United States Patent
Dugar et al.

(10) Patent No.: US 9,359,376 B2
(45) Date of Patent: Jun. 7, 2016

(54) SUBSTITUTED METHYLFORMYL REAGENTS AND METHOD OF USING SAME TO MODIFY PHYSICOCHEMICAL AND/OR PHARMACOKINETIC PROPERTIES OF COMPOUNDS

(75) Inventors: Sundeep Dugar, San Jose, CA (US); Dinesh Mahajan, Haryana (IN); Frank Peter Hollinger, Wayne, PA (US)

(73) Assignee: SPHAERA PHARMA PTE. LTD, Singapore (SG)

( * ) Notice: Subject to any disclaimer, the term of this patent is extended or adjusted under 35 U.S.C. 154(b) by 93 days.

(21) Appl. No.: 14/110,373

(22) PCT Filed: Apr. 9, 2012

(86) PCT No.: PCT/IN2012/000248
§ 371 (c)(1),
(2), (4) Date: Dec. 16, 2013

(87) PCT Pub. No.: WO2012/137225
PCT Pub. Date: Oct. 11, 2012

(65) Prior Publication Data
US 2014/0121367 A1 May 1, 2014

(30) Foreign Application Priority Data
Apr. 8, 2011 (IN) .......................... 1024/DEL/2011

(51) Int. Cl.
| | |
|---|---|
| C07D 307/77 | (2006.01) |
| C07D 305/00 | (2006.01) |
| C07D 413/00 | (2006.01) |
| C07D 405/00 | (2006.01) |
| C07D 495/14 | (2006.01) |
| C07D 401/14 | (2006.01) |
| C07D 405/14 | (2006.01) |
| C07D 213/80 | (2006.01) |
| C07D 213/81 | (2006.01) |
| C07D 213/82 | (2006.01) |
| C07D 401/04 | (2006.01) |
| C07D 401/12 | (2006.01) |
| C07D 405/12 | (2006.01) |
| C07D 471/04 | (2006.01) |
| C07D 487/04 | (2006.01) |
| C07D 487/22 | (2006.01) |
| C07D 491/22 | (2006.01) |
| C07D 295/20 | (2006.01) |
| C07D 305/14 | (2006.01) |
| C07D 213/803 | (2006.01) |
| C07D 491/147 | (2006.01) |

(52) U.S. Cl.
CPC ............ *C07D 495/14* (2013.01); *C07D 213/80* (2013.01); *C07D 213/803* (2013.01); *C07D 213/81* (2013.01); *C07D 213/82* (2013.01); *C07D 295/20* (2013.01); *C07D 305/14* (2013.01); *C07D 401/04* (2013.01); *C07D 401/12* (2013.01); *C07D 401/14* (2013.01); *C07D 405/12* (2013.01); *C07D 405/14* (2013.01); *C07D 471/04* (2013.01); *C07D 487/04* (2013.01); *C07D 487/22* (2013.01); *C07D 491/147* (2013.01); *C07D 491/22* (2013.01)

(58) Field of Classification Search
CPC .. C07D 495/14; C07D 401/04; C07D 401/12; C07D 401/14; C07D 405/12; C07D 405/14; C07D 471/04; C07D 487/04; C07D 487/22; C07D 491/22
USPC ........... 549/457, 510, 511; 544/137; 546/208, 546/255, 256, 268.1, 269.7; 548/112, 247, 548/100, 240
See application file for complete search history.

(56) References Cited

U.S. PATENT DOCUMENTS

| | | |
|---|---|---|
| 3,642,920 A | 2/1972 | Johnson et al. |
| 7,498,353 B2 | 3/2009 | Singh et al. |
| 2003/0050333 A1 | 3/2003 | Jo |
| 2005/0004080 A1 | 1/2005 | Baudy et al. |
| 2005/0119292 A1 | 6/2005 | Gravestock et al. |
| 2009/0069410 A1 | 3/2009 | Czarnik |
| 2011/0034434 A1 | 2/2011 | Heffernan et al. |

OTHER PUBLICATIONS

International Search Report and Written Opinion issued in related International Patent Application No. PCT/IN2012/000248, mailed Aug. 28, 2012.

*Primary Examiner* — Andrew D Kosar
*Assistant Examiner* — Raymond Covington
(74) *Attorney, Agent, or Firm* — Foley & Lardner LLP

(57) ABSTRACT

The present invention relates to the synthesis and application of novel chiral/achiral substituted methyl formyl reagents to modify pharmaceutical agents and/or biologically active substances to modify the physicochemical, biological and/or pharmacokinetic properties of the resulting compounds from the unmodified original agent.

14 Claims, No Drawings

SUBSTITUTED METHYLFORMYL REAGENTS AND METHOD OF USING SAME TO MODIFY PHYSICOCHEMICAL AND/OR PHARMACOKINETIC PROPERTIES OF COMPOUNDS

FIELD OF THE INVENTION

The present invention relates to the synthesis and application of novel chiral/achiral substituted methyl formyl reagents to modify pharmaceutical agents and/or biologically active substances to modify the physicochemical, biological and/or pharmacokinetic properties of the resulting compounds from the unmodified original agent.

BACKGROUND OF THE INVENTION

A chemical entity, which is potent in activity against its target, is the first step in the drug discovery process. However, a potent compound is only effective when an appropriate quantity is transported to the site of action at an acceptable rate after it has been administered. Even potent compounds benefit from optimization of these aspects. Many potent chemical entities do not have optimal pharmacokinetic parameters and hence the pharmacodynamic properties of these drugs are also suboptimal. In addition, there are several chemical entities that are already available in the market which have restricted pharmacokinetic properties and hence cannot be formulated in a manner convenient for patient administration.

The rate and extent of transportation into the blood circulation can be controlled by addition of certain groups to the original molecule, thereby modifying the molecule and its properties. Molecular modification is the chemical modification of a known and previously characterized lead compound for the purpose of enhancing its usefulness as a drug. This could mean enhancing its specificity for a particular target site, increasing its potency, improving its rate and extent of absorption, modifying the time course over which the active components become bio-available in the body (e.g., time release formulation), reducing its toxicity, and/or changing its physical or chemical properties (e.g., solubility) to optimize those aspects for particular applications.

However, the moiety used for molecular modification of the drug must be such that the therapeutic efficacy of the compound is retained and/or enhanced, while causing modification of the pharmacokinetic properties. Further, the modified compound, when administered, must not adversely affect the safety, toxicity and efficacy of the chemical entity beyond a tolerable degree.

The aforementioned strictures have resulted in limitations, some long standing, in the manner in which existing pharmaceuticals can be administered. For example, acetylsalicylic acid, the active ingredient in aspirin, is insufficiently soluble in saline to be administered intravenously. Hence, from the time it was discovered that chewing willow bark could reduce a fever, through the time aspirin was first compounded and till date, it is most frequently administered orally, and is not suitable for intravenous administration.

The strictures have also made it difficult to modify the pharmacodynamic properties of existing pharmaceuticals to optimize them for particular uses. Development of pharmaceuticals would be facilitated if it was possible to develop derivatization methods that could modify the pharmacokinetic and pharmacodynamic properties of a drug without detrimentally affecting a drug's efficacy, safety, and toxicity.

There is a need, as is illustrated by some of the examples shown herein, for a method of modifying chemical compounds that are useful as drugs such that one or more of their pharmacokinetic, physical, and/or pharmacodynamic properties are modified in the resultant compounds Hence, to address this need, the present invention, aims to provide novel substituted methyl formyl based agents that may be used to modify existing compounds modify in terms of their pharmacokinetic, physical, and/or pharmacodynamic properties. The present invention discloses agents for modification and methods for using them to enhance particular properties while preserving the safety, toxicity, and efficacy of the original compound.

ADVANTAGES

This invention permits one to achieve one or more of the following:
1) Providing novel substituted methyl formyl based agents for molecular modification of chemical entities;
2) Modifying the pharmacokinetic profile of the modified entity;
3) Modifying the pharmacodynamic profile of the modified entity;
4) Maintaining a desirable safety and toxicity profile of the modified entity;
5) Improving the safety and toxicity profile;
6) Making pharmaceutical agents and other biologically active substances more soluble in saline and/or at biologically useful pH ranges;
7) Modifying the pharmacokinetic properties of pharmaceutical agents and other biologically active substances;
8) Modifying the rate of conversion of the modified pharmaceutical agents and other biologically active substances to the original pharmaceutical agents and biologically active substances by either modification of the structure of the substituted methyl formyl agents or by causing a change in the biological system favored to affect this conversion due to specificity and selectivity; and/or
9) Modifying the favored location(s) of conversion of the modified pharmaceutical agents and other biologically active substances to the original pharmaceutical agents and biologically active substances by either modification of the structure of the substituted methyl formyl agents or by causing a change in the biological system favored to affect this conversion due to specificity and selectivity.

SUMMARY OF THE INVENTION

The present invention provides a novel methyl formyl derivatizing reagent of the general formula shown below in Figure 1:

Figure 1:

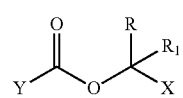

1

Figure 1 represents the structure of a substituted methyl formyl reagent;
Wherein:
X is selected from Cl, Br, I, OTs, OMs;
Y is selected from $R^2$, $OR^2$, or $N(R^2)_2$;

R and $R^1$ can independently be H, $C_1$-$C_8$ straight or branched chain alkyl—optionally containing 1-3 heteroatoms selected from O, N, S, SO, or $SO_2$; 3-7 membered cycloalkyl optionally containing 1-3 heteroatoms selected from O, N, S, SO, or $SO_2$ and or lower alkyl, straight or branched alkyl, alkoxy; alkaryl, aryl, heteroaryl, or alkheteroaryl;

R and $R^1$ can also be joined to form 3-7 membered carbocyclic ring optionally containing 1-2 heteroatoms selected from, O, N, S, SO, $SO_2$ and also be optionally substituted with alkoxy, F or Cl;

$R^2$ can independently be H, $C_1$-$C_8$ straight or branch chain alkyl—optionally containing 1-3 heteroatoms selected from O, N, S, SO, or $SO_2$; 3-7 membered cycloalkyl optionally containing 1-3 heteroatoms selected from O, N, S, SO, or $SO_2$ and or lower alkyl, straight or branched alkyl, alkoxy; alkaryl, aryl, heteroaryl, or alkheteroaryl; and $R^2$ can also be part of a 3-7 membered ring optionally containing additional 1-2 heteroatoms selected from O, N, S, SO, $SO_2$ and also be optionally substituted with alkoxy, F or Cl.

The methylformyl reagents of the present invention may be present in enantiomerically pure forms or as mixture of enantiomers or diastereomers.

Compounds that are derivatized with these substituted methyl formyl reagents have been found to possess notably enhanced aqueous solubility, and exhibit substantial and surprising improvements in pharmacokinetic and pharmacodynamic properties. These derivatizing agents are useful to favorably modify the physicochemical and pharmacodynamic properties of pharmaceutical compounds and other related uses.

The present invention therefore also includes a method of using these novel derivatizing agents to modify one or more of the physicochemical and pharmacokinetic, and pharmacodynamic properties of pharmaceutical compounds. As the examples shown herein demonstrate, the method of the present invention can readily be applied to a wide variety of compounds to modify their properties in desirable ways and obtain resultant compounds with improved properties.

DETAILED DESCRIPTION OF THE PREFERRED EMBODIMENTS

This invention provides novel substituted methyl formyl compounds suitable as a reagent for molecular modification, in which the modified entities exhibit improved properties and are suitable for to pharmaceutical use. The resultant modified compounds obtained by using the novel reagents of this invention are suitable for use as drugs and/or pharmaceutical agents with improved pharmacokinetic and/or pharmacodynamic profile(s), while maintaining a desirable safety and toxicity profile. The invention also provides a method for preparation of pharmaceutical agents and other biologically active substances more soluble in saline and/or at biologically useful pHs, a method to affect the pharmacokinetic properties of pharmaceutical agents and other biologically active substances, a method to affect the rate of conversion of the modified pharmaceutical agents and other biologically active substances to the original pharmaceutical agents and biologically active substances by either modification of the structure of the substituted methyl formyl agents or by causing a change in the biological system favored to affect this conversion due to specificity and selectivity, and a method to affect the favored location(s) of conversion of the modified pharmaceutical agents and other biologically active substances to the original pharmaceutical agents and biologically active substances by either modification of the structure of the substituted methyl formyl agents or by causing an change in the biological system favored to affect this conversion due to specificity and selectivity. Process for preparation and isolation of modified compounds are also provided.

A. Novel Substituted Methyl Formyl Reagents

B. A method of modifying a chemical compound by causing covalent attachment of a compound of formula 1, to a functional group or a heteroatom of a heterocyclic ring system to obtain a modified compound with improved chemical and biological properties;

Wherein in compound (I):

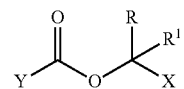

1

X is selected from Cl, Br, I, OTs, OMs;

Y is selected from $R^2$, $OR^2$, or $N(R^2)_2$; and

R and $R^1$ are independently H, $C_1$-$C_8$ straight or branched chain alkyl—optionally containing 1-3 heteroatoms selected from O, N, S, SO, or $SO_2$; 3-7 membered cycloalkyl optionally containing 1-3 heteroatoms selected from O, N, S, SO, or $SO_2$ and or lower alkyl, straight or branched alkyl, alkoxy; alkaryl, aryl, heteroaryl, or alkheteroaryl;

R and $R^1$ can also be joined to substituted methyl formyl to form a 3-7 membered carbocyclic ring optionally containing 1-2 heteroatoms selected from, O, N, S, SO, $SO_2$ and also be optionally substituted with alkoxy, F or Cl;

$R^2$ independently is H, $C_1$-$C_8$ straight or branch chain alkyl—optionally containing 1-3 heteroatoms selected from O, N, S, SO, or $SO_2$; 3-7 membered cycloalkyl optionally containing 1-3 heteroatoms selected from O, N, S, SO, or $SO_2$ and or lower alkyl, straight or branched alkyl, alkoxy; alkaryl, aryl, heteroaryl, or alkheteroaryl; and $R^2$ is independently part of a 3-7 membered ring optionally containing additional 1-2 heteroatoms selected from, O, N, S, SO, $SO_2$ and also be optionally substituted with alkoxy, F or Cl.

A.1 Novel Substituted Methyl Formyl Reagents

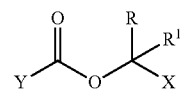

1

Where:

Figure 1 represents the structure of a substituted methyl formyl reagent;

X is selected from Cl, Br, I, OTs, OMs;

Y is selected from $R^2$, $OR^2$, or $N(R^2)_2$;

R and $R^1$ can independently be H, $C_1$-$C_8$ straight or branched chain alkyl—optionally containing 1-3 heteroatoms selected from O, N, S, SO, or $SO_2$; 3-7 membered cycloalkyl optionally containing 1-3 heteroatoms selected from O, N, S, SO, or $SO_2$ and or lower alkyl, straight or branched alkyl, alkoxy; alkaryl, aryl, heteroaryl, or alkheteroaryl;

R and $R^1$ can also be joined to substituted methyl formyl to form a 3-7 membered carbocyclic ring optionally containing 1-2 heteroatoms selected from, O, N, S, SO, $SO_2$ and also be optionally substituted with alkoxy, F or Cl;

$R^2$ can independently be H, $C_1$-$C_8$ straight or branch chain alkyl—optionally containing 1-3 heteroatoms selected from O, N, S, SO, or $SO_2$; 3-7 membered cycloalkyl optionally containing 1-3 heteroatoms selected from O, N, S, SO, or $SO_2$ and or lower alkyl, straight or branched alkyl, alkoxy; alkaryl, aryl, heteroaryl, or alkheteroaryl; and $R^2$ can also be part of a 3-7 membered ring optionally containing additional 1-2 heteroatoms selected from, O, N, S, SO, $SO_2$ and also be optionally substituted with alkoxy, F or Cl.

The terms "alk" or "alkyl" refer to straight or branched chain hydrocarbon groups having 1 to 12 carbon atoms, preferably 1 to 8 carbon atoms. The expression "lower alkyl" refers to alkyl groups of 1 to 4 carbon atoms.

The term "alkenyl" refers to straight or branched chain hydrocarbon groups of 2 to 10, preferably 2 to 4, carbon atoms having at least one double bond. Where an alkenyl group is bonded to a nitrogen atom, it is preferred that such group not be bonded directly through a carbon bearing a double bond.

The term "alkynyl" refers to straight or branched chain hydrocarbon groups of 2 to 10, preferably 2 to 4 carbon atoms having at least one triple bond. Where an alkynyl group is bonded to a nitrogen atom, it is preferred that such group not be bonded directly through a carbon bearing a triple bond.

The term "alkylene" refers to a straight chain bridge of 1 to 5 carbon atoms connected by single bonds (e.g., —$(CH_2)_x$— wherein x is 1 to 5), which may be substituted with 1 to 3 lower alkyl groups.

The term "alkenylene" refers to a straight chain bridge of 2 to 5 carbon atoms having one or two double bonds that is connected by single bonds and may be substituted with 1 to 3 lower alkyl groups. Exemplary alkenylene groups are —CH═CH—CH═CH—, —$CH_2$—CH═CH—, —$CH_2$—CH═CH—$CH_2$—, $C(CH_3)_2$CH═CH— and —CH($C_2H_5$)—CH═CH—.

The term "alkynylene" refers to a straight chain bridge of 2 to 5 carbon atoms that has a triple bond therein, is connected by single bonds, and may be substituted with 1 to 3 lower alkyl groups. Exemplary alkynylene groups are —C≡C—, —$CH_2$—C≡C—, —CH($CH_3$)—C≡C— and —C≡C—CH($C_2H_5$)$CH_2$—.

The terms "ar" or "aryl" refer to aromatic cyclic groups (for example 6 membered monocyclic, 10 membered bicyclic or 14 membered tricyclic ring systems) which contain 6 to 14 carbon atoms. Exemplary aryl groups include phenyl, naphthyl, biphenyl and anthracene.

The terms "cycloalkyl" and "cycloalkenyl" refer to cyclic hydrocarbon groups of 3 to 12 carbon atoms.

The terms "halogen" and "halo" refer to fluorine, chlorine, bromine and iodine.

The term "unsaturated ring" includes partially unsaturated and aromatic rings.

The terms "heterocycle", "heterocyclic" or "heterocyclo" refer to fully saturated or unsaturated, including aromatic (i.e. "heteroaryl") cyclic groups, for example, 4 to 7 membered monocyclic, 7 to 11 membered bicyclic, or 10 to 15 membered tricyclic ring systems, which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized.

The heterocyclic group may be attached at any heteroatom or carbon atom of the ring or ring system.

Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, triazinyl, and the like.

Exemplary bicyclic heterocyclic groups include indolyl, benzothiazolyl, benzoxazolyl, benzodioxolyl, benzothienyl, quinuclidinyl, quinolinyl, tetra-hydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b] pyridinyl), dihydroisoindolyl, dihydroquinazolinyl (such as 3,4-dihydro-4-oxo-quinazolinyl), tetrahydroquinolinyl and the like.

Exemplary tricyclic heterocyclic groups include carbazolyl, benzidolyl, phenanthrolinyl, acridinyl, phenanthridinyl, xanthenyl and the like.

The term "heteroaryl" refers to aromatic heterocyclic groups.

Exemplary heteroaryl groups include pyrrolyl, pyrazolyl, imidazolyl, oxazolyl, isoxazolyl, thiazolyl, thiadiazolyl, isothiazolyl, furyl, thienyl, oxadiazolyl, pyridinyl, pyrazinyl, pyrimidinyl, pyridazinyl, triazolyl, triazinyl, and the like.

The terms "alkylene" and "alkyl" in this text include both linear and branched, saturated and unsaturated (i.e. containing one double bond) divalent alkylene groups and monovalent alkyl groups, respectively. The term "alkanol" in this text likewise includes linear and branched, saturated and unsaturated alkyl components of the alkanol groups, in which the hydroxyl groups may be situated at any position on the alkyl moiety. The term "cycloalkanol" includes unsubstituted or substituted (e.g. methyl or ethyl)cyclic alcohols.

Pharmaceutical agents include any substance or agent considered to be a medicine, drug, or pharmaceutical agent.

Biologically active substances include any substance which exhibits a biological activity as understood by one skilled in the art.

Chemical and biological properties include pharmacokinetic and pharmacodynamic properties.

In a preferred embodiment, the novel substituted methyl formyl compounds Reagents of this invention have structures represented by Figure 1.

In another preferred embodiment, the present invention includes a method of using these novel derivatizing agents to modify one or more of the physicochemical and pharmacokinetic, and pharmacodynamic properties of pharmaceutical compounds. As the examples shown herein demonstrate, the method of the present invention can readily be applied to a wide variety of compounds to modify their properties in desirable ways.

Figure 1 reveals the general structure of the derivatizing agents of the present invention. The different structures related to Figure 1 may be divided in three classes i.e. Type I, where Y=$R^2$; Type II, where Y=$(NR^2)_2$ and Type III, where Y=$OR^2$.

A.2 General Methods for the Preparation of Novel Substituted Methyl Formyl Reagents The methyl formyl reagents (Type I, II, III) can be prepared from respective acids, amines and alcohols directly. An acid with or without activation can be reacted with a corresponding aldehyde in presence of a Lewis acid can provide Type I reagent. An alcohol can be reacted with a halomethylhaloacetate in presence of a base to provide Type III reagent. Similarly, an amine (primary or secondary) can be reacted with halomethyl haloacetate with or without the presence of base can provide Type II reagent.

A.2.2 General Method to Synthesize Type I Reagents

Scheme 1

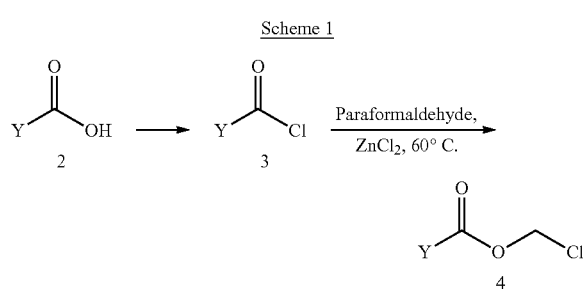

General Procedure:

Aldehydes such as paraformaldehyde and acid chlorides, [3], can be reacted under anhydrous conditions and at appropriate temperatures with Lewis acids such as zinc chloride (dry), typically between −10° C. and 60° C. for a time ranging up to 24 hours. The reaction mixture can be diluted with solvents such as dichloromethane, washed with aqueous dilute base such as a solution of $Na_2HCO_3$. Standard work up and purifications yield the desired substituted methyl formyl Reagents, [4].

Scheme 2

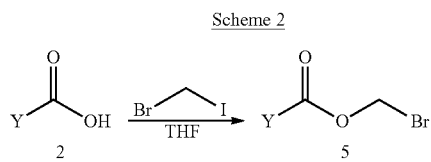

General Procedure:

Metal salt of desired acid such as caesium salt of Acid [2], can be treated with bromoiodomethane in Dry THF at appropriate temperatures, typically between 0° C. to RT for 16 hours and if required heating. The reaction mixture can be diluted with solvents such as ethyl acetate, washed with aqueous dilute base such as aqueous solution of $Na_2HCO_3$. Standard work up and purifications yield the desired substituted methyl formyl Reagents [5].

Scheme 3

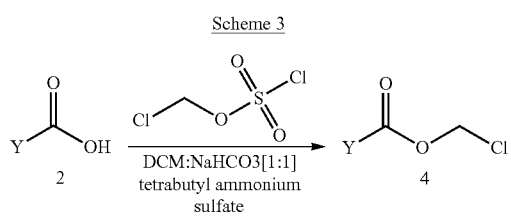

General Procedure:

To a vigorously stirred, solution of acid [2] in a solvent such as dichloromethane at room temperature, a base such as sodium bicarbonate and tetrabutylammonium bisulfate in water was added, followed by the drop-wise addition of a solution of chloromethyl chlorosulfate in a solvent such as dichloromethane. After completion of reaction, organic layer was washed with 5% aqueous $Na_2CO_3$. Standard work up and purifications yields desired substituted methyl formyl Reagents, [4].

As illustrated above and explained herein, $Y=R^2$, $R^4$ can be any of several moieties linking the compound to be modified to the methyl formyl reagent of the present invention. $R^2$ can independently be H, $C_1$-$C_8$ straight or branch chain alkyl—optionally containing 1-3 heteroatoms selected from O, N, S, SO, or $SO_2$; 3-7 membered cycloalkyl optionally containing 1-3 heteroatoms selected from O, N, S, SO, or $SO_2$ and or lower alkyl, straight or branched alkyl, alkoxy; alkaryl, aryl, heteroaryl, or alkheteroaryl.

$R^2$ can also be part of 3-7 membered ring optionally containing additional 1-2 heteroatoms selected from, O, N, S, SO, $SO_2$ and also be optionally substituted with alkoxy, F or Cl.

A.2.3: General Method to Synthesize Type II Reagents

Scheme 2

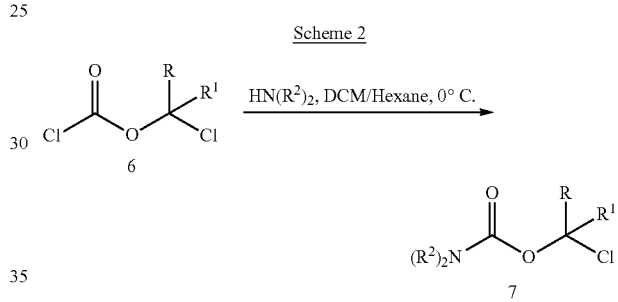

General Procedure:

Corresponding primary or secondary amines can be reacted with substituted or unsubstituted chloro methylchloroformate, [6], in a solvent such as hexane or DCM at 0° C. The reaction mixture can be filtered and the filtrate can be washed with 1.0 N HCl. The organics can be evaporated to get the desired reagent, [7]. If required, further purification can be achieved using any general purification method practiced in organic chemistry laboratory such as precipitation or crystallization or preparative column purification.

As illustrated above and explained herein, R and $R^1$ can independently be H, $C_1$-$C_8$ straight or branched alkyl chain—optionally containing 1-3 heteroatoms selected from O, N, S, SO, or $SO_2$; 3-7 membered cycloalkyl optionally containing 1-3 heteroatoms selected from O, N, S, SO, or $SO_2$ and or lower alkyl, straight or branched alkyl, alkoxy; alkaryl, aryl, heteroaryl, or alkheteroaryl.

R and $R^1$ can also be joined to substituted methyl formyl to form a 3-7 membered carbocyclic ring optionally containing 1-2 heteroatoms selected from, O, N, S, SO, $SO_2$ and also be optionally substituted with alkoxy, F or Cl.

$R^2$ can independently be H, $C_1$-$C_8$ straight or branch chain alkyl—optionally containing 1-3 heteroatoms selected from O, N, S, SO, or $SO_2$; 3-7 membered cycloalkyl optionally containing 1-3 heteroatoms selected from O, N, S, SO, or $SO_2$ and or lower alkyl, straight or branched alkyl, alkoxy; alkaryl, aryl, heteroaryl, or alkheteroaryl.

$R^2$ can also be part of a 3-7 membered ring optionally containing an additional 1-2 heteroatoms selected from, O, N, S, SO, $SO_2$ and also be optionally substituted with alkoxy, F or Cl.

A.2.4: General Method to Synthesize Type III Reagents

Scheme 3:

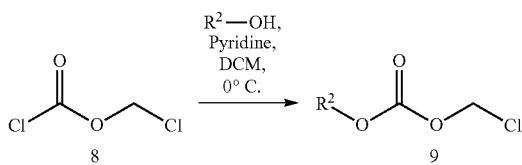

General Procedure:

To the solution of chloromethylchloroformate, [8], in a solvent such as hexane, can be added solution of pyridine in hexane, drop wise under ice cooling. To this reaction mixture, the corresponding alcohol can be added at the same temperature. The reaction mixture can be stirred for a time ranging up to 24 hrs. Standard work up and purifications yield the desired corresponding carbonate reagent, [9].

As illustrated above and explained herein, $R^2$ can be any of several moieties linking the compound to be modified to the methyl formyl reagent of the present invention.

$R^2$ can independently be H, $C_1$-$C_8$ straight or branch alkyl chain—optionally containing 1-3 heteroatoms selected from O, N, S, SO, or $SO_2$; 3-7 membered cycloalkyl optionally containing 1-3 heteroatoms selected from O, N, S, SO, or $SO_2$ and or lower alkyl, straight or branched alkyl, alkoxy; alkaryl, aryl, heteroaryl, or alkheteroaryl.

$R^2$ can also be part of a 3-7 membered ring optionally containing additional 1-2 heteroatoms selected from, O, N, S, SO, $SO_2$ and also be optionally substituted with alkoxy, F or Cl.

Scheme 4: General Synthetic Scheme for Halide Exchange:

Scheme 4.1:

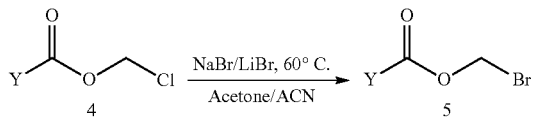

General Procedure:

Chloromethyl formyl Reagents [4] when treated with bromide suitable reagent such as lithium bromide or sodium bromide at appropriate temperatures, typically in the range of 40-80° C. for a time ranging up to 24 hours followed by standard work up and purification, yields desired bromo methyl formyl Reagents, [5].

Scheme 4.2:

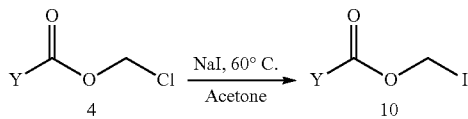

General Procedure:

Chloromethyl formyl Reagents [4] when treated with a reagent such as sodium iodide at appropriate temperatures, typically ranging from room temperature to 60° C. for a time ranging up to 24 hours followed by a standard work up and purification, yields desired iodo methyl formyl Reagents, [10].

Scheme 4.3:

General Procedure:

Chloromethyl formyl Reagents [4] when treated with silver salt of methane sulfonic acid at appropriate temperatures, typically ranging from room temperature to 60° C. to 90° C. for a time ranging up to 24 hours followed by standard work up and purification, yield desired ((methylsulfonyl)oxy)methyl formyl Reagents, [11].

Scheme 4.4:

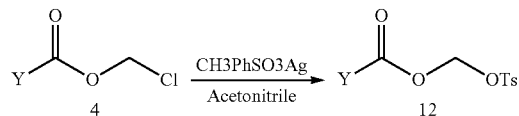

General Procedure:

Chloromethyl formyl Reagents [4] when treated with silver salt of p-methyl benzene sulfonic acid at appropriate temperatures, typically ranging from room temperature to 60° C. to 90° C. for a time ranging up to 24 hours followed by standard work up and purification yield the desired ((methylsulfonyl)oxy)methyl formyl Reagents, [12].

A.3 Substituted Methyl Formyl Reagents:

Based on the schemes as disclosed in A.2, a number of substituted methyl formyl reagents may be synthesized. Non limiting lists of substituted methyl formyl reagents of the present invention that may be synthesized as per schemes above are provided herein are as below and represented at Fig. 1:

Type I Reagents
i. chloromethyl isopropyl carbonate
ii. benzyl chloromethyl carbonate
iii. chloromethyl morpholinomethyl carbonate
iv. chloromethyl isobutyl carbonate
v. chloromethylmethyl carbonate
vi. (S)-sec-butyl chloromethyl carbonate
vii. (R)-sec-butyl chloromethyl carbonate
viii. chloromethyl((3S,5R)-3,5-dimethylmorpholino)methyl carbonate
ix. chloromethyl 2-methylcyclopropyl carbonate
x. chloromethyl 2-methoxyethyl carbonate
xi. chloromethyl propyl carbonate
xii. chloromethyl cyclobutyl carbonate
xiii. chloromethyl cyclopropyl carbonate
xiv. chloromethyl 2,2-dimethylcyclobutyl carbonate
xv. chloromethyl cyclopentyl carbonate
xvi. chloromethyl oxetan-3-yl carbonate
xvii. (S)-chloromethyl tetrahydrofuran-3-yl carbonate
xviii. chloromethyl cyclohexylmethyl carbonate
xix. chloromethyl 3-methoxycyclohexyl carbonate
xx. (R)-chloromethyl tetrahydrofuran-3-yl carbonate
xxi. chloromethyl ethoxymethyl carbonate
xxii. chloromethyl oxepan-4-yl carbonate
xxiii. (1R,2S,4S)-bicyclo[2.2.1]heptan-2-yl chloromethyl carbonate
xxiv. chloromethyl 2,3-dihydro-1H-inden-1-yl carbonate
xxv. benzyl chloromethyl carbonate xxvi. (S)-chloromethyl 1-phenylethyl carbonate
xxvii. chloromethyl cyclohexyl carbonate
xxviii. chloromethyl isobutyl carbonate
xxix. chloromethyl 4-methylcyclohexyl carbonate
xxx. chloromethyl 2-(methylthio)ethyl carbonate
xxxi. chloromethyl 3-methylcyclohexyl carbonate
xxxii. chloromethylpentan-2-yl carbonate
xxxiii. chloromethyl neopentyl carbonate
xxxiv. methyl 1-((chloromethoxy)carbonyloxy)cyclopropanecarboxylate
xxxv. chloromethyl cyclopropylmethyl carbonate
xxxvi. chloromethyl 2,2-diethoxyethyl carbonate
xxxvii. chloromethyl cyclopentylmethyl carbonate
xxxviii. methyl 2-((chloromethoxy)carbonyloxy)propanoate
xxxix. (S)-chloromethyl 2,2,4-trimethylcyclopent-3-enyl carbonate
xl. chloromethyl 1,3-dioxolan-2-yl carbonate
xli. chloromethyl (2,6-dimethylcyclohexyl)methyl carbonate
xlii. chloromethyl 2-(tetrahydro-2H-pyran-2-yl)ethyl carbonate
xliii. chloromethyl(tetrahydro-2H-pyran-4-yl)methyl carbonate
xliv. chloromethyl tetrahydro-2H-pyran-4-yl carbonate
xlv. chloromethyl 1-methylcyclopentyl carbonate
xlvi. chloromethyl 1-cyclopentylethyl carbonate
xlvii. chloromethyl 3-methylcyclopentyl carbonate
xlviii. chloromethyl 3,3-dimethylcyclohexyl carbonate
xlix. chloromethyl 2,5-dimethylcyclohexyl carbonate
l. chloromethyl 1-(4-methylcyclohexyl)ethyl carbonate
li. chloromethyl (3-methyloxetan-3-yl)methyl carbonate
lii. chloromethyl (3-methyloxetan-3-yl)methyl carbonate
liii. chloromethyl 2-isopropoxyethyl carbonate
liv. (chloromethyl carbonic)5-((3aS,4S,6aR)-2-oxohexahydro-1H-thieno[3,4-d]imidazol-4-yl)pentanoic anhydride
lv. 4-((chloromethoxy)carbonyloxy)-2-hydroxy-4-oxobutanoic acid
lvi. chloromethyl 4-formyl-2-methoxyphenyl carbonate
lvii. chloromethyl 3-oxobutan-2-yl carbonate
lviii. methyl 4-((chloromethoxy)carbonyloxy)benzoate
lix. (R)-2-amino-3-((chloromethoxy)carbonyloxy)propanoic acid
lx. 3-tert-butyl-4-methoxyphenyl chloromethyl carbonate
lxi. (R)-2-amino-3-(4-((chloromethoxy)carbonyloxy)phenyl)propanoic acid
lxii. (R)-2-amino-4-((chloromethoxy)carbonyloxy)-4-oxobutanoic acid
lxiii. (E)-chloromethyl 3,7-dimethylocta-2,6-dienyl carbonate
lxiv. methyl 4-((chloromethoxy)carbonyloxy)benzoate
lxv. chloromethyl 2-(4-methylcyclohex-3-enyl)propan-2-yl carbonate
lxvi. chloromethyl 3,7-dimethylocta-1,6-dien-3-yl carbonate
lxvii. 4-allyl-2-methoxyphenyl chloromethyl carbonate
lxviii. chloromethyl (1R,2S,5R)-2-isopropyl-5-methylcyclohexyl carbonate
lxix. propyl 4-((chloromethoxy)carbonyloxy)benzoate
lxx. (E)-chloromethyl 3,7-dimethylocta-2,6-dienyl carbonate TYPE I Reagents Fig 1: Some non limiting examples of type I Reagents.

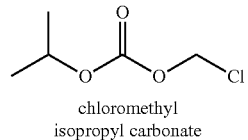

chloromethyl
isopropyl carbonate

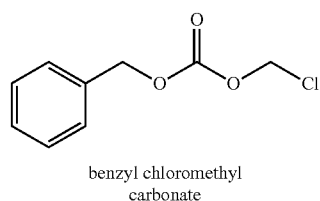

benzyl chloromethyl
carbonate

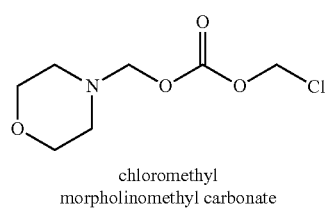

chloromethyl
morpholinomethyl carbonate

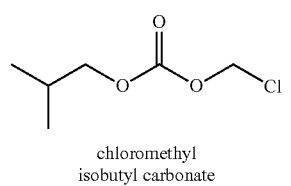

chloromethyl
isobutyl carbonate

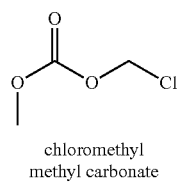

chloromethyl
methyl carbonate

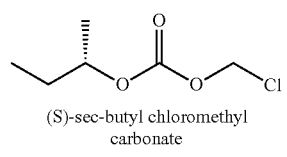

(S)-sec-butyl chloromethyl
carbonate

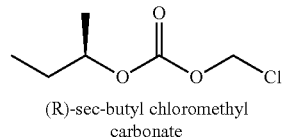

(R)-sec-butyl chloromethyl
carbonate

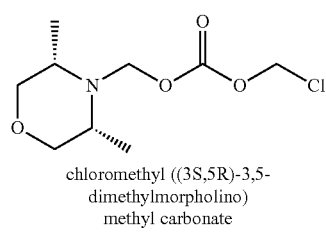

chloromethyl ((3S,5R)-3,5-
dimethylmorpholino)
methyl carbonate

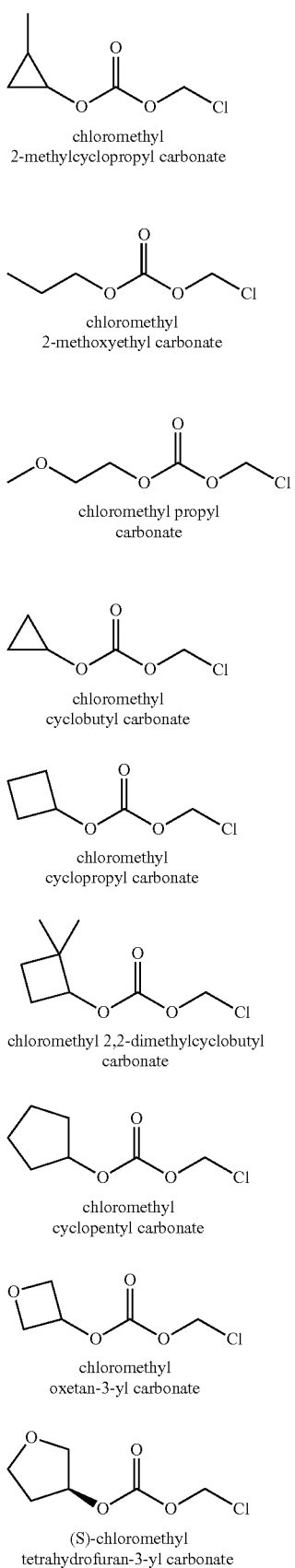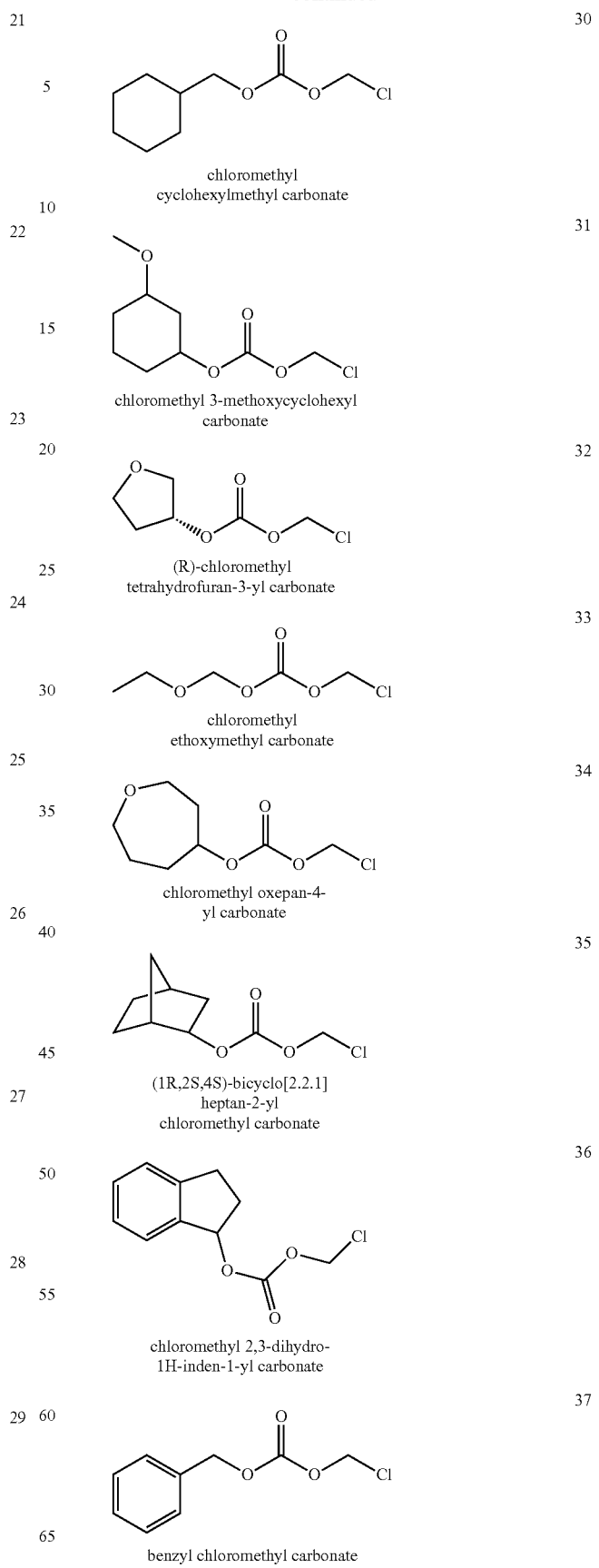

-continued

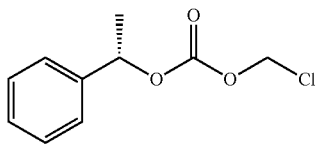

(S)-chloromethyl
1-phenylethyl carbonate

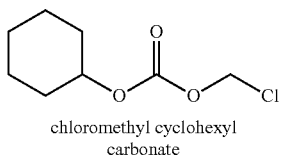

chloromethyl cyclohexyl
carbonate

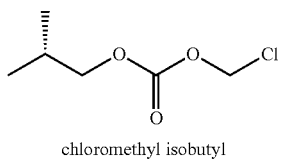

chloromethyl isobutyl
carbonate

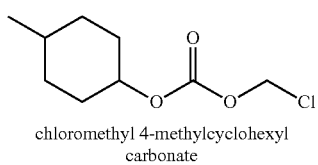

chloromethyl 4-methylcyclohexyl
carbonate

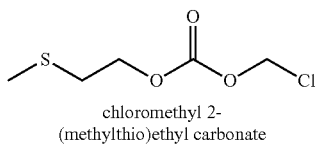

chloromethyl 2-
(methylthio)ethyl carbonate

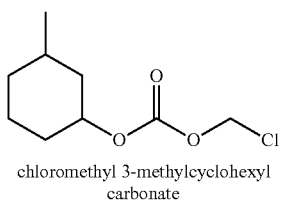

chloromethyl 3-methylcyclohexyl
carbonate

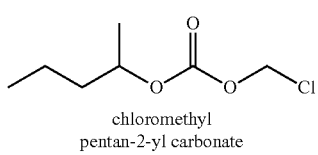

chloromethyl
pentan-2-yl carbonate

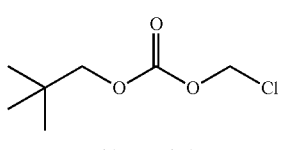

chloromethyl
neopentan carbonate

-continued

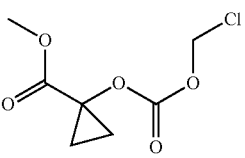

methyl 1-((chloromethoxy)carbonyloxy)
cyclopropanecarboxylate

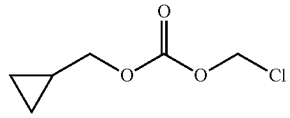

chloromethyl cyclopropylmethyl
carbonate

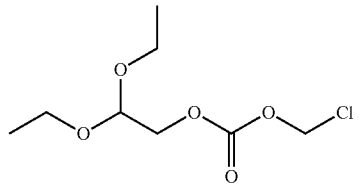

chloromethyl 2,2-diethoxyethyl
carbonate

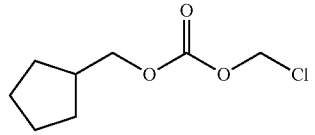

chloromethyl
cyclopentylmethyl carbonate

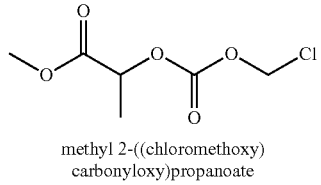

methyl 2-((chloromethoxy)
carbonyloxy)propanoate

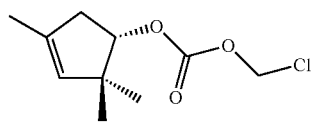

(S)-chloromethyl 2,2,4-
trimethylcyclopent-3-enyl
carbonate

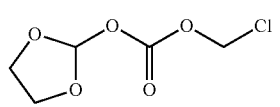

chloromethyl 1,3-dioxolan-2-yl
carbonate

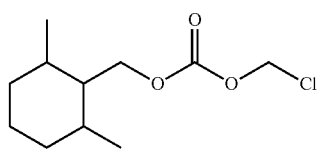

chloromethyl (2,6-dimethylcyclohexyl)
methyl carbonate

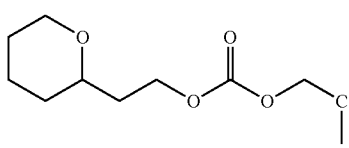

chloromethyl
2-(tetrahydro-2H-pyran-2-yl)
ethyl carbonate

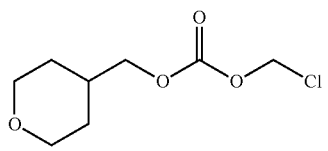

chloromethyl
(tetrahydro-2H-pyran-4-yl)
methyl carbonate

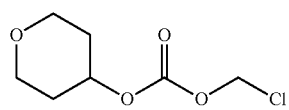

chloromethyl tetrahydro-2H-
pyran-4-yl carbonate
chloromethyl 1-(oxetan-3-yl)ethyl carbonate

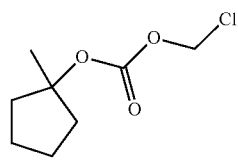

chloromethyl
1-methylcyclopentyl carbonate

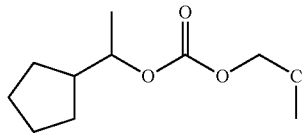

chloromethyl 1-
cyclopentylethyl carbonate

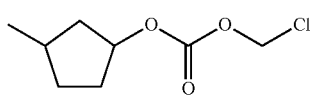

chloromethyl 3-
methylcyclopentyl
carbonate

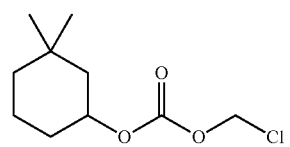

chloromethyl 3,3-dimethylcyclohexyl
carbonate

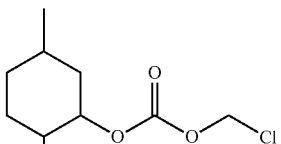

chloromethyl 2,5-dimethyl
cyclohexyl carbonate

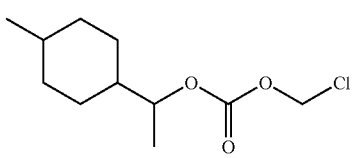

chloromethyl 1-(4-
methylcyclohexyl)ethyl carbonate

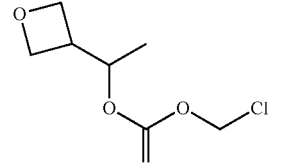

chloromethyl (3-methyloxetan-3-yl)
methyl carbonate

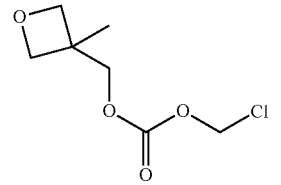

chloromethyl (3-methyloxetan-3-yl)
methyl carbonate

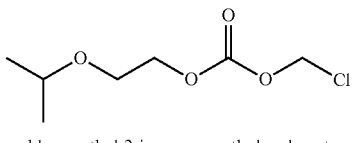

chloromethyl 2-isopropoxyethyl carbonate

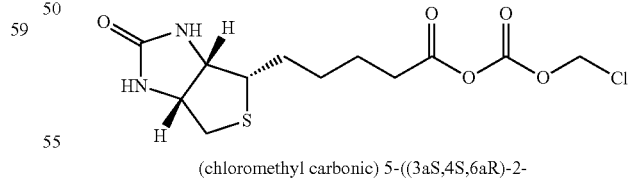

(chloromethyl carbonic) 5-((3aS,4S,6aR)-2-
oxohexahydro-1H-thieno[3,4-d]imidazol-4-
yl)pentanoic anhydride

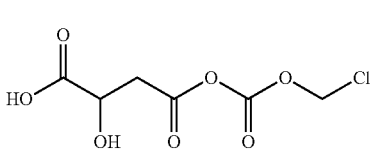

4-((chloromethoxy)carbonyloxy)-
2-hydroxy-4-oxobutanoic acid

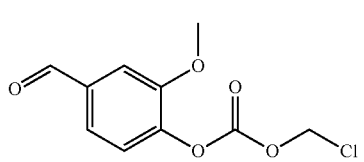

chloromethyl 4-formyl-2-
methoxyphenyl carbonate

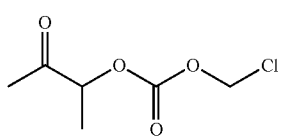

chloromethyl
3-oxobutan-2-yl carbonate

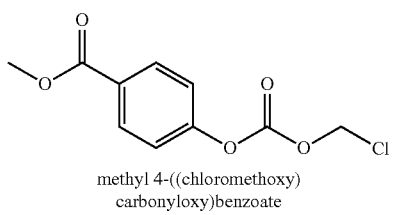

methyl 4-((chloromethoxy)
carbonyloxy)benzoate

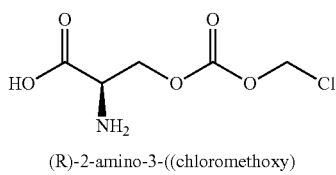

(R)-2-amino-3-((chloromethoxy)
carbonyloxy)propanoic acid

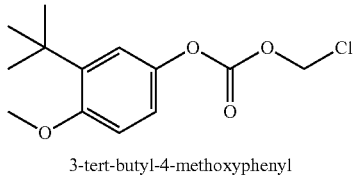

3-tert-butyl-4-methoxyphenyl
chloromethyl carbonate

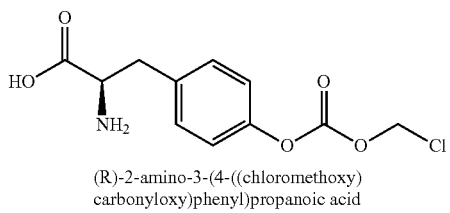

(R)-2-amino-3-(4-((chloromethoxy)
carbonyloxy)phenyl)propanoic acid

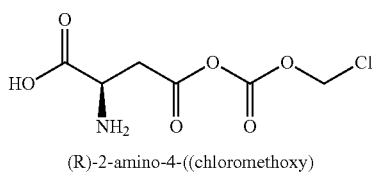

(R)-2-amino-4-((chloromethoxy)
carbonyloxy)-4-oxobutanoic acid

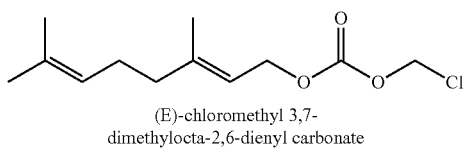

(E)-chloromethyl 3,7-
dimethylocta-2,6-dienyl carbonate

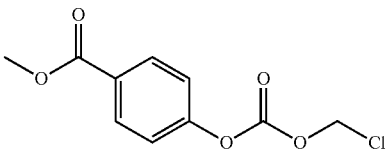

methyl 4-((chloromethoxy)
carbonyloxy)benzoate

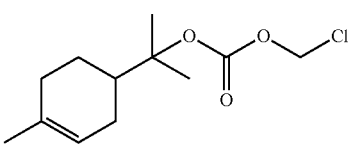

chloromethyl 2-(4-methylcyclohex-3-enyl)
propan-2-yl carbonate

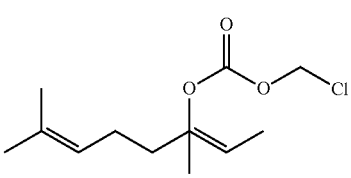

chloromethyl 3,7-
dimethylocta-1,6-dien-3-yl carbonate

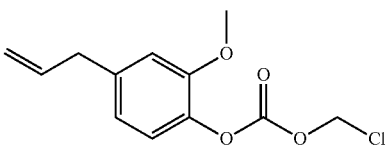

4-allyl-2-methoxyphenyl
chloromethyl carbonate

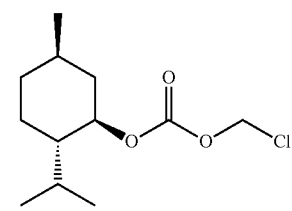

chloromethyl (1R,2S,5R)-2-isopropyl-5-
methylcyclohexyl carbonate

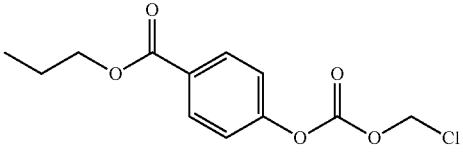

propyl-4-((chloromethoxy)
carbonyloxy)benzoate

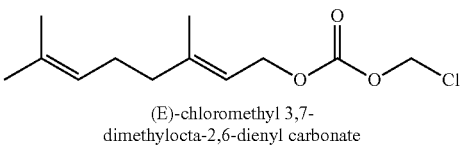

(E)-chloromethyl 3,7-
dimethylocta-2,6-dienyl carbonate

A non limiting examples of Type II reagents are listed herein below and represented at Figure 2.

Type II Reagents
i. chloromethyl cyclohexanecarboxylate
ii. chloromethyl 2-cyclohexylacetate iii. chloromethyl 4-methylcyclohexanecarboxylate
iv. chloromethyl 1-methylcyclohexanecarboxylate
v. chloromethyl cyclopentanecarboxylate
vi. chloromethyl 1-(trifluoromethyl)cyclopentanecarboxylate
vii. chloromethyl cyclobutanecarboxylate
viii. chloromethyl 2-ethylhexanoate
ix. chloromethyl 3-cyclopentylpropanoate
x. chloromethyl cyclopropanecarboxylate
xi. chloromethyl pentanoate
xii. chloromethyl 2-methylpentanoate
xiii. chloromethyl 3,5,5-trimethylhexanoate
xiv. chloromethyl 2,2-dimethylbutanoate
xv. chloromethyl 2-methylbutanoate
xvi. chloromethyl hexanoate
xvii. chloromethyl 2-ethylbutanoate
xviii. chloromethyl butyrate
xix. chloromethyl 3-phenylpropanoate
xx. chloromethyl 2-phenylpropanoate
xxi. (R)-chloromethyl 2-phenylpropanoate
xxii. (S)-chloromethyl 2-phenylpropanoate
xxiii. (1r,4r)-chloromethyl 4-methylcyclohexanecarboxylate
xxiv. chloromethyl 4-methoxycyclohexanecarboxylate
xxv. chloromethyl 4,4-difluorocyclohexanecarboxylate
xxvi. chloromethyl 3-methoxycyclohexanecarboxylate
xxvii. (2R)-chloromethyl 2-methylcyclopentanecarboxylate
xxviii. (R)-chloromethyl 2-methylbutanoate
xxix. (S)-chloromethyl 2-methylbutanoate
xxx. (S)-chloromethyl 2-methoxy-2-phenylacetate
xxxi. (S)-chloromethyl 2-phenylpropanoate
xxxii. (S)-chloromethyl 2-phenylbutanoate
xxxiii. (S)-chloromethyl 3-phenylbutanoate
xxxiv. bis(chloromethyl) 2,2-dimethylmalonate
xxxv. bis(chloromethyl)oxalate
xxxvi. chloromethyl 2-cyclopropylacetate
xxxvii. chloromethyl 2-cyclobutylacetate
xxxviii. chloromethyl 2-cyclopentylacetate
xxxix. chloromethyl 2-(tetrahydrofuran-3-yl)acetate
xl. chloromethyl 2-(tetrahydro-2H-pyran-4-yl)acetate
xli. chloromethyl 2-methylcyclopropanecarboxylate
xlii. chloromethyl 2-(1-methylcyclobutyl)acetate
xliii. chloromethyl 2-(1-methylcyclopropyl)'acetate
xliv. chloromethyl propionate
xlv. chloromethyl acetate
xlvi. chloromethyl isobutyrate
xlvii. chloromethyl 2-isopropyl-3-methylbutanoate
xlviii. chloromethyl 3,5-dimethylcyclohexanecarboxylate
xlix. chloromethyl 2-propylpentanoate
l. chloromethyl 4-methoxybenzoate
li. chloromethyl 4-methylbenzoate
lii. chloromethyl 3-methylbenzoate
liii. chloromethyl 2,2,2-trifluoroacetate
liv. chloromethyl 5,5-dimethyl-3-oxohexanoate
lv. bis(chloromethyl)cyclopropane-1,1-dicarboxylate
lvi. chloromethyl 1,2-dihydrocyclobutabenzene-1-carboxylate
lvii. chloromethyl 2-cyclopentenylacetate
lviii. chloromethyl 2-phenylbutanoate
lix. chloromethyl 2,2-difluoroacetate
lx. chloromethyl 4-fluorobenzoate
lxi. chloromethyl 3-cyclohexylpropanoate
lxii. chloromethyl 2-cyclohexylacetate
lxiii. chloromethyl 3-(tetrahydro-2H-pyran-4-yl)propanoate
lxiv. chloromethyl 2-(tetrahydro-2H-pyran-3-yl)acetate
lxv. chloromethyl 3-(tetrahydro-2H-pyran-3-yl)propanoate FIG 2: A non limiting set of compounds of Type II reagents.

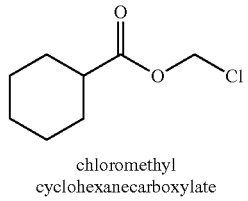

82 chloromethyl cyclohexanecarboxylate

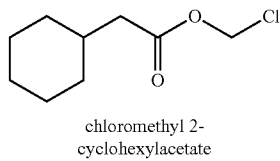

83 chloromethyl 2-cyclohexylacetate

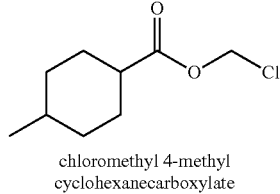

84 chloromethyl 4-methyl cyclohexanecarboxylate

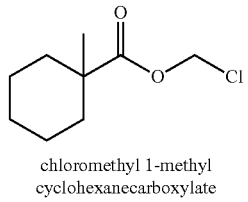

85 chloromethyl 1-methyl cyclohexanecarboxylate

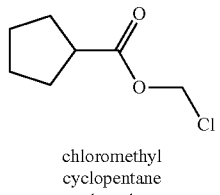

86 chloromethyl cyclopentane carboxylate

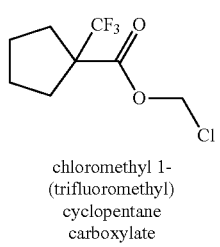

87 chloromethyl 1-(trifluoromethyl) cyclopentane carboxylate

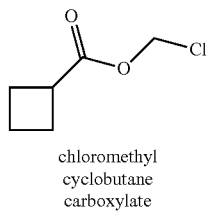

88 chloromethyl cyclobutane carboxylate

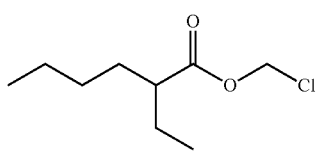

chloromethyl 2-ethylhexanoate

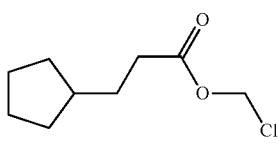

chloromethyl 3-cyclopentylpropanoate

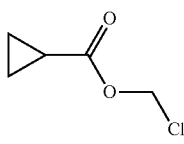

chloromethyl cyclopropane carboxylate

chloromethyl pentanoate

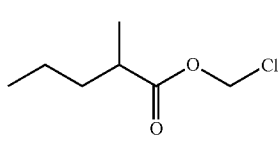

chloromethyl 2-methylpentanoate

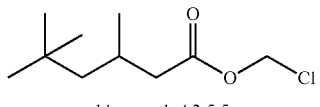

chloromethyl 3,5,5-trimethylhexanoate

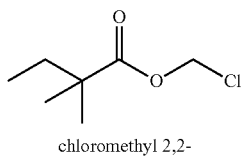

chloromethyl 2,2-dimethylbutanoate

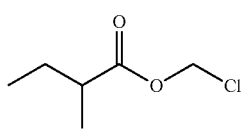

chloromethyl 2-methylbutanoate

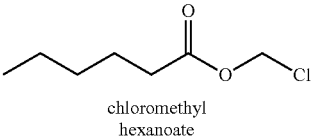

chloromethyl hexanoate

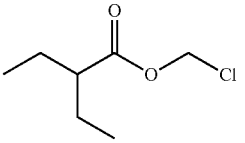

chloromethyl 2-ethylbutanoate

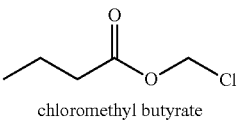

chloromethyl butyrate

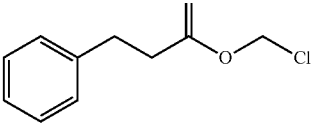

chloromethyl 3-phenylpropanoate

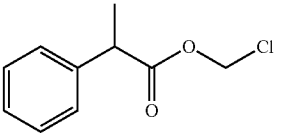

chloromethyl 2-phenylpropanoate

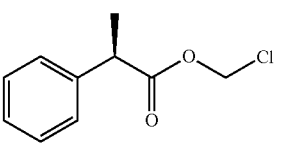

(R)-chloromethyl 2-phenylpropanoate

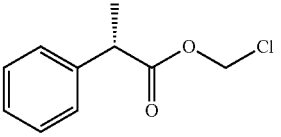

(S)-chloromethyl 2-phenylpropanoate

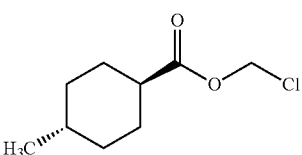

(1r,4r)-chloromethyl 4-methylcyclohexane carboxylate

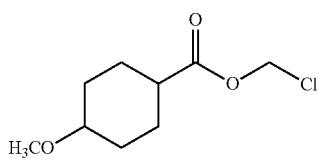

chloromethyl 4-methoxy
cyclohexanecarboxylate

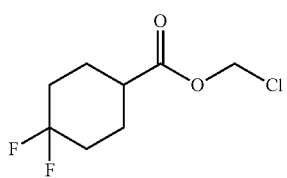

chloromethyl 4,4-difluoro
cyclohexanecarboxylate

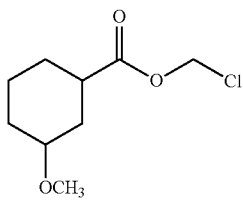

chloromethyl
3-methoxy
cyclohexane
carboxylate

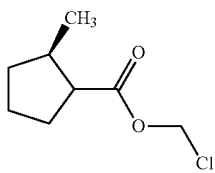

(2R)-chloromethyl
2-methylcyclo
pentanecarboxylate

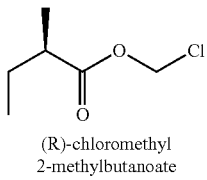

(R)-chloromethyl
2-methylbutanoate

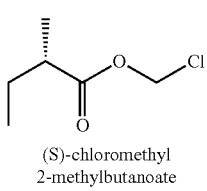

(S)-chloromethyl
2-methylbutanoate

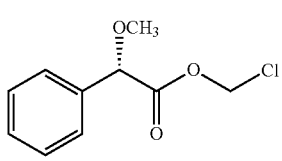

(S)-chloromethyl 2-
methoxy-2-phenylacetate

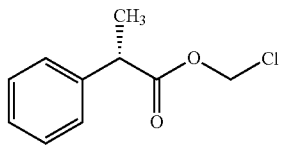

(S)-chloromethyl
2-phenylpropanoate

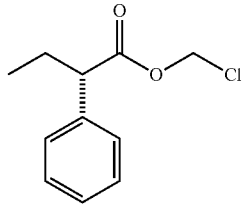

(S)-chloromethyl
2-phenylbutanoate

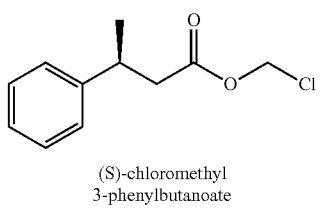

(S)-chloromethyl
3-phenylbutanoate

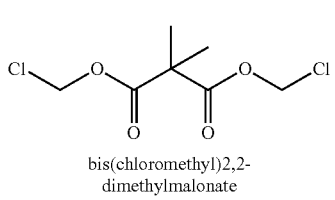

bis(chloromethyl)2,2-
dimethylmalonate

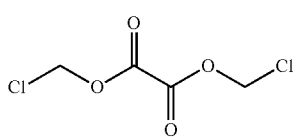

bis(chloromethyl) oxalate

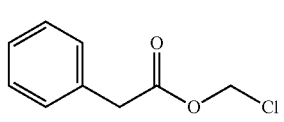

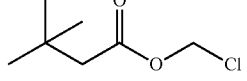

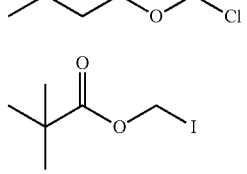

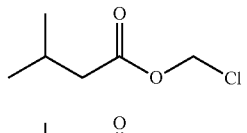

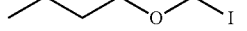

| | |
|---|---|
| 122 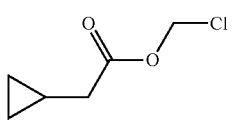<br>chloromethyl 2-cyclopropyl acetate | 129 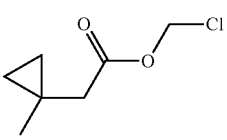<br>chloromethyl 2-(1-methylcyclopropyl) acetate |
| 123 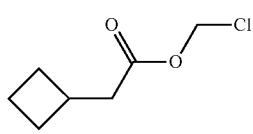<br>chloromethyl 2-cyclobutylacetate | 130 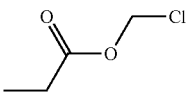<br>chloromethyl propionate |
| 124 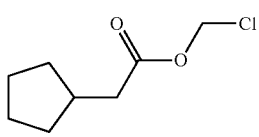<br>chloromethyl 2-cyclopentylacetate | 131 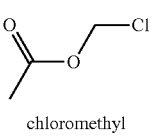<br>chloromethyl acetate |
| 125 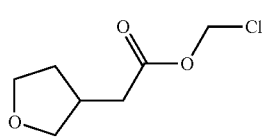<br>chloromethyl 2-(tetrahydrofuran-3-yl)acetate | 132 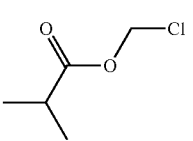<br>chloromethyl isobutyrate |
| 126 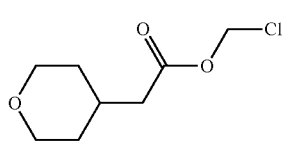<br>chloromethyl 2-(tetrahydro-2H-pyran-4-yl) acetate | 133 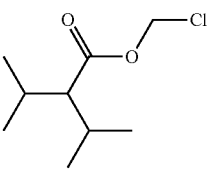<br>chloromethyl 2-isopropyl-3-methylbutanoate |
| 127 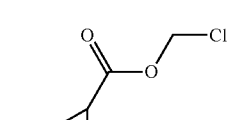<br>chloromethyl 2-methyl cyclopropanecarboxylate | 134 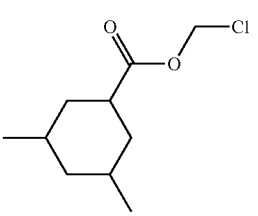<br>chloromethyl 3,5-dimethyl cyclohexane carboxylate |
| 128 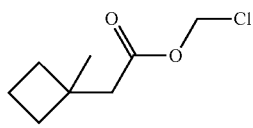<br>chloromethyl 2-(1-methylcyclobutyl) acetate | 135 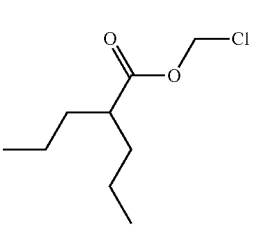<br>chloromethyl 2-propylpentanoate |

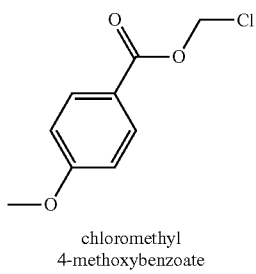
chloromethyl 4-methoxybenzoate

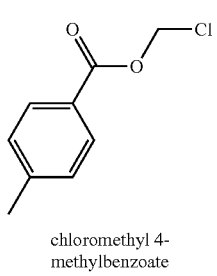
chloromethyl 4-methylbenzoate

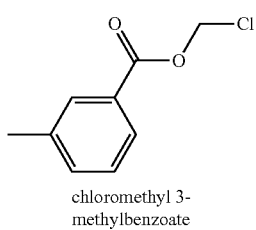
chloromethyl 3-methylbenzoate

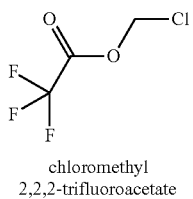
chloromethyl 2,2,2-trifluoroacetate

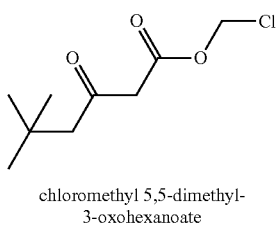
chloromethyl 5,5-dimethyl-3-oxohexanoate

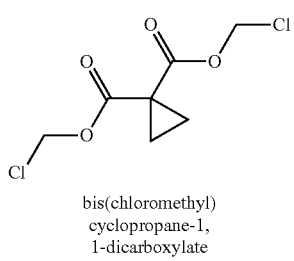
bis(chloromethyl) cyclopropane-1,1-dicarboxylate

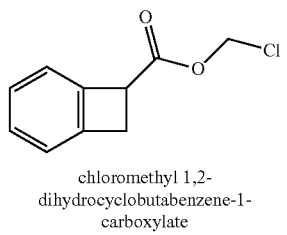
chloromethyl 1,2-dihydrocyclobutabenzene-1-carboxylate

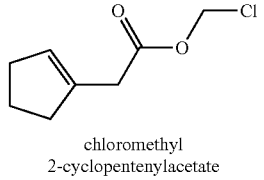
chloromethyl 2-cyclopentenylacetate

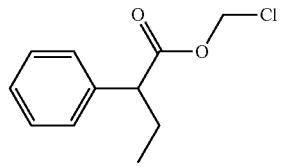
chloromethyl 2-phenylbutanoate

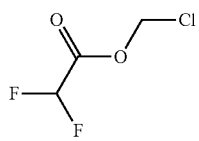
chloromethyl 2,2-difluoroacetate

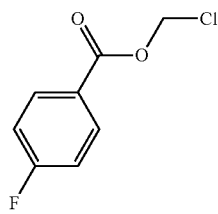
chloromethyl 4-fluorobenzoate

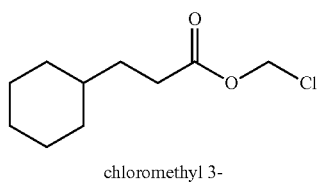
chloromethyl 3-cyclohexylpropanoate

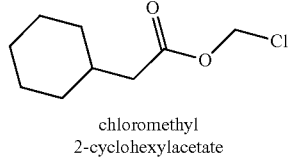
chloromethyl 2-cyclohexylacetate

-continued

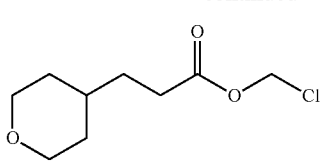
149 chloromethyl 3-(tetrahydro-2H-pyran-4-yl)propanoate

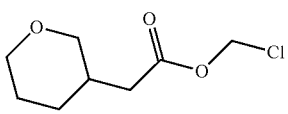
150 chloromethyl 2-(tetrahydro-2H-pyran-3-yl)acetate

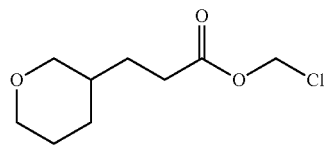
151 chloromethyl 3-(tetrahydro-2H-pyran-3-yl)propanoate

A non limiting set of compounds belonging to type III is listed herebelow and represented at Fig. 3.

Type III Reagents
 i. chloromethyl isopropylcarbamate
 ii. chloromethyl diisopropylcarbamate
 iii. chloromethyl dimethylcarbamate
 iv. chloromethyl isobutylcarbamate
 v. chloromethyl methylcarbamate
 vi. chloromethyl ethyl(isopropyl)carbamate
 vii. chloromethylisobutyl(methyl)carbamate
 viii. (S)-chloromethyl sec-butylcarbamate
 ix. chloromethyl methylcarbamate
 x. chloromethyl isopropyl(methyl)carbamate
 xi. chloromethyl propylcarbamate
 xii. chloromethyl 2-methoxyethylcarbamate
 xiii. chloromethyl methyl(propyl)carbamate
 xiv. chloromethyl diisobutylcarbamate
 xv. chloromethyl tert-butyl(isopropyl)carbamate
 xvi. chloromethyl di-sec-butylcarbamate
 xvii. chloromethyl aziridine-1-carboxylate
 xviii. chloromethyl 2-methylcyclopropylcarbamate
 xix. chloromethyl cyclopropylcarbamate
 xx. chloromethyl cyclopropylmethyl(propyl)carbamate
 xxi. chloromethyl cyclopropyl(methyl)carbamate
 xxii. chloromethyl azetidine-1-carboxylate
 xxiii. chloromethyl cyclobutylcarbamate
 xxiv. chloromethyl 2,2-dimethylcyclobutylcarbamate
 xxv. chloromethyl 3-methoxyazetidine-1-carboxylate
 xxvi. chloromethyl cyclobutyl(methyl)carbamate
 xxvii. chloromethyl oxetan-3-ylcarbamate
 xxviii. (S)-chloromethyl 2-methylpyrrolidine-1-carboxylate
 xxix. chloromethyl cyclopentylcarbamate
 xxx. chloromethyl cyclopentyl(methyl)carbamate
 xxxi. chloromethyl tetrahydrofuran-3-ylcarbamate
 xxxii. chloromethyl piperidine-1-carboxylate
 xxxiii. (2R,6S)-chloromethyl 2,6-dimethylpiperidine-1-carboxylate
 xxxiv. (R)-chloromethyl 2-methylpiperidine-1-carboxylate
 xxxv. chloromethyl piperidine-1-carboxylate
 xxxvi. chloromethyl 3-methoxycyclohexylcarbamate
 xxxvii. chloromethyl cyclohexylmethylcarbamate
 xxxviii. chloromethyl cyclohexylmethyl(methyl)carbamate
 xxxix. chloromethyl morpholine-4-carboxylate
 xl. (3S,5R)-chloromethyl 3,5-dimethylmorpholine-4-carboxylate
 xli. (3R,5S)-chloromethyl 3,5-dimethylmorpholine-4-carboxylate
 xlii. (2S,6R)-chloromethyl 2,6-dimethylmorpholine-4-carboxylate
 xliii. chloromethyl 4-methylpiperazine-1-carboxylate
 xliv. chloromethylazepane-1-carboxylate
 xlv. chloromethylcycloheptylcarbamate
 xlvi. chloromethyl oxepan-4-ylcarbamate
 xlvii. chloromethyl (1R,2S,4S)-bicyclo[2.2.1]heptan-2-ylcarbamate
 xlviii. chloromethyl 2,3-dihydro-1H-inden-1-ylcarbamate
 xlix. chloromethyl benzylcarbamate
 l. (S)-chloromethyl 1-phenylethylcarbamate
 li. ethyl 2-((chloromethoxy)carbonylamino)-3-methylbutanoate
 lii. ethyl 2-((chloromethoxy)carbonylamino)-3-phenylpropanoate
 liii. (S)-diethyl 2-((chloromethoxy)carbonylamino)pentanedioate
 liv. ethyl((chloromethoxy)carbonylamino)propanoate
 lv. ethyl 2-amino-6-((chloromethoxy)carbonylamino)hexanoate
 lvi. ethyl 2-((chloromethoxy)carbonylamino)-4-methylpentanoate
 llvii. ethyl 2-((chloromethoxy)carbonylamino)-3-methylpentanoate
 lviii. (S)-dimethyl 2-((chloromethoxy)carbonylamino)succinate
 lix. (S)-ethyl 2-((chloromethoxy)carbonylamino)-5-guanidinopentanoate
 lx. (S)-ethyl 4-amino-2-((chloromethoxy)carbonylamino)-4-oxobutanoate
 lxi. (S)-ethyl 2-amino-5-((chloromethoxy)carbonylamino)pentanoate
 lxii. (S)-ethyl 5-amino-2-((chloromethoxy)carbonylamino)-5-oxopentanoate
 lxiii. ethyl 2-((chloromethoxy)carbonylamino)-4-(methylthio)butanoate
 lxiv. 1-chloromethyl 3-methyl 2-methyl-5,6-dihydropyridine-1,3(2H)-dicarboxylate
 lxv. (S)-chloromethyl (1-methylpyrrolidin-2-yl)methyl carbonate
 lxvi. (R)-chloromethyl (1-methylpyrrolidin-2-yl)methyl carbonate
 lxvii. (S)-(1-benzylpyrrolidin-2-yl)methyl chloromethyl carbonate
 lxviii. chloromethyl 1H-pyrrole-1-carboxylate
 lxix. chloromethyl 2-nicotinoylhydrazinecarboxylate
 lxx. (6S)-3-chloro-7-((chloromethoxy)carbonylamino)-8-oxo-5-thia-1-azabicyclo[4.2.0]oct-2-ene-2-carboxylic acid
 lxxi. (6S)-7-((chloromethoxy)carbonylamino)-8-oxo-3-vinyl-5-thia-1-azabicyclo[4.2.0]oct-2-ene-2-carboxylic acid
 lxxii. (6S)-7-((chloromethoxy)carbonylamino)-3-(methoxymethyl)-8-oxo-5-thia-1-azabicyclo[4.2.0]oct-2-ene-2-carboxylic acid lxxiii. (6R,7R)-7-((chloromethoxy)carbonylamino)-3-methoxy-8-oxo-5-thia-1-azabicyclo[4.2.0]oct-2-ene-2-carboxylic acid lxxiv. chloromethyl 3-(4-chlorophenyl)-1H-pyrazole-1-carboxylate lxxv. chloromethyl 3-(4-fluorophenyl)-1H-pyrazole-1-carboxylate lxxvi. chloromethyl 3-phenyl-1H-pyrazole-1-carboxylate lxxvii. chloromethyl 3-(4-bromophenyl)-1H-pyrazole-1-carboxylate lxxviii. chloromethyl 2-cyano-1H-pyrrole-1-carboxylate lxxix. chloromethyl 4-oxopiperidine-1-carboxylate lxxx. 1-chloromethyl 3-ethyl 2-oxopiperidine-1,3-dicarboxylate lxxxi. chloromethyl 2,2,6,6-tetramethyl-4-oxopiperidine-1-carboxylate lxxxii. chloromethyl 2-oxopiperidine-1-carboxylate FIG 3: List of Type III compounds.

152

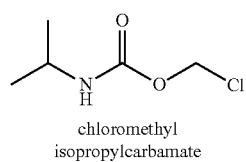

chloromethyl isopropylcarbamate

153

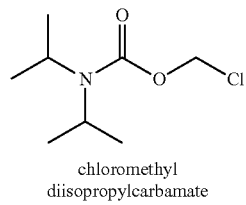

chloromethyl diisopropylcarbamate

154

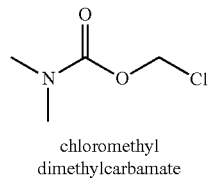

chloromethyl dimethylcarbamate

155

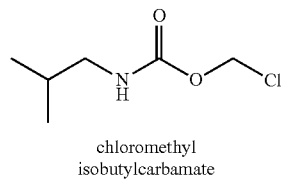

chloromethyl isobutylcarbamate

156

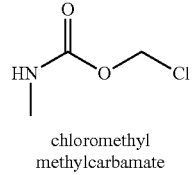

chloromethyl methylcarbamate

157

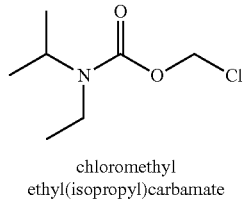

chloromethyl ethyl(isopropyl)carbamate

158

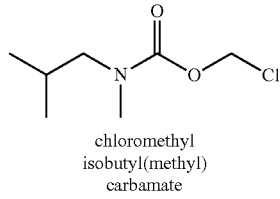

chloromethyl isobutyl(methyl)carbamate

159

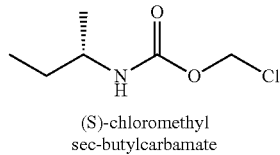

(S)-chloromethyl sec-butylcarbamate

160

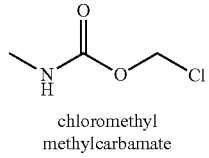

chloromethyl methylcarbamate

161

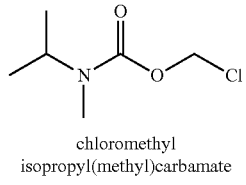

chloromethyl isopropyl(methyl)carbamate

162

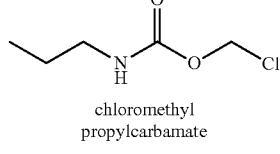

chloromethyl propylcarbamate

163

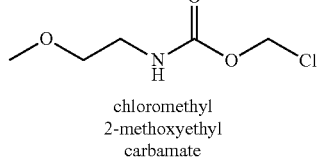

chloromethyl 2-methoxyethyl carbamate

164

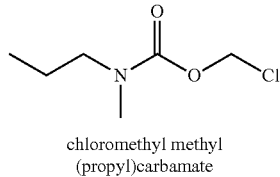

chloromethyl methyl (propyl)carbamate

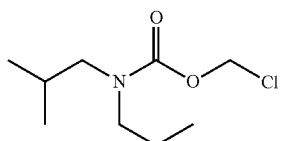

chloromethyl diisobutylcarbamate

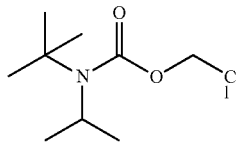

chloromethyl tert-butyl(isopropyl)carbamate

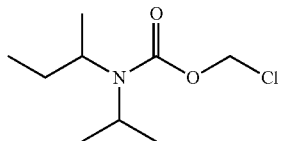

chloromethyl di-sec-butylcarbamate

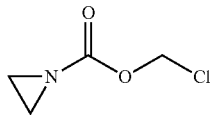

chloromethyl aziridine-1-carboxylate

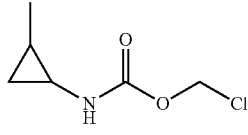

chloromethyl 2-methyl cyclopropylcarbamate

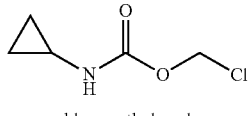

chloromethyl cyclopropylcarbamate

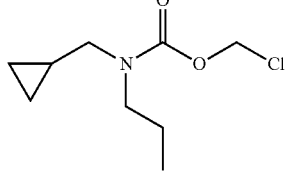

chloromethyl cyclopropylmethyl(propyl)carbamate

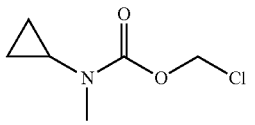

chloromethyl cyclopropyl(methyl)carbamate

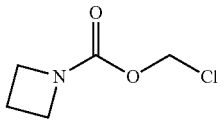

chloromethyl azetidine-1-carboxylate

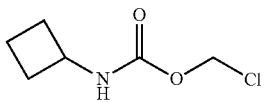

chloromethyl cyclobutylcarbamate

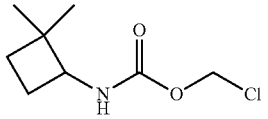

chloromethyl 2,2-dimethylcyclobutylcarbamate

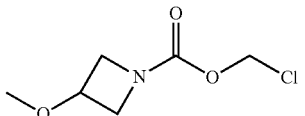

chloromethyl 3-methoxyazetidine-1-carboxylate

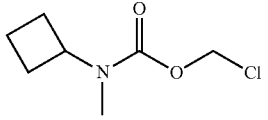

chloromethyl cyclobutyl(methyl)carbamate

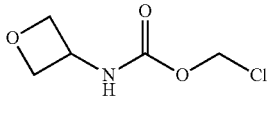

chloromethyl oxetan-3-ylcarbamate

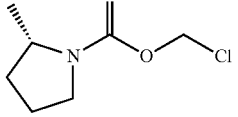

(S)-chloromethyl 2-methyl pyrrolidine-1-carboxylate

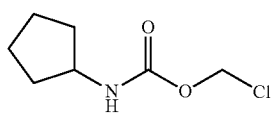

chloromethyl cyclo
pentylcarbamate

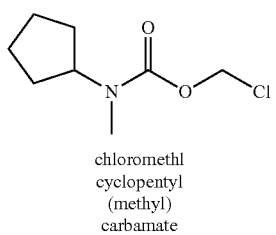

chloromethl
cyclopentyl
(methyl)
carbamate

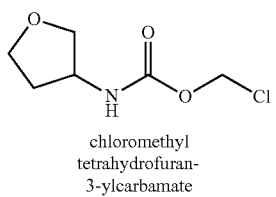

chloromethyl
tetrahydrofuran-
3-ylcarbamate

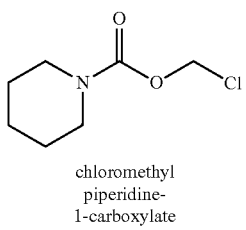

chloromethyl
piperidine-
1-carboxylate

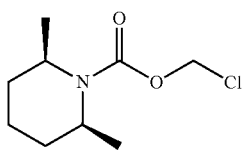

(2R,6S)-chloromethyl
2,6-dimethylpiperidine-
1-carboxylate

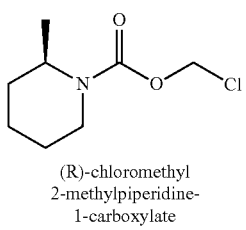

(R)-chloromethyl
2-methylpiperidine-
1-carboxylate

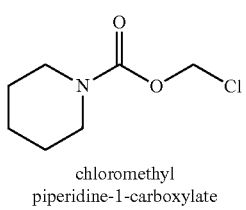

chloromethyl
piperidine-1-carboxylate

180

181

182

183

184

185

186

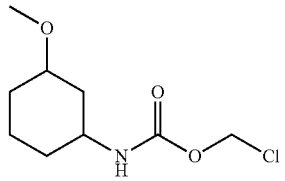

chloromethyl 3-
methoxycyclo
hexylcarbamate

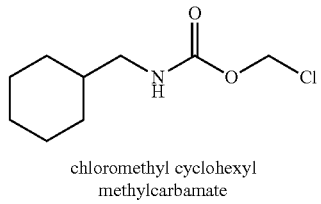

chloromethyl cyclohexyl
methylcarbamate

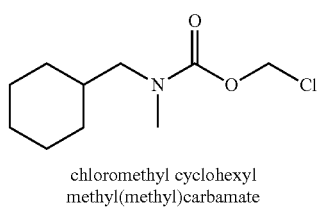

chloromethyl cyclohexyl
methyl(methyl)carbamate

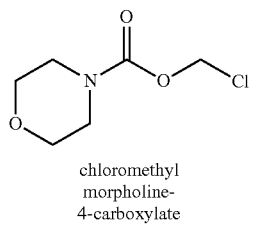

chloromethyl
morpholine-
4-carboxylate

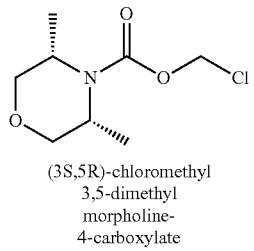

(3S,5R)-chloromethyl
3,5-dimethyl
morpholine-
4-carboxylate

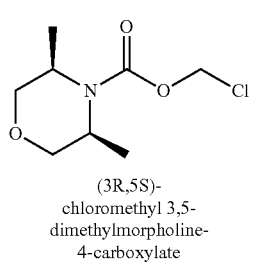

(3R,5S)-
chloromethyl 3,5-
dimethylmorpholine-
4-carboxylate

187

188

189

190

191

192

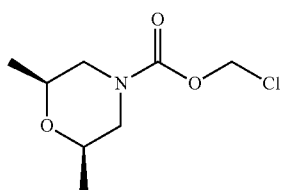

(2S,6R)-chloromethyl 2,6-dimethyl morpholine-4-carboxylate

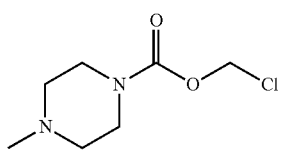

chloromethyl 4-methyl piperazine-1-carboxylate

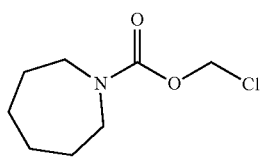

chloromethyl azepane-1-carboxylate

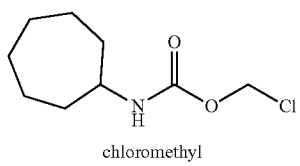

chloromethyl cycloheptylcarbamate

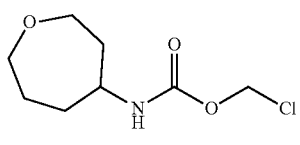

chloromethyl oxepan-4-ylcarbamate

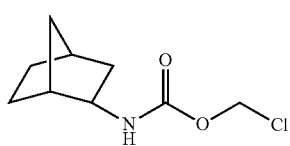

chloromethyl (1R,2S,4S)-bicyclo[2.2.1]heptan-2-ylcarbamate

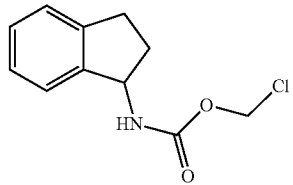

chloromethyl 2,3-dihydro-1H-inden-1-ylcarbamate

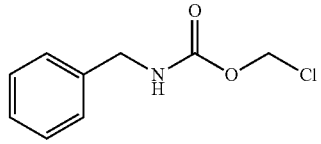

chloromethyl benzylcarbamate

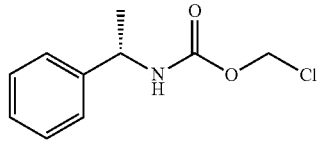

(S)-chloromethyl 1-phenylethylcarbamate

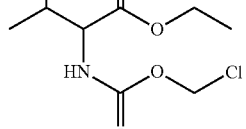

ethyl 2-((chloromethoxy)carbonylamino)-3-methylbutanoate

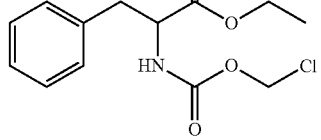

ethyl 2-((chloromethoxy)carbonylamino)-3-phenylpropanoate

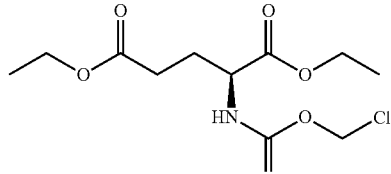

(S)-diethyl 2-((chloromethoxy)carbonylamino)pentanedioate

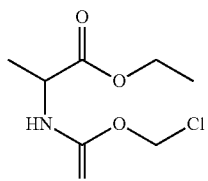

ethyl((chloromethoxy)
carbonylamino)
propanoate

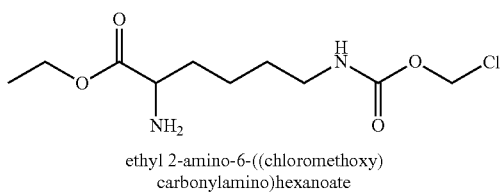

ethyl 2-amino-6-((chloromethoxy)
carbonylamino)hexanoate

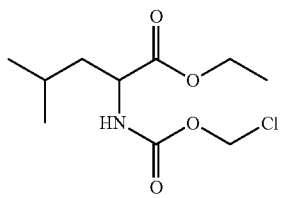

ethyl 2-((chloromethoxy)
carbonylamino)-4-
methylpentanoate

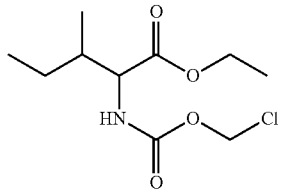

ethyl 2-((chloromethoxy)
carbonylamino)-
3-methylpentanoate

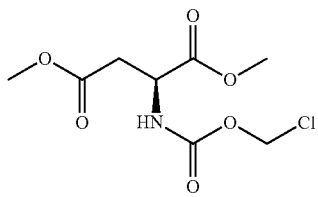

(S)-dimethyl 2-
((chloromethoxy)
carbonylamino)succinate

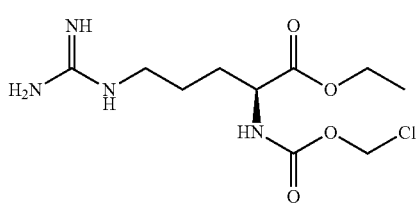

(S)-ethyl 2-((chloromethoxy)
carbonylamino)-5-
guanidinopentanoate

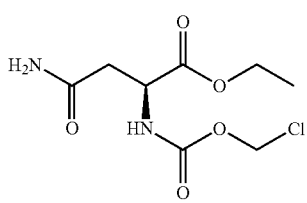

(S)-ethyl 4-amino-2-
((chloromethoxy)
carbonylamino)-4-oxobutanoate

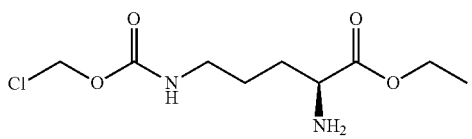

(S)-ethyl 2-amino-5-
((chloromethoxy)
carbonylamino)pentanoate

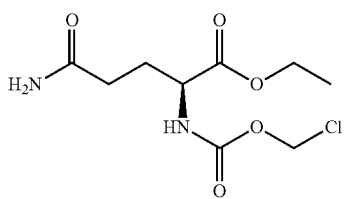

(S)-ethyl 5-amino-2-
((chloromethoxy)carbonylamino)-
5-oxopentanoate

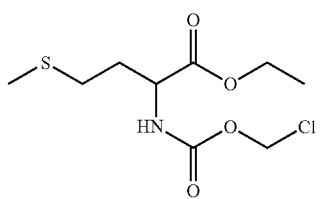

ethyl 2-((chloromethoxy)
carbonylamino)-4-
(methylthio)butanoate

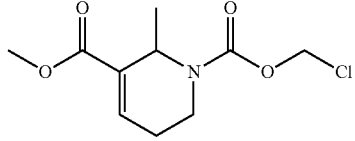

1-chloromethyl 3-methyl
2-methyl-5,6-dihydropyridine-
1,3(2H)-dicarboxylate

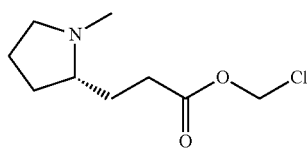

(S)-chloromethyl (1-
methyopyrrolidin-2-
yl)methyl carbonate

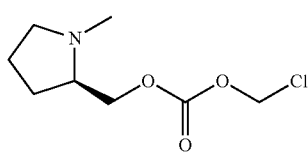

(R)-chloromethyl (1-methyl pyrrolidin-2-yl)methyl carbonate

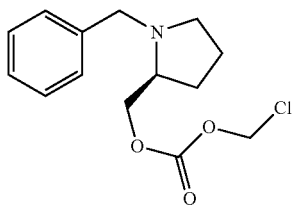

(S)-(1-benzylpyrrolidin-2-yl)methyl chloromethyl carbonate

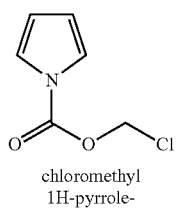

chloromethyl 1H-pyrrole-1-carboxylate

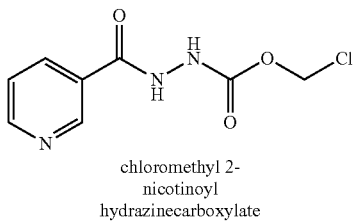

chloromethyl 2-nicotinoyl hydrazinecarboxylate

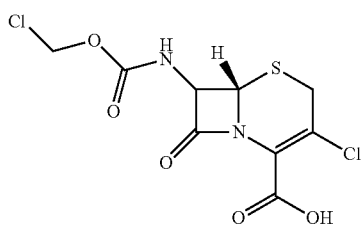

(6S)-3-chloro-7-((chloromethoxy) carbonylamino)-8-oxo-5-thia-1-azabicyclo[4.2.0]oct-2-ene-2-carboxylic acid

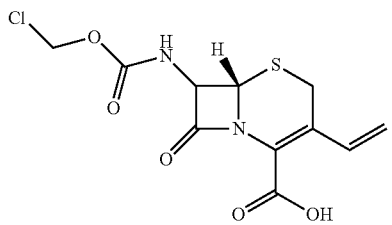

(6S)-7-((chloromethoxy) carbonylamino)-8-oxo-3-vinyl-5-thia-1-azabicyclo[4.2.0]oct-2-ene-2-carboxylic acid

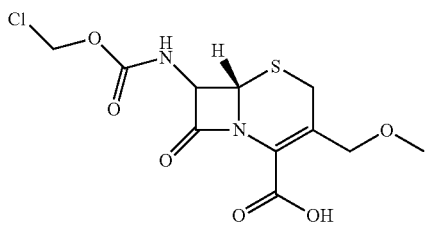

(6S)-7-((chloromethoxy) carbonylamino)-3-(methoxymethyl)-8-oxo-5-thia-1-azabicyclo[4.2.0]oct-2-ene-2-carboxylic acid

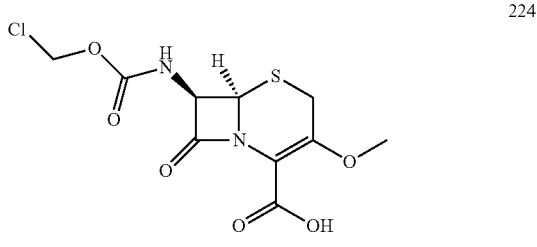

(6R,7R)-7-((chloromethoxy) carbonylamino)-3-methoxy-8-oxo-5-thia-1-azabicyclo[4.2.0]oct-2-ene-2-carboxylic acid chloromethyl 3-(4-chlorophenyl)-1H-pyrazole-1-carboxylate chloromethyl 3-(4-fluorophenyl)-1H-pyrazole-1-carboxylate

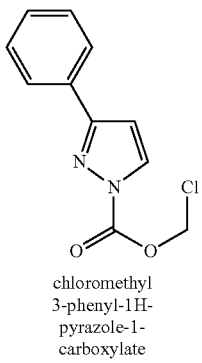

chloromethyl 3-phenyl-1H-pyrazole-1-carboxylate

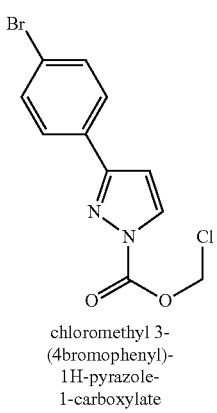

chloromethyl 3-(4bromophenyl)-1H-pyrazole-1-carboxylate

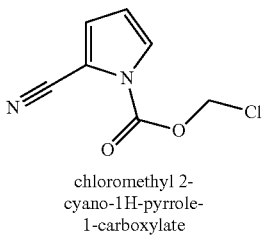

chloromethyl 2-cyano-1H-pyrrole-1-carboxylate

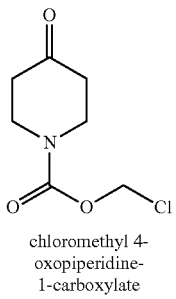

chloromethyl 4-oxopiperidine-1-carboxylate

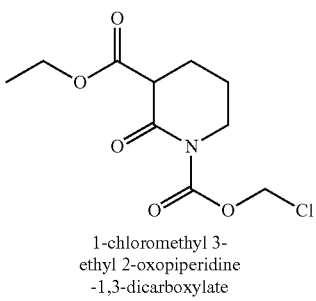

1-chloromethyl 3-ethyl 2-oxopiperidine-1,3-dicarboxylate

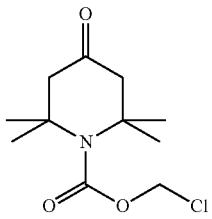

chloromethyl 2,2,6,6-tetramethyl-4-oxopiperidine-1-carboxylate

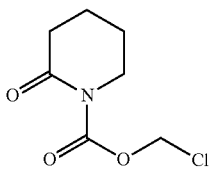

chloromethyl 2-oxopiperidine-1-carboxylate chloromethyl 2-oxopiperidine-1-carboxylate C. Modifications of Chemical Compounds by Substituted Methyl Formyl Reagents The novel substituted methyl formyl Reagents of the present invention are used to modify the properties of any chemical molecule that may be used for pharmaceutical, nutraceutical or other purposes. Such modification may be carried out on a wide variety of substrates to modify several parameters. This modification may be carried out by reacting a functional group of the chemical molecule, with the substituted methyl formyl reagents of the present invention. The modification may also be carried out by effecting a chemical reaction of the substituted methyl formyl reagents of the present invention with a heteroatom of a heterocyclic ring system.

The modification may be carried out by converting any functional group present in the chemical molecule of interest of type I, II or III and then reacting with an suitable external quaternization agent, or by reaction of the reagent on a heteroatom present on molecule of interest to make a quart.

The term 'Chemical compound' includes within its scope, all molecules that are currently present in the market as drugs, including antibiotics and orphan drugs, molecules currently undergoing clinical trials, molecules awaiting approval, molecules meant for use as nutraceuticals or as nutrients, molecules meant for agricultural purposes as pesticide, herbicide, insecticide, fungicide and other similar applications.

The term 'functional group' includes the specific groups of atoms and/or bonds within molecules that are responsible for the characteristic chemical reactions of those molecules and include hydrocarbons, groups containing halogens, groups containing oxygen, groups containing nitrogen, groups containing sulfur, groups containing phosphorus, groups containing boron. The functional groups may be aliphatic or aromatic in nature.

Preferred groups for modification by the substituted methyl formyl reagents, which may be termed as sites of translation are the carboxylic group, amino group, the heteroatom of the ring, alcoholic group, amide, etc.

The heteroatom of the heterocyclic ring system may be any heteroatom, but is preferably O, N, S or P.

B.1. General Synthetic Schemes for the Modification of Chemical Compounds

The general schemes of modification various functional groups using the methyl formyl Reagents are provided below as a means of illustration.

B. 1.1: Nitrogen Containing Aromatic Rings

Scheme 5: Modification of drugs/biologically active molecules with nitrogen-containing aromatic rings such as pyridine, imidazole, triazole, etc.

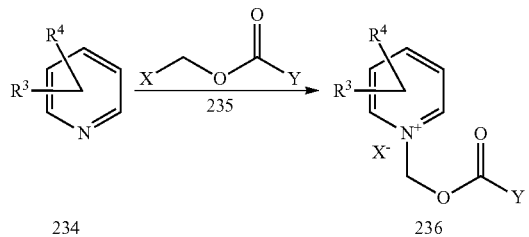

234    236

$R^3$ and $R^4$ can independently be H, $C_1$-$C_8$ straight or branched alkyl chain—optionally containing 1-3 heteroatoms selected from O, N, S, SO, or $SO_2$; 3-7 membered cycloalkyl optionally containing 1-3 heteroatoms selected from O, N, S, SO, or $SO_2$ and/or lower alkyl, straight or branched alkyl, alkoxy; alkaryl, aryl, heteroaryl, or alkheteroaryl.

$R^3$ and/or $R^4$ can also be part of 3-7 membered ring optionally containing additional 1-2 heteroatoms selected from, O, N, S, SO, $SO_2$ and also be optionally substituted with alkoxy, F or Cl. Appropriately, $R^3$ and $R^4$ may be connected to form 3-8 membered aliphatic or aromatic ring fused to the heteroaromatic ring. One skilled in the art would know which rings would be appropriately aliphatic and which would be aromatic.

General Procedure:

Drugs or biological active molecules with nitrogen containing aromatic rings such as [234] can be reacted with a Type I reagent such as [235] using a solvent such as DCM or ACN under anhydrous conditions at room temperature for a time ranging up to 24 hours. The reaction mixture can be evaporated to dryness and triturated with ether. The standard work up yields desired product [236].

Any drug or molecule of biological importance having an aromatic nitrogen such as pyridine can be reacted with a desired methyl formyl reagent (Type I ($Y=R^2$) or Type II ($Y=NR^2)_2$) or Type III ($Y=OR^2$) in a solvent such as ACN at temperatures typically ranging from RT to 60° C. After completion, the reaction was concentrated by evaporating excess of organic solvent to get the desired product, which can be purified if required by any general purification method practiced in organic chemistry laboratory such as precipitation or crystallization or preparative column purification.

B.1.2 Amines

Scheme 6: Modification of drugs/biologically active molecules containing aliphatic tertiary amines such as piperidine, piperazine and trialkyl amines.

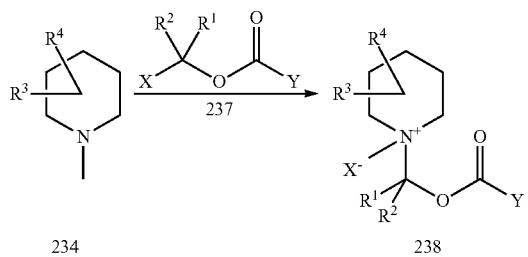

234    238

$R^3$ and $R^4$ can independently be H, $C_1$-$C_8$ straight or branched chain alkyl—optionally containing 1-3 heteroatoms selected from O, N, S, SO, or $SO_2$; 3-7 membered cycloalkyl optionally containing 1-3 heteroatoms selected from O, N, S, SO, or $SO_2$ and or lower alkyl, straight or branched alkyl, alkoxy; alkaryl, aryl, heteroaryl, or alkheteroaryl.

$R^3$ and/or $R^4$ can also be part of 3-7 membered ring optionally containing additional 1-2 heteroatoms selected from, O, N, S, SO, $SO_2$ and also be optionally substituted with alkoxy, F or Cl. Appropriately, $R^3$ and $R^4$ may be connected to form 3-8 membered aliphatic or aromatic ring fused to the heteroalicyclic ring. One skilled in the art would know which rings would be appropriately aliphatic and which would be aromatic.

General Procedure:

Drugs or biologically active molecules with aliphatic tertiary amines such as [234] can be reacted with a Type I reagent such as [237] using acetonitrile/tetrahydrofuran/dichloromethane as solvents under anhydrous conditions at room temperature for a time ranging up to 24 hours. The reaction mixture can be evaporated to dryness and triturated with ether. The standard work up yields the desired product such as [238].

Any drug or molecule of biological importance having an aliphatic tertiary nitrogen such as piperidine can be reacted with a desired methyl formyl reagent (Type I ($Y=R^2$) or Type II ($Y=N(R^2)_2$) or Type 111 ($Y=OR^2$)) in a solvent such as ACN at temperatures typically ranging from RT to 60° C. After completion of the reaction, evaporation of the excess of the organic solvent will yield the desired product which can be purified if required by any general purification method practiced in organic chemistry such as precipitation or crystallization or preparative column purification.

Drugs or biologically active molecules with alcohols and/or phenols and/or amines can also be modified by conversion to a respective methyl formyl reagent followed by making a quaternary ammonium cation using amines such as pyridine, for example nicotinamide is a preferred embodiment. Non-limiting examples of such conversions with drugs or biologically active molecules with alcohols and/or phenols are shown in Schemes below. Non-limiting examples of such conversions of drugs or biologically active molecules with primary or secondary amines are shown in Schemes 7 and 8.

Modification of drugs/biologically active molecules with primary or secondary aliphatic amines

Scheme 7:

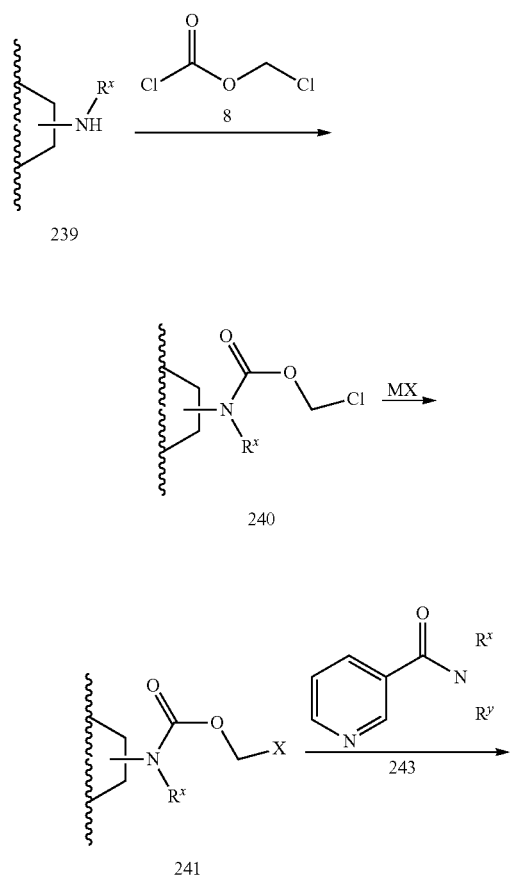

Rx/Ry = H or alkyl;

In a similar fashion, Drugs or biological active molecules containing amine such as [239] were reacted first with chloromethyl chloroformate such as [8] using pyridine as a base and DCM as solvent. Standard workup of the reaction mixture yields intermediate [240]. This intermediate when further reacted with iodide suitable metal salt such as NaI in acetone or acetonitrile at room temperature or under heating followed by standard workup of the reaction mixture yielded intermediate [241]. This intermediate on reaction with a quaternizing reagent such as nicotinamide [243] using solvent such as DCM or ACN at room temperature Followed by evaporation of organic solvent under vacuum to yield the desired modified drug or biological active molecule [242].

Scheme 8:

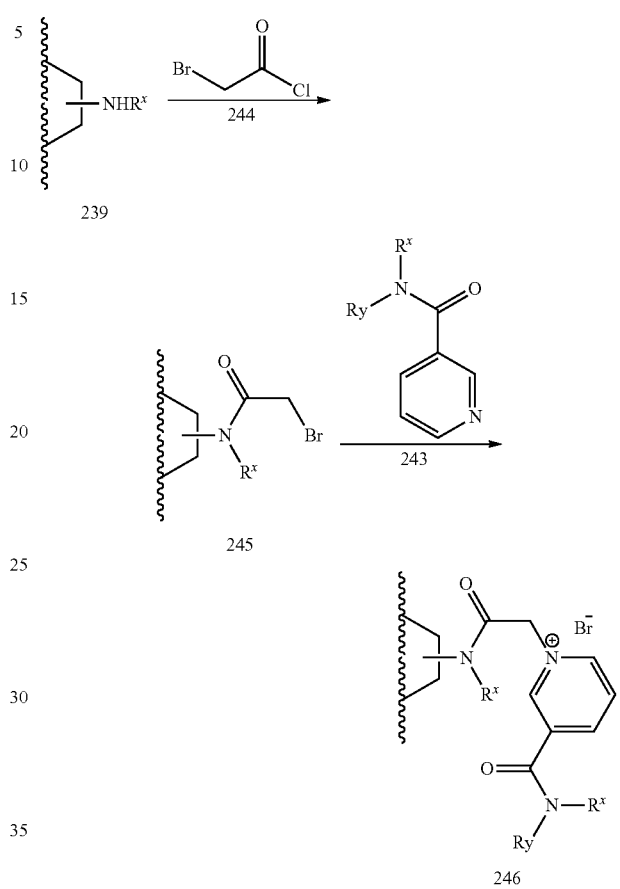

Wherein Rx/Ry = H or alkyl;

Similarly, drugs or biological active molecules with a primary or secondary amino group [239] can be reacted first with a suitable halo actetyl chloride such as bromo acetylchloride [244] using DCM as solvent. Standard workup of the reaction mixture yields the intermediate [245]. This intermediate [245] can be further reacted with a quaternization reagent such as nicotinamide [243] using a solvent such as DCM at room temperature. The reaction mixture can be evaporated to yield the desired final modified drug or biological active molecule [246].

Scheme 9:

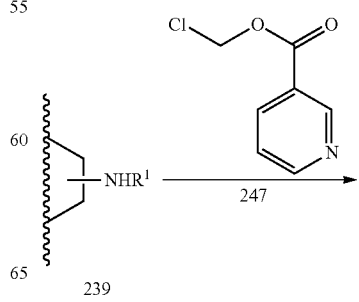

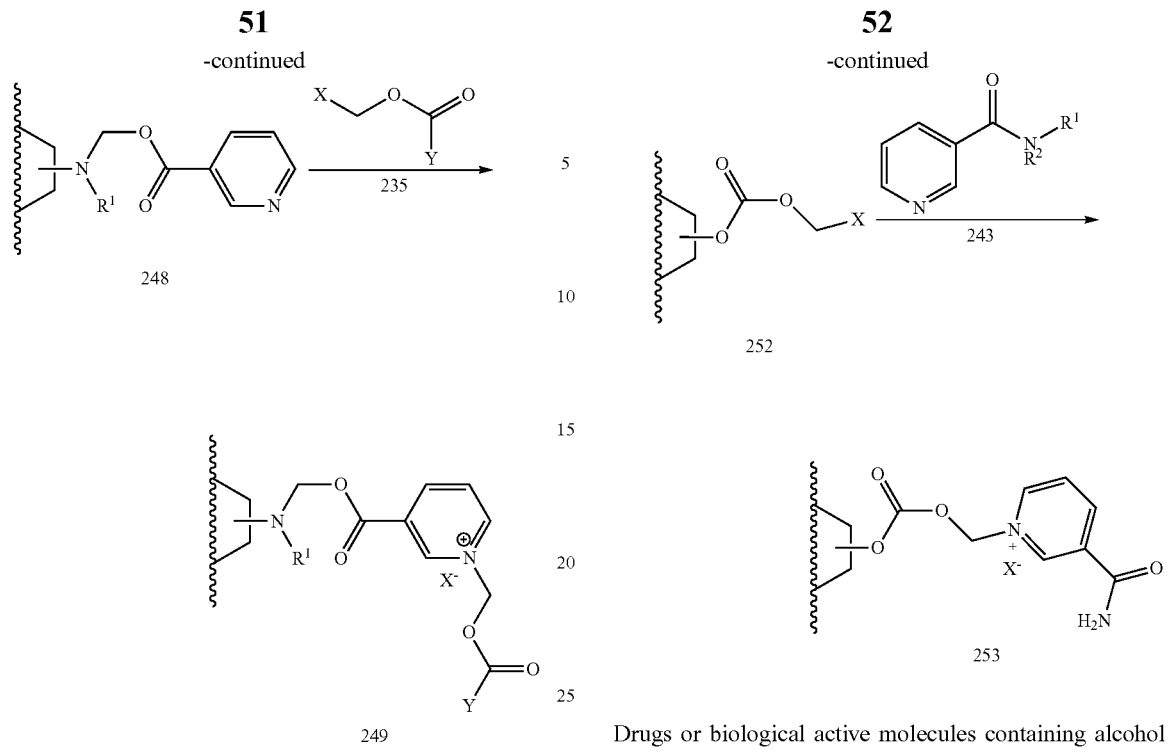

In a similar fashion, a corresponding drug or biologically active molecule with a primary or secondary amino group, such as [239], can be reacted with chloromethyl nicotinic acid [247] using DCM as solvent at room temperature. Standard work up of the reaction yields the intermediate [248], which can be further treated with suitable methyl formyl reagents [235] ($Y=R^2$, $N(R^2)_2$, or $OR^2$) using DCM as solvent at room temperature. A similar work up yields the desired modified biologically active molecule [249].

B.1.3 Alcohols

Scheme for Modification of Drugs/Biologically Active Molecules with Alcohols/Phenols Drugs or biological active molecules containing alcohol such as [250] can be reacted with chloromethyl chloroformate [8] in presence of a base such as pyridine and a solvent such as DCM. Standard workup of the reaction mixture yields an intermediate [251]. This intermediate on reaction with a suitable metal salt such as sodium iodide in a solvent such as acetone at a desired temperature starting from ambient to heating followed by a standard workup yields compound [252]. Compound [252] on reaction with a suitable quaternization reagent such as nicotinamide [243] using solvent such as DCM at room temperature followed by evaporation of organic solvent provides the desired modified drug or biological active molecule [253].

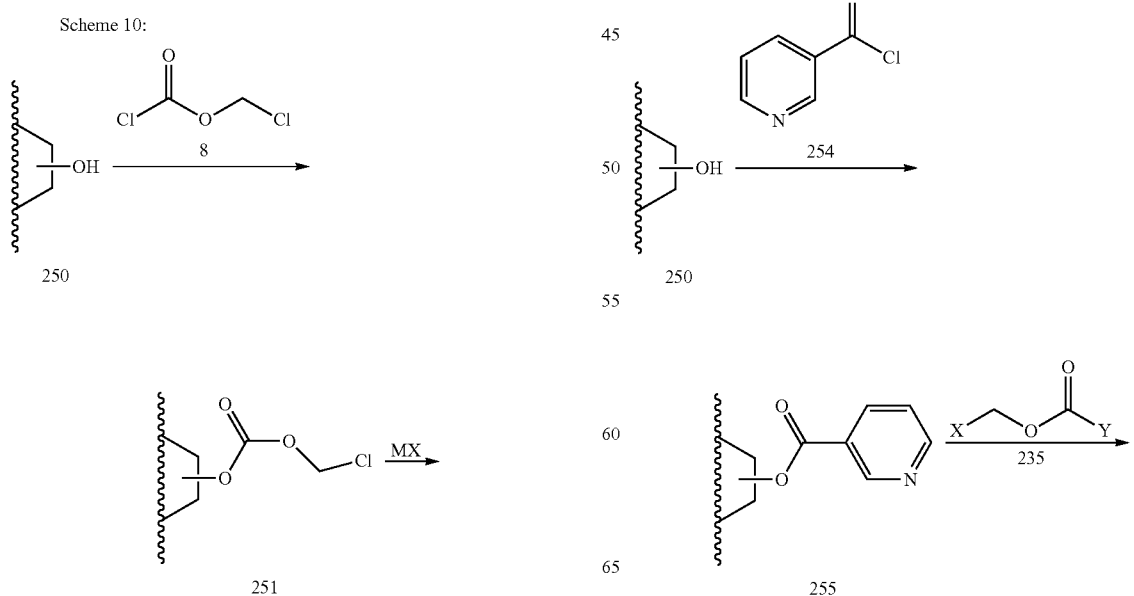

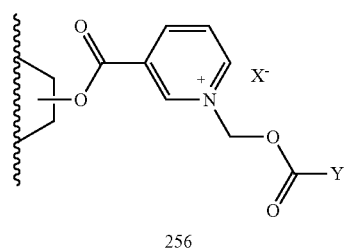

256

In a similar fashion, the corresponding drug or biological active molecule [250] were reacted with a suitable acid chloride such as nicotinoyl chloride [254] in a solvent such as DCM in presence of a base such as pyridine at a desire temperature ranging from ambient to refluxing followed by a standard work up to yield intermediate [255]. which on further treatment with suitable methyl formyl reagents [235] ($Y=R^2$, $N(R^2)_2$, or $OR^2$) using a solvent such as acetonitrile at a desired temperature ranging from ambient to refluxing yield the desired modified biological active molecule [256].

Scheme 12:

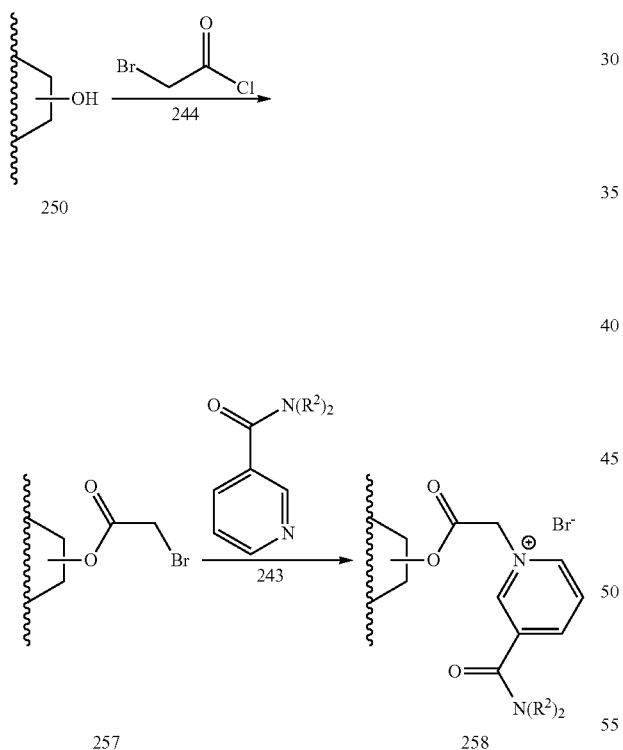

Drugs or biological active molecules containing alcohol such as [250] can be reacted first with a suitable haloacetyl-halides such as bromoacetylchloride [244] in a solvent such as DCM at a desired temperature followed by a standard workup yield compound [257]. Compound [257] can be further reacted with a suitable quaternizing agent such as nicotinamide [243] using solvent such as ACN at desired temperature. Upon evaporation the reaction mixture yields the desired final modified drug or biological active molecule [258].

Scheme 13:

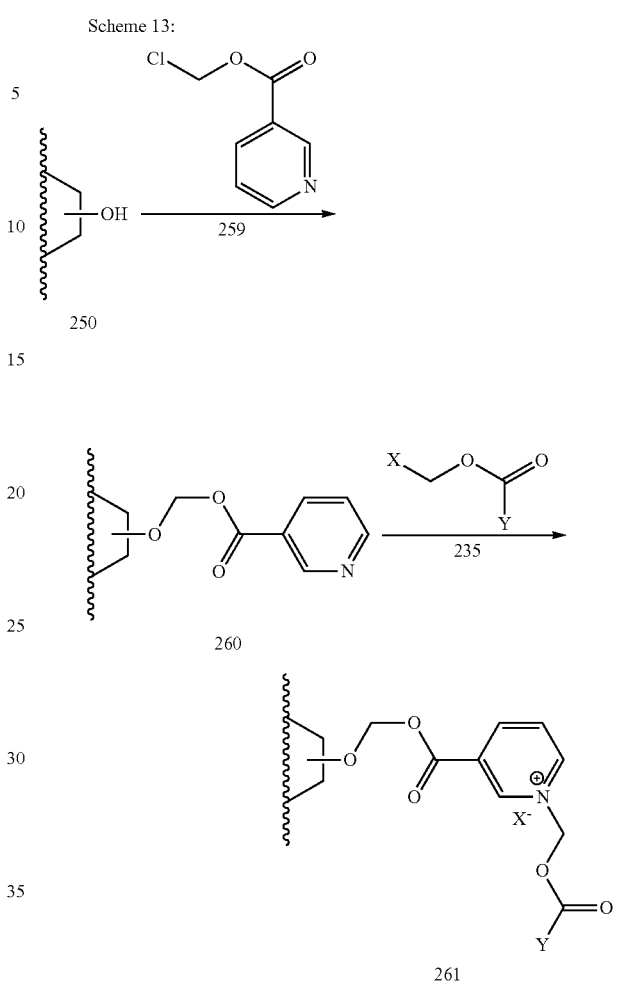

In a similar fashion, the corresponding drug or biological active molecule [250] can be reacted with suitable halomethyl reagents such as chloromethyl nicotinate [259] in a solvent such as DCM at a desired temperature ranging from ambient to refluxing. The standard work up of the reaction yields intermediate [260], which can be further treated with suitable methyl formyl reagents such as [10] ($Y=R^2$, $N(R^2)_2$, or $OR^2$) using DCM as solvent at room temperature. A similar work up yields the desired modified biological active molecule [261].

B.1.4 Carboxylic Acids—Modification of Drugs/Biologically Active Molecules with a Carboxylic Acid Moiety Scheme 14:

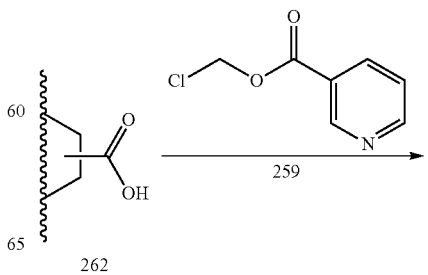

262

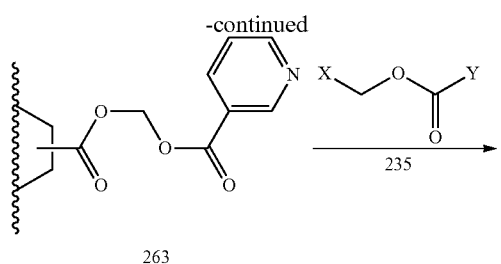

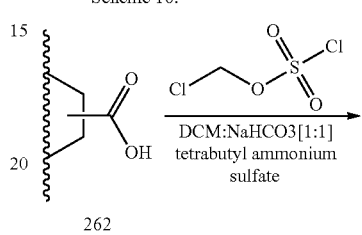

Drugs or biological active molecules with a carboxylic group [262] can be reacted with a suitable halomethyl reagent such as chloromethyl nicotinate [259] in a solvent such as DCM at desired temperature. Standard work up of the reaction yields the intermediate [263], which can be further treated with suitable methyl formyl reagents [235] (Y=R$^2$, N(R$^2$)$_2$, or OR$^2$) using DCM as solvent at room temperature to yield the desired modified biological active molecule [264].

In a similar fashion, the corresponding drug or biological active molecule with a carboxylic acid group [262] can be reacted with Lewis acids such as Zinc chloride (dry) and aldehydes such as paraformaldehyde at temperatures ranging from −10° C. to 60° C. for a time ranging up to 20-24 hours. Standard work up of the reaction mixture yields the intermediate [265], which can be further reacted with nicotinamide [322] using DCM or ACN as a solvent at room temperature. The reaction mixture can be evaporated to yield the desired final modified drug or biological active molecule [266].

Scheme 16:

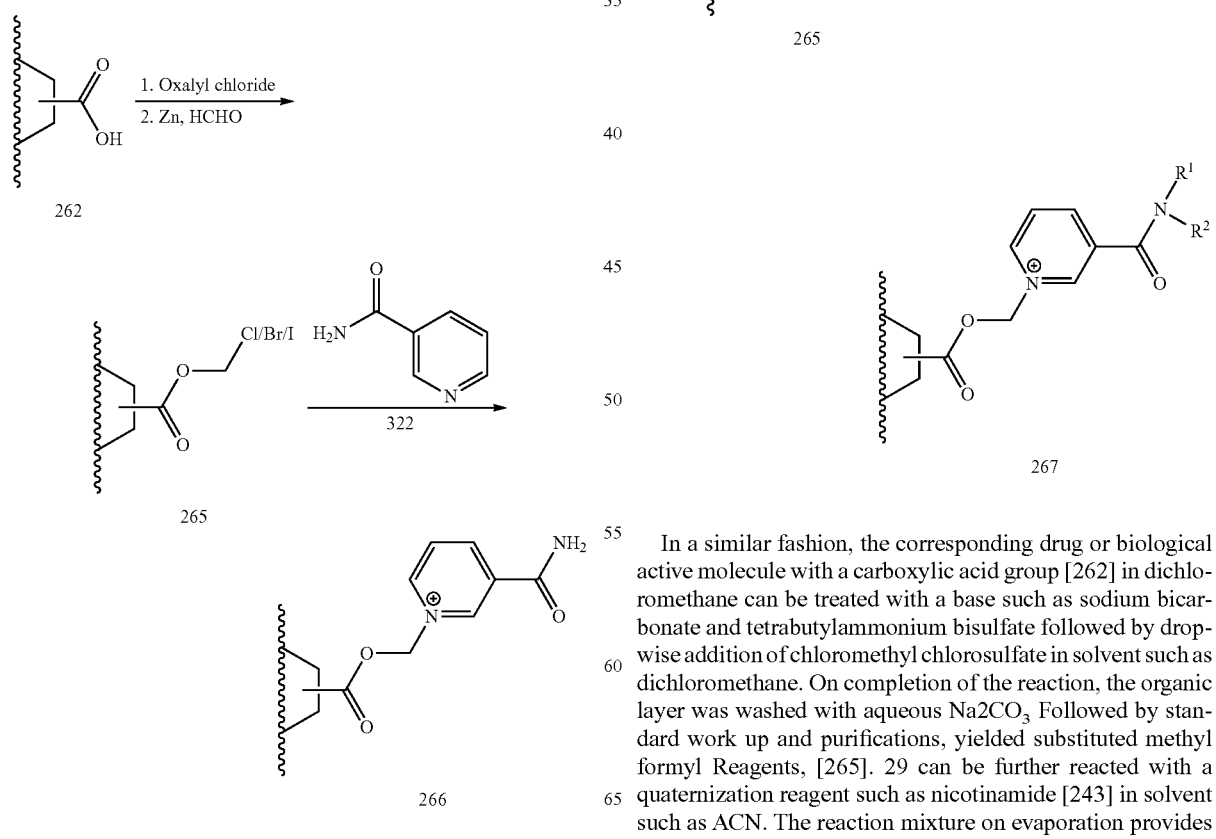

In a similar fashion, the corresponding drug or biological active molecule with a carboxylic acid group [262] in dichloromethane can be treated with a base such as sodium bicarbonate and tetrabutylammonium bisulfate followed by dropwise addition of chloromethyl chlorosulfate in solvent such as dichloromethane. On completion of the reaction, the organic layer was washed with aqueous Na2CO$_3$ Followed by standard work up and purifications, yielded substituted methyl formyl Reagents, [265]. 29 can be further reacted with a quaternization reagent such as nicotinamide [243] in solvent such as ACN. The reaction mixture on evaporation provides modified drug or biological active molecule [267].

Scheme 17:

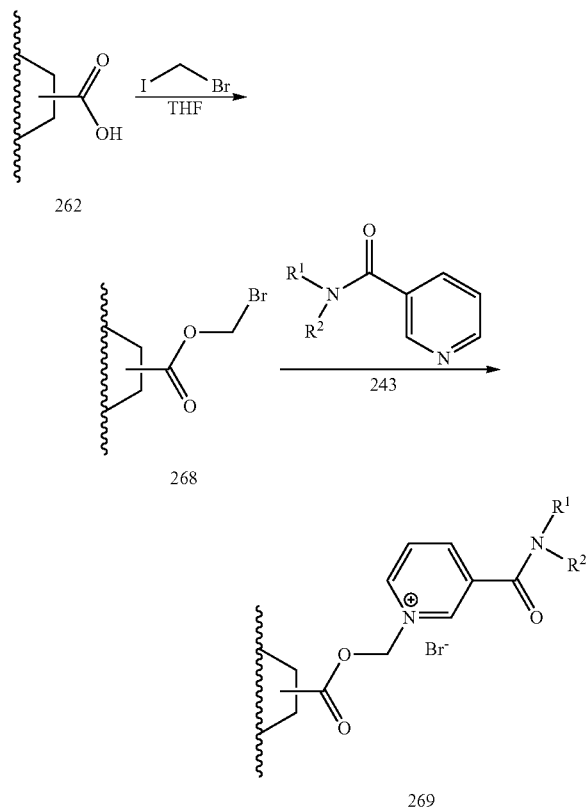

In a similar fashion, the corresponding drug or biological active molecule with a carboxylic acid group [262] can be reacted with a base such as cesium carbonate followed by the addition of a reagent such as bromo iodomethane in a solvent such as THF. On completion of the reaction followed by standard work up and purifications, yield substituted methyl formyl Reagents, [268], which can be further reacted with a quaternization reagent such as nicotinamide [243] in a solvent such as ACN. The reaction mixture on evaporation yields desired products [269].

Scheme 18: Anion Exchnage on quaternary salts:

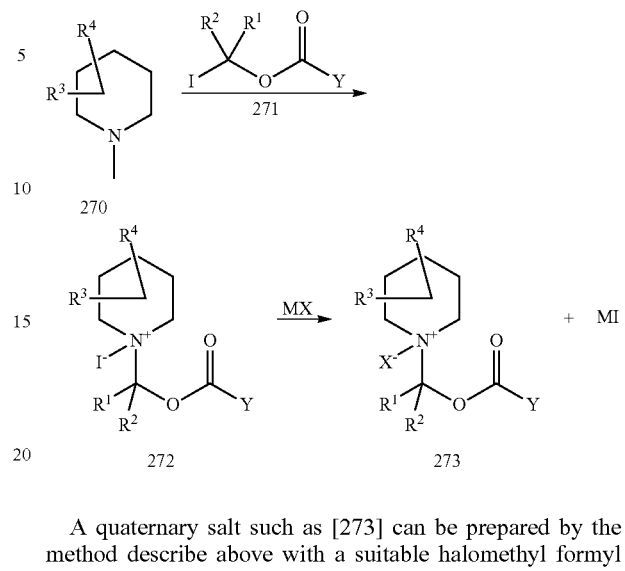

A quaternary salt such as [273] can be prepared by the method describe above with a suitable halomethyl formyl reagent such as iodo methyl formyl (Type I or Type II or Type III). The quat [272] can be treated with a suitable metal salt such as silver mesylate in a solvent such as acetonitrile at a desired temperature ranging from ambient to refluxing which results in the precipitation of silver iodide and formation of desired product. The insoluble silver halide can be filtered out to get reasonably pure desired product [273].

The above method is applicable to do anion exchange on all type of quat salts having any halide such as chloride, bromide or iodide as the counter ion. The various types of silver salts can be used such as silver acetate, silver mesylate or silver tosylate etc.

B.2. Examples of Chemical Compounds Modified by the Substituted Methyl Formyl Groups The substituted methyl formyl reagents as referred herein may be utilized in modifying the chemical compounds by schemes as explained above. A non-limiting set of compounds modified using the method and reagents of the present invention are illustrated at Table 1. The list is meant only for illustration and may not be construed as limiting the scope of the invention.

| Structure | Molecular Formula (Parent) | Molecular Formula (Salt) | Molecular Weight (Parent) | M/Z | IUPAC Name |
|---|---|---|---|---|---|
| C₂₃H₂₄N₅O₆(+) | C23H24N5O6(+) | Cl- | 466.47 | 466 | 3-(dimethylcarbamoyl)-1-[((2-{2,6-dioxopiperidin-3-yl}-1-oxoisoindolin-4-yl)carbamoyl)methyl]pyridin-1-ium |
| C₂₅H₂₈N₅O₇+ | C25H28N5O7 (+) | I- | 510.52 | 511 | 3-((3-{4-amino-1-oxoisoindolin-2-yl}-2,6-dioxopiperidin-1-yl)methoxy)carbonyl]-1-(((isopropylcarbamoyl)oxy)methyl]pyridin-1-ium |
| C₂₅H₃₅N₆O₆S+ | C25H35N6O6S (+) | I- | 547.65 | 548 | 1-(acetoxymethyl)-4-((4-ethoxy-3-(1-methyl-7-oxo-3-propyl-4,7-dihydro-1H-pyrazolo[4,3-d]pyrimidin-5-yl)phenyl)sulfonyl)-1-methylpiperazin-1-ium |

| Structure | Molecular Formula (Parent) | Molecular Formula (Salt) | Molecular Weight (Parent) | M/Z | IUPAC Name |
|---|---|---|---|---|---|
| 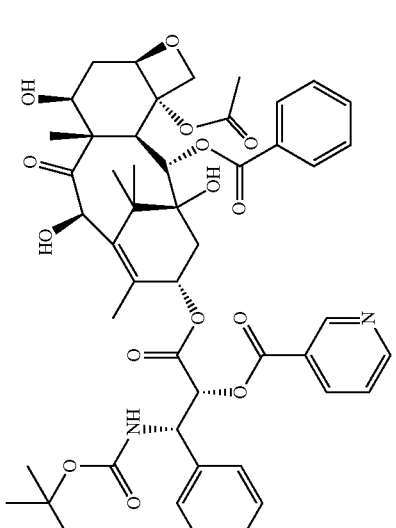 $C_{49}H_{56}N_2O_{15}$ | C49H56N2O15 | | 912.97 | 913 | {2R,3S}-1-({(2aR,4S,4aS,6R,9S,11S,12S,12aR,12bS)-12b-acetoxy-12-(benzoyloxy)-4,6,11-trihydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxet-9-yl}oxy)-3-((tert-butoxycarbonyl)amino)-1-oxo-3-phenylpropan-2-yl nicotinate |
| 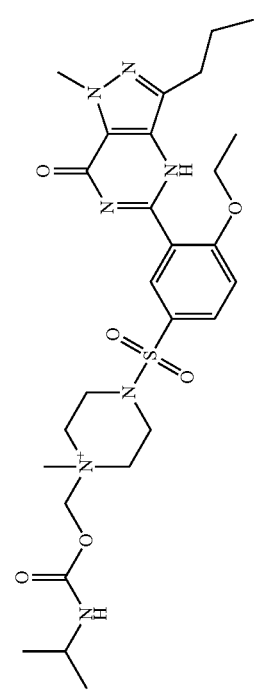 $C_{20}H_{18}N_4O_5$ | C20H18N4O5 | HCl | 394.38 | 394 | (3-(4-amino-1-oxoisoindolin-2-yl)-2,6-dioxopiperidin-1-yl) methyl nicotinate |
| 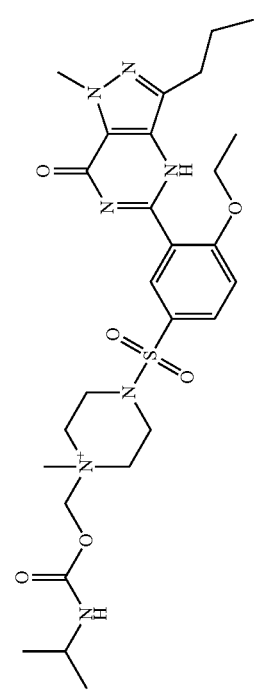 $C_{27}H_{40}N_7O_6S+$ | C27H40N7O6S(+) | I- | 590.71 | 591 | 4-((4-ethoxy-3-(1-methyl-7-oxo-3-propyl-4,7-dihydro-1H-pyrazolo[4,3-d]pyrimidin-5-yl)phenyl)sulfonyl)-1-(((isopropylcarbamoyl)oxy)methyl)-1-methylpiperazin-1-ium |

-continued

| Structure | Molecular Formula (Parent) | Molecular Formula (Salt) | Molecular Weight (Parent) | M/Z | IUPAC Name |
|---|---|---|---|---|---|
| 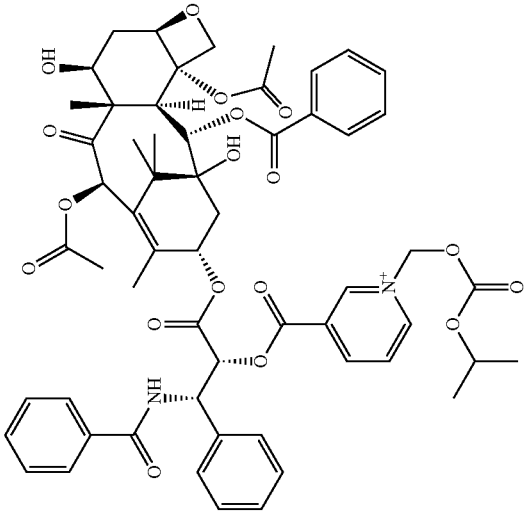 $C_{58}H_{63}N_2O_{18}^+$ | C58H63N2O18(+) | I- | 1076 | 1076 | 3-(({[1S,2R]-1-benzamido-3-(({2aR,4S,4aS,6R,9S,11S,12S,12aR,12bS}-6,12b-diacetoxy-12-(benzoyloxy)-4,11-dihydroxy-4a,8,13,13-tetramethyl-5-oxo-2a,3,4,4a,5,6,9,10,11,12,12a,12b-dodecahydro-1H-7,11-methanacyclodeca[3,4]benzo[1,2-b]oxet-9-yl}oxy)-3-oxo-1-phenylpropan-2-yl}oxy)carbonyl)oxy)methyl)pyridin-1-ium |
| 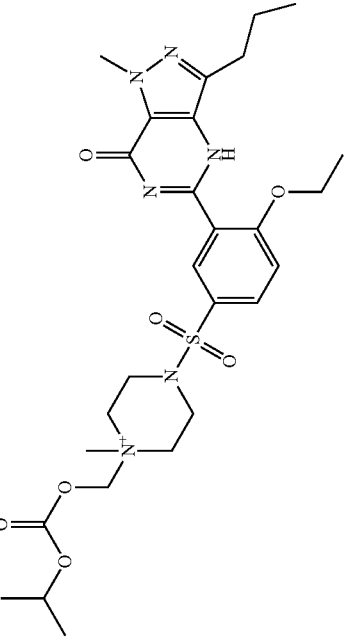 $C_{27}H_{39}N_6O_7S^+$ | C27H39N6O7S(+) | I- | 591.7 | 592 | 4-{[4-ethoxy-3-[1-methyl-7-oxo-3-propyl-4,7-dihydro-1H-pyrazolo[4,3-d]pyrimidin-5-yl]phenyl]sulfonyl}-1-((((isopropoxycarbonyl)oxy)methyl)-1-methylpiperazin-1-ium |

| Structure | Molecular Formula (Parent) | Molecular Formula (Salt) | Molecular Weight (Parent) | M/Z | IUPAC Name |
|---|---|---|---|---|---|
| 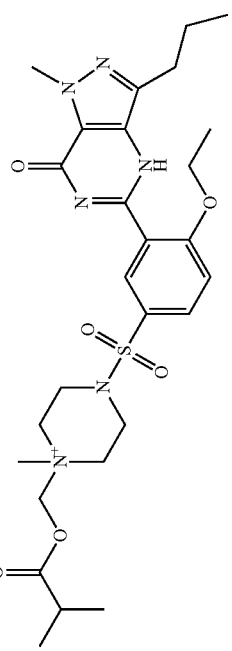<br>$C_{27}H_{39}N_6O_6S^+$ | C27H39N6O6S(+)<br>C27H39N6O6S(+) | I-<br>CH4O3S- | 575.19 | 575 | 4-((4-ethoxy-3-(1-methyl-7-oxo-3-propyl-4,7-dihydro-1H-pyrazolo[4,3-d]pyrimidin-5-yl)phenyl)sulfonyl)-1-((isobutyryloxy)methyl)-1-methylpiperazin-1-ium |
| 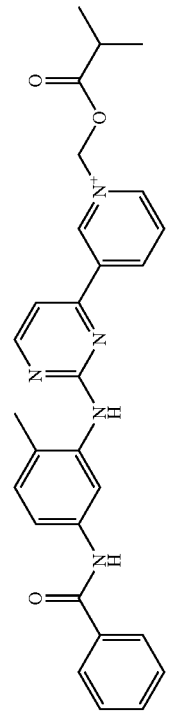<br>$C_{28}H_{28}N_5O_3^+$ | C28H28N5O3(+) | I- | 482.22 | 482 | 3-(2-((5-benzamido-2-methylphenyl)amino)pyrimidin-4-yl)-1-((isobutyryloxy)methyl)pyridin-1-ium |

| Structure | Molecular Formula (Parent) | Molecular Formula (Salt) | Molecular Weight (Parent) | M/Z | IUPAC Name |
|---|---|---|---|---|---|
| 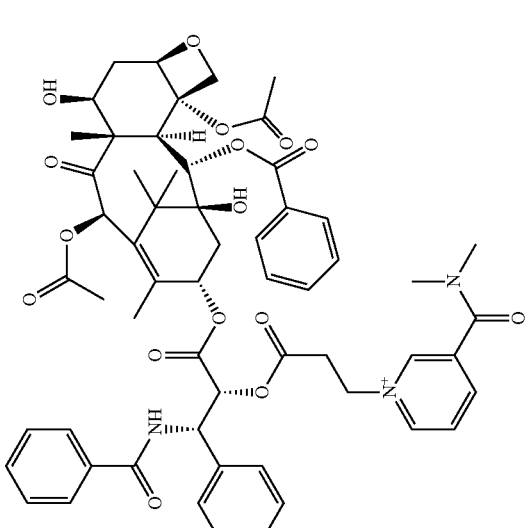 $C_{57}H_{62}N_3O_{17}+$ | C57H62N3O17(+) | 1- | 1061 | 1061 | 1-[(((1S,2R)-1-benzamido-3-(((2aR,4S,4aS,6R,9S,11S,12S,12aR,12bS)-6,12b-diacetoxy-12-(benzoyloxy)-4,11-dihydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxet-9-yl)oxy)-3-oxo-1-phenylpropan-2-yl)oxy)carbonyl)methyl)-3-(dimethylcarbamoyl)pyridin-1-ium |
| 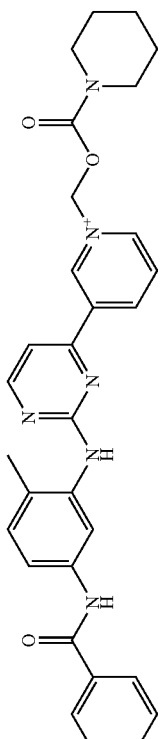 $C_{30}H_{31}N_6O_3+$ | C30H31N6O(1+) | 1- | 491.61 | 492 | 3-(2-((5-benzamido-2-methylphenyl)amino)pyrimidin-4-yl)-1-(((piperidine-1-carbonyl)oxy)methyl)pyridin-1-ium |

| Structure | Molecular Formula (Parent) | Molecular Formula (Salt) | Molecular Weight (Parent) | M/Z | IUPAC Name |
|---|---|---|---|---|---|
| C29H39N8O5+ | C29H39N8O5(+) | I- | 579.67 | 580 | 2-amino-1-(((diisopropylcarbamoyl)oxy)methyl)-5-[4-(4-(dimethylcarbamoyl)phenoxy]-6-morpholino-1,3,5-triazin-2-yl)pyridin-1-ium |
| C29H29N6O3+ | C29H29N6O3(+) | I- | 509.58 | 510 | 3-(2-{(5-benzamido-2-methylphenyl)amino}pyrimidin-4-yl)-1-(((pyrrolidine-1-carbonyl)oxy)methyl)pyridin-1-ium |
| C26H23O5N3Cl+ | C26H23O5N3Cl(+) | I- | 492.93 | 493 | 3-carbamoyl-1-((2-(1-(4-chlorobenzoyl)-5-methoxy-2-methyl-1H-indol-3-yl)acetoxy)methyl)pyridin-1-ium |

-continued

| Structure | Molecular Formula (Parent) | Molecular Formula (Salt) | Molecular Weight (Parent) | M/Z | IUPAC Name |
|---|---|---|---|---|---|
| 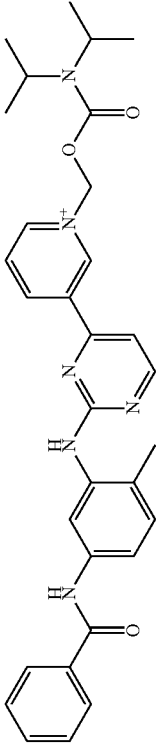 $C_{31}H_{35}N_6O_3^+$ | C31H35N6O3(+) | I- | 539.65 | 540 | 3-[2-((5-benzamido-2-methylphenyl)amino)pyrimidin-4-yl]-1-((((diisopropylcarbamoyl)oxy)methyl)pyridin-1-ium |
| 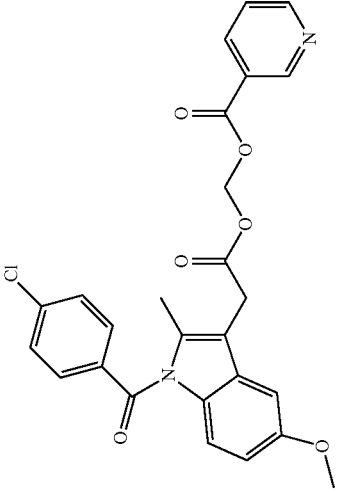 $C_{26}H_{21}ClN_2O_6$ | C26H21O6N2Cl | | 492.91 | 493 | (2-(1-(4-chlorobenzoyl)-5-methoxy-2-methyl-1H-indol-3-yl)acetoxy)methyl nicotinate |
| 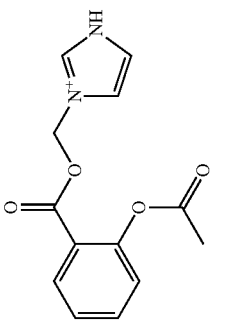 $C_{13}H_{13}N_2O_4^+$ | C13H13O4N2(+) | I- | 261.25 | 261 | 3-(((2-acetoxybenzoyl)oxy)methyl)-1H-imidazol-3-ium |

-continued
| Structure | Molecular Formula (Parent) | Molecular Formula (Salt) | Molecular Weight (Parent) | M/Z | IUPAC Name |
|---|---|---|---|---|---|
| 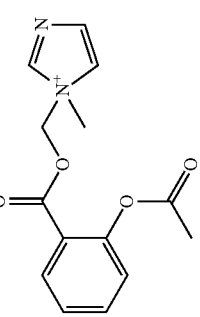 $C_{14}H_{15}N_2O_4^+$ | C14H15O4N2(+) | I- | 275.28 | 275 | 1-(((2-acetoxybenzoyl)oxy)methyl)-1-methyl-1H-imidazol-1-ium |
| 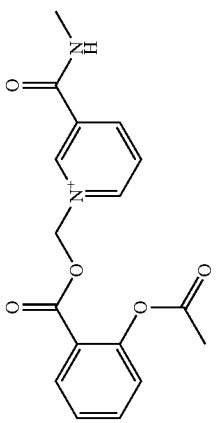 $C_{17}H_{17}N_2O_5^+$ | C17H17O5N2(+) | I- | 329.33 | 329 | 1-(((2-acetoxybenzoyl)oxy)methyl)-3-(methylcarbamoyl)pyridin-1-ium |
| 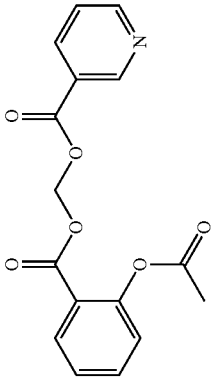 $C_{16}H_{13}NO_6$ | C16H13O6N | | 315.28 | 315 | ((2-acetoxybenzoyl)oxy)methyl nicotinate |

-continued

| Structure | Molecular Formula (Parent) | Molecular Formula (Salt) | Molecular Weight (Parent) | M/Z | IUPAC Name |
|---|---|---|---|---|---|
| C₁₆H₁₅N₂O₅⁺ | C16H15N2O5 | I- | 315.3 | 315 | 1-(((2-acetoxybenzoyl)oxy)methyl)-3-carbamoylpyridin-1-ium |
| C₄₈H₅₉N₆O₅⁺ | C48H59N6O5(+) | I- | 799.45 | 799 | Compound No. 337 |

-continued

| Structure | Molecular Formula (Parent) | Molecular Formula (Salt) | Molecular Weight (Parent) | M/Z | IUPAC Name |
|---|---|---|---|---|---|
| 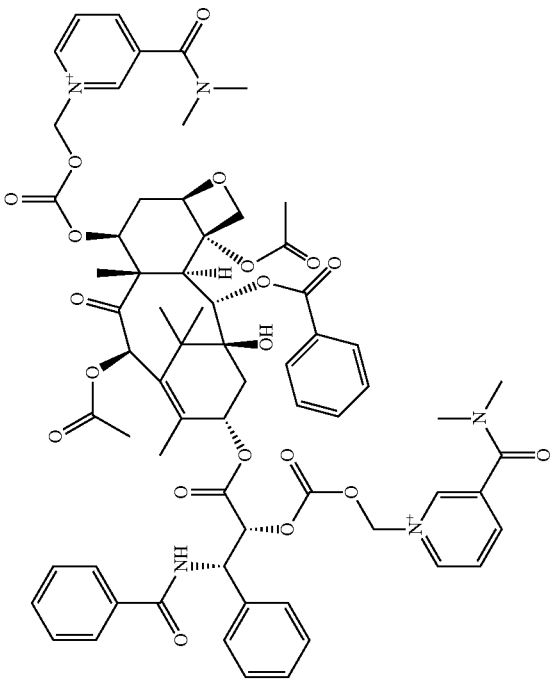 $C_{67}H_{73}N_5O_{20}^{2+}$ | C67H73N5O20 | 2I- | 1268 | 1268 | 1-((((1S,2R)-1-benzamido-3-((2aR,4S,4aS,6R,9S,11S,12S,12aR,12bS)-6,12b-diacetoxy-12-(benzoyloxy)-4-((((3-(dimethylcarbamoyl)pyridin-1-ium-1-yl)methoxy)carbonyl)oxy)-11-hydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxet-9-yl)oxy)-3-oxo-1-phenylpropan-2-yl)oxy)carbonyl)oxy)methyl)-3-(dimethylcarbamoyl)pyridin-1-ium |
| 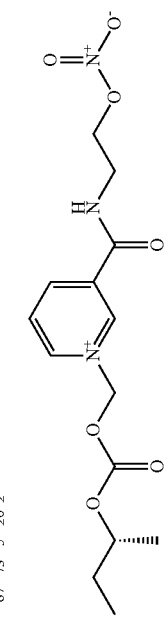 $C_{14}H_{20}N_3O_7+$ | C14H20N3O7(+) | I- | 342.32 | 342 | (R)-1-(((sec-butoxycarbonyl)oxy)methyl)-3-((2-(nitroxy)ethyl)carbamoyl)pyridin-1-ium |
| 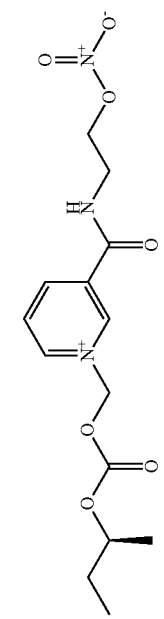 $C_{14}H_{20}N_3O_7+$ | C14H20N3O7(+) | I- | 342.32 | 342 | (S)-1-(((sec-butoxycarbonyl)oxy)methyl)-3-((2-(nitroxy)ethyl)carbamoyl)pyridin-1-ium |

-continued

| Structure | Molecular Formula (Parent) | Molecular Formula (Salt) | Molecular Weight (Parent) | M/Z | IUPAC Name |
|---|---|---|---|---|---|
|  C18H27N4O6+ | C18H27N4O6(+) | I- | 395.43 | 395 | (R)-1-(((1-cyclohexylethyl)carbamoyl)oxy)methyl)-3-((2-(nitroxy)ethyl)carbamoyl)pyridin-1-ium |
|  C18H27N4O6+ | C18H27N4O6(+) | I- | 395.43 | 395 | (S)-1-(((1-cyclohexylethyl)carbamoyl)oxy)methyl)-3-((2-(nitroxy)ethyl)carbamoyl)pyridin-1-ium |
| 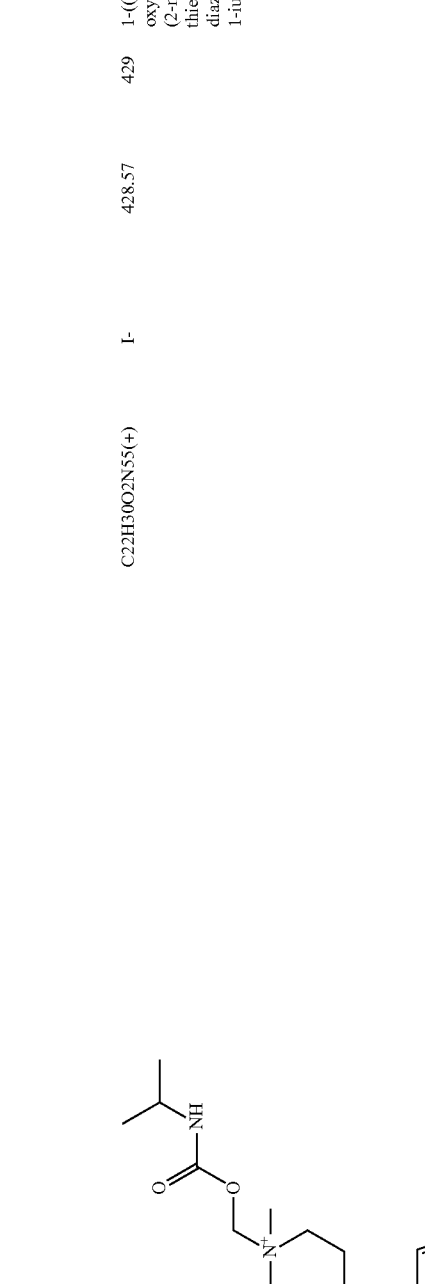 C22H30N5O2S+ | C22H30O2N5S(+) | I- | 428.57 | 429 | 1-(((isopropylcarbamoyl)oxy)methyl)-1-methyl-4-(2-methyl-10H-benzo[b]thieno[2,3-c][1,4]diazepin-4-yl)piperazin-1-ium |

-continued

| Structure | Molecular Formula (Parent) | Molecular Formula (Salt) | Molecular Weight (Parent) | M/Z | IUPAC Name |
|---|---|---|---|---|---|
|  $C_{18}H_{18}N_3O_8+$ | C18H18O8N3(+) | I- | 404.35 | 404 | 1-(((2-acetoxybenzoyl)oxy)methyl)-3-((2-(nitrooxy)ethyl)carbamoyl)pyridin-1-ium |
|  $C_{25}H_{31}N_2O_5+$ | C25H33O5N2(+) | I- | 441.54 | 442 | 3-(2-hydroxy-2,2-diphenylacetoxy)-1-(((isopropylcarbamoyl)oxy)methyl)-1-methylpiperidin-1-ium |
|  $C_{28}H_{27}ClN_3O_5+$ | C28H27O5N3Cl(+) | I- | 520.98 | 521 | 1-(2-(1-(4-chlorobenzoyl)-5-methoxy-2-methyl-1H-indol-3-yl)acetoxy)methyl)-3-(dimethylcarbamoyl)pyridin-1-ium |

-continued

| Structure | Molecular Formula (Parent) | Molecular Formula (Salt) | Molecular Weight (Parent) | M/Z | IUPAC Name |
|---|---|---|---|---|---|
| 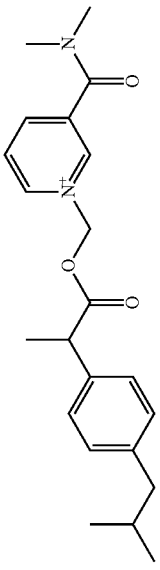<br>$C_{22}H_{29}N_2O_3+$ | C22H29N2O3(+) | I- | 369.48 | 369 | 3-(dimethylcarbamoyl)-1-(((2-(4-isobutylphenyl)propanoyl)oxy)methyl)pyridin-1-ium |
| 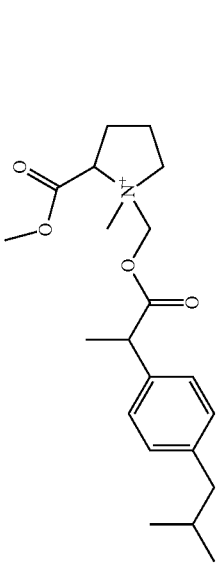<br>$C_{22}H_{32}NO_4+$ | C21H32O4N(+) | I- | 362.48 | 362 | 1-(((2-(4-isobutylphenyl)propanoyl)oxy)methyl)-2-(methoxycarbonyl)-1-methylpyrrolidin-1-ium |
| 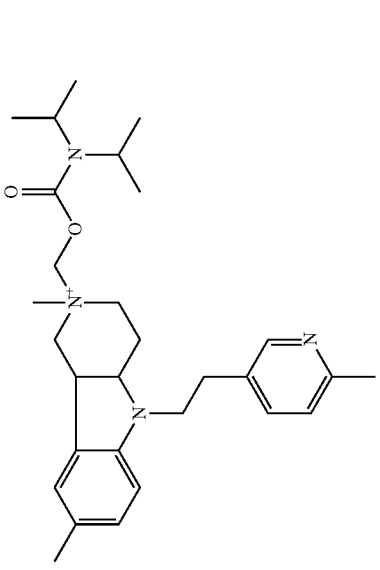<br>$C_{29}H_{43}N_4O_2+$ | C29H43N4O2(+) | I- | 606 | 606 | 2-((((diisopropylcarbamoyl)oxy)methyl)-2,8-dimethyl-5-(2-(6-methylpyridin-3-yl)ethyl)-2,3,4,4a,5,9b-hexahydro-1H-pyrido[4,3-b]indol-2-ium |

-continued

| Structure | Molecular Formula (Parent) | Molecular Formula (Salt) | Molecular Weight (Parent) | M/Z | IUPAC Name |
|---|---|---|---|---|---|
| 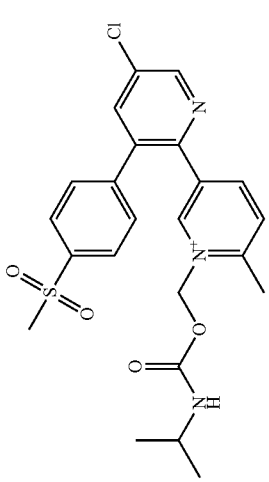 $C_{23}H_{25}ClN_3O_4S+$ | C23H25ClN3O4(+) | I- | 474.98 | 475 | 5-chloro-1'-(((isopropylcarbamoyl)oxy)methyl)-6'-methyl-3-(4-(methylsulfonyl)phenyl)-[2,3'-bipyridin]-1'-ium |
| 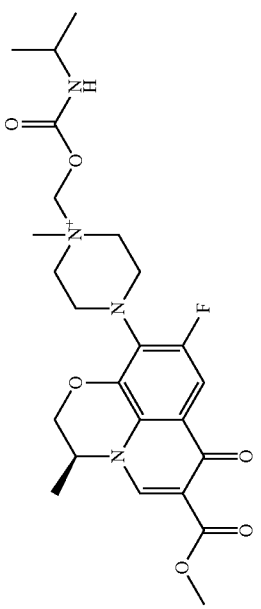 $C_{24}H_{32}FN_4O_6+$ | C24H32FN4O6(+) | I- | 491.53 | 492 | (S)-4-(9-fluoro-6-(methoxycarbonyl)-3-methyl-7-oxo-3,7-dihydro-2H-[1,4]oxazino[2,3,4-ij]quinolin-10-yl)-1-(((isopropylcarbamoyl)oxy)methyl)-1-methylpiperazin-1-ium |

| Structure | Molecular Formula (Parent) | Molecular Formula (Salt) | Molecular Weight (Parent) | M/Z | IUPAC Name |
|---|---|---|---|---|---|
| 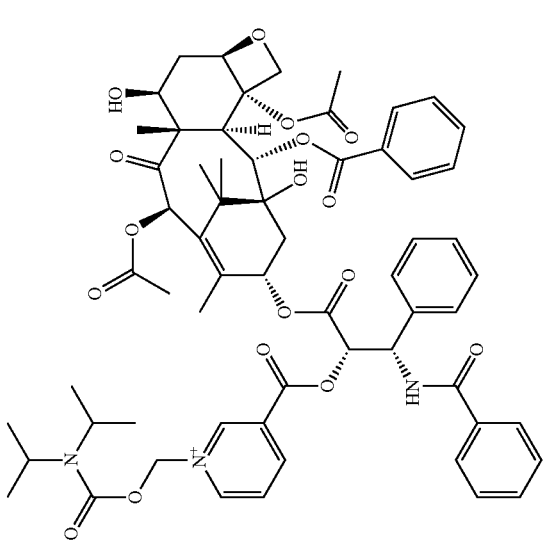 C61H70N3O17+ | C61H70N3O17(+) | I- | 1117 | 1117 | 3-(((1S,2S)-1-benzamido-3-(((2aR,4S,4aS,6R,9S,11S,12S,12aR,12bS)-6,12b-diacetoxy-12-(benzyloxy)-4,11-dihydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxet-9-yl)oxy)-3-oxo-1-phenylpropan-2-yl)oxy)carbonyl)-1-(((diisopropylcarbamoyl)oxy)methyl)pyridin-1-ium |
| 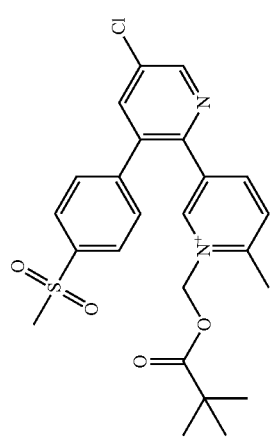 C24H26ClN2O4S+ | C24H25N2ClO4S(+) | I- | 599.89 | 600 | 5-chloro-6'-methyl-3-(4-(methylsulfonyl)phenyl)-1'-((pivaloyloxy)methyl)-[2,3'-bypyridin]-1'-ium |

-continued

| Structure | Molecular Formula (Parent) | Molecular Formula (Salt) | Molecular Weight (Parent) | M/Z | IUPAC Name |
|---|---|---|---|---|---|
| $C_{23}H_{22}Cl_2N_3O_3^+$ | C23H22Cl2N3O3(+) | I- | 459.34 | 459 | 1-((2-(2-((2,6-dichlorophenyl)amino)phenyl)acetoxy)methyl)-3-(dimethylcarbamoyl)pyridin-1-ium |
| $C_{22}H_{24}NO_8^+$ | C22H24NO8(+) | I- | 430.43 | 430 | 3-(((2-acetoxybenzoyl)oxy)methoxy)carbonyl)-1-((pivaloyloxy)methyl)pyridin-1-ium |
| $C_{18}H_{19}N_2O_5^+$ | C18H19N2O5(+) | I- | 343.35 | 343 | 1-(((2-acetoxybenzoyl)oxy)methyl)-3-(dimethylcarbamoyl)pyridin-1-ium |
| $C_{18}H_{20}N_3O_5^+$ | C18H20N3O5(+) | I- | 358.37 | 358 | 1-((((4-acetamidophenoxy)carbonyl)oxy)methyl)-3-(dimethylcarbamoyl)pyridin-1-ium |

-continued

| Structure | Molecular Formula (Parent) | Molecular Formula (Salt) | Molecular Weight (Parent) | M/Z | IUPAC Name |
|---|---|---|---|---|---|
| $C_{19}H_{21}N_2O_5+$ | C19H21N2O5(+) | I- | 357.38 | 357 | 3-((4-acetamidophenoxy)carbonyl)-1-((isobutyryloxy)methyl)pyridin-1-ium |
| $C_{31}H_{31}N_2O_9+$ | C31H31N2O9(+) | I- | 575.59 | 576 | 3-(dimethylcarbamoyl)-1-((((4-((1E,3Z,6E)-3-hydroxy-7-[4-hydroxy-3-methoxyphenyl)-5-oxohepta-1,3,6-trien-1-yl]-2-methoxyphenoxy)carbonyl)oxy)methyl]pyridin-1-ium |
| $C_{22}H_{28}N_3O_5+$ | C22H28N3O5(+) | I- | 414.47 | 414 | 3-[(4-acetamidophenoxy)carbonyl]-1-((((diisopropylcarbamoyl)oxy)methyl)pyridin-1-ium |

-continued

| Structure | Molecular Formula (Parent) | Molecular Formula (Salt) | Molecular Weight (Parent) | M/Z | IUPAC Name |
|---|---|---|---|---|---|
| C26H29N2O7+ | C26H29N2O7(+) | I- | 481.52 | 482 | (S)-1-(((isopropylcarbamoyl)oxy)methyl)-3-(((2-(6-methoxynaphthalen-2-yl)propanoyl)oxy)methoxy)carbonyl)pyridin-1-ium |
| C28H38N3O6+ | C28H38N3O6(+) | I- | 512.62 | 513 | (E)-3-(dimethylcarbamoyl)-1-((((2-methoxy-4-((8-methylnon-6-enamido)methyl)phenoxy)carbonyl)oxy)methyl)pyridin-1-ium |
| C58H64N3O17+ | C58H46N3O17(+) | I- | 1075 | 1075 | 3-(((1S,2R)-1-benzamido-3-(((2aR,4S,4aS,6R,9S,11S,12S,12aR,12bS)-6,12b-diacetoxy-12-(benzoyloxy)-4,11-dihydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxet-9-yl)oxy)-3-oxo-1-phenylpropan-2-yl)oxy)carbonyl)-1-((((isopropylcarbamoyl)oxy)methyl)pyridin-1-ium |

-continued

| Structure | Molecular Formula (Parent) | Molecular Formula (Salt) | Molecular Weight (Parent) | M/Z | IUPAC Name |
|---|---|---|---|---|---|
| 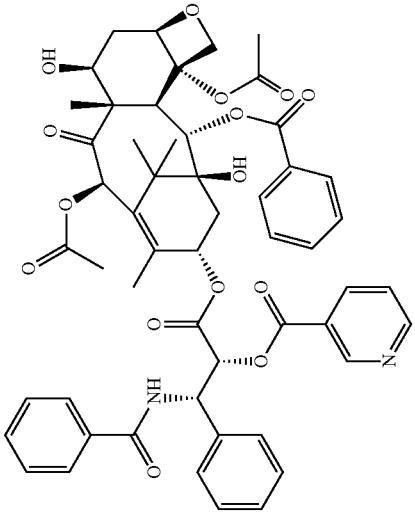<br>$C_{53}H_{54}N_2O_{15}$ | C53H54N2O15 | C53H54N2O15 | 959 | 959 | (2aR,4S,4aS,6R,9S,11S,12S,12aR,12bS)-9-((2R,3S)-3-benzamide-2-(nicotinoyloxy)-3-phenylpropanoyl)oxy)-12-(benzyloxy)-4,11-dihydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxete-6,12b-diyl diacetate |
| 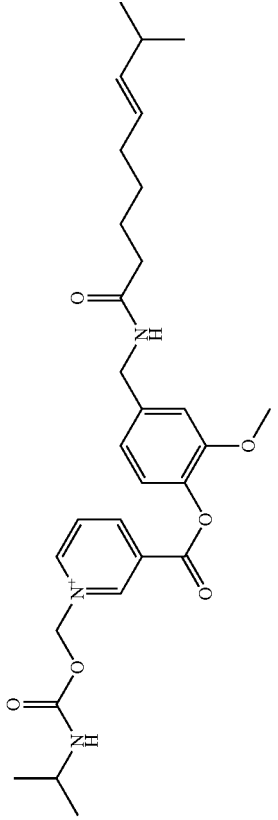<br>$C_{29}H_{40}N_3O_{6+}$ | C29H40N3O6(+) | I- | 526.64 | 527 | (E)-1-(((isopropylcarbamoyl)oxy)methyl)-3-((2-methoxy-4-((8-methylnon-6-enamido)methyl)phenoxy)carbonyl)pyridin-1-ium |

| Structure | Molecular Formula (Parent) | Molecular Formula (Salt) | Molecular Weight (Parent) | M/Z | IUPAC Name |
|---|---|---|---|---|---|
| 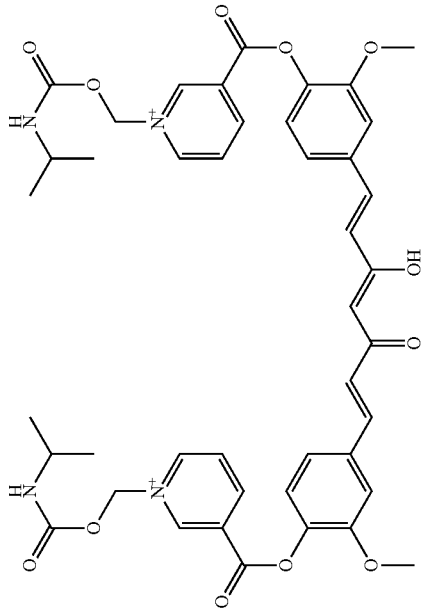 $C_{43}H_{46}N_4O_{12}^{+2}$ | C43H46N4O12(+2) | 2I- | 810.84 | 811 | 3,3'-((((((1E,3Z,6E)-3-hydroxy-5-oxohepta-1,3,6-triene-1,7-diyl)bis(2-methoxy-4,1-phenylene)bis(oxy))bis(carbonyl))bis(1-(((isopropylcarbamoyl)oxy)methyl)pyridin-1-ium |
| 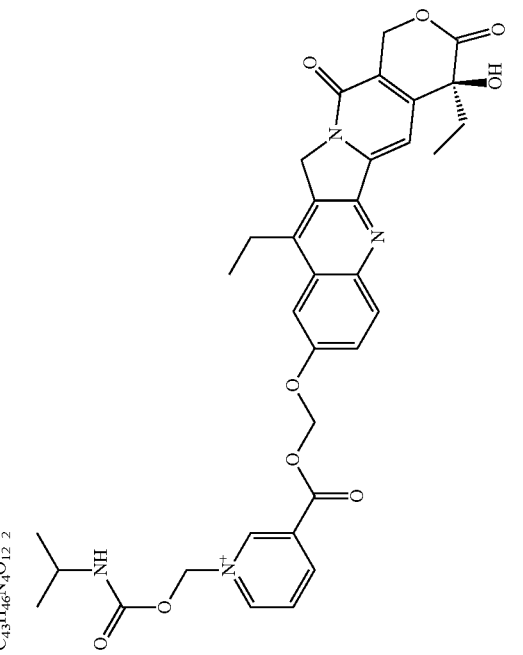 $C_{34}H_{35}N_4O_9^{+}$ | C43N35N4O9(+) | I- | 643.66 | 644 | (S)-3-{{((4,11-diethyl-4-hydroxy-3,14-dioxo-3,4,12,14-tetrahydro-1H-pyrano[3',4':6,7]indolizino[1,2-b]quinolin-9-yl)oxy)methoxy)carbonyl)-1-(((isopropylcarbamoyl)oxy)methyl)pyridin-1-ium |

-continued
| Structure | Molecular Formula (Parent) | Molecular Formula (Salt) | Molecular Weight (Parent) | M/Z | IUPAC Name |
|---|---|---|---|---|---|
| 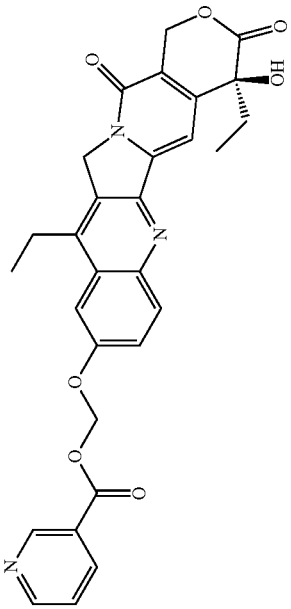 $C_{29}H_{25}N_3O_7$ | C29H25N3O7 | | 527.52 | 528 | (S)-(4,11-diethyl-4-hydroxy-3,14-dioxo-3,4,12,24-tetrahydro-1H-pyrano[3',4':6,7]indolizino[1,2-b]quinolin-9-yl)oxy)methyl nicotinate |
| 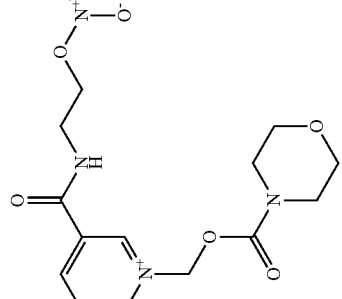 $C_{14}H_{15}N_4O_7+$ | C14H19N4O7(+) | I- | 355.32 | 355 | 1-(((morpholine-4-carbonyl)oxy)methyl)-3-((2-(nitrooxy)ethyl)carbamoyl)pyridin-1-ium |

-continued

| Structure | Molecular Formula (Parent) | Molecular Formula (Salt) | Molecular Weight (Parent) | M/Z | IUPAC Name |
|---|---|---|---|---|---|
| C14H19N4O6(+) | C14H19N4O6(+) | I- | 339.32 | 339 | 3-((2-(nitrooxy)ethyl)carbamoyl)-1-(((pyrrolidine-1-carbonyl)oxy)methyl)pyridin-1-ium |
| C30H38N4O6 | C30H38N4O6 | I- | 550.65 | 551 | (((6,7-bis[2-methoxyethoxy)quinazolin-4-yl](3-ethynylphenyl)amino)methyl diisopropylcarbamate |

-continued
| Structure | Molecular Formula (Parent) | Molecular Formula (Salt) | Molecular Weight (Parent) | M/Z | IUPAC Name |
|---|---|---|---|---|---|
| 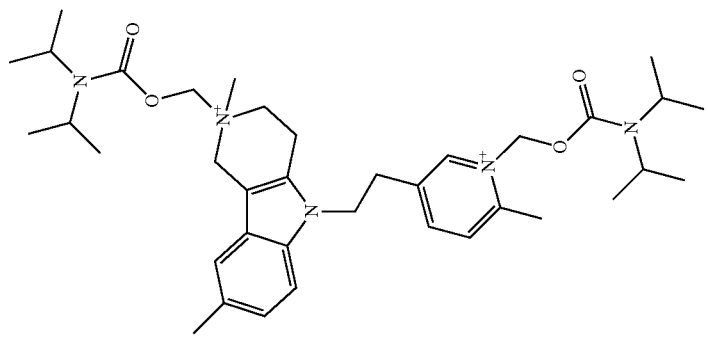<br>$C_{37}H_{57}N_5O_4^{+}{}_2$ | C37H57N5O4(+2) | 2I- | 635.88 | 636 | 2-(((diisopropylcarbamoyl)methyl)-5-[2-(1-(((diisopropylcarbamoyl)oxy)methyl)-6-methylpyridin-1-ium-3-yl)ethyl]-2,8-dimethyl-2,3,4,5-tetrahydro-1H-pyrido[4,3-b]indol-2-ium |

| Structure | Molecular Formula (Parent) | Molecular Formula (Salt) | Molecular Weight (Parent) | M/Z | IUPAC Name |
|---|---|---|---|---|---|
| C₂₈H₂₉N₆O₃⁺ | C28H29N6O3(+) | I- | 497.57 | 498 | 3-[2-((5-benzamido-2-methylphenyl)amino)pyrimidin-4-yl]-1-(((isopropylcarbamoyl)oxy)methyl)pyridin-1-ium |
| C₁₄H₂₀N₃O₇⁺ | C14H20N3O7(+) | I- | 342.32 | 342 | 1-(((tert-butoxycarbonyl)oxy)methyl)-3-((2-(nitrooxy)ethyl)carbamoyl)pyridin-1-ium |

-continued

| Structure | Molecular Formula (Parent) | Molecular Formula (Salt) | Molecular Weight (Parent) | M/Z | IUPAC Name |
|---|---|---|---|---|---|
| C20H21N2O8(+) | C20H21N2O8(+) | I- | 417.39 | 417 | 3-(((2-acetoxybenzoyl)oxy)methoxy)carbonyl)-1-(((dimethylcarbamoyl)oxy)methyl)pyridin-1-ium |
| C13H19N4O6+ | C13H19N4O6(+) | I- | 327.31 | 327 | 1-(((isopropylcarbamoyl)oxy)methyl)-3-((2-(nitrooxy)ethyl)carbamoyl)pyridin-1-ium |

-continued

| Structure | Molecular Formula (Parent) | Molecular Formula (Salt) | Molecular Weight (Parent) | M/Z | IUPAC Name |
|---|---|---|---|---|---|
| $C_{12}H_{17}N_4O_6+$ | C12H17N4O6(+) | I- | 313.29 | 313 | 1-(((dimethylcarbamoyl)oxy)methyl)-3-((2-(nitrooxy)ethyl)carbamoyl)pyridin-1-ium |
| $C_{13}H_{18}N_3O_7+$ | C13H18N3O7(+) | I- | 328.3 | 328 | 1-((((isopropylcarbonyl)oxy)methyl)-3-((2-(nitrooxy)ethyl)carbamoyl)pyridin-1-ium |
| $C_{29}H_{30}N_5O_3+$ | C29H30N5O3(+) | I- | 496.58 | 497 | 3-(2-(5-benzamido-2-methylphenyl)amino)pyrimidin-4-yl)-1-((pivaloyloxy)methyl)pyridin-1-ium |

| Structure | Molecular Formula (Parent) | Molecular Formula (Salt) | Molecular Weight (Parent) | M/Z | IUPAC Name |
|---|---|---|---|---|---|
|  C12H16N3O7+ | C12H16N3O7(+) | I- | 314.27 | 314 | 1-(((ethoxycarbonyl)oxy)methyl)-3-((2-(nitrooxy)ethyl)carbamoyl)pyridin-1-ium |
|  C15H21N4O6+ | C15H21N4O6(+) | I- | 353.35 | 353 | 3-((2-(nitrooxy)ethyl)carbamoyl)-1-(((piperidine-1-carbonyl)oxy)methyl)pyridin-1-ium |
|  C16H25N4O6+ | C16H25N4O6(+) | I- | 369.39 | 369 | 1-(((diisopropylcarbamoyl)oxy)methyl)-3-((2-(nitrooxy)ethyl)carbamoyl)pyridin-1-ium |

-continued
| Structure | Molecular Formula (Parent) | Molecular Formula (Salt) | Molecular Weight (Parent) | M/Z | IUPAC Name |
|---|---|---|---|---|---|
| 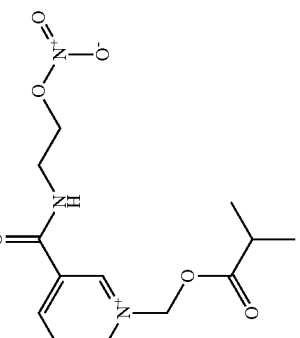<br>$C_{13}H_{18}N_3O_6+$ | C13H18N3O6(+) | I- | 312.3 | 312 | 1-(((isobutyryloxy)methyl)-3-((2-(nitrooxy)ethyl)carbamoyl)pyridin-1-ium |
| 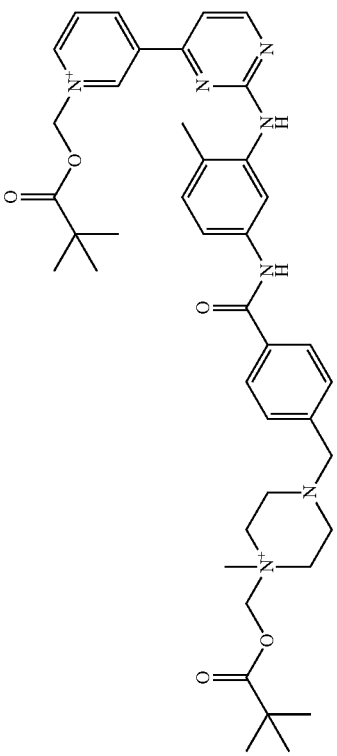<br>$C_{41}H_{53}N_7O_5{}^{+}{}_{2}$ | C41H53N7O5(+2) | 2I- | 723.9 | 724 | 1-methyl-4-(4-([4-methyl-3-((4-(1-((pivaloyloxy)methyl)pyridin-1-ium-3-yl)pyrimidin-2-yl)amino)phenyl)carbamoyl)benzyl)-1-((pivaloyloxy)methyl)piperazin-1-ium |

-continued

| Structure | Molecular Formula (Parent) | Molecular Formula (Salt) | Molecular Weight (Parent) | M/Z | IUPAC Name |
|---|---|---|---|---|---|
| C₁₄H₂₀N₃O₆⁺ | C14H20N3O6(−) | I- | 326.32 | 326 | 1-[((3-methylbutanoyl)oxy)methyl]-3-((2-(nitrooxy)ethyl)carbamoyl)pyridin-1-ium |
| C₂₄H₃₀N₃O₃⁺ | C24H30N3O3(+) | Cl- | 408.51 | 409 | 2-methyl-1-[(9-methyl-4-oxo-2,3,4,9-tetrahydro-1H-carbazol-3-yl)methyl]-3-((pivaloyloxy)methyl)-1H-imidazol-3-ium |
| C₁₅H₂₂N₃O₆⁺ | C15H22N3O6(+) | I- | 340.35 | 340 | 1-(((3,3-dimethylbutanoyl)oxy)methyl)-3-((2-(nitrooxy)ethyl)carbamoyl)pyridin-1-ium |

| Structure | Molecular Formula (Parent) | Molecular Formula (Salt) | Molecular Weight (Parent) | M/Z | IUPAC Name |
|---|---|---|---|---|---|
| C35H42N7O3(+) | C35H42N7O3(+) | I- | 608.75 | 609 | 1-methyl-4-(4-((4-methyl-3-((4-(pyridin-3-yl)pyrimidin-2-yl)amino)phenyl)carbamoyl)benzyl)-1-((pivaloyloxy)methyl)piperazin-1-ium |
| C14H20N3O6(+) | C14H20N3O6(+) | I- | 326.32 | 326 | 3-((2-(nitrooxy)ethyl)carbamoyl)-1-((pivaloyloxy)methyl)pyridin-1-ium |

C. Use of Substituted Methyl Formyl Reagents to Modify Chemical Compounds to Modify the Rate and Site Specificity of Conversion in the Body.

Substituted methyl formyl reagents of the present invention are used to generate New Chemical Entities (NCEs) so that the rate and site of conversion of these NCEs to the parent drugs/biologically active compounds can be controlled. This can be achieved, due to the presence of the converting enzyme(s) or other converting parameters and reagents that are involved in the transformation of the NCEs to the parent drugs/biologically active substances which may only (or even predominantly) be selectively present at the site of conversion. The rate of conversion can be modified as the structure of the modified drug/biologically active molecule or the concentration/amount of the converting enzyme present at the site of conversion can influence the rate of conversion of the NCEs to the drug/biologically active compound. Endogenous enzymes that are capable of converting these compounds belong to four International Union of Pure and Applied Chemistry classes. Enzymes from class 1 are the oxidoreductases, enzymes from class 2 are the transferases, enzymes from class 3 are hydrolases, and enzymes from class 4 are the lysases. Numerous modified compounds have been developed for the delivery of higher concentrations of a drug to the target than could otherwise be obtained by the administration of the unmodified compound itself. Four main modes of delivery have been identified which modified drugs or biologically active molecules as described in this patent may exploit: (1) passive drug enrichment in the target organ; (2) transporter mediated delivery; (3) selective metabolic activation through enzymes; and (4) antigen targeting.

This application of the present invention achieves more than simply modifying the pharmacokinetic and physicochemical properties of the drug/biologically active molecule. This results in the ability to use less, overall, of the drug/biologically active compound than would be required of the unmodified drug. This offers several benefits, including potential decrease or even elimination of unwanted side effects.

Accordingly, as one of ordinary skill in the art will appreciate, the methyl formyl reagents of the present invention are designed to be cleaved from the drug they are attached to by the endogenous systems, such as enzymes present, to a greater or lesser extent, in humans and most animals kept as pets or livestock. Accordingly, unlike making many other possible covalent modifications to an effective drug, derivatization according to the present invention permits modification of the modified compound's characteristics without sacrificing the safety, efficacy, or toxicology of the original, un-modified drug. Based upon this principle, one of ordinary skill in the art will readily comprehend that the method of the present invention can be used, along with the agents disclosed and taught herein, to make a variety of derivatized compounds with modified pharmacokinetic, pharmacodynamic, and physiochemical properties without decreasing the potency of the original drug. As such, one of ordinary skill in the art will understand that the examples shown herein are simply illustrations of the present invention and its application and do not in any manner limit the scope and breadth of the invention disclosed or the teachings of the present invention.

Table 2, shows an exemplary but a non-limiting list of currently-existing drugs/biologically active compounds that can be modified using the methods and modification agents described in this invention. The first column provides the reference number for the drug and/or biologically active compound. The second column gives the generic name for the drug and/or biologically active compound. The third column gives the trade name under which the drug is sold (where applicable). The fourth column gives the IUPAC name of the drug and/or biologically active compound. The fifth column shows the chemical structure of the drug. For example, dimebon [4149] has two functional groups which can undergo derivation. One group is a tertiary amine and the other is an aromatic amine. Non-limiting examples of these derivations are illustrated in Schemes 31 and 32. As one of ordinary skill in the art would readily apprehend, the present invention teaches that novel derivatized compounds of the present invention could be formed with any of a variety of drugs which have one or more of the functional groups referenced according to Schemes 1, 2 and/or 3 by practicing the method of the present invention.

TABLE 2

A Non-limiting List of Drugs or Biologically Active Molecules which can be derivatized according to the embodiment of the invention.

| No. | Drug or Biologically Active Molecule | Trade Name | IUPAC Name | Chemical Structure |
| --- | --- | --- | --- | --- |
| 4101 | Tadalafil | Cialis | (6R-trans)-6-(1,3-benzodioxol-5-yl)-2,3,6,7,12,12a-hexahydro-2-methyl-pyrazino [1',2':1,6] pyrido[3,4-b]indole-1,4-dione | 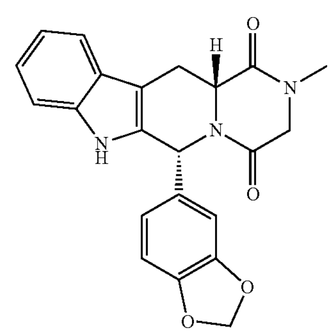 [SMILES: CN1CC(=O)N2[C@H](c3ccc4c(c3)OCO4)c3[nH]c4ccccc4c3C[C@@H]2C1=O] |

TABLE 2-continued

A Non-limiting List of Drugs or Biologically Active Molecules which can be derivatized according to the embodiment of the invention.

| No. | Drug or Biologically Active Molecule | Trade Name | IUPAC Name | Chemical Structure |
|---|---|---|---|---|
| 4102 | Sildenafil | Viagra | 1-[4-ethoxy-3-(6,7-dihydro-1-methyl-7-oxo-3-propyl-1H-pyrazolo[4,3-d]pyrimidin-5-yl)phenylsulfonyl]-4-methylpiperazine | 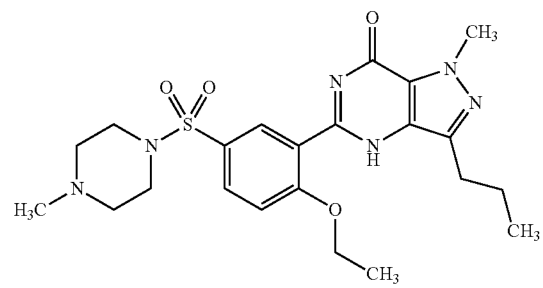 [SMILES: CCCc1nn(C)c2c(=O)nc(-c3cc(S(=O)(=O)N4CCN(C)CC4)ccc3OCC)[nH]c12] |
| 4103 | Amprenavir | | (3S)-oxolan-3-yl N-[(2S,3R)-3-hydroxy-4-[N-(2-methylpropyl)(4-aminobenzene)sulfonamido]-1-phenylbutan-2-yl]carbamate | 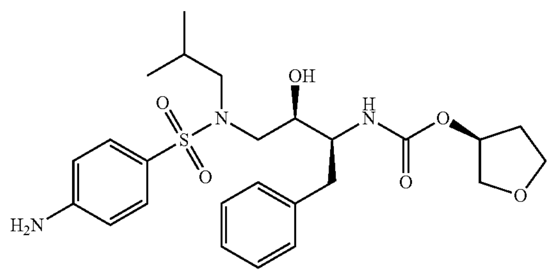 [SMILES: CC(C)CN(C[C@@H](O)[C@H](Cc1ccccc1)NC(=O)O[C@H]1CCOC1)S(=O)(=O)c1ccc(N)cc1] |
| 4104 | Fosamprenavir | Lexiva/ Telzir | {[(2R,3S)-1-[N-(2-methylpropyl)(4-aminobenzene)sulfonamido]-3-({[(3S)-oxolan-3-yloxy]carbonyl}amino)-4-phenylbutan-2-yl]oxy}phosphonic acid | 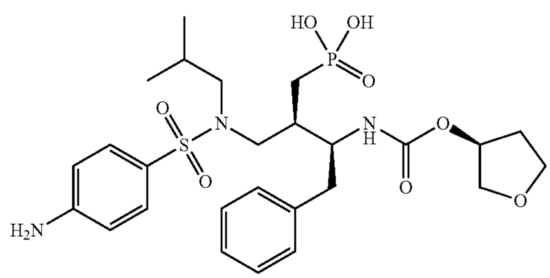 [SMILES: CC(C)CN(C[C@@H](CP(=O)(O)O)[C@H](Cc1ccccc1)NC(=O)O[C@H]1CCOC1)S(=O)(=O)c1ccc(N)cc1] |
| 4105 | Buproprion | Wellbutrin, Zyban, Voxra Budeprion, or Aplenzin | (±)-2-(tert-Butylamino)-1-(3-chlorophenyl)propan-1-one | 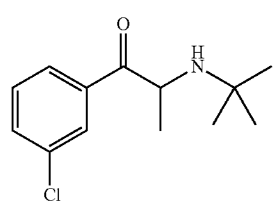 [SMILES: CC(NC(C)(C)C)C(=O)c1cccc(Cl)c1] |
| 4106 | Duloxetine | Cymbalta | (±)-(S)-N-Methyl-3-(naphthalen-1-yloxy)-3-(thiophen-2-yl)propan-1-amine | 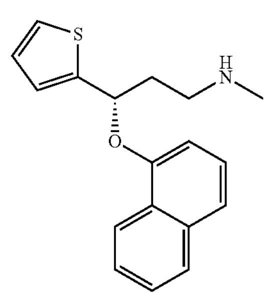 [SMILES: CNCC[C@H](Oc1cccc2ccccc12)c1cccs1] |

TABLE 2-continued

A Non-limiting List of Drugs or Biologically Active Molecules which can be derivatized according to the embodiment of the invention.

| No. | Drug or Biologically Active Molecule | Trade Name | IUPAC Name | Chemical Structure |
|---|---|---|---|---|
| 4107 | Finasteride | Proscar | N-(1,1-dimethylethyl)-3-oxo-(5α,17β)-4-azaandrost-1-ene-17-carboxamide | 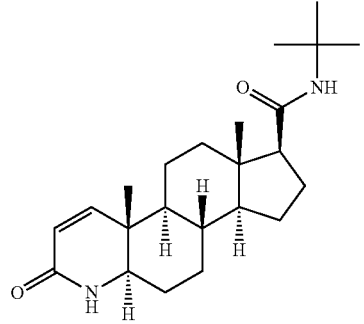 |
| 4108 | Latanoprost | Xalatan | isopropyl (Z)-7-[(1R,2R,3R,5S)-3,5-dihydroxy-2-[(3R)3-hydroxy-5-phenylpentyl]-cyclopentyl] hept-5-enoate | 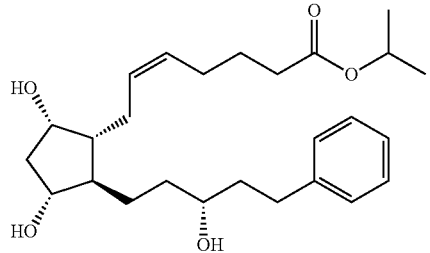 [SMILES: CC(C)OC(=O)CCC/C=C\C[C@@H]1[C@@H](CC[C@@H](O)CCc2ccccc2)[C@H](O)C[C@@H]1O] |
| 4109 | Lopinavir | Kaletra/ Aluvia | (2S)-N-[(2S,4S,5S)-5-[2-(2,6-dimethylphenoxy)acetamido]-4-hydroxy-1,6-diphenylhexan-2-yl]-3-methyl-2-(2-oxo-1,3-diazinan-1-yl)butanamide | 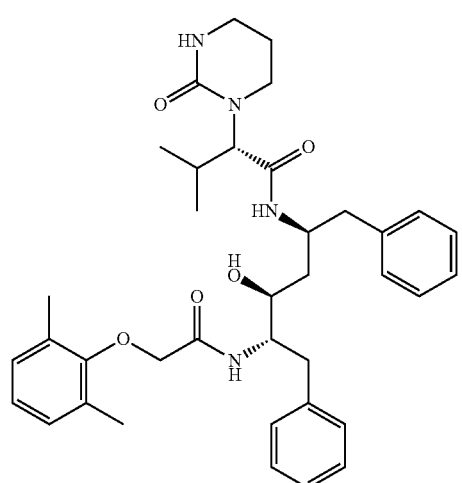 |

TABLE 2-continued

A Non-limiting List of Drugs or Biologically Active Molecules which can be derivatized according to the embodiment of the invention.

| No. | Drug or Biologically Active Molecule | Trade Name | IUPAC Name | Chemical Structure |
|---|---|---|---|---|
| 4110 | Raloxifene | Evista | [6-hydroxy-2-(4-hydroxyphenyl)-benzothiophen-3-yl]-[4-[2-(1-piperidyl)ethoxy]phenyl]-methanone | 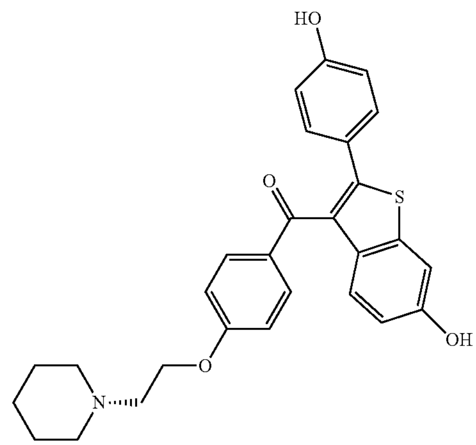 |
| 4111 | Tropicamide | Paremyd | N-ethyl-3-hydroxy-2-phenyl-N-(pyridin-4-ylmethyl) propanamide | 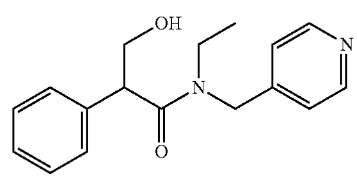 [SMILES: CCN(Cc1ccncc1)C(=O)C(CO)c1ccccc1] |
| 4112 | Geldanamycin | | (4E,6Z,8S,9S,10E,12S,13R,14S,16R)-13-hydroxy-8,14,19-trimethoxy-4,10,12,16-tetramethyl-3,20,22-trioxo-2-azabicyclo[16.3.1]docosa-1(21),4,6,10,18-pentaen-9-yl carbamate | 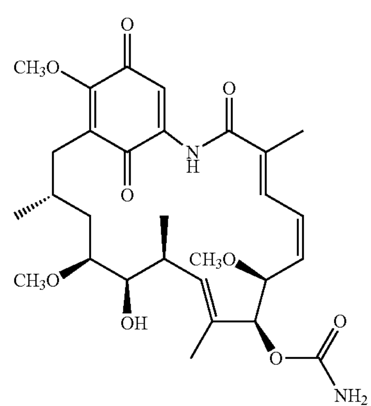 |
| 4113 | Metformin | Fortamet, Glucophage, Glumetza | N,N-dimethylimidodicarbonimidic diamide | 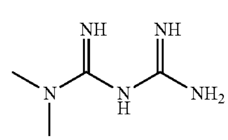 |

TABLE 2-continued

A Non-limiting List of Drugs or Biologically Active Molecules which can be derivatized according to the embodiment of the invention.

| No. | Drug or Biologically Active Molecule | Trade Name | IUPAC Name | Chemical Structure |
|---|---|---|---|---|
| 4114 | Paclitaxel | Taxol | (2α,4α,5β,7β,10β,13α)-4,10-bis(acetyloxy)-13-{[(2R,3S)-3-(benzoylamino)-2-hydroxy-3-phenylpropanoyl]oxy}-1,7-dihydroxy-9-oxo-5,20-epoxytax-11-en-2-yl benzoate | 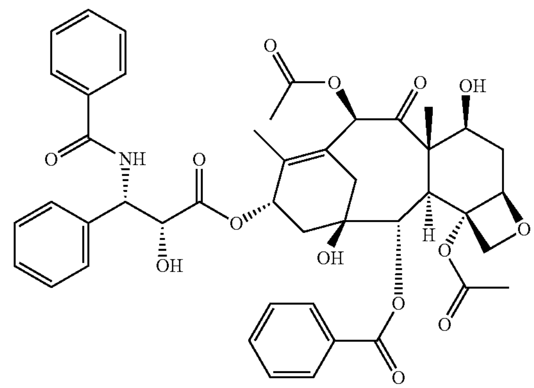 [SMILES: CC(=O)O[C@H]1C(=O)[C@@]2(C)[C@H]([C@H](OC(=O)c3ccccc3)[C@@]3(O)CC1=C(C)[C@@H](OC(=O)[C@H](O)[C@@H](NC(=O)c1ccccc1)c1ccccc1)C3)[C@]1(OC(C)=O)CO[C@@H]1C[C@@H]2O] |
| 4115 | Doxorubicin | Adriamycin | (8S,10S)-10-(4-amino-5-hydroxy-6-methyl-tetrahydro-2H-pyran-2-yloxy)-6,8,11-trihydroxy-8-(2-hydroxyacetyl)-1-methoxy-7,8,9,10-tetrahydrotetracene-5,12-dione | 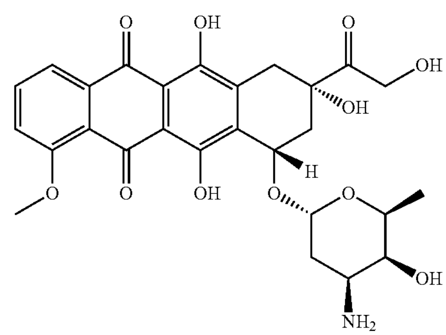 [SMILES: COc1cccc2c1C(=O)c1c(O)c3c(c(O)c1C2=O)C[C@@](O)(C(=O)CO)C[C@@H]3O[C@H]1C[C@H](N)[C@H](O)[C@H](C)O1] |
| 4116 | Nelfinavir | Viracept | (3S,4aS,8aS)-N-tert-butyl-2-[(2R,3R)-2-hydroxy-3-[(3-hydroxy-2-methylphenyl)formamido]-4-(phenylsulfanyl)butyl]-decahydroisoquinoline-3-carboxamide | 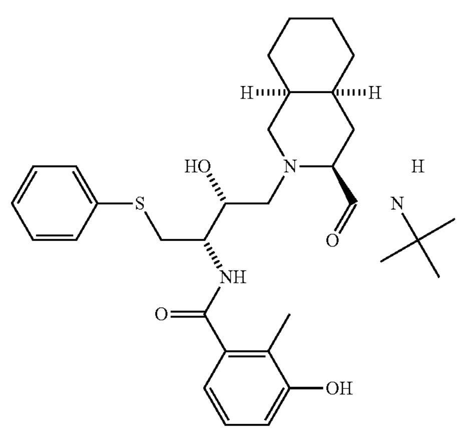 |

TABLE 2-continued

A Non-limiting List of Drugs or Biologically Active Molecules which can be derivatized according to the embodiment of the invention.

| No. | Drug or Biologically Active Molecule | Trade Name | IUPAC Name | Chemical Structure |
|---|---|---|---|---|
| 4117 | Rapamycin | Rapamune | (3S,6R,7E,9R,10R,12R,14S, 15E,17E,19E,21S,23S,26R, 27R,34aS)-9,10,12,13,14,21,22,23,24, 25,26,27,32,33,34,34a-hexadecahydro-9,27-dihydroxy-3-[(1R)-2-[(1S,3R,4R)-hexamethyl-23,27-epoxy-3H-pyrido[2,1-c][1,4]-oxaazacyclohentriacontine-1,5,11,28,29(4H,6H,31H)-pentonel-methylethyl]-10,21-dimethoxy-6,8,12,14,20,26-4-hydroxy-3-methoxycyclohexyl]- | 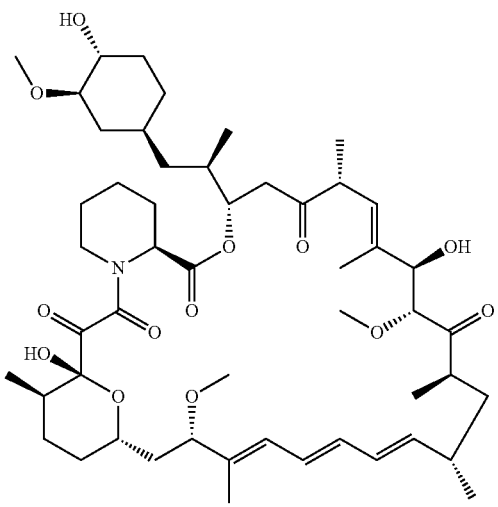 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC(=O)[C@H](C)/C=C(\C)[C@@H](O)[C@@H](OC)C(=O)[C@H](C)C[C@H](C)/C=C/C=C/C=C/1C] |
| 4118 | Piroxicam | Feldene | (8E)-8-[hydroxy-(pyridin-2-ylamino)methylidene]-methyl-10,10-dioxo-10λ6-thia-9-azabicyclo[4.4.0]deca-1,3,5-trien-7-one | 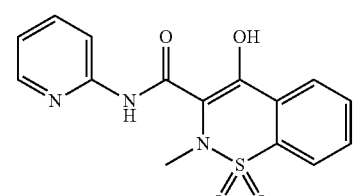 |
| 4119 | Amlexanox | Aphthasol/ Solfa | 2-amino-7-isopropyl-5-oxo-5H-chromeno[2,3-b]pyridine-3-carboxylic acid | 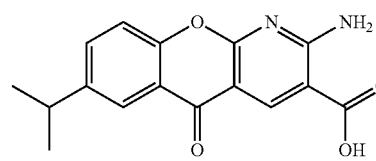 |
| 4120 | Rosoxacin | Eradacil | 1-Ethyl-4-oxo-7-pyridin-4-ylquinoline-3-carboxylic acid | 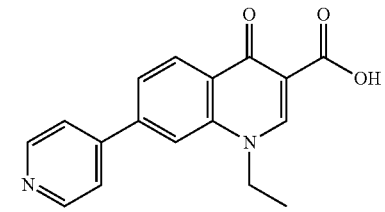 [SMILES: CCn1cc(C(=O)O)c(=O)c2ccc(-c3ccncc3)cc21] |
| 4121 | Etoricoxib | Arcoxia | 5-chloro-6'-methyl-3-[4-(methylsulfonyl)phenyl]-2,3'-bipyridine | 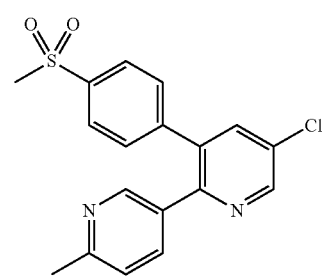 [SMILES: Cc1ccc(-c2ncc(Cl)cc2-c2ccc(S(C)(=O)=O)cc2)cn1] |

TABLE 2-continued

A Non-limiting List of Drugs or Biologically Active Molecules which can be derivatized according to the embodiment of the invention.

| No. | Drug or Biologically Active Molecule | Trade Name | IUPAC Name | Chemical Structure |
|---|---|---|---|---|
| 4122 | Sumatriptan | Imitrex | 1-[3-(2-dimethylaminoethyl)-1H-indol-5-yl]-N-methyl-methanesulfonamide | 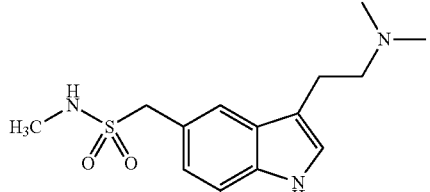 |
| 4123 | Vardenafil | Levitra | 4-[2-ethoxy-5-(4-ethylpiperazin-1-yl)sulfonyl-phenyl]-9-methyl-7-propyl-3,5,6,8-tetrazabicyclo[4.3.0]nona-3,7,9-trien-2-one | 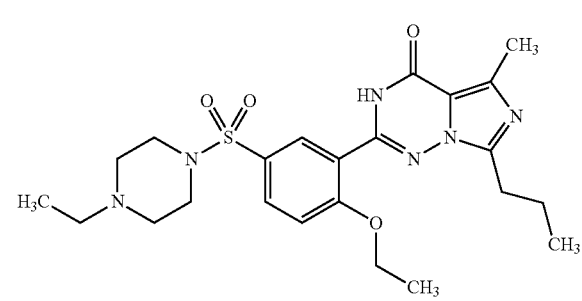 [SMILES: CCCc1nc(C)c2c(=O)[nH]c(-c3cc(S(=O)(=O)N4CCN(CC)CC4)ccc3OCC)nn12] |
| 4124 | Quinacrine | Mepacrine | (RS)-N'-(6-chloro-2-methoxy-acridin-9-yl)-N,N-diethyl-pentane-1,4-diamine | 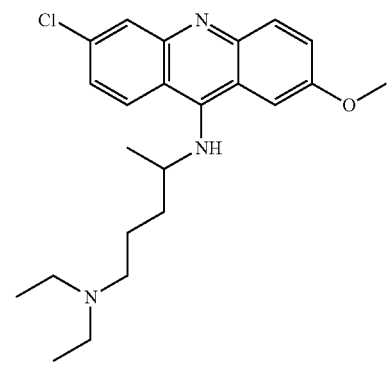 [SMILES: CCN(CC)CCCC(C)Nc1c2ccc(Cl)cc2nc2ccc(OC)cc12] |
| 4125 | Atorvastatin | Lipitor | (3R,5R)-7-[2-(4-fluorophenyl)-3-phenyl-4-(phenylcarbamoyl)-5-(propan-2-yl)-1H-pyrrol-1-yl]-3,5-dihydroxyheptanoic acid | 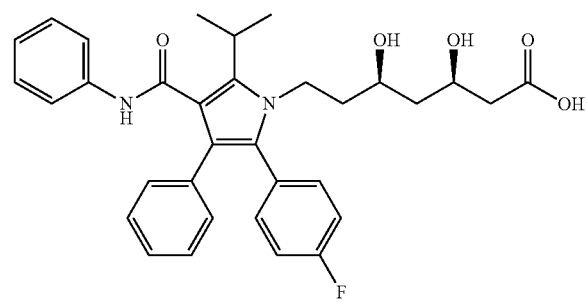 [SMILES: CC(C)c1c(C(=O)Nc2ccccc2)c(-c2ccccc2)c(-c2ccc(F)cc2)n1CC[C@@H](O)C[C@@H](O)CC(=O)O] |
| 4126 | Valciclovir Hydrochloride | Valtrex | (S)-2-[(2-amino-6-oxo-6,9-dihydro-3H-purin-9-yl)methoxy]ethyl-2-amino-3-methylbutanoate | 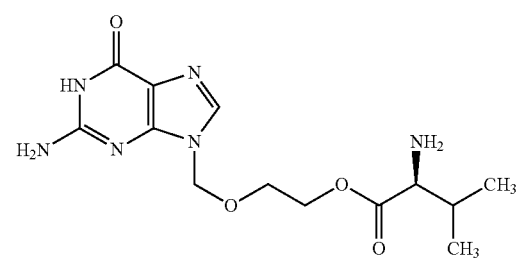 [SMILES: CC(C)[C@H](N)C(=O)OCCOCn1cnc2c(=O)[nH]c(N)nc21] |

TABLE 2-continued

A Non-limiting List of Drugs or Biologically Active Molecules which can be derivatized according to the embodiment of the invention.

| No. | Drug or Biologically Active Molecule | Trade Name | IUPAC Name | Chemical Structure |
|---|---|---|---|---|
| 4127 | Atovaquone | Mepron | trans-2-[4-(4-chlorophenyl)cyclohexyl]-3-hydroxy-1,4-naphthalenedione | 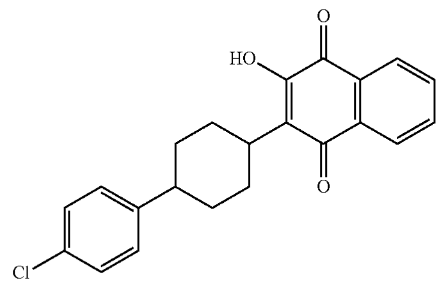 [SMILES: O=C1C(O)=C(C2CCC(c3ccc(Cl)cc3)CC2)C(=O)c2ccccc21] |
| 4128 | Dihydro-ergotamine | Migranal | (2R,4R,7R)-N-[(1S,2S,4R,7S)-7-benzyl-2-hydroxy-4-methyl-5,8-dioxo-3-oxa-6,9-diazatricyclo[7.3.0.0$^{2,6}$]dodecan-4-yl]-6-methyl-6,11-diazatetracyclo[7.6.1.0$^{2,7}$.0$^{12,16}$]hexadeca-1(16),9,12,14-tetraene-4-carboxamide | 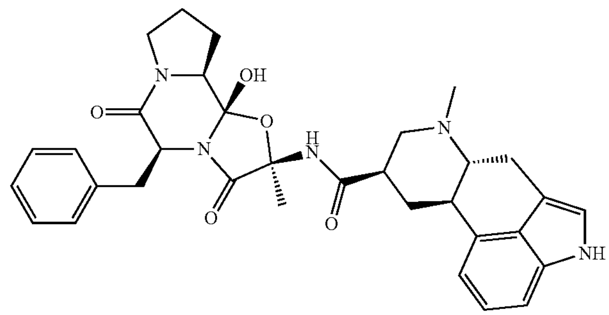 [SMILES: CN1C[C@H](C(=O)N[C@]2(C)O[C@@]3(O)[C@@H]4CCCN4C(=O)[C@H](Cc4ccccc4)N3C2=O)C[C@@H]2c3cccc4[nH]cc(c34)C[C@H]21] |
| 4129 | Donepezil | Aricept | (RS)-2-[(1-benzyl-4-piperidyl)methyl]-5,6-dimethoxy-2,3-dihydroinden-1-one | 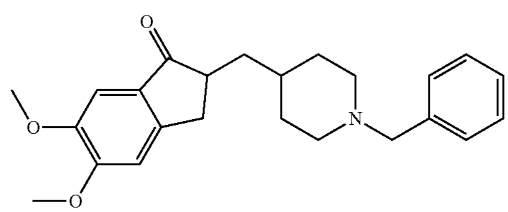 [SMILES: COc1cc2c(cc1OC)C(=O)C(CC1CCN(Cc3ccccc3)CC1)C2] |
| 4130 | Levofloxacin | Levaquin | (S)-7-fluoro-6-(4-methylpiperazin-1-yl)-10-oxo-4-thia-1-azatricyclo[7.3.1.0$^{5,13}$]trideca-5(13),6,8,11-tetraene-11-carboxylic acid | 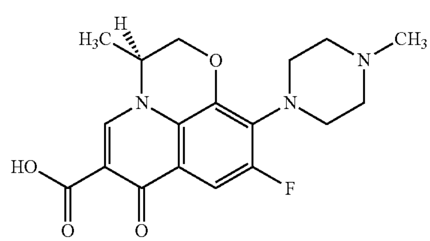 [SMILES: C[C@H]1COc2c(N3CCN(C)CC3)c(F)cc3c(=O)c(C(=O)O)cn1c23] |
| 4131 | Topotecan | Hycamtin | (S)-10-[(dimethylamino)methyl]-4-ethyl-4,9-dihydroxy-1H-pyrano[3',4':6,7]indolizino[1,2-b]quinoline-3,14(4H,12H)-dione monohydrochloride | 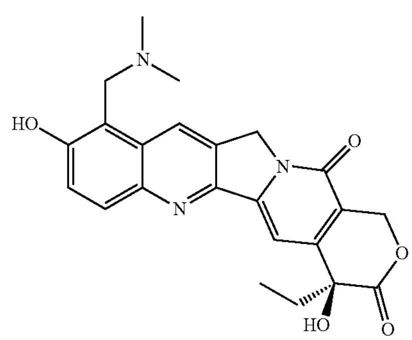 [SMILES: CC[C@@]1(O)C(=O)OCc2c1cc1n(c2=O)Cc2cc3c(CN(C)C)c(O)ccc3nc2-1] |

TABLE 2-continued

A Non-limiting List of Drugs or Biologically Active Molecules which can be derivatized according to the embodiment of the invention.

| No. | Drug or Biologically Active Molecule | Trade Name | IUPAC Name | Chemical Structure |
|---|---|---|---|---|
| 4132 | Estadiol | Climara | (17β)-estra-1,3,5(10)-triene-3,17-diol | 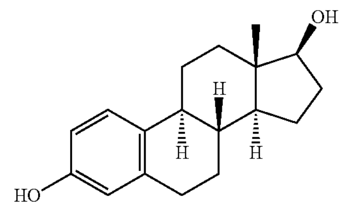 |
| 4133 | Quetiapine | Seroquel | 2-(2-(4-dibenzo[b,f][1,4]thiazepine-11-yl-1-piperazinyl)ethoxy)ethanol | 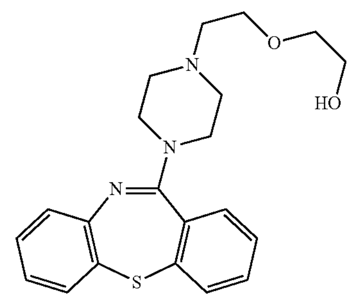 [SMILES: OCCOCCN1CCN(C2=Nc3ccccc3Sc3ccccc32)CC1] |
| 4134 | Olanzapine | Zyprexa | 2-methyl-4-(4-methyl-1-piperazinyl)-10H-thieno[2,3-b][1,5]benzodiazepine | 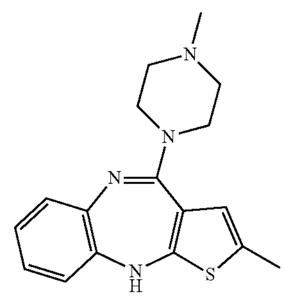 [SMILES: Cc1cc2c(s1)Nc1ccccc1N=C2N1CCN(C)CC1] |
| 4135 | Venlafaxine | Effexor | (RS)-1-[2-dimethylamino-1-(4-methoxyphenyl)-ethyl]cyclohexanol | 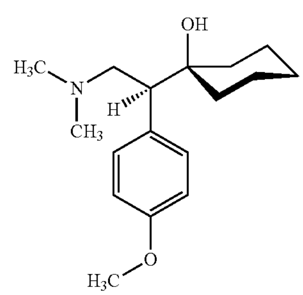 |
| 4136 | Azelastine | Asetlin | (RS)-4-[(4-chlorophenyl)methyl]-2-(1-methylazepan-4-yl)-phthalazin-1-one | | ns
TABLE 2-continued

A Non-limiting List of Drugs or Biologically Active Molecules which can be derivatized according to the embodiment of the invention.

| No. | Drug or Biologically Active Molecule | Trade Name | IUPAC Name | Chemical Structure |
|---|---|---|---|---|
| 4137 | Pioglitazone | Actos | (RS)-5-(4-[2-(5-ethylpyridin-2-yl)ethoxy]benzyl)thiazolidine-2,4-dione | 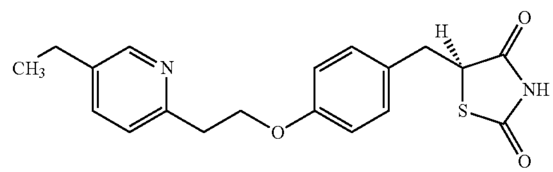 [SMILES: CCc1ccc(CCOc2ccc(C[C@@H]3SC(=O)NC3=O)cc2)nc1] |
| 4138 | Nevirapine | Viramune | 11-cyclopropyl-4-methyl-5,11-dihydro-6H-dipyrido[3,2-b:2',3'-e][1,4]diazepin-6-one | 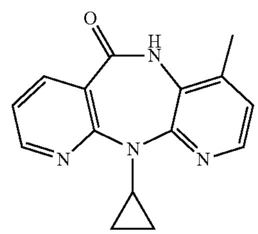 [SMILES: Cc1ccnc2c1NC(=O)c1cccnc1N2C1CC1] |
| 4139 | Rizatriptan | Maxalt | N,N-dimethyl-2-[5-(1H-1,2,4-triazol-1-ylmethyl)-1H-indol-3-yl]ethanamine | 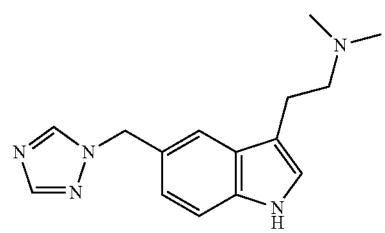 [SMILES: CN(C)CCc1c[nH]c2ccc(Cn3cncn3)cc12] |
| 4140 | Escitalopram | Lexapro/Cipralex | (S)-1-[3-(dimethylamino)propyl]-1-(4-fluorophenyl)-1,3-dihydroisobenzofuran-5-carbonitrile | 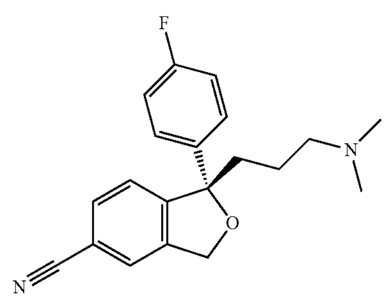 [SMILES: CN(C)CCC[C@@]1(c2ccc(F)cc2)OCc2cc(C#N)ccc21] |
| 4141 | Losartan | Cozaar | (2-butyl-4-chloro-1-{[2'-(1H-tetrazol-5-yl)biphenyl-4-yl]methyl}-1H-imidazol-5-yl)methanol | 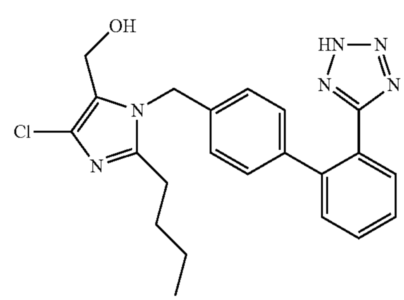 [SMILES: CCCCc1nc(Cl)c(CO)n1Cc1ccc(-c2ccccc2-c2nn[nH]n2)cc1] |

TABLE 2-continued

A Non-limiting List of Drugs or Biologically Active Molecules which can be derivatized according to the embodiment of the invention.

| No. | Drug or Biologically Active Molecule | Trade Name | IUPAC Name | Chemical Structure |
|---|---|---|---|---|
| 4142 | Saquinavir | Invirase | (2S)-N-[(2S,3R)-4-[(3S)-3-(tert-butylcarbamoyl)-decahydroisoquinolin-2-yl]-3-hydroxy-1-phenylbutan-2-yl]-2-(quinolin-2-ylformamido)butanediamide | 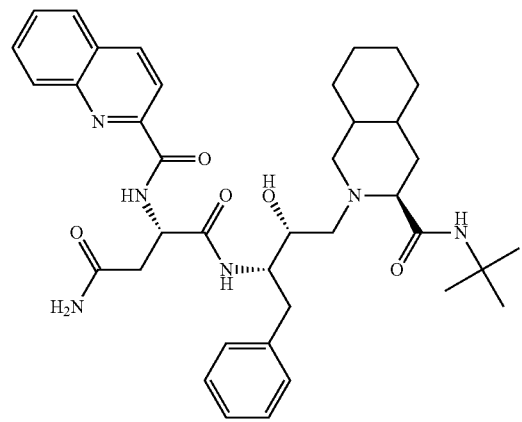 [SMILES: CC(C)(C)NC(=O)[C@@H]1CC2CCCCC2CN1C[C@@H](O)[C@H](Cc1ccccc1)NC(=O)[C@H](CC(N)=O)NC(=O)c1ccc2ccccc2n1] |
| 4143 | Fluticasone/salmeterol | Advair | S-(fluoromethyl) {6S,8S,9R,10S,11S,13S,14S,16R,17R)-6,9-difluoro-11,17-dihydroxy-10,13,16-trimethyl-3-oxo-6,7,8,11,12,14,15,16-octahydrocyclopenta[a]phenanthrene-17-carbothioate | 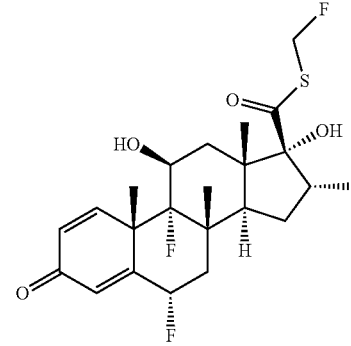 |
| 4144 | Rosuvastatin | Crestor | (3R,5S,6E)-7-[4-(4-fluorophenyl)-2-(N-methylmethanesulfonamido)-6-(propan-2-yl)pyrimidin-5-yl]-3,5-dihydroxyhept-6-enoic acid | 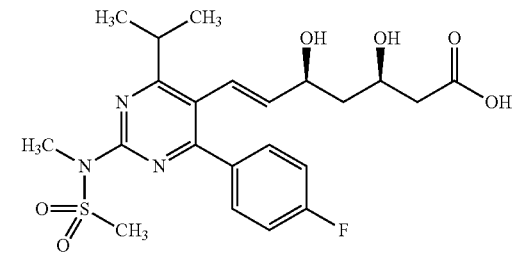 [SMILES: CC(C)c1nc(N(C)S(C)(=O)=O)nc(-c2ccc(F)cc2)c1/C=C/[C@@H](O)C[C@@H](O)CC(=O)O] |
| 4145 | Budesonide/Formoterol | Symbiocort | 16,17-(butylidenebis(oxy))-11,21-dihydroxy-, (11-β,16-α)-pregna-1,4-diene-3,20-dione | 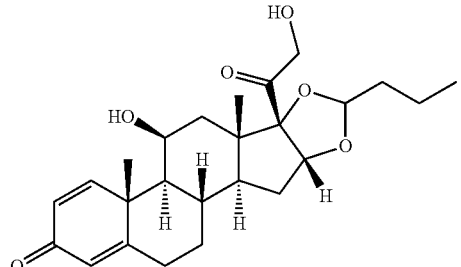 |

TABLE 2-continued

A Non-limiting List of Drugs or Biologically Active Molecules which can be derivatized according to the embodiment of the invention.

| No. | Drug or Biologically Active Molecule | Trade Name | IUPAC Name | Chemical Structure |
|---|---|---|---|---|
| 4146 | Montelukast | Singulair | (S,E)-2-(1-((1-(3-(2-(7-chloroquinolin-2-yl)vinyl)phenyl)-3-(2-(2-hydroxypropan-2-yl)phenyl)propylthio)methyl)cyclopropyl)acetic acid | 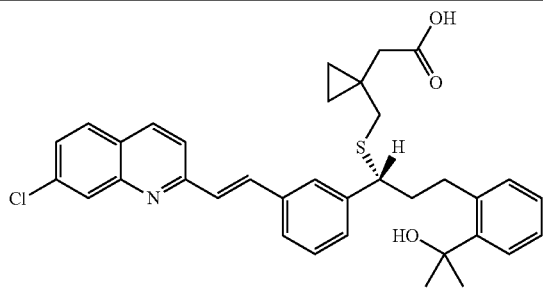 |
| 4147 | Acetaminophen | Paracetamol/ Tylenol | N-(4-hydroxyphenyl)acetamide | 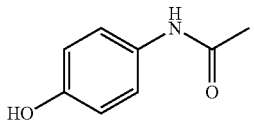 |
| 4149 | Dimebon | Dimebon | 2,8-dimethyl-5-(2-(6-methylpyridin-3-yl)ethyl)-2,3,4,5-tetrahydro-1H-pyrido[4,3-b]indole | |
| 4150 | SN-38 | SN-38 | (S)-4,11-diethyl-4,9-dihydroxy-1H-pyrano[3',4':6,7]indolizino[1,2-b]quinoline-3,14(4H,12H)-dione | |
| 4151 | Curcumin | | (1E,4Z,6E)-5-hydroxy-1,7-bis(4-hydroxy-3-methoxyphenyl)hepta-1,4,6-trien-3-one | |
| 4152 | Hydroxy Fasudil | | 5-((1,4-diazepan-1-yl)sulfonyl)isoquinolin-1-ol | 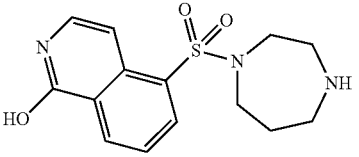 [SMILES: O=S(=O)(c1cccc2c(O)nccc12)N1CCCNCC1] |
| 4153 | Fasudil | | 5-((1,4-diazepan-1-yl)sulfonyl)isoquinoline | 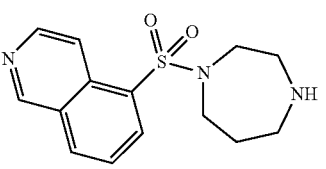 [SMILES: O=S(=O)(c1cccc2cnccc12)N1CCCNCC1] |
| 4154 | Aspirin | Aspirin | 2-acetoxybenzoic acid | 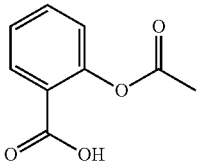 |
| 4155 | Nicorandil | Ikorel, Dancor, Nikoran, Aprior, Nitrorubin, Sigmart | 2-(nicotinamido)ethyl nitrate | 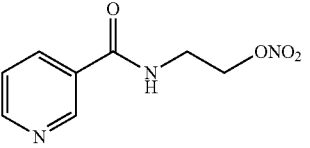 |

The reagents of the present invention may be used to modify drugs which belong to the class of compounds may be selected from, but are not limited to: Central Nervous System Drugs, such as CNS/Respiratory Stimulants, Analgesics, Narcotic Agonists, Narcotic agonist/antagonists, Nonsteroidal Anti-inflammatory/Analgesic Agents, Behavior-Modifying Agents, Tranquilizers/Sedatives, Anesthetic Agents, Inhalants, Narcotics, Reversal Agents, Anticonvulsants, Muscle Relaxants, Skeletal, Muscle Relaxants, Smooth, Euthanasia Agent, Cardiovascular Agents, Inotropic Agents, Antiarrhythmic Drugs, Anticholinergics, Vasodilating Agents, Agents Used in Treatment of Shock, Alpha-Adrenergic Blocking Agents, Beta-Adrenergic Blocking Agents, Respiratory Drugs, Bronchodilators, Sympathomimetics, Antihistamines, Antitussives, Renal and Urinary Tract, Agents for Urinary Incontinence/Retention, Urinary Alkalinizers, Urinary Acidifiers, Cholinergic Stimulants, Agents for Urolithiasis, Gastrointestinal Agents, Antiemetic Agents, Antacids, H2 Antagonists, Gastromucosal Protectants, Proton Pump Inhibitors, Appetite Stimulants, GI Antispasmodics-Anticholinergics, GI Stimulants, Laxatives, Saline, Bulk producing, Lubricant, Surfactant, Antidiarrheals, Hormones/Endocrine/Reproductive Agents, Sex Hormones, Anabolic steroids, Posterior Pituitary Hormones, Adrenal Cortical Steroids, Glucocorticoids, Antidiabetic Agents, Thyroid Drugs, Thyroid Hormones, Misc. Endocrine/Reproductive Drugs, Prostaglandins, Antiinfective Drugs, Antiparasitics, Anticoccidial Agents, Antibiotics, Anti-tuberculosis, Aminocyclitols, Cephalosporins, Macrolides, Penicillins, Tetracyclines, Lincosamides, Quinolones, Sulfonamides, Miscellaneous Antibacterials, Antifungal Agents, Antiviral Agents, Blood Modifying Agents, Clotting Agents, Anticoagulants, Erythropoietic Agents, Antineoplastics/Immunosuppresives, Alkylating Agents, Antidotes, Bone/Joint Agents, Dermatologic Agents (Systemic), Vitamins and Minerals/Nutrients, Systemic Acidifiers, Systemic Alkalinizers, anti-cancer agents, anti-viral agents, etc.

The compounds of the present invention after being modified include but are not limited to:

i. 1-(((3,3-dimethylbutanoyl)oxy)methyl)-3-((2-(nitrooxy)ethyl)carbamoyl)pyridin-1-ium iodide;
ii. 3-((2-(nitrooxy)ethyl)carbamoyl)-1-((pivaloyloxy)methyl)pyridin-1-ium iodide;
iii. 1-((isobutyryloxy)methyl)-3-((2-(nitrooxy)ethyl)carbamoyl)pyridin-1-ium iodide;
iv. 1-(((diisopropylcarbamoyl)oxy)methyl)-3-((2-(nitrooxy)ethyl)carbamoyl)pyridin-1-ium iodide;
v. 1-(((ethoxycarbonyl)oxy)methyl)-3-((2-(nitrooxy)ethyl)carbamoyl)pyridin-1-ium iodide;
vi. 3-((2-(nitrooxy)ethyl)carbamoyl)-1-(((piperidine-1-carbonyl)oxy)methyl)pyridin-1-ium iodide;
vii. 1-(((isopropoxycarbonyl)oxy)methyl)-3-((2-(nitrooxy)ethyl)carbamoyl)pyridin-1-ium iodide;
viii. 1-(((isopropylcarbamoyl)oxy)methyl)-3-((2-(nitrooxy)ethyl)carbamoyl)pyridin-1-ium iodide;
ix. 1-(((tert-butoxycarbonyl)oxy)methyl)-3-((2-(nitrooxy)ethyl)carbamoyl)pyridin-1-ium iodide;
x. 2-(((diisopropylcarbamoyl)oxy)methyl)-2,8-dimethyl-5-(2-(6-methylpyridin-3-yl)ethyl)-2,3,4,5-tetrahydro-1H-pyrido[4,3-b]indol-2-ium iodide;
xi. 2-(((diisopropylcarbamoyl)oxy)methyl)-5-(2-(1-(((diisopropylcarbamoyl)oxy)methyl)-6-methylpyridin-1-ium-3-yl)ethyl)-2,8-dimethyl-2,3,4,5-tetrahydro-1H-pyrido[4,3-b]indol-2-ium diiodide;
xii. (S)-((4,11-diethyl-4-hydroxy-3,14-dioxo-3,4,12,14-tetrahydro-1H-pyrano[3',4':6,7]indolizino[1,2-b]quinolin-9-yl)oxy)methyl nicotinate;
xiii. (S)-3-((((4,11-diethyl-4-hydroxy-3,14-dioxo-3,4,12,14-tetrahydro-1H-pyrano[3',4':6,7]indolizino[1,2-b]quinolin-9-yl)oxy)methoxy)carbonyl)-1-(((isopropylcarbamoyl)oxy)methyl)pyridin-1-ium iodide;
xiv. 4-((1E,4Z,6E)-5-hydroxy-7-(4-hydroxy-3-methoxyphenyl)-3-oxohepta-1,4,6-trien-1-yl)-2-methoxyphenyl nicotinate;
xv. ((1E,3Z,6E)-3-hydroxy-5-oxohepta-1,3,6-triene-1,7-diyl)bis(2-methoxy-4,1-phenylene)dinicotinate;
xvi. 3,3'-((((((1E,3Z,6E)-3-hydroxy-5-oxohepta-1,3,6-triene-1,7-diyl)bis(2-methoxy-4,1-phenylene))bis(oxy))bis(carbonyl))bis(1-(((isopropylcarbamoyl)oxy)methyl)pyridin-1-ium)diiodide;
xvii. (2aR,4S,4aS,6R,9S,11S,12S,12aR,12bS)-9-(((2R,3S)-3-benzamido-2-(nicotinoyloxy)-3-phenylpropanoyl)oxy)-12-(benzoyloxy)-4,11-dihydroxy-4a,8,13,13-tetramethyl-5-oxo-2a,3,4,4a,5,6,9,1,11,12,12a,12b-dodecahydro-1H-7,11-methanocyclodeca[3,4]benzo[1,2-b]oxete-6,12b-diyl diacetate;
xviii. 3-((((1S,2R)-1-benzamido-3-(((2aR,4S,4aS,6R,9S,11S,12S,12aR,12bS)-6,12b-diacetoxy-12-(benzoyloxy)-4,11-dihydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxet-9-yl)oxy)-3-oxo-1-phenylpropan-2-yl)oxy)carbonyl)-1-(((isopropylcarbamoyl)oxy)methyl)pyridin-1-ium iodide;
xix. (2aR,4S,4aS,6R,9S,11S,12S,12aR,12bS)-9-(((2R,3S)-3-benzamido-2-(((chloromethoxy)carbonyl)oxy)-3-phenylpropanoyl)oxy)-12-(benzoyloxy)-4-(((chloromethoxy)carbonyl)oxy)-11-hydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxete-6,12b-diyl diacetate;
xx. (2a R,4S,4aS,6R,9S,11S,12S,12aR,12bS)-9-(((2R,3S)-3-benzamido-2-(((iodomethoxy)carbonyl)oxy)-3-phenylpropanoyl)oxy)-12-(benzoyloxy)-11-hydroxy-4-(((iodomethoxy)carbonyl)oxy)-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxete-6,12b-diyl diacetate;
xxi. mono(1-((((((1S,2R)-1-benzamido-3-(((2aR,4S,4aS,6R,9S,11S,12S,12aR,12bS)-6,12b-diacetoxy-12-(benzoyloxy)-4-((((3-(dimethylcarbamoyl)pyridin-1-ium-1-yl) methoxy)carbonyl)oxy)-11-hydroxy-4a,8,13,13-tetrammethyl-5-oxo-2a,3,4,4a,5,6,9,10,11,12,12a,12b-dodecahydro-1H-7,11-methanocyclodeca[3,4]benzo[1,2-b]oxet-9-yl)oxy)-3-oxo-1-phenylpropan-2-yl)oxy)carbonyl)oxy)methyl)-3-(dimethylcarbamoyl)pyridin-1-ium)diiodide;
xxii. ((2-acetoxybenzoyl)oxy)methyl nicotinate;
xxiii. 3-((((2-acetoxybenzoyl)oxy)methoxy)carbonyl)-1-(((dimethylcarbamoyl)oxy)methyl)pyridin-1-ium iodide.

D. Salts and Isomers and Counter Ions

The present invention includes within its scope the salts and isomers. Compounds of the present invention after being modified by the substituted methyl formyl reagent may in some cases form salts which are also within the scope of this invention. The term "salt(s)", as employed herein, denotes acidic and/or basic salts formed with inorganic and/or organic acids and bases. Zwitterions (internal or inner salts) are included within the term "salt(s)" as used herein (and may be formed, for example, where the R substituents comprise an acid moiety such as a carboxyl group). Also included herein are quaternary ammonium salts such as alkyl ammonium salts.

Pharmaceutically acceptable (i.e., non-toxic, physiologically acceptable) salts are preferred, although other salts are useful, for example, in isolation or purification steps which may be employed during preparation. Salts of the compounds of may be formed, for example, by reacting a compound with an amount of acid or base, such as an equivalent amount, in a medium such as one in which the salt precipitates or in an aqueous medium followed by lypholization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxy ethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates, undecanoates, and the like.

Exemplary basic salts (formed, for example, wherein the substituent comprise an acidic moiety such as a carboxyl group) include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines, N-methyl-D-glucamines, N-methyl-D-glucamides, t-butyl amines, and salts with amino acids such as arginine, lysine and the like. The basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Solvates of the compounds of the invention are also contemplated herein. Solvates of the compounds of formula I are preferably hydrates or any other pharmaceutically acceptable solvate.

All stereoisomers of the present compounds, such as those which may exist due to asymmetric carbons on the R substituents of the compound, including enantiomeric and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration.

The present invention also envisages within its scope the effect of selection of suitable counter ions. The counter ion of the compounds of the present invention may be chosen by selecting the dissociation constant for the drug capable of ionization within the said pH range. By estimating the ionized and un-ionized drug concentration of any compound (using well established equations such a Henderson-Hasselbach equation), the solubility and consequently the absorption of the drug may be modified.

The present invention includes in its scope, the modification of deuterated compounds. Deuterated compounds are those wherein the compounds have selective incorporation of deuterium in place of hydrogen. Deuterated compounds may be further modified by the substituted methyl formyl reagents of the present invention as per procedures as disclosed herein.

E. Composition Containing the Modified Entities of the Invention

The invention thus also provides the use of the modified entity as defined herein for use in human or veterinary medicine. The compound for use as a pharmaceutical may be presented as a pharmaceutical formulation.

The invention therefore provides in a further aspect a pharmaceutical formulation comprising the modified compounds of the invention with a pharmaceutically acceptable carrier thereof and optionally other therapeutic and/or prophylactic ingredients. The carriers must be "acceptable" in the sense of being compatible with the other ingredients of the formula and not deleterious to the recipient thereof. Suitably the pharmaceutical formulation will be in an appropriate unit dosage form.

The pharmaceutical formulations may be any formulation and include those suitable for oral, intranasal, intraocular or parenteral (including intramuscular and intravenous) administration. The formulations may, where appropriate, be conveniently presented in discrete dosage units and may be prepared by any of the methods well known in the art of pharmacy. All methods include the step of bringing into association the active compound with liquid carriers or finely divided solid carriers or both, and then, if necessary, shaping the product into the desired formulation.

For these purposes the compounds of the present invention may be administered orally, topically, intranasally, intraocularly, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasteral injection or infusion techniques. In addition to the treatment of warm-blooded animals such as mice, rats; horses, dogs, cats, etc., the compounds of the invention are effective in the treatment of humans.

EXAMPLES

Numerous modifications and variations of the present invention are possible in light of the above teachings. It is therefore to be understood that within the scope of the appended claims, the invention may be practiced other than as specifically exemplified herein.

EXPERIMENTAL

Scheme 19: Example of a typical Synthetic Procedure for the synthesis of Type III reagents

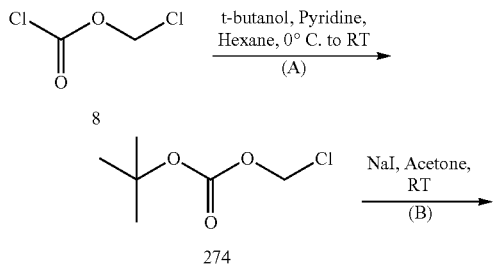

274

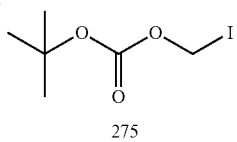

275

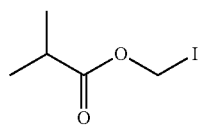

278

Procedures:

Step (A):

To a solution of chloromethylchloroformate [8] (7.75 mmol, 1 eq) in hexane was added a solution of pyridine (19.3 mmol, 2.5 eq) in hexane drop wise under ice cooling. After the complete addition, a white solid precipitate formed. t-Butanol (11.62 mmol, 1.5 eq) was added in hexane at the same temperature. After the addition of t-butanol the reaction mixture became a clear solution. The resulting mixture was stirred for 2 hours under ice cooling and then 1 hour at room temperature (RT). Reaction completion was monitored by TLC, which showed one non-polar spot compared to starting material. The reaction was worked up by diluting the reaction mixture with hexane and washing with saturated $NaHCO_3$ solution, followed by 2N HCl solution, followed by a second washing with saturated $NaHCO_3$ solution, and lastly by water. The organic layer was separated, dried over $Na_2SO_4$ and evaporated under reduced pressure to give the reagent tert-butyl (chloromethyl)carbonate [274] as a colorless sticky liquid (0.900 g, 70%).

$^1$H NMR: [$CDCl_3$, 300 MHz]: –δ 5.774 (s, 2H), 1.518 (s, 9H).

Step (B):

To a solution of tert-butyl(chloromethyl)carbonate [274] (9.87 mmol, 1 eq) dissolved in acetone was added sodium iodide (29.61 mmol, 3 eq). The resulting reaction mixture was stirred overnight at RT. The TLC showed consumption of starting material and one new non polar spot compared to starting material. The reaction was worked up by filtering out any precipitated solid and evaporating the acetone layer. The solid obtained was dissolved in DCM. The solution was filtered once again to eliminate any solid not dissolved in the DCM. The DCM layer obtained was evaporated. The crude product was passed through column chromatography by using 100-200 mesh size silica and 1% MeOH-DCM as a solvent system to yield the product tert-butyl(iodomethyl)carbonate [275] as colorless liquid (136 mg, 30%).

$^1$H NMR [$CDCl_3$, 300 MHz]: δ 5.90 (s, 2H), 1.518 (s, 9H).

Scheme 20: Example of a typical Synthetic Procedure for the synthesis of Type I reagents

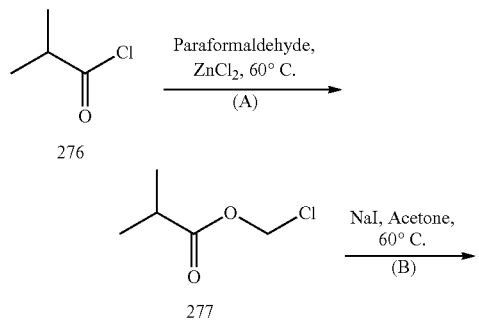

Step (A):

An appropriate Lewis acid such as zinc chloride (catalytic amount-0.50 g) was fused in a dried 2-neck round bottomed flask under inert atmosphere. Iso-butyryl chloride [276] (46.72 mmol, 1 eq) and paraformaldehyde (47.0 mmol, 10 eq) are added to the prepared Lewis Acid at RT. The reaction mixture was heated to 60° C. overnight. The reaction was monitored by TLC. The reaction was stopped by addition of DCM and washed with saturated $NaHCO_3$ then brine. The organic layer was separated, dried over $Na_2SO_4$ and evaporated under reduced pressure to yield the product, chloromethyl isobutyrate [277], as colorless oil (2.0 g, 31%).

$^1$H NMR [$CDCl_3$, 300 MHz]: δ 5.71-5.76 (d, 2H), 2.54-2.64 (m, 1H), 1.17-1.21 (d, 6H)

Step (B):

Sodium iodide (43.9 mmol, 3 eq) was added to a solution of chloromethyl isobutyrate [277] (14.6 mmol, 1 eq) in acetone. The resulting reaction mixture was stirred at RT overnight. Reaction completion was monitored by TLC. The reaction was worked up by filtering out precipitated solid and evaporation of excess of acetone under reduced pressure. A solid was obtained and washed with DCM while filtering under suction using a Buchner funnel. The DCM layer obtained was evaporated to provide crude product which was further purified using silica gel column chromatography (100-200 mesh) and DCM as an eluent. The product, iodomethyl isobutyrate [278], (1.6 g, 50% yield) was obtained as a brownish liquid.

$^1$H NMR [$CDCl_3$, 300 MHz]: δ 6.21 (s, 2H), 2.54-2.64 (m, 1H), 1.17-1.21 (d, 6H).

Scheme 21: Synthesis of ((methylsulfonyl)oxy)methyl 3-methylbutanoate:

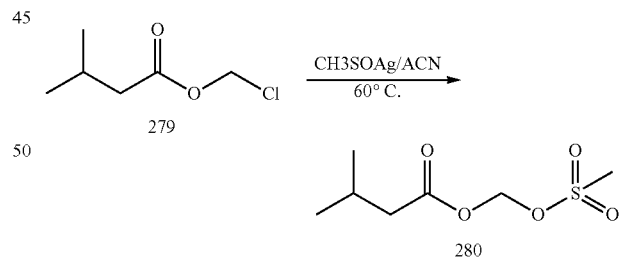

Procedure:

Silver salt of methane sulfonic acid [0.34 g, 1.6 mmol, 0.5 eq] was taken in acetonitrile (8 ml) and chloromethyl 3-methylbutanoate [279] (0.5 g, 3.3 mmol, 1.0 eq) was added to it. The resulting solution was heated to 60° C. for 5 h. Reaction progress was monitored by TLC. After completion, the reaction was filtered and solvent was evaporated under vacuum to yield colorless oil. The crude compound was purified by silica gel column chromatography (10% EtOAc: Cyclohexane, 100-200 mesh) which afforded [280]((methylsulfonyl)oxy) methyl 3-methylbutanoate [0.25 g, 40%] as a colorless oil.

Scheme 22: Type I reagent (chloro methyl nicotinate)

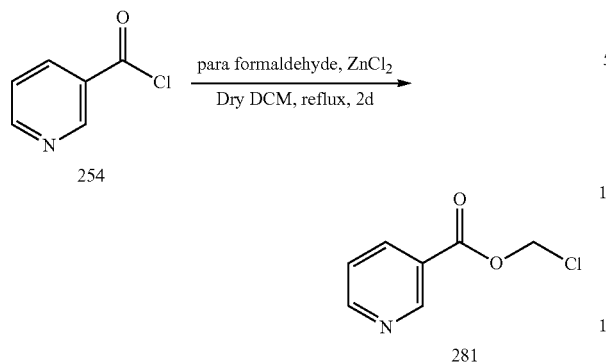

254

281

To a three necked oven dried R.B.F equipped with dry condenser, take-off and stopper, was added zinc chloride (0.3 g, 10%) and fused using hot gun under dry conditions. After cooling to RT dry DCM (60 ml) was added, followed by addition of paraformaldehyde (5.2 g, 170 mmol, 10.0 eq) and compound [254] (3.0 g, 17 mmol, 1.0 eq). The reaction was refluxed for two days under dry conditions. After cooling the reaction was treated with saturated solution of NaHCO$_3$ and extracted with DCM. Combined organic layer were dried over Na$_2$SO$_4$ and evaporated under vacuum to get [281] as colorless oil (0.6 g, 16.6%). $^1$HNMR (300 MHz; CDCl3) δ: 9.28-9.27 (s, 1H); 8.89-8.83 (dd, 1H); 8.34-8.33 (d, 1H); 7.47-7.42 (dd, 1H); 5.97 (s, 2H).

M+1=172

Scheme 23: Modifynative Procedure to Synthesis of Type I reagent (chloro methyl nicotinate):

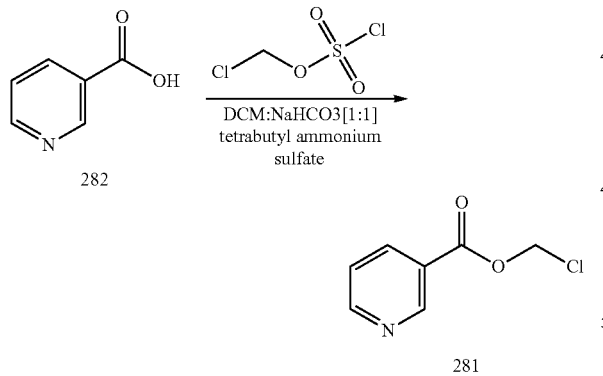

282

281

To a vigorously stirred, solution of nicotinic acid [282] (1.0 g, 10.0 mmol, 1.0 eq) at room temperature, sodium bicarbonate (3.2 g, 40.0 mmol, 4.0 eq), and tetrabutylammonium bisulfate (0.175 g, 0.1 mmol, 0.1 eq) in water (10 ml) was added dichloromethane (10 ml) followed by the dropwise addition of a solution of chloromethyl chlorosulfate (0.1 g, 12.5 mmol, 1.1 eq) in dichloromethane (5 ml). After stirring the reaction at room temperature for 1 h, the dichloromethane layer was separated, washed with 5% aqueous Na2CO$_3$ solution (1×25 ml), organic layer separated and dried over Na$_2$SO$_4$, followed filtering and concentrating under vacuum to yield chloro methyl nicotinate [281] as a colorless oil (0.70 g, 50%).

Scheme 24: Synthesis of reagent ((methylsulfonyl)oxy)methyl nicotinate:

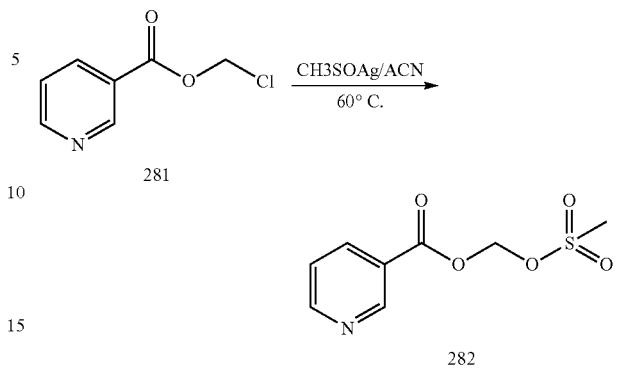

281

282

Procedure:

Silver salt of methane sulfonic acid [0.096 g, 0.47 mmol, 0.8 eq] was taken in acetonitrile (8 ml) and chloromethyl nicotinate [281] (0.1 g, 0.59 mmol, 1.0 eq) was added to it. The resulting solution was heated to 60° C. for 5 h. Reaction progress was monitored by TLC. After completion the reaction was filtered and solvent evaporated under vacuum to yield colorless oil. The crude compound was purified by silica gel column chromatography (35% EtOAc: Cyclohexane, 100-200 mesh) to afforded [282]((methylsulfonyl)oxy)methyl nicotinate [0.035 g, 25%] as a colorless oil.

m/z: 232

Scheme 25: Example of a typical Synthetic Procedure for the synthesis of Type II reagents

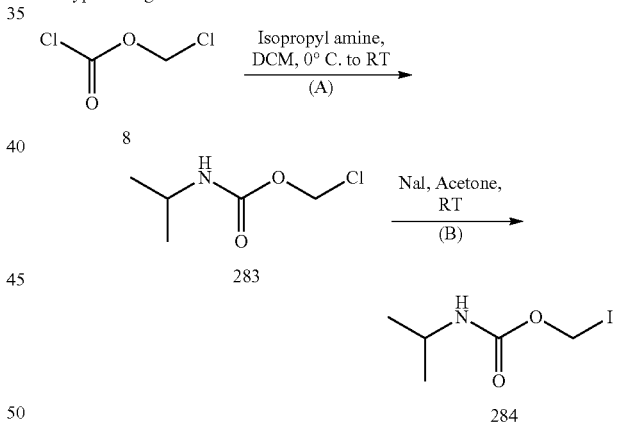

8

283

284

Step (A):

To the solution of chloromethylchloroformate [8] (1.00 g, 7.75 mmol, 1.0 eq) in DCM (y ml) was added a solution of isopropyl amine (1.14 g, 19.30 mmol, 2.5 eq) in DCM drop wise at 0° C. White solid precipitated out in the reaction mixture on addition. The resulting mixture was stirred for 2 hours at 0° C. and then at RT for 1 hour. Reaction was monitored by TLC. The reaction was worked up by diluting the reaction mixture with DCM, washing with saturated NaHCO$_3$ solution, followed by a wash with 2N HCl solution, again washing with saturated NaHCO$_3$ solution, and lastly with water. The organic layer was separated, dried over Na$_2$SO$_4$ and evaporated under reduced pressure to give chloromethyl isopropylcarbamate [283] as colorless oil (0.50 g, 44%).

¹H NMR [CDCl₃, 300 MHz]: δ 5.73 (s, 2H), 4.73 (s, —NH), 3.78-3.91 (m, 1H), 1.17-1.19 (d, 6H)

Step (B):

Sodium iodide (0.89 g, 5.94 mmol, 3.0 eq) was added to a solution of chloromethyl isopropylcarbamate [283] (0.30 g, 1.98 mmol, 1.0 eq) in acetone. The resulting reaction mixture was stirred at RT overnight. Reaction was monitored by TLC. The reaction was worked up by filtering out precipitated solid and evaporating the acetone layer under vacuum. The solid obtained was dissolved in DCM and filtered to get rid of residual solid. The DCM layer thus obtained was evaporated under reduced pressure to get a crude product, which was purified using silica gel column chromatography (2% MeOH: DCM, 100-200 mesh yield pure iodomethyl isopropylcarbamate [284] as colorless sticky material (0.12 g, 37%). ¹H NMR [CDCl₃, 300 MHz]: δ 5.96 (s, 2H), 4.65 (s, —NH), 3.80-3.91 (m, 1H), 1.17-1.19 (d, 6H).

Scheme 26: Synthesis of bromomethyl morpholine-4-carboxylate

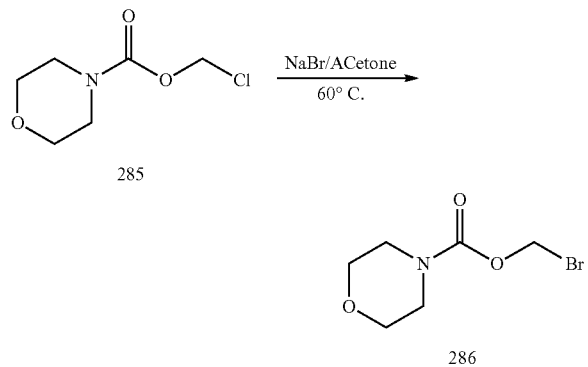

Procedure:

Chloromethyl morpholine-4-carboxylate [285] (0.3 g, 1.67 mmol, 1.0 eq) and sodium bromide (0.86 g, 8.3 mmol, 5.0 eq) was taken in acetone (10 ml). The reaction was refluxed at 60° C. for 24 h. Reaction progress was monitored by TLC/¹H NMR. The reaction was filtered off and filtrate was evaporated to dryness under reduced pressure to yield light brown gel, bromomethyl morpholine-4-carboxylate [286] (0.30 g, 80%)

¹H NMR (CDCl3): δ ppm 5.92 (s, 2H), 3.72 (t, 4H), 3.54 δ(t, 4H)s

Scheme 27:

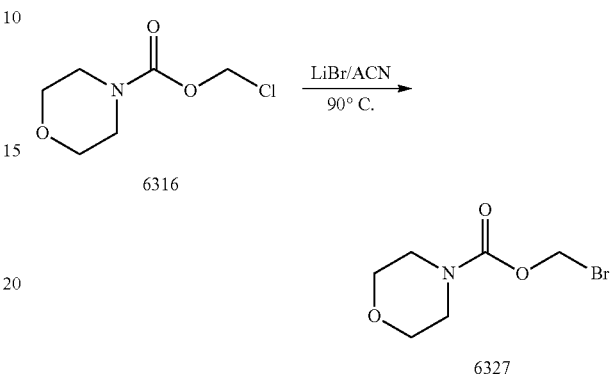

Procedure:

Chloromethyl morpholine-4-carboxylate [6316] (0.3 g, 1.67 mmol, 1.0 eq) and lithium bromide (0.72 g, 8.3 mmol, 5.0 eq) was taken in acetonitrile (10 ml). The reaction was refluxed at 90° C. for 30 h. Reaction progress was monitored by TLC/¹H NMR. The reaction was filtered off and filtrate was evaporated to dryness under reduced pressure to yield light brown gel, bromomethyl morpholine-4-carboxylate [6327](0.30 g, 80%)

¹H NMR (CDCl3): δ ppm 5.92 (s, 2H), 3.72 (t, 4H), 3.54 (t, 4H)

Other methyl formyl reagents were synthesized using the synthetic procedures disclosed above and herein with various substituted or unsubstituted alcohols, phenols, amines and acids to get structures in Tables 3, 4 and 5 which were characterized using spectroscopic techniques such as MS and/or ¹H NMR.

TABLE 3

Examples of Type I Reagents

| No. | STRUCTURE | NMR, ¹HNMR (300 MHz; CDCl3) δ | IUPAC Name |
| --- | --- | --- | --- |
| 277 | 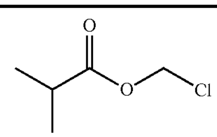 | 5.75(s, 2H), 2.50-2.70 (m, 1H), 1.15-1.25 (m, 6H). | chloromethyl isobutyrate |
| 5202 | 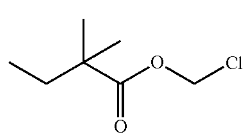 | 5.70 (2H, s); 1.80-1.90 (2H, q); 1.50 (6H, s); 1.6-1.82 (6H, m); 0.90-1.00 (3H, m). | chloromethyl 2,2-dimethylbutanoate |
| 5203 | 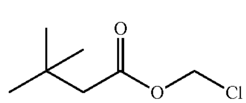 | 5.37 (s, 2H), 2.21(s, 2H), 1.05(s, 9H). | chloromethyl 3,3-dimethylbutanoate |
| 279 | 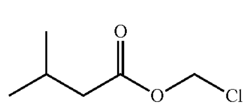 | 5.65 (s, 2H), 2.21-2.30 (m, 2H), 2.10-2.20 (m, 1H), 0.90-1.00 (m, 6H). | chloromethyl 3-methylbutanoate |

TABLE 3-continued

Examples of Type I Reagents

| No. | STRUCTURE | NMR, ¹HNMR (300 MHz; CDCl3) δ | IUPAC Name |
|---|---|---|---|
| 5205 | methoxyacetate chloromethyl ester structure | 5.50 (s, 2H), 4.15(s, 2H), 3.42(s, 3H). | chloromethyl 2-methoxyacetate |
| 5206 | | 1.16-1.21 (m, 6H), 2.54-2.64 (m, 6H), 6.21-6.25(s, 2H) | iodomethyl isobutyrate |
| 5207 | phenylacetate chloromethyl ester structure | 7.20-7.40 (m, 5H), 5.30 (s, 2H), 3.85 (s, 2H). | chloromethyl 2-phenylacetate |
| 281 | nicotinate chloromethyl ester structure | 8.89-8.83 (1H, dd); 8.34-8.33 (1H, d); 7.47-7.42 (1H, dd); 5.97 (2H, s) | chloromethyl nicotinate |
| 5209 | | 5.92(s, 2H), 1.28(s, 9H). | idomethyl pivalate |
| 5210 | | 1.9(d, 3H); 1.15-1.25(d, 6H); 6.1(q, 1H); 2.6(m, 1H) | 1-chloroethyl isobutyrate |
| 5211 | | 1.25(m, 6H); 5.94(t, 1H); 2.6(m, 1H); 1.85 (m, 2H); 0.9(t, 3H) | 1-chloropropyl isobutyrate |
| 5212 | | 5.74(s, 2H); 2.1(s, 3H) | chloromethyl acetate |
| 280 | | 5.81 (2H, s); 3.1 (3H, s); 2.3 (2H, d); 2.10 (2H, m); 0.99 (6H, d) | ((methylsulfonyl)oxy)methyl 3-methylbutanoate |
| 5214 | | 7.8 (2H, d); 7.35 (2H, d); 5.74 (2H, s); 2.45 (3H, s); 1.96 (2H, d): 1.85 (1H, m): 0.85 (6H, d) | (tosyloxy)methyl 3-methylbutanoate |
| 282 | | 9.28-9.27 (1H, d); 8.89-8.83 (1H, dd); 8.34-8.33 (1H, d); 7.47-7.42 (1H, dd); 6.08 (2H, s): 3.14 (3H, s) | ((methylsulfonyl)oxy)methyl nicotinate |

TABLE 4

Examples of Type II Reagents

| No. | STRUCTURE | NMR, ¹HNMR (300 MHz; CDCl3) δ | IUPAC Name |
|---|---|---|---|
| 6301 | benzylcarbamate chloromethyl ester structure | 7.27-7.38 (m, 5H), 5.78-5.81 (d, 2H), 5.192 (s, 1H), 4.39-4.43 (m, 2H), | chloromethyl benzylcarbamate |
| 6302 | isopropylcarbamate chloromethyl ester structure | 1.17-1.19 (d, 6 H), 3.78-3.91 (m, 1 H), 4.73 (s, —NH), 5.73 (s, 2 H) | chloromethyl isopropylcarbamate |
| 6303 | diisopropylcarbamate chloromethyl ester structure | 1.09-1.25 (m, 12H), 3.20-3.40 (m, 2H), 5.75-5.85 (d, 2H) | chloromethyl diisopropylcarbamate |
| 6304 | diisopropylcarbamate iodomethyl ester structure | 1.09-1.25 (m, 12H), 3.20-3.40 (m, 2H), 6.01 (d, 2H) | iodomethyl diisopropylcarbamate |

TABLE 4-continued

Examples of Type II Reagents

| No. | STRUCTURE | NMR, ¹HNMR (300 MHz; CDCl3) δ | IUPAC Name |
|---|---|---|---|
| 6305 | 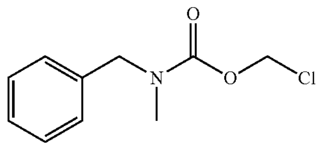 | 7.20-7.40 (m, 5H), 6.83(s, 2H), 4.42-4.55 (m, 2H), 2.82-2.95(m, 2H) | chloromethyl benzyl(methyl)carbamate |
| 6306 | 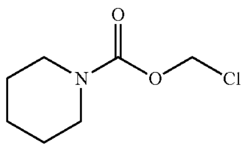 [SMILES: O=C(OCCl)N1CCCCC1] | 1.10-2.05 (m, 3H), 1.30-1.45 (m, 2H), 1.55-1.65 (m, 1H), 1.65-1.80 (m, 2H), 1.90-2.00 (m, 2H), 3.45-3.60 (m, 1H), 4.75-4.95 (s, 1H), 5.75 (s, 2H) | chloromethyl piperidine-1-carboxylate |
| 6307 | 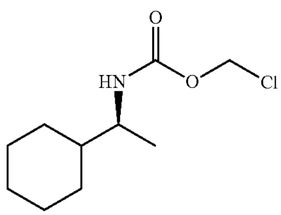 | : 5.71-5.80 (2H, s); 5.85-5.95 (1H, bs); 3.58-3.70 (1H, q); 1.6-1.82 (6H, m); 0.8-1.45 (7H, m). | (S)-chloromethyl (1-cyclohexylethyl)carbamate |
| 6308 | 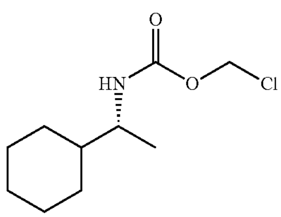 | 5.71-5.80 (2H, s); 5.85-5.95 (1H, bs); 3.58-3.60 (1H, q); 1.6-1.8 (4H, m); 0.8-1.45 (7H, m). | (R)-chloromethyl (1-cyclohexylethyl)carbamate |
| 6309 | 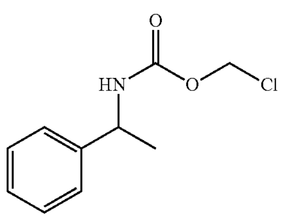 | 7.21-7.41 (5H, m); 5.71-5.92 (1H, dd); 5.31-5.40 (1H, bs); 4.82-4.95 (1H, t); 1.42-1.51 (3H, d). | chloromethyl (1-phenylethyl)carbamate |
| 6310 | 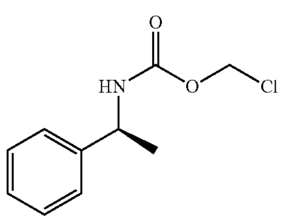 | 7.21-7.41 (5H, m); 5.71-5.92 (1H, dd); 5.1-5.25 (1H, bs); 4.91-5.00 (1H, t); 1.55-1.63 (3H, d). | (S)-chloromethyl (1-phenylethyl)carbamate |
| 6311 | 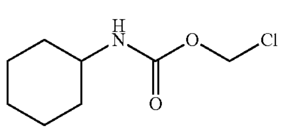 [SMILES: O=C(NC1CCCCC1)OCCl] | 1.10-2.05 (m, 3H), 1.30-1.45 (m, 2H), 1.55-1.65 (m, 1H), 1.65-1.80 (m, 2H), 1.90-2.00 (m, 2H), 3.45-3.60 (m, 1H), 4.75-4.95 (s, 1H), 5.75 (s, 2H) | chloromethyl cyclohexylcarbamate |
| 6312 | 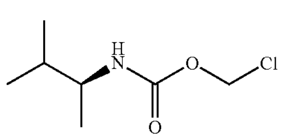 | 0.80-1.00 (m, 6H), 1.10-1.20 (m, 3H), 1.65-1.80 (m, 1H), 3.55-3.65 (m, 1H), 4.70-4.90 (s, 1H), 5.75 (s, 2H) | (S)-chloromethyl (3-methylbutan-2-yl)carbamate |
| 6313 | 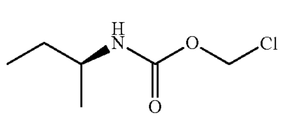 | 0.80-1.00 (m, 3H), 1.10-1.20 (m, 3H), 1.40-1.55 (m, 2H), 3.6-3.75 (m, 1H), 4.70-4.85 (m, 1H), 5.75 (s, 2H) | (S)-chloromethyl sec-butylcarbamate |

TABLE 4-continued

Examples of Type II Reagents

| No. | STRUCTURE | NMR, ¹HNMR (300 MHz; CDCl3) δ | IUPAC Name |
| --- | --- | --- | --- |
| 6314 | 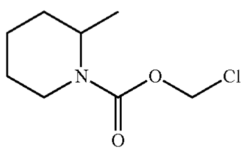 | 1.15-1.23 (m, 3H), 1.35-1.50 (m, 1H), 1.50-1.55 (m, 1H), 1.55-1.80 (m, 4H), 2.85-3.00 (m, 1H), 3.9-4.1 (m, 1H), 4.4-4.55 (m, 1H), 5.75-5.85 (m, 2H) | chloromethyl 2-methylpiperidine-1-carboxylate |
| 6315 | 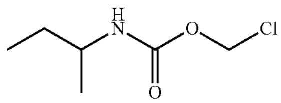 | 0.80-1.00 (m, 3H), 1.1-1.2 (m, 3H), 1.45-1.55 (m, 2H), 3.5-3.8 (m, 1H), 4.75-4.95 (s, 1H), 5.75 (s, 2 H) | chloromethyl sec-butylcarbamate |
| 6316 | 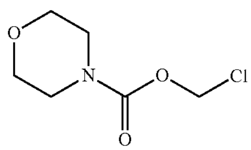 [SMILES: O=C(OCCl)N1CCOCC1] | 3.45-3.60 (m, 4H), 3.60-3.80 (m, 4H), 5.8 (s, 2H) | chloromethyl morpholine-4-carboxylate |
| 6317 | 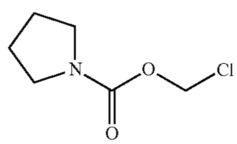 | 1.80-1.90 (m, 4H), 3.30-3.50 (m, 4H), 5.80 (s, 2H) | chloromethyl pyrrolidine-1-carboxylate |
| 6318 | 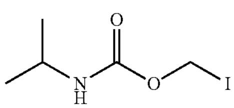 | 6.01δ(2H, s); 4.70 δ (1H, bs); 3.83δ(1H, septet); 1.19 δ (6H, d). | iodomethyl isopropylcarbamate |
| 6319 | 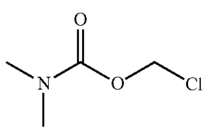 | 5.76 (2H, s); 2.99-2.94 (6H, d). | chloromethyl dimethylcarbamate |
| 6320 | 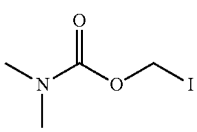 | 6.01 (2H, s); 2.96-2.89 (6H, d). | iodomethyl dimethylcarbamate |
| 6321 | 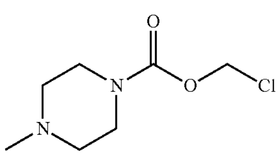 | 6.17(s, 2H); 2.26(s, 3H); 2.27(d, 4H); 3.2(d, 4H) | chloromethyl 4-methylpiperazine-1-carboxylate |
| 6322 | 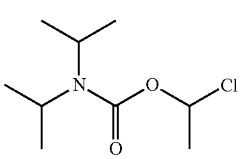 | 1.09-1.25 (m, 12H), 1.3 (d, 3H), 3.20-3.40 (m, 2H), 6.01 (q, 1H); | 1-chloroethyl diisopropylcarbamate |
| 6323 | 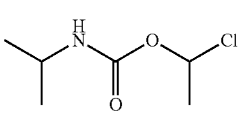 | 1.17-1.19 (d, 6 H), 3.78-3.91 (m, 1 H), 4.73 (s, —NH), 5.73 (q, 1H); 1.3 (d, 3H) | 1-chloroethyl isopropylcarbamate |
| 6324 | 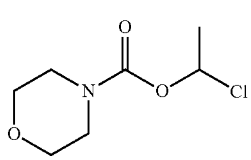 | 3.45-3.60 (m, 4H), 3.50-3.80 (m, 4H), 5.8 (q, 1H); 1.9(d, 3H) | 1-chloroethyl morpholine-4-carboxylate |

TABLE 4-continued

Examples of Type II Reagents

| No. | STRUCTURE | NMR, ¹HNMR (300 MHz; CDCl3) δ | IUPAC Name |
| --- | --- | --- | --- |
| 6325 | 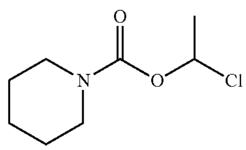 | 1.10-2.05 (m, 3H), 1.30-1.45 (m, 2H), 1.55-1.65 (m, 1H), 1.65-1.80 (m, 2H), 1.90-2.00 (m, 2H), 3.45-3.60 (m, 1H), 4.75-4.95 (s, 1H), 6.2 (q, 1H); 1.9(d, 3H) | 1-chloroethyl piperidine-1-carboxylate |
| 6326 | 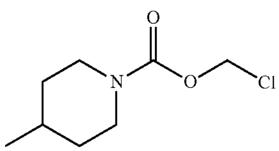 | 1.10 (d, 3H), 1.30-1.45 (q, 4H), 1.55-1.65 (m, 1H), 1.65-1.80 (t, 4H), 6.1 (s, 2H) | chloromethyl 4-methylpiperidine-1-carboxylate |
| 6327 | 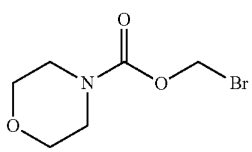 [SMILES: O=C(OCBr)N1CCOCC1] | 5.92 δ (2H, S), 3.72 δ(4H, t), 3.54 δ(4H, t) | bromomethyl morpholine-4-carboxylate |

TABLE 5

Examples of Type III Reagents

| No. | STRUCTURE | NMR, ¹HNMR (300 MHz; CDCl3) δ | IUPAC Name |
| --- | --- | --- | --- |
| 7401 | 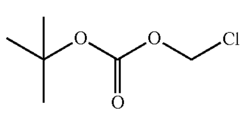 | 1.50 (s, 9H), 5.65 (s, 2H) | tert-butyl (chloromethyl) carbonate |
| 7402 | 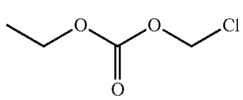 | 1.25-1.40 (t, 3H), 4.25-4.35 (q, 2H), 5.75 (s, 2H) | chloromethyl ethyl carbonate |
| 7403 | 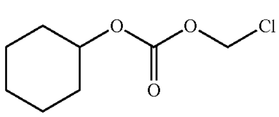 [SMILES: O=C(OCCl)OC1CCCCC1] | 1.20-1.40 (m, 3H), 1.45-1.6 (m, 3H), 1.70-1.80 (m, 2H), 1.90-2.0 (m, 2H), 4.75-4.75 (m, 1H), 5.75 (s, 2H) | chloromethyl cyclohexyl carbonate |
| 7404 | 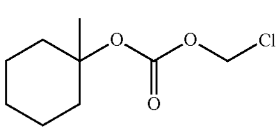 | 1.40-1.60 (m, 10H), 2.10-2.20 (m, 3H), 1.70-1.80 (m, 2H), 5.65 (s, 2H) | chloromethyl (1-methylcyclohexyl) carbonate |
| 7405 | 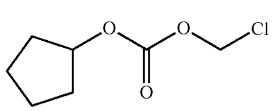 [SMILES: O=C(OCCl)OC1CCCC1] | 1.55-1.65 (m, 3H), 1.65-1.95 (m, 7H), 5.10-5.20 (m, 1H), 5.7 (s, 2H) | chloromethyl cyclopentyl carbonate |
| 7406 | 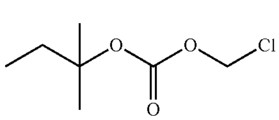 | 5.70 (2H, s); 1.80-1.90 (2H, q); 1.50 (6H, s); 1.6-1.82 (6H, m); 0.90-1.00 (3H, t). | chloromethyl tert-pentyl carbonate |

TABLE 5-continued

Examples of Type III Reagents

| No. | STRUCTURE | NMR, ¹HNMR (300 MHz; CDCl3) δ | IUPAC Name |
| --- | --- | --- | --- |
| 7407 | 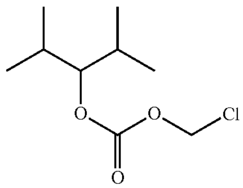 | 5.70 (2H, s); 4.40-4.50 (1H, t); 1.50 (6H, s); 1.90-2.00 (2H, q); 0.90-1.00 (14H, s). | chloromethyl (2,4-dimethylpentan-3-yl) carbonate |
| 7408 | 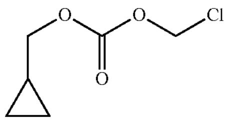 | 5.80 (2H, s); 4.10-4.18 (2H, q); 1.10-1.30 (1H, t); 0.60-0.70 (2H, m); 0.42-0.50 (2H, m). | chloromethyl (cyclopropylmethyl) carbonate |
| 7409 | 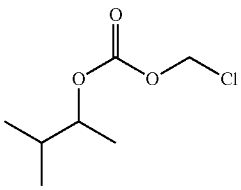 | 5.70 (2H, s); 4.60-4.70 (1H, t); 1.80-1.85 (1H, q); 1.20 (3H, d); 0.95 (6H, d). | chloromethyl (3-methylbutan-2-yl) carbonate |
| 7410 | 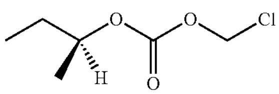 | 5.70 (2H, s); 4.65-4.75 (1H, m); 1.40-1.60 (2H, m); 1.20-1.30 (3H, d); 0.95 (3H, m). | (S)-sec-butyl (chloromethyl) carbonate |
| 7411 | 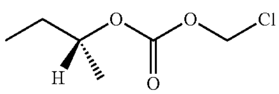 | 5.78 (2H, s); 4.65-4.75 (1H, m); 1.40-1.60 (2H, m); 1.30 (3H, d); 0.95 (3H, m). | (R)-sec-butyl (chloromethyl) carbonate |
| 7412 | 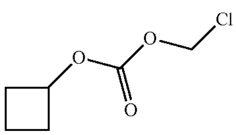 | 4.98-5.00 (1H, m); 2.36-2.42 (2H, m); 2.10-2.20 (2H, m); 1.80-1.90 (1H, m), 1.59-1.61 (1H, m). | chloromethyl cyclobutyl carbonate |
| 7413 | 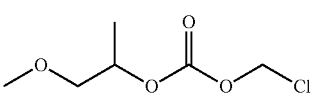 | 5.65-5.80 (m, 2H), 4.95-5.15 (m, 1H), 3.40-3.45 (m, 2H), 3.35 (s, 3H), 1.25-1.35 (m, 2H). | chloromethyl (1-methoxypropan-2-yl) carbonate |
| 7414 | 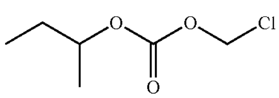 | 5.75 (s, 2H), 4.70-4.90 (m, 1H), 1.60-1.80 (m, 2H), 1.25-1.35 (m, 2H), 0.80-0.95(m, 3H). | sec-butyl (chloromethyl) carbonate |
| 7415 | 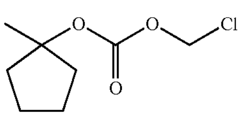 | 5.75(m, 2H), 2.15-2.25 (m, 2H), 1.60 (s, 3H), 1.62-1.90 (m, 9H). | chloromethyl (1-methylcyclopentyl) carbonate |
| 7416 | 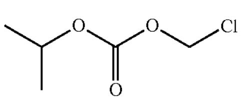 | 1.25-1.40 (d, 6H), 4.25-4.35 (m, 1H), 5.75 (s, 2H) | chloromethyl isopropyl carbonate |
| 7417 | 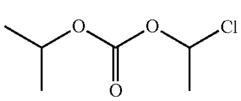 | 1.25-1.40 (d, 6H), 4.25-4.35 (m, 1H), 5.75 (q, 2H); 1.9(d, 3H) | 1-chloroethyl isopropyl carbonate |

TABLE 5-continued

Examples of Type III Reagents

| No. | STRUCTURE | NMR, $^1$HNMR (300 MHz; CDCl3) δ | IUPAC Name |
|-----|-----------|----------------------------------|------------|
| 7418 | Ph–CH$_2$–O–C(=O)–O–CH$_2$–I | 7.38-7.45(m, 5H); 5.1(s, 2H); 6.1(s, 2H) | benzyl (iodomethyl) carbonate |
| 7419 | Ph–CH(CH$_3$)–O–C(=O)–O–CH$_2$–I | 1.6(d, 3H); 7.38-7.40(m, 5H); 5.4(q, 1H); 6.1(s, 2H); | (S)-iodomethyl (1-phenylethyl) carbonate |
| 7420 | Ph–CH(CH$_3$)–O–C(=O)–O–CH$_2$–I | 1.6(d, 3H); 7.38-7.40(m, 5H); 5.4(q, 1H); 6.1(s, 2H); | (R)-iodomethyl (1-phenylethyl) carbonate |

Accordingly, as a person of ordinary skill in the art will readily apprehend from the teachings herein, the modifying reagents of the present invention can be synthesized in wide variety as taught and disclosed, including but not limited to the specific examples provided herein, including those in Tables 3, 4 and 5. As such, one aspect of the present invention is therefore the ability to tailor the substituents to the family of reagents disclosed in Figure 1 to suit a particular application or obtain the desired result.

Example of Chemical Modifications of Drugs/Biologically Active Compounds with Aromatic Nitrogen as a Heteroatom.

Scheme 28: Synthesis of modified form of Nicorandil

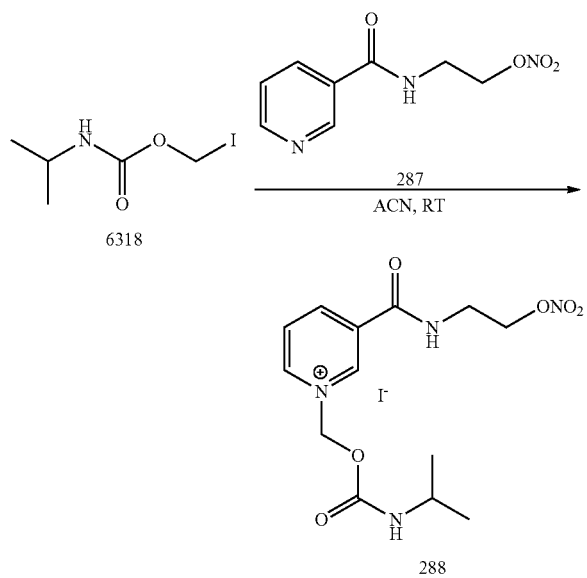

To a solution of nicorandil, (2-(nicotinamido)-ethyl nitrate) [287], (0.28 mmol, 1 eq) in acetonitrile (3 ml) was added iodomethyl isopropyl carbamate [6318] (0.28 mmol, 1.2 eq) drop wise. The resulting reaction mixture was stirred overnight at RT. Reaction completion was monitored by TLC. The excess of acetonitrile was removed under vacuum with a Buchi rotavapor. The resulting crude was dissolved in a minimum amount of MeOH and washed with an excess of ether. This process was repeated twice to get nearly pure solid product, 1-(((isopropylcarbamoyl)oxy)methyl)-3-((2-(nitrooxy)ethyl)carbamoyl)pyridin-1-ium iodide [288], which was dried under high vacuum to obtain the product as a yellow sticky solid (0.085 g, 88%).

m/z: 327 (M$^+$)

$^1$H NMR [DMSO, 300 MHz]: δ ppm 9.54 (s, 1H), 9.43-9.46 (m, 1H), 9.27-9.29 (d, 1H), 9.01-9.04 (d, 1H), 8.33-8.38 (m, 1H), 7.86-7.88 (m, 1H), 6.41 (s, 2H), 4.67-4.70 (t, 2H), 3.69-3.74 (m, 2H), 3.52-3.63 (m, 1H), 1.04-1.11 (m, 6H)

Other chemical modifications of nicorandil were accomplished using similar synthetic procedure with various substituted methyl formyl reagents to get structures in Table 6 which were characterized using spectroscopic techniques such as MS and/or $^1$H NMR.

These compounds were tested for their Pharmacokinetic parameters and were found to be more active than nicorandril. The Pk data corresponding to the compounds are presented at Table 6.

The PK data of the compounds were tested by following the protocol as below:

Female Sprague Dawley (SD) rats 3 per group after overnight fasting were dosed orally (via gavage) with imatinib and its modified drugs in distilled water (5 ml/kg) at a dose level of 3 mg/kg. Blood was collected by serial bleeding at 0.16 h, 0.5 h, 1 h, 2 h, 4 h, 6 h, 8 h and 24 h in heparinized tubes. Blood samples were centrifuged at 10,000 rpm for 10 min. at 4° C. to obtain the plasma, which were aspirated into separate labeled tubes and stored at –80° C. 400 ng/ml of Verapmil in acetonitrile was used as the drug extraction solvent for extracting drug from plasma. Extraction solvent was added to plasma was vortexed and shaken on shaker for 10 minutes, centrifuged at 10000 rpm for 10 minutes at 4° C. Supernatant was kept for analysis.

Acetonitrile and plasma calibration curves were generated and percentage of drug recovery from plasma determined. Quantitative analysis was done by liquid chromatography tandem mass spectrometry using multiple reaction monitoring (API3000 LC-MS/MS). $C_{max}$, $T_{max}$, AUC and $t_{1/2}$ were calculated using Graph Pad PRISM version 5.04.

TABLE 6

Some examples of chemical modifications of nicorandil and their Pharmacokinetic Parameters
determined in Swiss mice at 3 mpk orally ($T_{max}$, $C_{max}$, AUC and $T_{1/2}$)

| Structure | Compound Number | Compound Name | PK Value (AUC) [nM * hr] |
|---|---|---|---|
| $C_8H_9N_3O_4$ | 4155 | Nicorandil | 20441 |
| $C_{15}H_{22}N_3O_6^+$ | 8501 | Nicorandil Mod Drug | 20634 |
| $C_{14}H_{20}N_3O_6^+$ | 8502 | Nicorandil Mod Drug | 10278 |
| $C_{13}H_{18}N_3O_6^+$ | 8503 | Nicorandil Mod Drug | 15024 |
| $C_{16}H_{25}N_4O_6^+$ | 8504 | Nicorandil Mod Drug | 32164 |

TABLE 6-continued

Some examples of chemical modifications of nicorandil and their Pharmacokinetic Parameters
determined in Swiss mice at 3 mpk orally ($T_{max}$, $C_{max}$, AUC and $T_{1/2}$)

| Structure | Compound Number | Compound Name | PK Value (AUC) [nM * hr] |
|---|---|---|---|
| 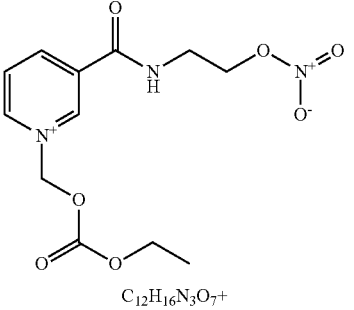 $C_{12}H_{16}N_3O_7+$ | 8505 | Nicorandil Mod Drug | 11062 |
| 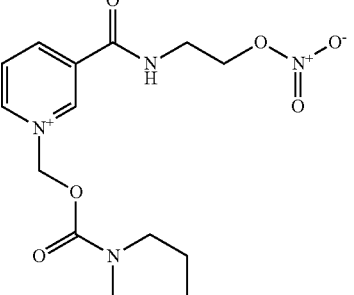 $C_{15}H_{21}N_4O_6+$ | 8506 | Nicorandil Mod Drug | 57049 |
| $C_{13}H_{18}N_3O_7+$ | 8507 | Nicorandil Mod Drug | 4476 |
| 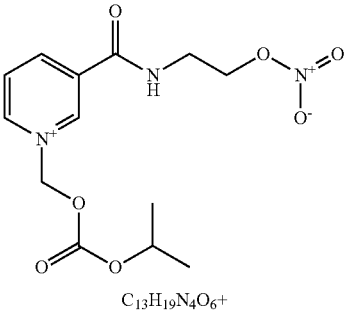 $C_{13}H_{19}N_4O_6+$ | 8508 | Nicorandil Mod Drug | 28461 |
| 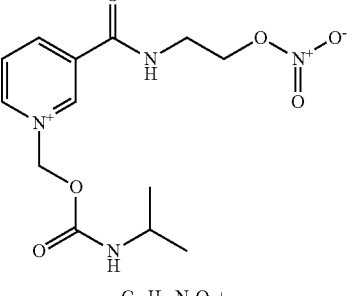 $C_{14}H_{20}N_3O_7+$ | 8509 | Nicorandil Mod Drug | 12472 |

TABLE 6-continued

Some examples of chemical modifications of nicorandil and their Pharmacokinetic Parameters determined in Swiss mice at 3 mpk orally ($T_{max}$, $C_{max}$, AUC and $T_{1/2}$)

| Structure | Compound Number | Compound Name | PK Value (AUC) [nM * hr ] |
|---|---|---|---|
| 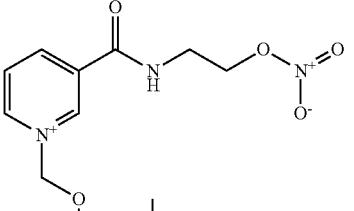 $C_{17}H_{27}N_4O_6^+$ | 8510 | Nicorandil Mod Drug | 16135 |
| 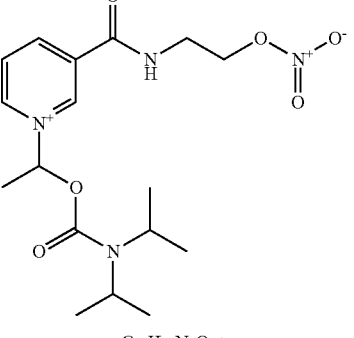 $C_{18}H_{27}N_4O_6^+$ | 8515 | Nicorandil Mod Drug | 46438 |
| 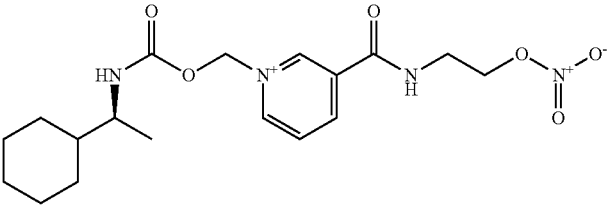 $C_{16}H_{23}N_4O_6^+$ | 8520 | Nicorandil Mod Drug | 19488 |
| 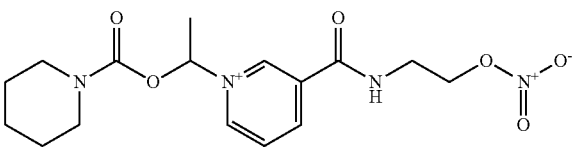 $C_{18}H_{27}N_4O_6^+$ | 8525 | Nicorandil Mod Drug | 33154 |
| 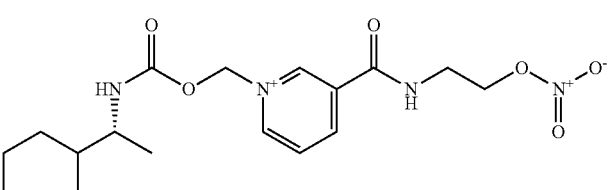 $C_{14}H_{20}N_3O_7^+$ | 8530 | Nicorandil Mod Drug | 10007 |

TABLE 6-continued

Some examples of chemical modifications of nicorandil and their Pharmacokinetic Parameters determined in Swiss mice at 3 mpk orally ($T_{max}$, $C_{max}$, AUC and $T_{1/2}$)

| Structure | Compound Number | Compound Name | PK Value (AUC) [nM * hr] |
|---|---|---|---|
| 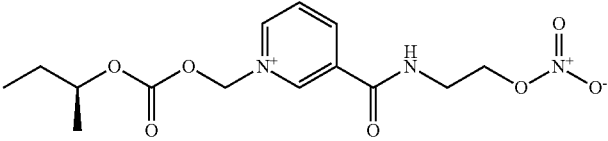 $C_{14}H_{20}N_3O_7^+$ | 8535 | Nicorandil Mod Drug | 23680 |
| 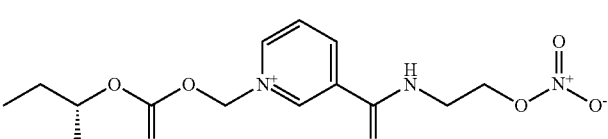 $C_{17}H_{27}N_4O_6^+$ | 8540 | Nicorandil Mod Drug | 16135 |
| 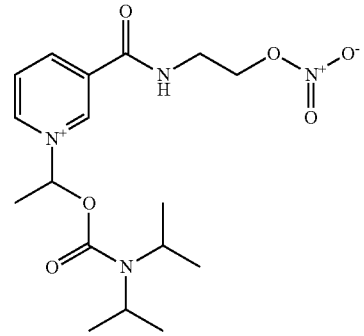 $C_{18}H_{27}N_4O_6^+$ | 8545 | Nicorandil Mod Drug | 46438 |
| 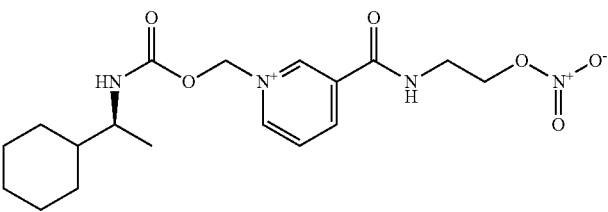 $C_{16}H_{23}N_4O_6^+$ | 8550 | Nicorandil Mod Drug | 19488 |
| 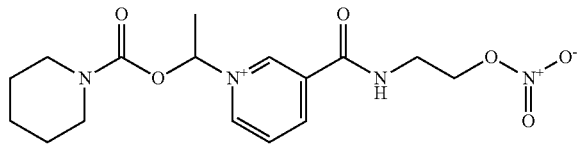 $C_{18}H_{27}N_4O_6^+$ | 8555 | Nicorandil Mod Drug | 33154 |
| 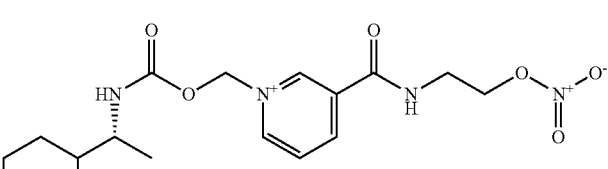 $C_{14}H_{20}N_3O_7^+$ | 8560 | Nicorandil Mod Drug | 10007 |

TABLE 6-continued

Some examples of chemical modifications of nicorandil and their Pharmacokinetic Parameters determined in Swiss mice at 3 mpk orally ($T_{max}$, $C_{max}$, AUC and $T_{1/2}$)

| Structure | Compound Number | Compound Name | PK Value (AUC) [nM * hr] |
|---|---|---|---|
| 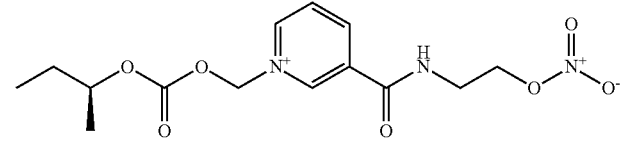 $C_{14}H_{20}N_3O_7+$ | 8565 | Nicorandil Mod Drug | 23680 |

Accordingly, as a person of ordinary skill in the art will readily apprehend from the teachings herein, the modifying reagents of the present invention can be synthesized in wide variety as taught and disclosed, including but not limited to the specific examples provided herein. As taught herein, and exemplified in herein, modification according to the teachings of the present invention provides a ready and flexible method of varying various pharmacokinetic parameters of a biologically active compound.

Example of Chemical Modifications of Drugs/Biologically Active Compounds with Aliphatic Tertiary Nitrogen as a Heteroatom Scheme 31: Synthesis of modified form of Dimebon, Derivative I

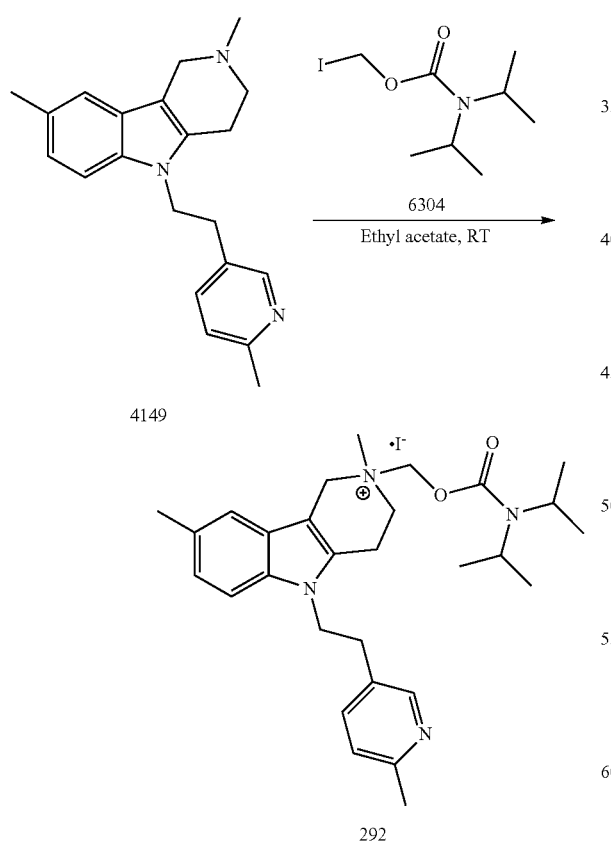

Procedure:

To a stirred solution of dimebon, 2,8-dimethyl-5-(2-(6-methylpyridin-3-yl)ethyl)-2,3,4,5-tetrahydro-1H-pyrido[4,3-b]indole [4149], (0.070 g, 0.22 mmol, 1.0 eq) in ethyl acetate was added iodomethyl diisopropyl carbonate [6304] (0.057 g, 0.20 mmol, 0.9 eq) at RT. The reaction mixture was stirred at RT for 4 to 6 hours. The resulting precipitate was collected by filtration under suction and washed four times with ethyl acetate followed by an additional wash by diethyl ether. to get a pale yellow, solid which was dried under vacuum at RT to yield the desired product, 2-(((diisopropylcarbamoyl)oxy)methyl)-2,8-dimethyl-5-(2-(6-methylpyridin-3-yl)ethyl)-2,3,4,5-tetrahydro-1H-pyrido[4,3-b]indol-2-ium iodide [292] (0.020 g, 15%).

m/z: 477.3

Scheme 32: Synthesis of modified form of Dimebon, Derivative II

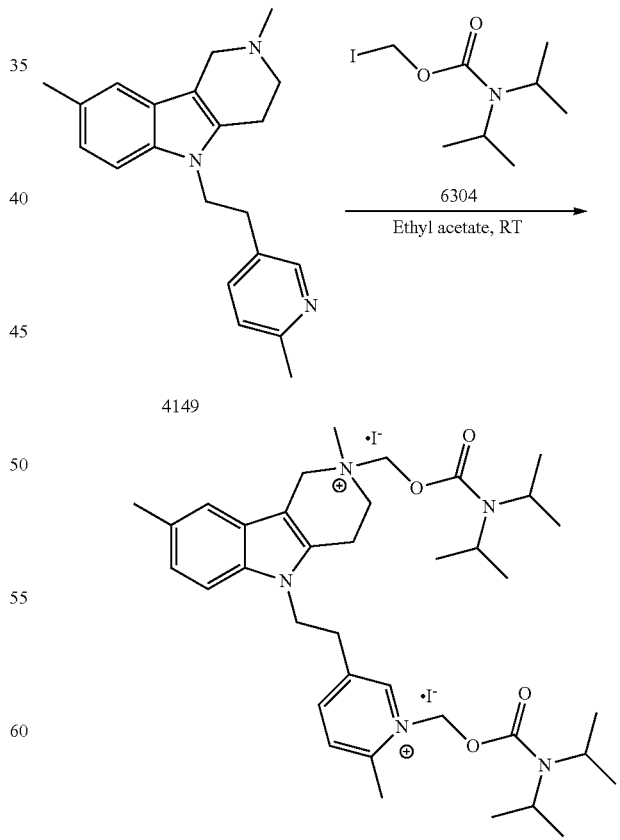

Procedure:

Iodomethyl diisopropyl carbamate [6304] (0.134 g, 0.47 mmol, 5.0 eq) was added to a stirred solution of dimebon [4149] (0.030 g, 0.094 mmol, 1.0 eq) in ethyl acetate at RT. The reaction mixture was stirred at RT for 4 to 6 hours. The resulting precipitate was filtered under suction and washed four times with ethyl acetate followed by an additional wash with diethyl ether to get a pale yellow solid, which was dried under vacuum at RT to yield the desired product, 2-(((diisopropylcarbamoyl)oxy)methyl)-5-(2-(1-(((diisopropylcarbamoyl)oxy)methyl)-6-methylpyridin-1-ium-3-yl)ethyl)-2,8-dimethyl-2,3,4,5-tetrahydro-1H-pyrido[4,3-b]indol-2-ium diiodide [293] (0.033 g, 39%)

m/z: 317.8

Scheme 33: Synthesis of modified forms of Olanzapine

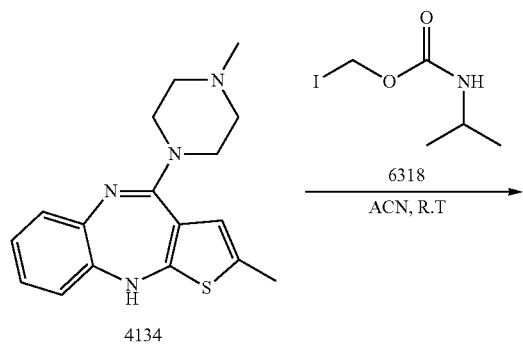

4134

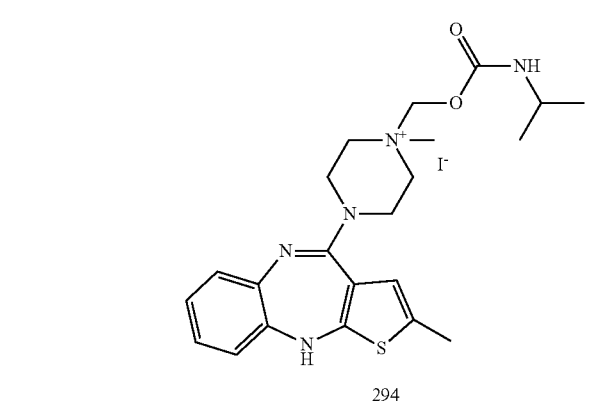

294

Procedure:

To a stirred solution of Olanzapine, (2-methyl-4-(4-methylpiperazin-1-yl)-10H-benzo[b]thieno[2,3-e][1,4]diazepine) [4134] (0.025 g, 0.086 mmol, 1.0 eq) in ACN was added iodomethyl isopropylcarbamate [6318] (0.20 g, 0.086 mmol, 1.0 eq) at RT. The reaction mixture was stirred at RT for four to 16 h. Reaction progress was monitored by TLC. Solvent was removed under vacuum to get a crude product. The crude product obtained was triturated with diethyl ether (5 ml×2) to give the desired product [294], 1-(((isopropylcarbamoyl)oxy)methyl)-1-methyl-4-(2-methyl-10H-benzo[b]thieno[2,3-e][1,4]diazepin-4-yl)piperazin-1-ium iodide (0.013 g, 41%) as yellow solid.

Scheme 34: Synthesis of modified forms of Sildenafil

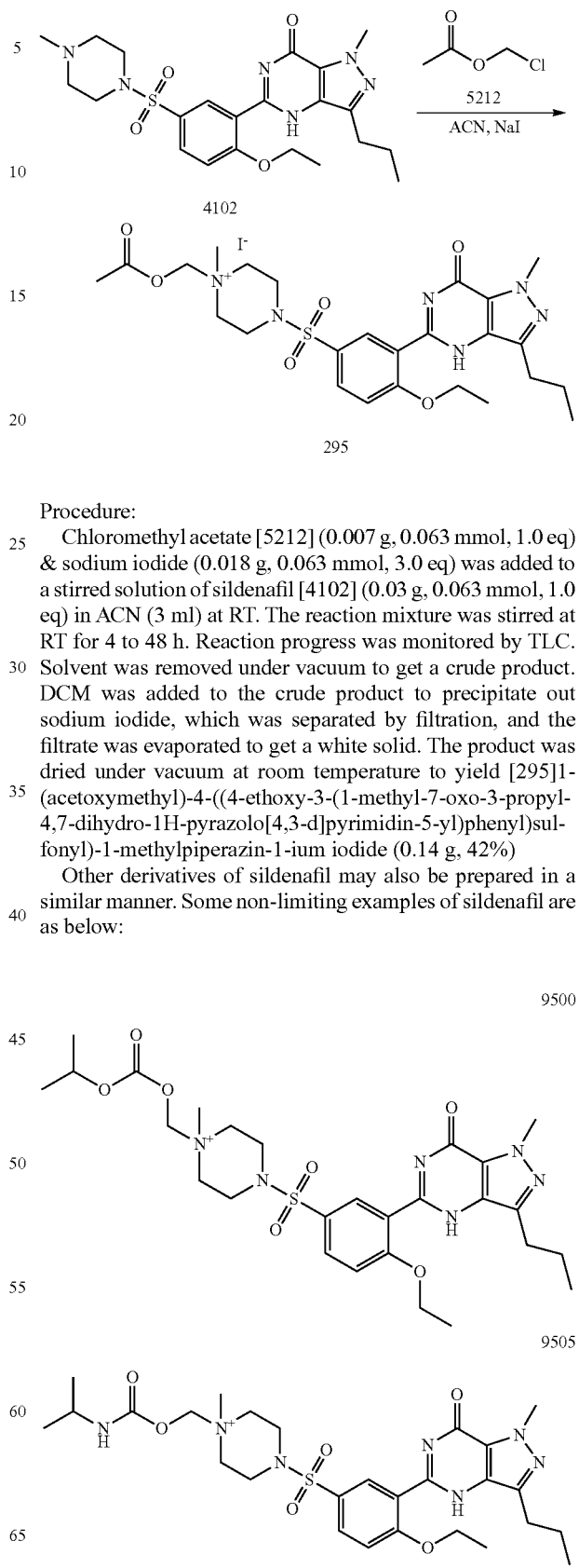

Procedure:

Chloromethyl acetate [5212] (0.007 g, 0.063 mmol, 1.0 eq) & sodium iodide (0.018 g, 0.063 mmol, 3.0 eq) was added to a stirred solution of sildenafil [4102] (0.03 g, 0.063 mmol, 1.0 eq) in ACN (3 ml) at RT. The reaction mixture was stirred at RT for 4 to 48 h. Reaction progress was monitored by TLC. Solvent was removed under vacuum to get a crude product. DCM was added to the crude product to precipitate out sodium iodide, which was separated by filtration, and the filtrate was evaporated to get a white solid. The product was dried under vacuum at room temperature to yield [295]1-(acetoxymethyl)-4-((4-ethoxy-3-(1-methyl-7-oxo-3-propyl-4,7-dihydro-1H-pyrazolo[4,3-d]pyrimidin-5-yl)phenyl)sulfonyl)-1-methylpiperazin-1-ium iodide (0.14 g, 42%)

Other derivatives of sildenafil may also be prepared in a similar manner. Some non-limiting examples of sildenafil are as below:

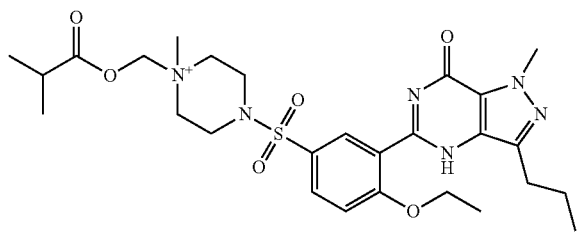
9510

Examples of Chemical Modifications of Drugs/Biologically Active Compounds with Alcohol/Phenol as a Functional Group Scheme 35: Synthesis of modified forms of Paracetamol, Derivative I

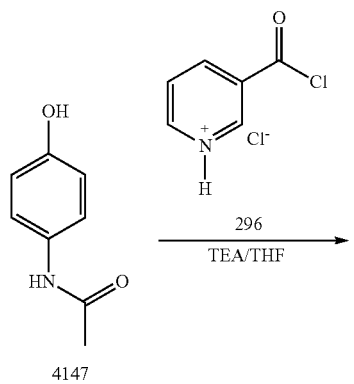

Step 1:

TEA (1.2 ml, 8.6 mmol, 5.0 eq) was added to a solution of paracetamol [4147] (0.26 g, 1.7 mmol, 1.0 eq) in dry THF under argon atmosphere. At 0° C., nicotinoyl chloride hydrochloride [296] (1.53 gm, 8.6 mmol, 5.0 eq) was added to the above reaction mixture. The reaction mixture was stirred at room temperature for 24 h. After 24 h, organic solvent was evaporated under vacuum and residue was dissolved in dichloromethane (50 ml) and washed with a 10% solution of NaHCO$_3$ (15 ml) and then with brine (10 ml) followed by drying of organic layer over anhydrous sodium sulfate. Evaporation of the solvents provided white solid which was purified by silica gel column chromatography (4% MeOH: DCM, 100-200 mesh silica) to give the product 4-acetamidophenyl nicotinate [297] (0.34 g, 78%).

m/z: 257

Step 2:

To a solution of 4-acetamidophenyl nicotinate [297], (0.05 g, 1.95 mmol, 1.0 eq) in acetonitrile (4 ml) was added iodomethyl diisopropylcarbamate [6304] (0.055 g, 1.95 mmol, 1.0 eq). The resulting reaction mixture was stirred overnight at RT. The reaction was monitored by TLC. Acetonitrile was removed under vacuum and the resulting crude mixture was washed with diethyl ether (10 ml) to give pale yellow solid product 3-((4-acetamidophenoxy)carbonyl)-1-(((diisopropylcarbamoyl)oxy)methyl)pyridin-1-ium iodide [298] (0.086 g, 81%).

m/z: 414

Scheme 36: Synthesis of modified forms of Paracetamol, Derivative II

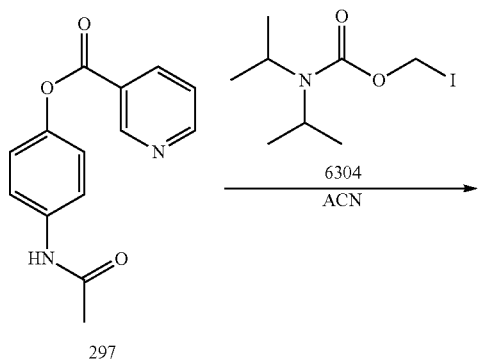

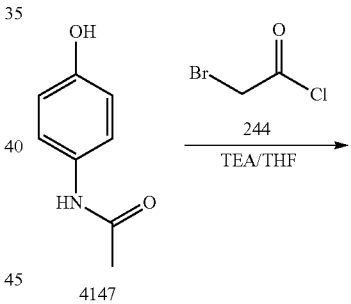

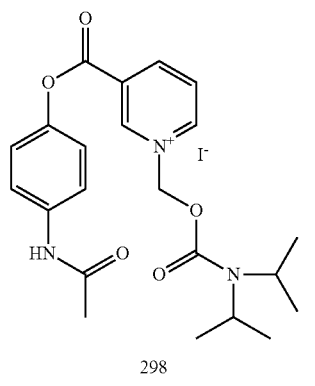

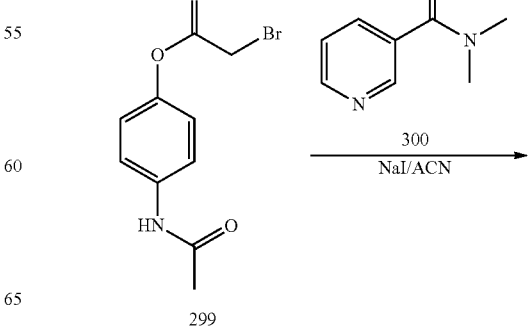

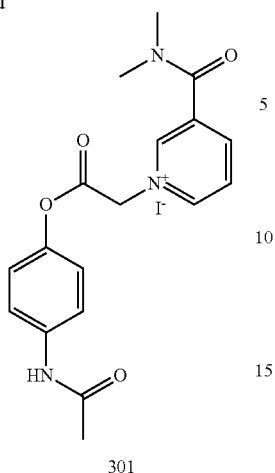

301

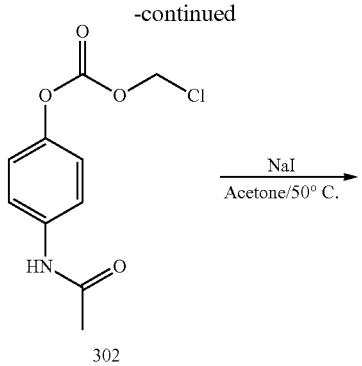

302

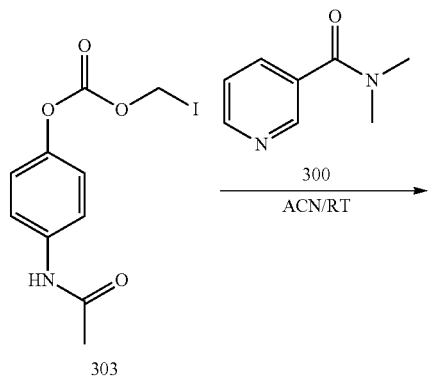

303

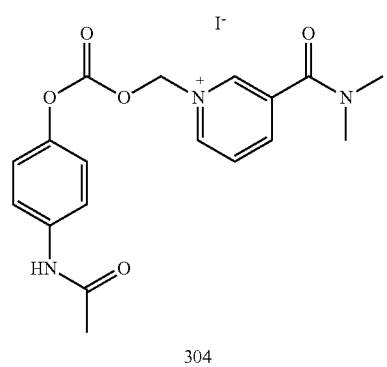

304

Step 1:
TEA (0.28 ml, 1.98 mmol, 3.0 eq) was added to a solution of paracetamol [4147] (0.10 g, 0.66 mmol, 1.0 eq) of in dry THF under argon atmosphere. At 0° C., bromoacetyl chloride [244] (0.123 g, 0.79 mmol, 1.2 eq) was added. The reaction mixture was stirred at room temperature for 24 h. After 24 h, solvent was evaporated under vacuum and residue was taken in dichloromethane (50 ml) and washed with a 10% solution of NaHCO$_3$ (15 ml) and then with brine (10 ml), followed by drying of the organic layer over anhydrous sodium sulfate. Evaporation of the solvent provided white solid which was purified by silica gel column chromatography (0.5% MeOH: DCM, 100-200 mesh silica) to give the product 4-acetamidophenyl 2-bromoacetate [299] (0.05 g, 28%).
m/z: 272

Step 2:
Sodium iodide (0.083 g, 5.52 mmol, 3.0 eq.) was added to a solution of 4-acetamidophenyl 2-bromoacetate [299] (0.05 g, 1.84 mmol, 1.0 eq.) in acetonitrile (5 ml) followed by the addition of dimethyl nicotinamide [300] (0.027 g, 1.84 mmol, 1.0 eq). The resulting reaction mixture was stirred at 40° C. for 48 h. Reaction progress was monitored by TLC. Solvent was removed under vacuum to get crude product. The crude product obtained was taken in DCM to precipitate excess of sodium iodide and sodium bromide, which was removed by filtration and filtrate was evaporated to get a yellow solid, which was washed with diethyl ether (10 ml) and then dried under vacuum to yield light yellow solid, 1-(2-(4-acetamidophenoxy)-2-oxoethyl)-3-(dimethylcarbamoyl)pyridin-1-ium iodide[301], (0.038 g, 44%)
m/z: 342

Scheme 37: Synthesis of modified forms of Paracetamol, Derivative III

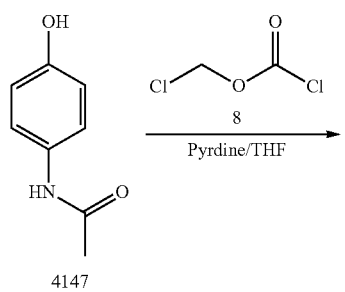

4147

Step 1:
Pyridine (0.375 g, 47.5 mmol, 2.5 eq) was added to a solution of chloromethyl chloroformate (CMCF) [8](0.294 g, 22.8 mmol, 1.2 eq) in dry THF (10 ml) under an argon atmosphere at 0° C. At 0° C., a solution of Paracetamol [4147] (0.30 g, 19.0 mmol, 1.0 eq) in dry THF was added to the above reaction mixture. The reaction mixture was stirred at RT for 20 h. Reaction progress was monitored by TLC. After 20 h, the reaction mixture was diluted with dichloromethane (50 ml), washed with water (15 ml), 10% solution of NaHCO$_3$ (15 ml), dilute HCl (10 ml), followed with brine (10 ml). The organic layer dried over anhydrous sodium sulfate. Evaporation of the solvents under vacuum gave crude product. The crude product was purified by silica gel column chromatography (2% MeOH: DCM, 100-200 mesh) to yield a off white product, 4-acetamidophenyl(chloromethyl)carbonate [302] (0.33 g, 68%).

m/z: 244

Step 2:

Sodium iodide (0.454 g, 107 mmol 3.7 eq) was added to a solution of 4-acetamidophenyl(chloromethyl)carbonate [302] (0.20 g, 29 mmol, 1.0 eq) in acetone. The resulting reaction mixture was heated for 6 h at 50° C. Reaction progress was monitored by TLC. The reaction mixture was cooled to room temperature and passed through a bed of silica (mesh 100-200). The silica bed was washed several times with acetone and fractions collected and evaporated under vacuum to yield the desired product, 4-acetamidophenyl(iodomethyl)carbonate [303] (0.27 gm, 98%).

m/z: 336

Step 2:

Dimethyl nicotinamide [300] (0.022 g, 15 mmol, 1.0 eq) was added to a solution of 4-acetamidophenyl(iodomethyl) carbonate [303] (0.05 g, 15.0 mmol, 1.0 eq) in dry acetonitrile (2 ml) under argon atmosphere. The resulting reaction mixture was stirred for 2 days at RT. Reaction progress was monitored by TLC. Solvent was removed under vacuum to get a crude product. The crude product obtained was triturated with diethyl ether (2×10 ml) to give the desired product, 1-((((4-acetamidophenoxy)carbonyl)oxy)methyl)-3-(dimethylcarbamoyl)pyridin-1-ium iodide [304] (0.021 g, 29%).

m/z: 358

Scheme 38: Synthesis of modified forms of SN-38 procedure

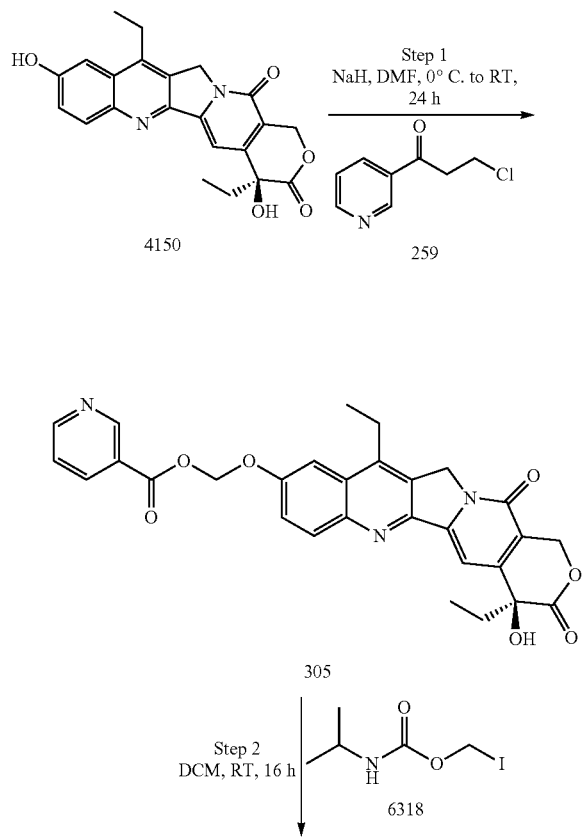

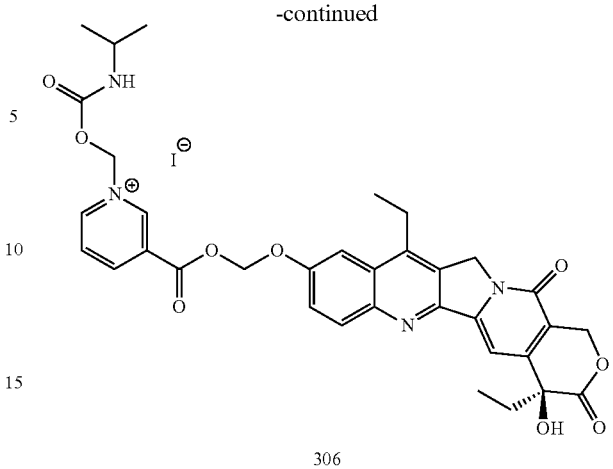

Step 1:

NaH (0.012 g, 0.51 mmol, 1.0 eq) was added portion wise to a solution of SN-38, (S)-4,11-diethyl-4,9-dihydroxy-1H-pyrano[3',4':6,7]indolizino[1,2-b]quinoline-3,14(4H,12H)-dione [4150] (0.20 g, 0.51 mmol, 1.0 eq) in DMF (2 ml) under $N_2$ atmosphere at 0° C. The resulting reaction mixture was stirred at 0° C. for an additional 30 min. To the reaction mixture, chloromethyl nicotinate [259] (0.087 g, 0.51 mmol, 1.0 eq) dissolved in DMF was added dropwise while maintaining the temperature at 0° C. The reaction was then allowed to come to RT and stirred overnight. The reaction mass was quenched with addition of water. The reaction mixture was extracted with DCM (2×100 ml). The organic layers were combined and washed with brine, dried over $Na_2SO_4$ and evaporated. The resultant crude product was purified on column chromatography (2% MeOH: DCM, silica gel 100-200 mesh) to yield a pale yellow solid, (S)-column chromatography (2% MeOH: DCM, silica gel 100-200 mesh) to yield a pale yellow solid, (S)-((4,11-diethyl-4-hydroxy-3,14-dioxo-3,4,12,14-tetrahydro-1H-pyrano[3',4':6,7]indolizino[1,2-b] quinolin-9-yl)oxy)methyl nicotinate [305] (0.036 g, 13%).

m/z=528

$^1$H NMR (DMSO, 300 MHz): δ ppm 9.36 (s, 1H); 8.95 (d, 1H); 8.58 (d, 1H); 8.23-8.25 (dd, 2H); 7.84 (d, 1H); 7.69-7.72 (m, 1H), 7.29 (d, 1H); 6.50-6.53 (m, 1H); 6.01-6.04 (d, 1H); 5.75 (s, 1H); 5.29 (s, 2H); 4.80-4.84 (bs, 1H); 4.67 (br, 1H); 4.03-4.09 (bs, 1H); 3.31-3.33 (m, 2H); 1.82-1.92 (m, 2H); 1.29-1.34 (t, 3H); 0.85-0.93 (t, 3H)

Step 2:

Iodomethyl isopropylcarbamate [6318] (0.007 g, 0.028 mmol, 1.0 eq) was added to a solution of (S)-((4,11-diethyl-4-hydroxy-3,14-dioxo-3,4,12,14-tetrahydro-1H-pyrano[3',4':6,7]indolizino[1,2-b]quinolin-9-yl)oxy)methyl nicotinate [305] (0.015 g, 0.028 mmol, 1.0 eq) in DCM (5 ml). The reaction mixture was stirred at RT for 16 hours. The DCM was evaporated under reduced pressure and washed thoroughly with diethyl ether to yield [306], as a yellow solid (S)-3-(((((4,11-diethyl-4-hydroxy-3,14-dioxo-3,4,12,14-tetrahydro-1H-pyrano[3',4':6,7]indolizino[1,2-b]quinolin-9-yl)oxy)methoxy)carbonyl)-1-(((isopropylcarbamoyl)oxy)methyl)pyridin-1-ium iodide (0.018 g, 85%).

m/z: 643

$^1$H NMR (300 MHz; DMSO): δ 9.98 (s, 1H); 9.39-9.46 (d, 1H); 9.36 (d, 1H); 8.45-8.49 (t, 1H); 8.28-8.29 (dd, 2H); 7.25 (s, 1H); 6.50-6.53 (m, 3H); 6.04-6.07 (d, 1H); 5.39-5.42 (s, 2H); 4.80-4.87 (br, 1H); 4.72 (br, 1H); 4.03-4.09 (br, 1H); 3.36 (m, 1H); 3.07-3.11 (m, 2H); 1.84-1.90 (m, 2H); 1.29-1.34 (t, 3H); 1.06-1.11 (m, 6H); 0.85-0.93 (t, 3H)

Scheme 39: Synthesis of modified forms of Curcumin

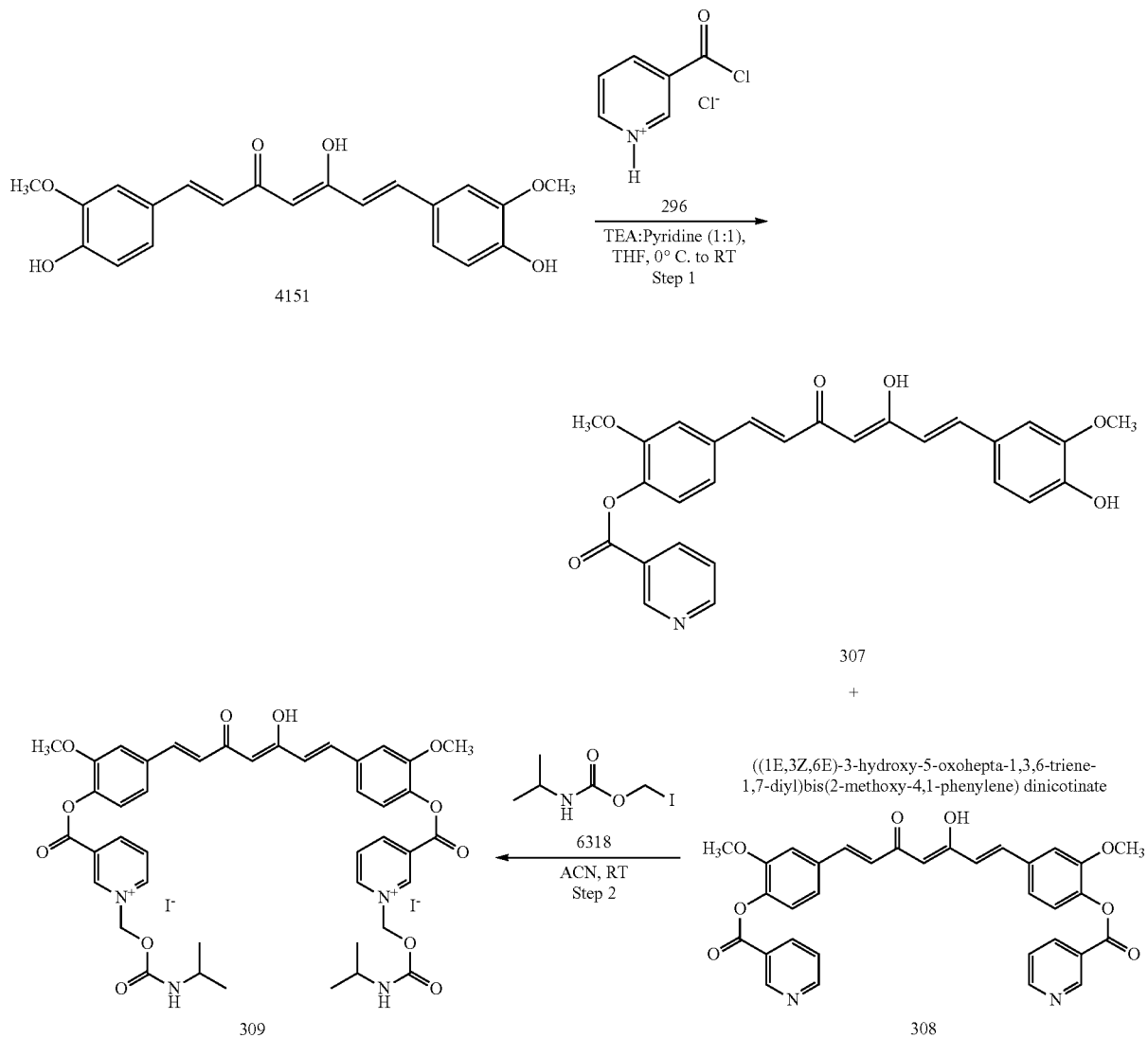

Step 1:

To a solution of nicotinoyl chloride hydrochloride [296] (0.725 g, 4.0 mmol, 1.5 eq) in THF (30 ml) was added TEA (1 ml, x mmol, y eq) drop-wise at 0° C. A solution of curcumin, (1E,4Z,6E)-5-hydroxy-1,7-bis(4-hydroxy-3-methoxyphenyl)hepta-1,4,6-trien-3-one [4151] (1.0 g, 2.7 moles, 1.0 eq) and pyridine (1 ml) in THF (10 ml) was then added at the same temperature. The reaction temperature was gradually increased to RT. The reaction mixture was stirred for 20 h at RT. Reaction was monitored by TLC. The reaction mixture was diluted with EtOAc (200 ml), washed by saturated NaHCO$_3$ solution (75 ml) and water (100 ml) successively. The EtOAc layer was separated, dried with sodium sulphate and concentrated under reduced pressure to yield a crude product. The crude product was purified by column chromatography using (2% MeOH: DCM, 100-200 mesh) get the desired product, 4-((1E,4Z,6E)-5-hydroxy-7-(4-hydroxy-3-methoxyphenyl)-3-oxohepta-1,4,6-trien-1-yl)-2-methoxyphenyl nicotinate [307] as yellow solid (0.30 g, 23%).

m/z: 579

A yellow solid was also generated corresponding to ((1E,3Z,6E)-3-hydroxy-5-oxohepta-1,3,6-triene-1,7-diyl)bis(2-methoxy-4,1-phenylene)dinicotinate [308] (0.03 g, 2.3%).

m/z: 474.

Step 2:

Compound [308][((1E,3Z,6E)-3-hydroxy-5-oxohepta-1,3,6-triene-1,7-diyl)bis(2-methoxy-4,1-phenylene)dinicotinate] (0.02 g, 0.035 mmol, 1.0 eq) was dissolved in solvent ACN (1 ml) followed by the addition of [6318] (0.018 g, 0.076 mmol, 2.2 eq) at room temperature under stirring. Resulting reaction mixture was further stirred for overnight at RT. Reaction was monitored by TLC. Excess of acetonitrile was evaporated under vacuum to get a crude product which on trituration by ethyl acetate (5 ml) followed by diethyl ether (10 ml) gave a yellow solid 3,3'-(((((1E,3Z,6E)-3-hydroxy-5-oxohepta-1,3,6-triene-1,7-diyl)bis(2-methoxy-4,1-phenylene))bis(oxy))bis(carbonyl))bis(1-(((isopropylcarbamoyl)oxy)methyl)pyridin-1-ium)diiodide, [309] (0.017 g, 46%).

m/z: 405.

Scheme 40: Synthesis of modified forms of Paclitaxel, Derivative I

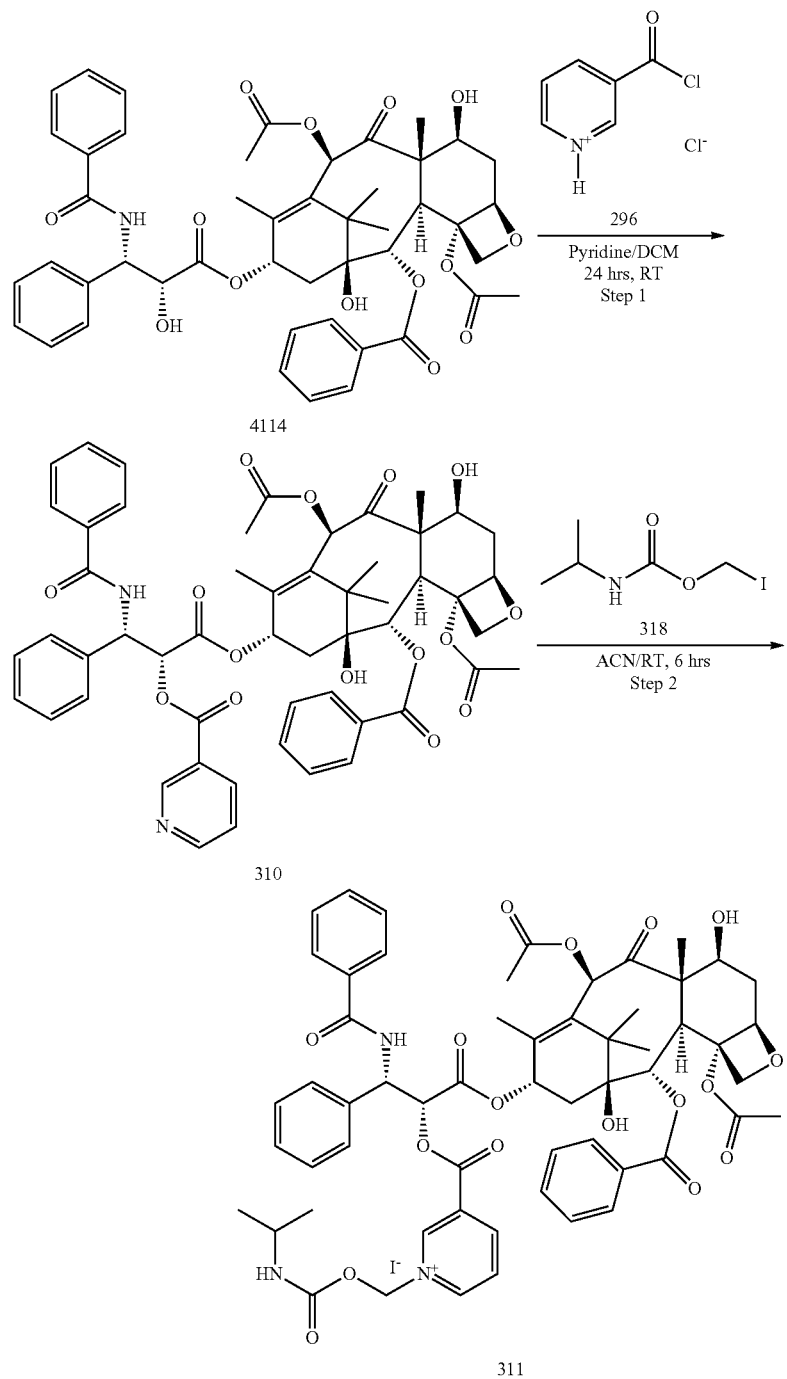

Step 1:
4 drops of pyridine were added to a solution of paclitaxel [4114] (0.10 g, 0.117 mmol 1.0 eq) of in dry dichloromethane under argon atmosphere. At 0° C., nicotinoyl chloride hydrochloride [296] (0.17 g, 1.17 mmol 10.0 eq) was added. The reaction mixture was stirred at room temperature for 24 hours. After 24 hours, the mixture was diluted with dichloromethane (25 ml) and washed with a 10% solution of NaHCO$_3$ (15 ml) and brine (10 ml) followed by drying over anhydrous sodium sulfate. Evaporation of the solvents provided residual yellow solid which was purified by silica gel column chromatography (30% ethyl acetate: cyclohexane, 100-200 mesh silica) to get a white solid [310], (2aR,4S,4aS, 6R,9S,11S,12S,12aR,12bS)-9-(((2R,3S)-3-benzamido-2-(nicotinoyloxy)-3-phenylpropanoyl)oxy)-12-(benzoyloxy)-4,11-dihydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxete-6,12b-diyl diacetate, (0.05 g, 45%)
m/z: 959.2

Step 2:
Iodomethyl isopropylcarbamate [6318] (0.003 g, 10 mmol, 1.0 eq) was added to a solution of [310] (0.01 g, 10.0 mmol, 1.0 eq) in dry Acetonitrile under an argon atmosphere. The resulting reaction mixture was stirred for 6 hours at RT. Reaction progress was monitored by TLC. Solvent was evaporated under high vacuum pump to give crude product. Crude product obtained was triturated with diethyl ether (2×10 ml) to get a yellow solid [311], 3-((((1S,2R)-1-benzamido-3-(((2aR,4S, 4aS,6R,9S,11S,12S,12aR,12bS)-6,12b-diacetoxy-12-(benzoyloxy)-4,11-dihydroxy-4a,8,13,13-tetramethyl-5-oxo-2a, 3,4,4a,5,6,9,10,11,12,12a,12b-dodecahydro-1H-7,11-methanocyclodeca[3,4]benzo[1,2-b]oxet-9-yl)oxy)-3-oxo-1-phenylpropan-2-yl)oxy)carbonyl)-1-(((isopropylcarbamoyl)oxy)methyl)pyridin-1-ium iodide, (0.01 g, 90%).

m/z: 1075.2

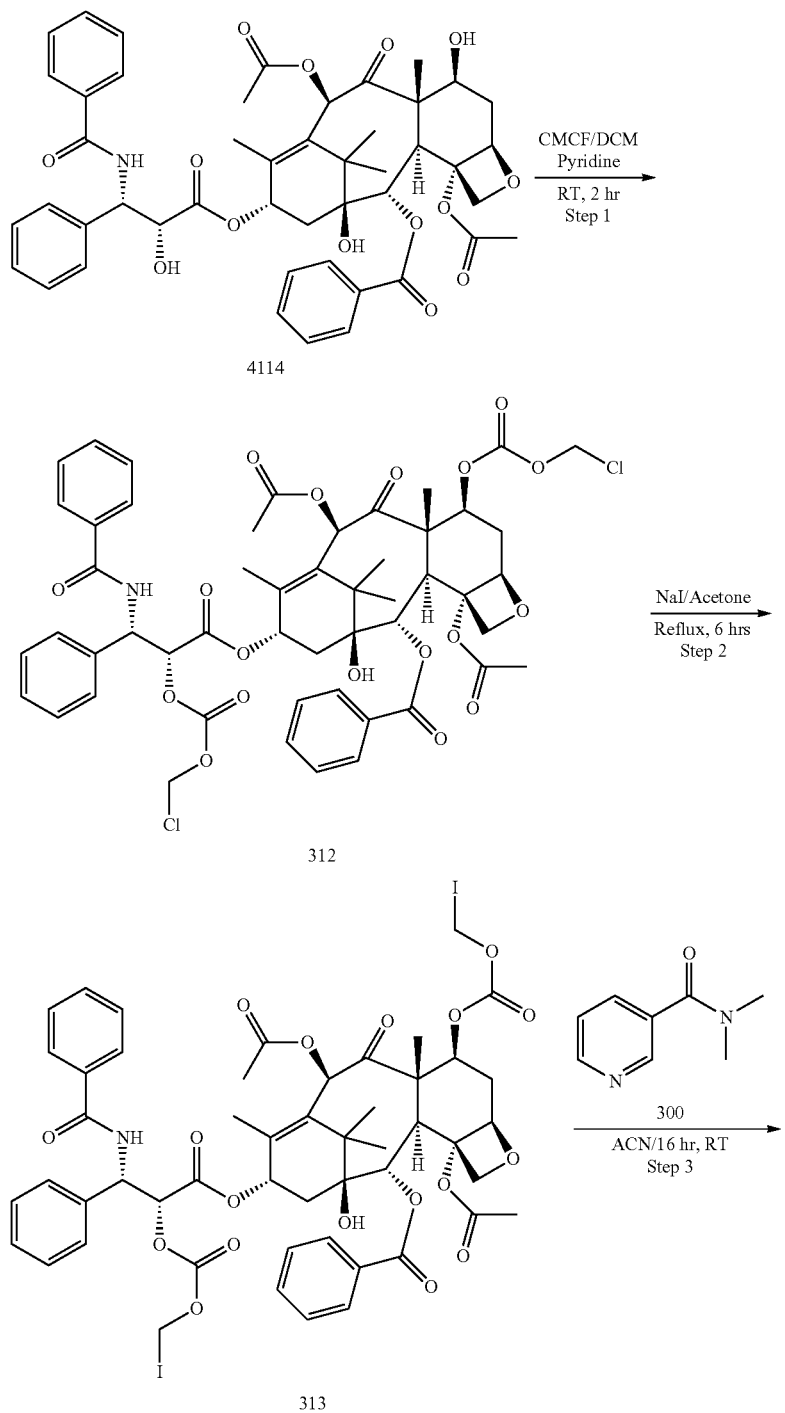

Scheme 41: Synthesis of modified forms of Paclitaxel, Derivative II

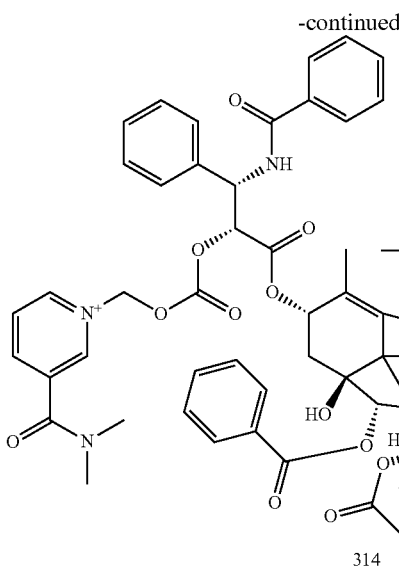
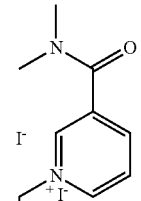

314

Step 1:
Pyridine (0.026 g, 23.0 mmol, 2.0 eq) was added to a solution of chloromethyl chloroformate (CMCF) [8](0.02 g, 23.0 mmol, 2.0 eq) in dry dichloromethane under an argon atmosphere at 0° C. At 0° C., a solution of paclitaxel [4114] (0.10 g, 11.7 mmol, 1.0 eq) in dry dichloromethane was added to the above reaction mixture. The reaction mixture was stirred at room temperature for 2 h. The reaction progress was monitored by TLC. After 2 h the reaction mixture was diluted with dichloromethane (25 ml), washed with a 10% solution of NaHCO$_3$ (15 ml), brine (10 ml), and then dried over anhydrous sodium sulfate. Evaporation of the solvent under vacuum gave a white solid, [312], (2aR,4S,4aS,6R,9S,11S,12S,12aR,12bS)-9-(((2R,3S)-3-benzamido-2-(((chloromethoxy)carbonyl)oxy)-3-phenylpropanoyl)oxy)-12-(benzoyloxy)-4-(((chloromethoxy)carbonyl)oxy)-11-hydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxete-6,12b-diyl diacetate, (0.11 g, 90%)
m/z: 1038.3

Step 2:
Sodium iodide (0.022 g, 145.0 mmol, 5 eq) was added to a solution of [312] (0.03 g, 29.0 mmol, 1 eq) in acetone. The resulting reaction mixture was refluxed for 6 h at 60° C. Reaction progress was monitored by TLC. The reaction mixture was cooled to room temperature and passed through a bed of silica (mesh 100-200). The silica bed was washed with acetone which was collected and evaporated under vacuum to yield a white solid [313], (2aR,4S,4aS,6R,9S,11S,12S,12aR,12bS)-9-(((2R,3S)-3-benzamido-2-(((iodomethoxy)carbonyl)oxy)-3-phenylpropanoyl)oxy)-12-(benzoyloxy)-11-hydroxy-4-(((iodomethoxy)carbonyl)oxy)-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxete-6,12b-diyl diacetate, (0.02 g, 70%)
m/z: 1221.7

Step 3:
Dimethyl nicotinate [300] (0.003 g, 20.0 mmol, x eq) was added to a solution of [313] (0.01 g, 10.0 mmol, x eq) in dry acetonitrile (y ml) under argon atmosphere. The resulting reaction mixture was stirred for 16 h at RT. Reaction progress was monitored by TLC. Solvent was removed under high vacuum pump to give a crude product. The crude product obtained was triturated with diethyl ether (10 ml×2) to give a yellow solid [314], mono(1-((((((1S,2R)-1-benzamido-3-(((2aR,4S,4aS,6R,9S,11S,12S,12aR,12bS)-6,12b-diacetoxy-12-(benzoyloxy)-4-((((3-(dimethylcarbamoyl)pyridin-1-ium-1-yl)methoxy)carbonyl)oxy)-11-hydroxy-4a,8,13,13-tetramethyl-5-oxo-2a,3,4,4a,5,6,9,10,11,12,12a,12b-dodeca hydro-1H-7,11-methanocyclodeca[3,4]benzo[1,2-b]oxet-9-yl)oxy)-3-oxo-1-phenylpropan-2-yl)oxy)carbonyl)oxy)methyl)-3-(dimethylcarbamoyl)pyridin-1-ium)doiodide (0.014 g, 60%).
m/z: 1268

Scheme 42: Synthesis of modified forms of Paclitaxel, Derivative III

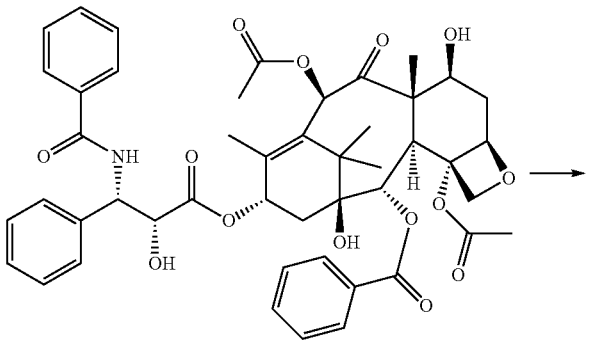

4114

-continued

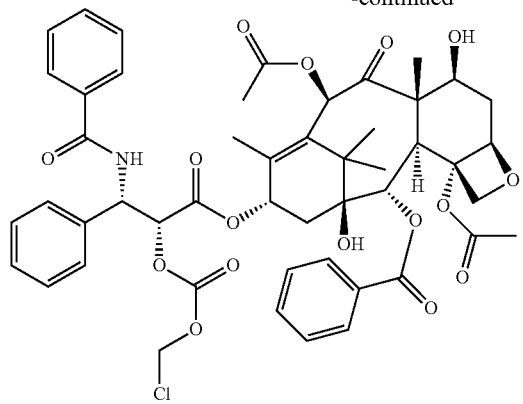

315

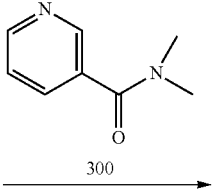

300

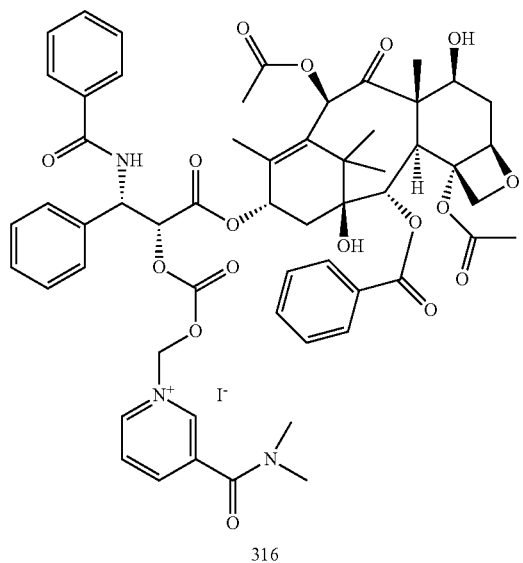

316

Step 1:

DIPEA (0.026 g, 46.0 mmol, 4.0 eq) was added to a solution of chloromethyl chloroformate (CMCF) [8] (0.04 g, 23.0 mmol, 4.0 eq) in dry dichloromethane under an argon atmosphere at 0° C. To the above reaction mixture at 0° C., a solution of paclitaxel 14114 (0.10 g, 11.7 mmol, 1.0 eq) in dry dichloromethane (y ml) was added. The reaction mixture was stirred at room temperature for 16 h. reaction progress was monitored by TLC. After 16 h the reaction mixture was diluted with dichloromethane (25 ml), washed with a 10% solution of NaHCO$_3$ (15 ml), brine (10 ml), and then dried over anhydrous Na$_2$SO$_4$. Evaporation of the solvents under vacuum gave a white solid, (2aR,4S,4aS,6R,9S,11S,12S,12aR,12bS)-9-(((2R,3S)-3-benzamido-2-(((chloromethoxy)carbonyl)oxy)-3-phenylpropanoyl)oxy)-12-(benzoyloxy)-4,11-dihydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxete-6,12b-diyl diacetate [315], (0.08 g, 70%)

m/z=946

Step 2:

Sodium iodide (0.14 g, 0.42 mmol, 4.0 eq) was added to a solution of [315] (0.10 g, 0.116 mmol, 1.0 eq) in Acetonitrile (5 ml) followed by the addition of dimethyl nicotinamide [300] (0.034 g, 0.233 mmol, 2.0 eq). The resulting reaction mixture was stirred at 50° C. for 24 h. Reaction progress was monitored by TLC. Solvent was removed under vacuum to get a crude product. DCM was added to the crude product to precipitate out sodium iodide, which was separated by filtration, and the filtrate was evaporated under vacuum to get a yellow oil 1-((((((1S,2R)-1-benzamido-3-(((2aR,4S,4aS,6R,9S,11S,12S,12aR,12bS)-6,12b-diacetoxy-12-(benzoyloxy)-4,11-dihydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxet-9-yl)oxy)-3-oxo-1-phenylpropan-2-yl)oxy)carbonyl)oxy)methyl)-3-(dimethylcarbamoyl)pyridin-1-ium iodide iodomethyl 2-(4-isobutylphenyl)propanoate [316] (0.012 g, 10%).

m/z: 1060.

Other derivatives of paclitaxel may also be synthesized in a similar manner, for instance see compound number 9400 and 9405 as below:

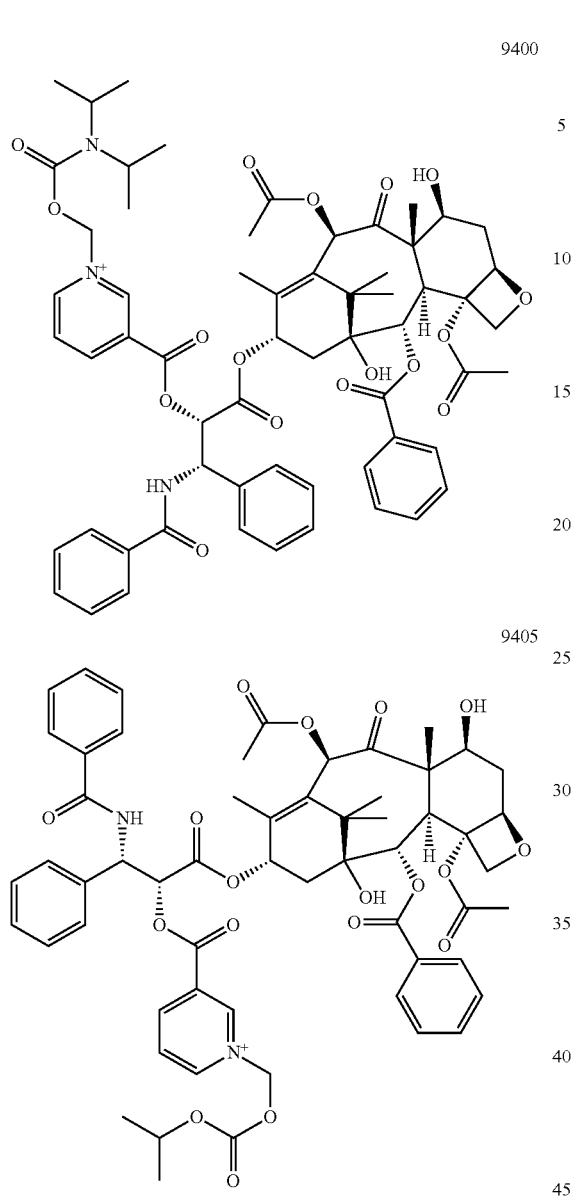

Examples of Chemical Modifications of Drugs/Biologically Active Compounds with a Carboxylic Acid as a Functional Group Scheme 43: Synthesis of modified forms of Aspirin, Derivative I:

Derivative I:

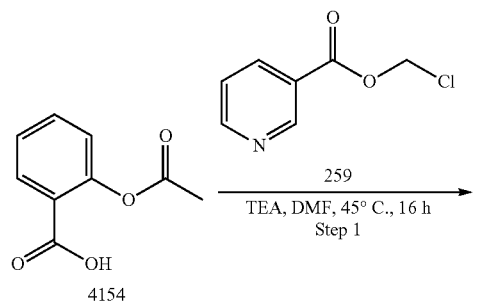

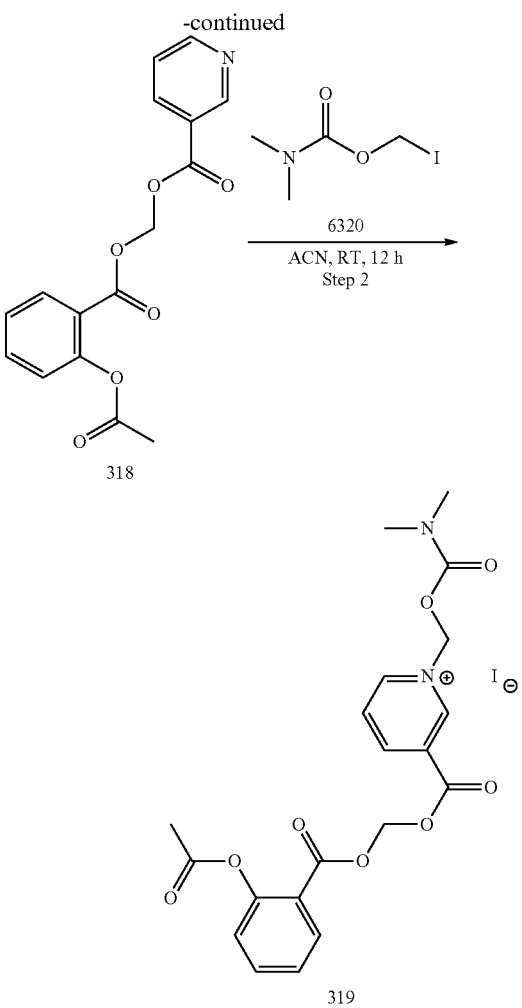

TEA (0.08 ml, 0.68 mmol, 1.2 eq) and methyl formyl reagent [259] (0.1 g, 0.56 mmol, 1.0 eq) was added to a solution of aspirin [4154] and 2-acetoxybenzoic acid, (0.1 g, 0.56 mmol, 1.0 eq) in DMF (2 ml). The reaction mixture was heated at 45° C. for 16 h, followed by cooling to room temperature and dilution with water. The organic material was extracted with ethyl acetate, was washed with water dried over $Na_2SO_4$ and evaporated under vacuum to get crude product. The crude product was purified by silica gel column chromatography (ethyl acetate in cyclohexane 100-200 mesh) to yield a dark colored sticky product [318], ((2-acetoxybenzoyl)oxy)methyl nicotinate, (0.09 g, 50%).

m/z: 316

[318] (0.09 g, 0.28 mmol, 1.0 eq) was dissolved in ACN (2 ml) followed by addition of iodomethyl dimethylcarbamate reagent [6320] (0.078 g, 0.34 mmol, 1.2 eq) and stirred at RT for 12 h. Excess solvent was evaporated under vacuum to obtain crude product. Compound was purified by precipitation of crude product using DCM: diethyl ether, which provided solid [319], 3-((((2-acetoxybenzoyl)oxy)methoxy)carbonyl)-1-(((dimethylcarbamoyl)oxy)methyl)pyridin-1-ium iodide (0.085 g, 71%).

m/z: 417

$^1$H NMR [CDCl$_3$, 300 MHz]: δ 9.82-9.80, (d, 1H); 9.588, (s, 1H); 9.07-9.03, (d, 1H); 8.39-8.34, (t, 1H); 8.11-8.06, (d, 1H); 7.66-7.63, (t, 1H), 7.38-7.33, (t, 1H); 7.15-7.12, (d, 1H), 6.26, (s, 2H), 3.014, (s, 3H); 2.89, (s, 3H); 2.34, (s, 3H)

Scheme 44: Synthesis of modified forms of Aspirin, Derivative II:

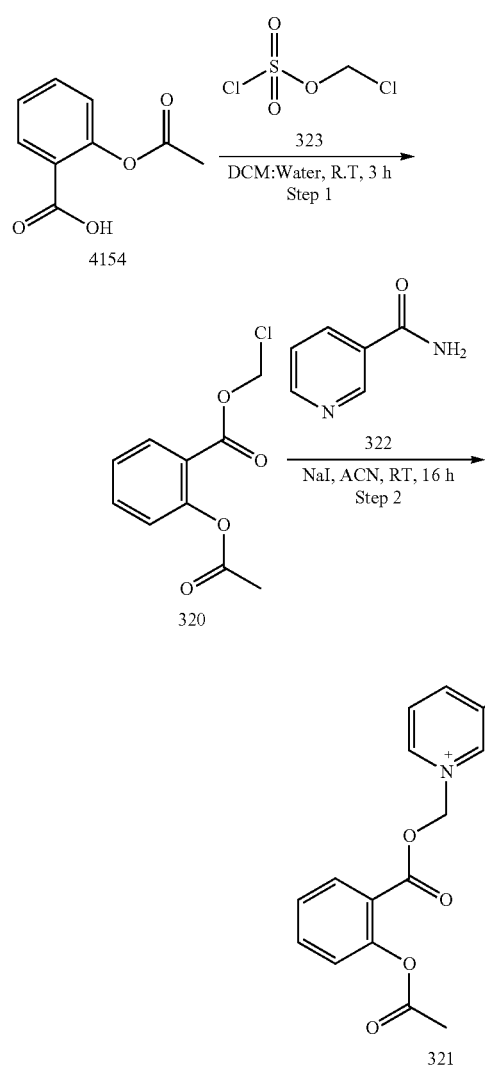

Step 1:

To a vigorously stirred solution of Aspirin [4154] (0.2 g, 1.11 mmol, 1.0 eq) at room temperature, sodium bicarbonate (0.3 g, 4.1 mmol, 3.81 eq), and tetrabutylammonium bisulfate (0.035 g, 0.11 mmol, 0.1 eq) in water (5 ml) was added dichloromethane (5 ml) followed by the dropwise addition of a solution of chloromethyl chlorosulfate [323] (0.02 ml, 1.2 mmol, 1.1 eq) in dichloromethane (5 ml). After stirring at room temperature for 1 h, dichloromethane layer was separated, washed with 5% aqueous sodium bicarbonate solution (1×25 ml), separated and dried over Na$_2$SO$_4$, filtered and concentrated under vacuum to get a colorless oil [320] (Chloromethyl 2-acetoxybenzoate), (0.18 mg, 71%)

m/z: 229.

Step 2:

Chloromethyl 2-acetoxybenzoate [320] (0.050 g, 0.21 mmol, 1.0 eq) sodium iodide (0.098 g, 0.6 mmol, 3.0 eq) and nicotinamide [322] (0.026 g, 0.2 mmol, 1.0 eq) were added in ACN (3 ml). The reaction mixture was stirred at RT for 16 h Reaction progress was monitored by TLC. After completion of the reaction solvent was removed vacuum to get a crude product. The crude product obtained was triturated with diethyl ether (2×10 ml) to give the desired product [321], 1-(((2-acetoxybenzoyl)oxy)-3-carboylpyridin-1-ium iodide (0.01 g, 14%)

m/z: 315

Scheme 45: Synthesis of modified forms of Indomethacin

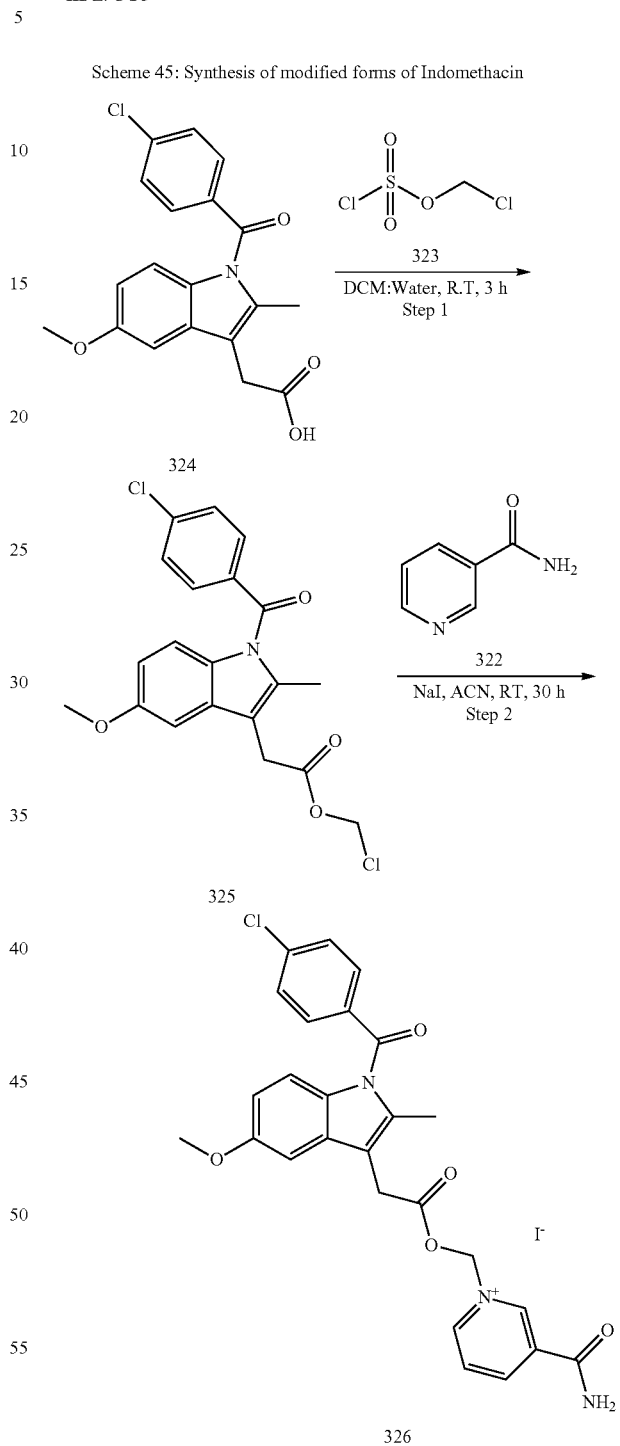

Step 1:

A mixture of Indomethacin [324] (0.2 g, 0.56 mmol, 1.0 eq), DCM (1 ml), water (1 ml), sodium bicarbonate (0.126 g, 1.78 mmol, 3.81 eq) and tetrabutylammonium hydrogen sulfate (0.018 g, 0.056 mmol, 0.1 eq) were stirred room temperature for 2 min. A solution of chloromethyl chlorosulfate [323] (0.1 ml, 0.61 mmol, 1.1 eq) in DCM (1 ml) was added dropwise. This biphasic system was stirred at RT for 1 h. The organic layer was separated and dried over Na$_2$SO$_4$. Evaporation of the solvent under vacuum gave a yellow oil [325] (Chloromethyl 2-(-1-(4-chlorobenzoyl)-5methoxy-2-methyl-1H-indol-3-yl)acetate), (0.16 ml, 70%)

Step 2:

Chloromethyl 2-(-1-(4-chlorobenzoyl)-5-methoxy-2-methyl-1H-indol-3-yl)acetate [325] (0.05 g, 0.12 mmol, 1.0 eq) sodium iodide (0.055 g, 0.36 mmol, 3.0 eq) and nicotinamide (0.015 g, 0.12 mmol, 1.0 eq) were added in ACN (3 ml). The reaction mixture was stirred at RT for 16 h Reaction progress was monitored by TLC. After completion solvent was removed under vacuum to get a crude product. The crude product obtained was triturated with diethyl ether (2×10 ml) to get the desired product [326], 3-carbamoyl-1-((2-(-1-(4-chlorobenzoyl)-5-methoxy-2-methyl-1H-indol-3-yl)acetoxy)methyl)pyridine-1-ium iodide (0.015 g, 25%).

Scheme 46: Synthesis of modified forms of Ibuprofen:

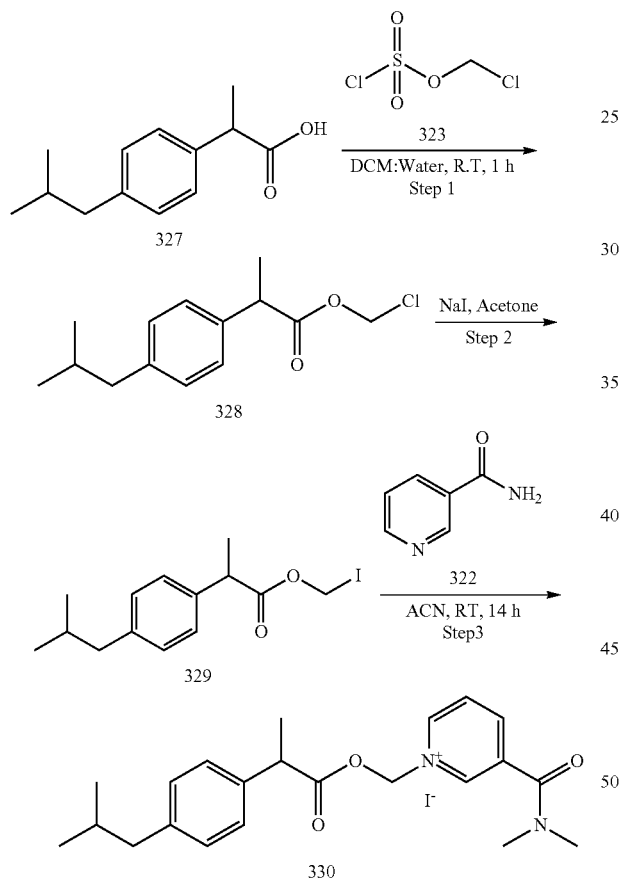

Step 1:

Ibuprofen [327] (0.1 g, 0.48 mmol, 1.0 eq) DCM (2 ml), water (2 ml), sodium bicarbonate (0.131 g, 1.8 mmol, 3.81 eq) and tetrabutylammonium hydrogen sulfate (0.016 g, 0.05 mmol, 0.1 eq) were stirred at 25° C. for 2 min. to the above reaction mixture, a solution of chloromethyl chlorosulfate [323] (0.08 ml, 0.51 mmol, 1.1 eq) in DCM (1 ml) was added dropwise and the biphasic system was stirred at RT for 1 h. The organic layer was separated and dried over anhydrous Na$_2$SO$_4$. Evaporation of the solvent under vacuum gave the desired product as a colorless oil [328] (chloromethyl 2-(4-isobutylphenyl)propanoate), (0.06 ml, 50%)

Step 2:

Sodium iodide (0.14 g, 0.925 mmol, 4.0 eq) was added to a solution of [328] (0.06 g, 0.22 mmol, 1.0 eq) in acetone (5 ml). The resulting reaction mixture was stirred at RT for 14 h. Reaction progress was monitored by TLC. Solvent was removed under vacuum to get a crude product. Then DCM was added to the crude product to precipitate out sodium iodide which was separated by filtration, and filtrate was evaporated under vacuum to get a yellow oil [329]iodomethyl 2-(4-isobutylphenyl)propanoate (0.07 g, 86%).

Step 3:

Iodomethyl 2-(4-isobutylphenyl)propanoate [329] (0.07 g, 0.23 mmol, 1.0 eq) and nicotinamide [322](0.03 g, 0.22 mmol, 1.0 eq) were added in ACN (3 ml). The reaction mixture was stirred at RT for 16 h. Reaction progress was monitored by TLC. Solvent was removed under vacuum to get a crude product. The crude product obtained was triturated with diethyl ether (2×5 ml) to give the desired product

[330], 3-(dimethylcarbamoyl)-1-(((2-(4-isobutylphenyl)propanoyl)oxy)methyl)pyridin-1-ium iodide (0.045 g, 60%).

Scheme 47: Synthesis of modified forms of Diclofenac

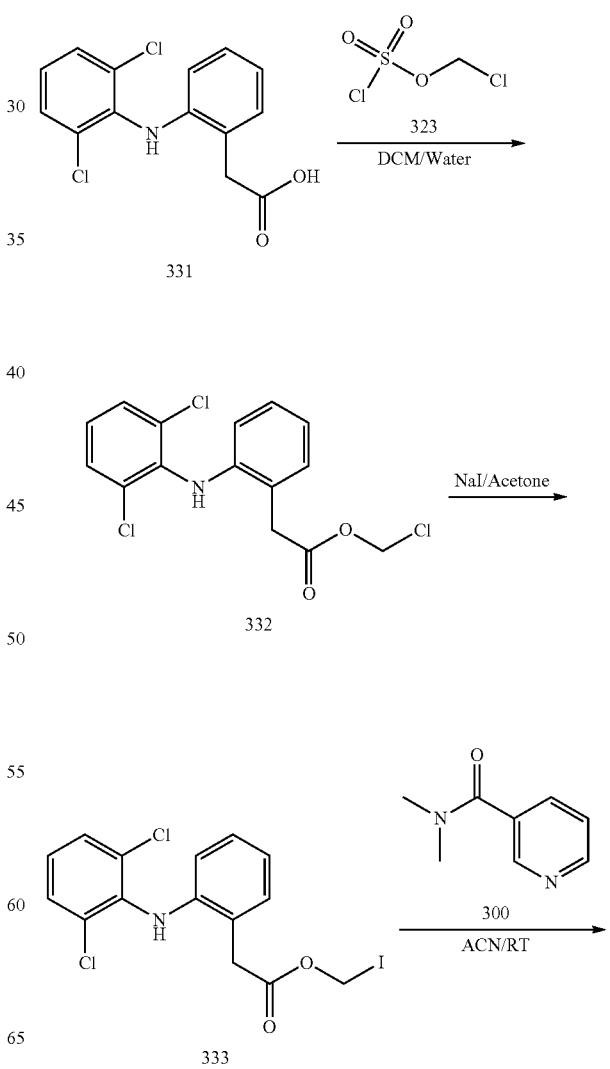

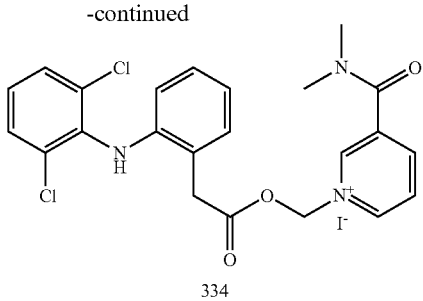

334

Step 1:

Diclofenac sodium [331] (0.1 g, 0.33 mmol, 1.0 eq) DCM (2 ml), water (2 ml), sodium bicarbonate (0.105 g, 0.125 mmol, 3.81 eq) and tetrabutylammonium hydrogen sulfate (0.011 g, 0.033 mmol, 0.1 eq) were stirred at 25° C. for 2 min. A solution of chloromethyl chlorosulfate [323] (0.06 g, 0.363 mmol, 1.1 eq) in DCM (1 ml) was added dropwise. This biphasic system was stirred at RT for 1 h. The organic layer was separated and dried over anhydrous $Na_2SO_4$. Evaporation of the solvent under vacuum gave the product as a white solid, chloromethyl 2-(2-((2,6-dichlorophenyl)amino)phenyl)acetate [332] (0.11 g, 95%)

m/z: 343

Step 2:

Sodium iodide (0.192 g, 1.28 mmol, 4.0 eq) was added to a solution of [332] (0.11 g, 0.32 mmol, 1.0 eq) in acetone (5 ml). The resulting reaction mixture was stirred at RT for 16 h. Reaction progress was monitored by TLC. Solvent was removed under vacuum to get a crude product. DCM was added to the crude product to precipitate out sodium iodide, which was separated by filtration, and the filtrate was evaporated to get a yellow oil [333]iodomethyl 2-(2-((2,6-dichlorophenyl)amino)phenyl)acetate (0.1 g, 71%)

m/z: 436

Step 3:

Iodomethyl 2-(2-((2,6-dichlorophenyl)amino)phenyl)acetate [333] (0.1 g, 0.23 mmol, 1.0 eq) & dimethyl Nicotinamide (0.034 g, 0.23 mmol, 1.0 eq) were added in ACN (3 ml). The reaction mixture was stirred at RT for 16 h. Reaction progress was monitored by TLC. Solvent was removed under vacuum to get a crude product. The crude product obtained was triturated with diethyl ether (2×5 ml) to get the desired product 1-((2-(2-((2,6-dichlorophenyl)amino)phenyl)acetoxy)methyl)-3-(dimethylcarbamoyl)pyridin-1-ium iodide [334] (0.082 g, 61%).

m/z: 585

Scheme 48: Synthesis of modified forms of HPPH:

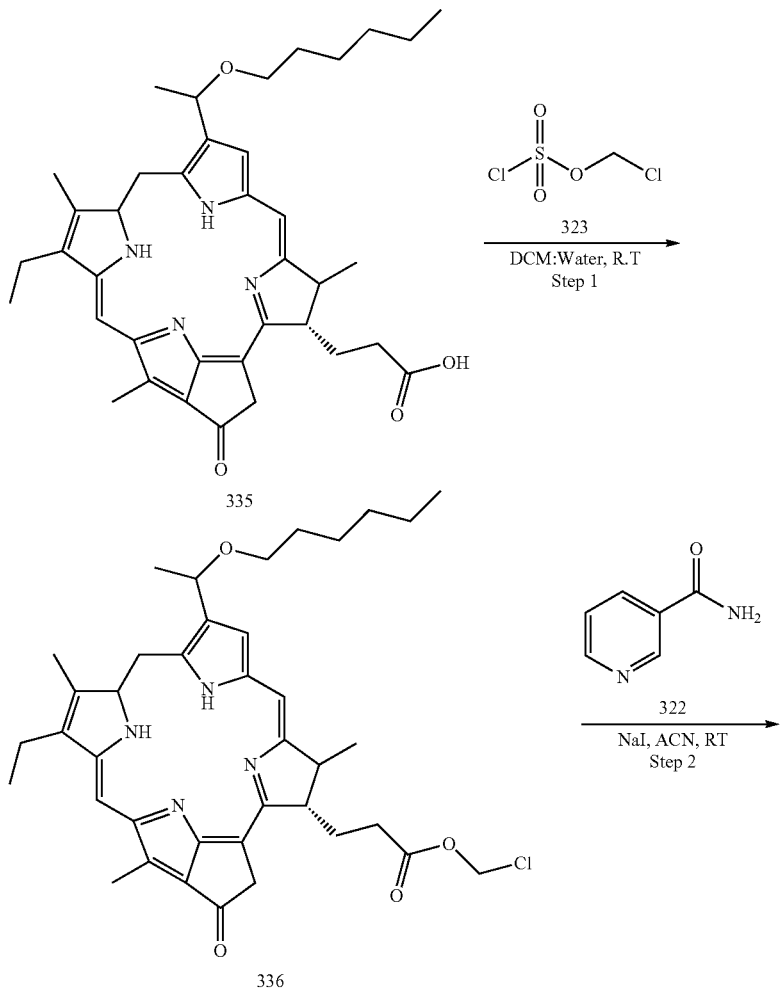

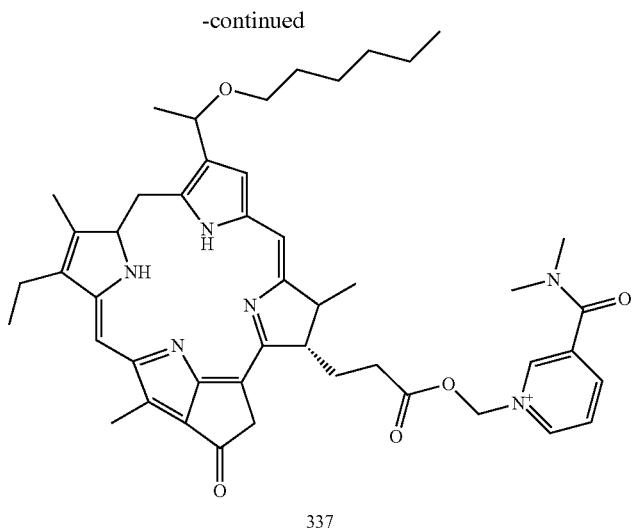

337

Step 1:

HPPH [335] (0.4 g, 0.62 mmol, 1.0 eq) DCM (5 ml), water (5 ml), sodium bicarbonate (0.17 g, 2.3 mmol, 3.81 eq) and tetrabutylammonium hydrogen sulfate (0.02 g, 0.05 mmol, 0.1 eq) were stirred at 25° C. for 2 min in dark. A solution of chloromethyl chlorosulfate [323] (0.11 ml, 0.69 mmol, 1.1 eq) in DCM (1 ml) was added dropwise. This biphasic system was stirred at RT in dark for 1 h. The organic phase was separated and dried over anhydrous $Na_2SO_4$. Evaporation of the solvent under vacuum gave the desired product [336] as black solid (0.42 g, 80%)

Step 2:

[336] (0.05 g, 0.072 mmol, 1.0 eq) sodium iodide (0.038 g, 0.21 mmol, 3.0 eq) and nicotinamide [322](0.011 g, 0.072 mmol, 1.0 eq) were added in ACN (3 ml). The reaction mixture was stirred at RT for 16 h in dark. Reaction progress was monitored by TLC. Solvent was removed under vacuum to get a crude product. The crude product obtained was triturated with diethyl ether (2×10 ml) to get the desired product [337], as black solid (0.044 g, 75%).

Examples of Chemical Modifications of Drugs/Biologically Active Compounds with an Amide as a Functional Group Scheme 49: Synthesis of modified forms of linalidomide

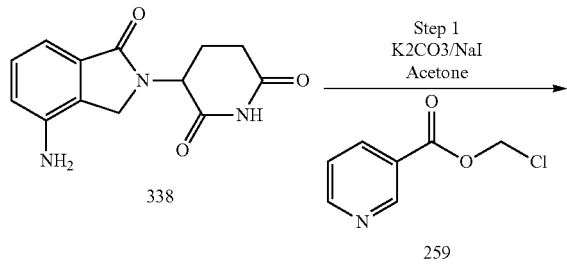

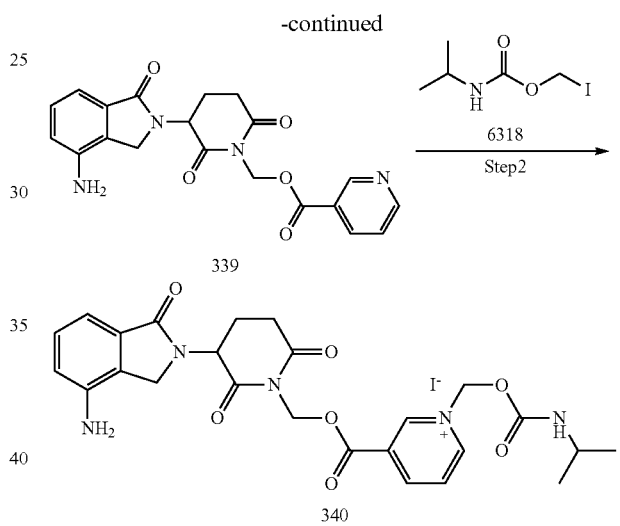

339

340

Step 1:

$K_2CO_3$ (0.105 g, 0.76 mmol, 2.0 eq) was added to a solution of 3-(4-amino-1-oxoisoindolin-2-yl)piperidine-2,6-dione [338] (0.2 g, 0.38 mmol, 1.0 eq) in Acetone (17 ml) under $N_2$ atmosphere at room temperature and heated at 60° C. for 30 min followed by the addition of methyl formyl reagent [259](0.164 g, 0.48 mmol, 1.25 eq) and sodium Iodide (0.29 g, 0.95 mmol, 2.5 eq). The resulting reaction mixture was refluxed at 60° C. for 24 h. Reaction progress was monitored by TLC and mass spectroscopy. Then, the reaction mass was filtered through cellite bed and washed with acetone (2×25 ml). The acetone layer was then evaporated to dryness under vacuum to yield a brown gel. The resultant crude product was purified on column chromatography (2% MeOH in DCM as eluent 100-200 mesh silica) to yield a white powder, (3-(4-amino-1-oxoisoindolin-2-yl)-2,6-dioxopiperidin-1-yl)methyl nicotinate [339](0.032 g, 20%).

m/z: 395

Step 2:

Iodomethyl isopropylcarbamate [6318] (0.018 g, 0.028 mmol, 1.0 eq) was added to a solution of (3-(4-amino-1-oxoisoindolin-2-yl)-2,6-dioxopiperidin-1-yl)methyl nicotinate [339] (0.03 g, 0.028 mmol, 1.0 eq) in DCM (5 ml). The reaction mixture was stirred at RT for 16 h. The DCM was evaporated under reduced pressure and washed thoroughly with diethyl ether to yield a yellow powder [340], 3-(((3-(4-amino-1-oxoisoindolin-2-yl)-2,6-dioxopiperidin-1-yl)methoxy)carbonyl)-1-(((isopropylcarbamoyl)oxy)methyl)pyridin-1-ium iodide, (0.015 g, 40%).

m/z: 510

Example of Chemical Modifications of Drugs/Biologically Active Compounds with Aliphatic Tertiary Nitrogen as a Heteroatom Synthesis of Modified Forms of Imatinib flask, and iodomethyl pivalate [40] (0.049 g, 0.2 mmol, 1 eq) was added at RT. After stirring for 3-4 hours, the precipitate formed was filtered and washed with DCM to give the product, 1-methyl-4-(4-((4-methyl-3-((4-(pyridin-3-yl)pyrimidin-2-yl)amino)phenyl)carbamoyl)benzyl)-1-((pivaloyloxy)methyl)piperazin-1-ium iodide, [41] as a yellow solid. (0.040 g, 27% yield).

m/z 608.

$^1$H NMR (DMSO): δ 1.24 (s, 9H), 2.20 (s, 3H), 2.7 (m, 4H), 3.10 (s, 3H), 3.07 (s, 3H), 3.48 (br s, 4H), 3.71 (s, 2H), 5.39 (s,

Scheme 50: Derivatization at an aliphatic tertiary amine with a Type I agent

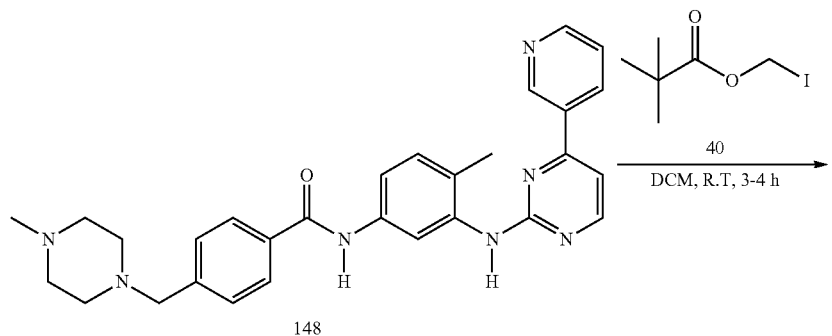

Imatinib, N-(4-methyl-3-((4-(pyridin-3-yl)pyrimidin-2-yl)amino)phenyl)-4-((4-methylpiperazin-1-yl)methyl)benzamide, [148] (0.100 g, 0.2 mmol, 1 eq) was dissolved in dichloromethane (10 ml) in a 25 ml two-necked round bottom

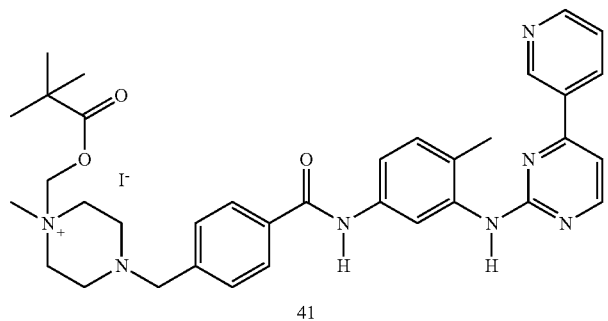

2H), 7.19 (d, 1H), 7.42-7.54 (m, 5H), 7.9 (d, 2H), 8.06 (d, 1H), 8.45-8.52 (m, 2H), 8.60 (dd, 1H), 9.0 (s, 1H), 9.27 (d, 1H), 10.18 (s, 1H).

Scheme 51: Derivatization at both an aromatic nitrogen and an aliphatic tertiary amine, with a Type I derivatizing agent

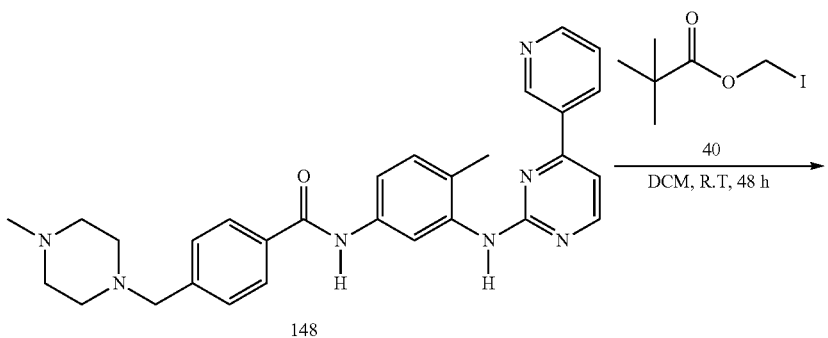

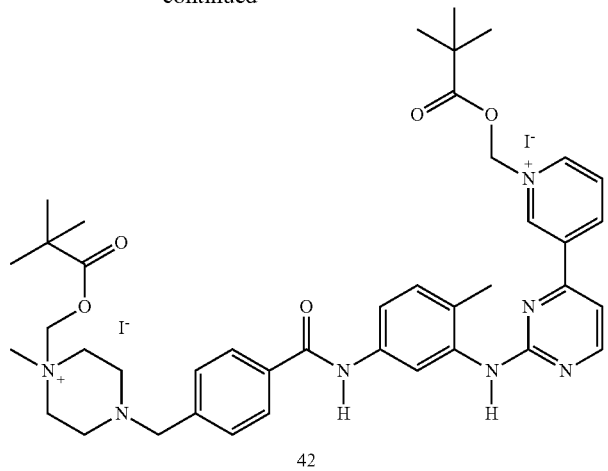

42

Imatinib [148] (0.100 g, 0.2 mmol, 1 eq) was dissolved in DCM (10 ml) in a 25 ml two-necked round bottomed flask and iodomethyl pivalate [40] (0.185 g, 0.77 mmol, 3.8 eq) was added while stirring at RT. After 48 h stirring, the precipitate formed was filtered under vacuum and washed with DCM to give the product, 1-methyl-4-(4-((4-methyl-3-((4-(1-((pivaloyloxy)methyl)pyridin-1-ium-3-yl)pyrimidin-2-yl)amino)phenyl)carbamoyl)benzyl)-1-((pivaloyloxy)methyl)piperazin-1-ium diiodide [42], as a yellow solid. (0.050 g, 25% yield).

m/z=361

$^1$H NMR (DMSO, 300 MHz): δ 1.10 (s, 9H), 1.24 (s, 9H), 2.24 (s, 3H), 2.78 (m, 4H), 3.11 (s, 3H), 3.48 (br s, 4H), 3.72 (s, 2H), 5.40 (s, 2H), 6.50 (s, 2H), 7.21-7.24 (d, 1H), 7.32 (d, 1H), 7.44 (dd, 1H), 7.58 (d, 1H), 7.98 (d, 2H), 8.20 (s, 1H), 8.36 (dd, 1H), 8.72 (d, 1H), 9.23 (s, 1H), 9.28 (d, 1H), 9.36 (d, 1H), 9.9 (s, 1H), 10.25 (s, 1H)

Scheme 52: Modification of Docetaxol.

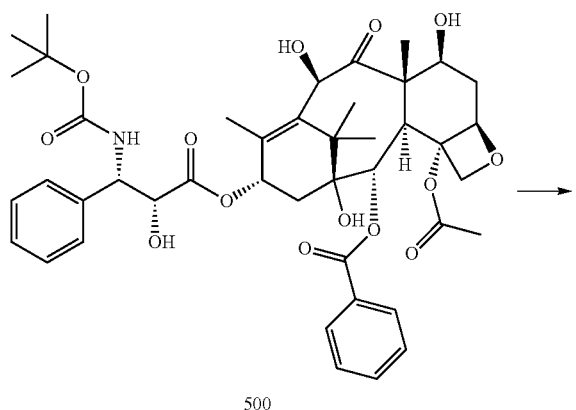

500

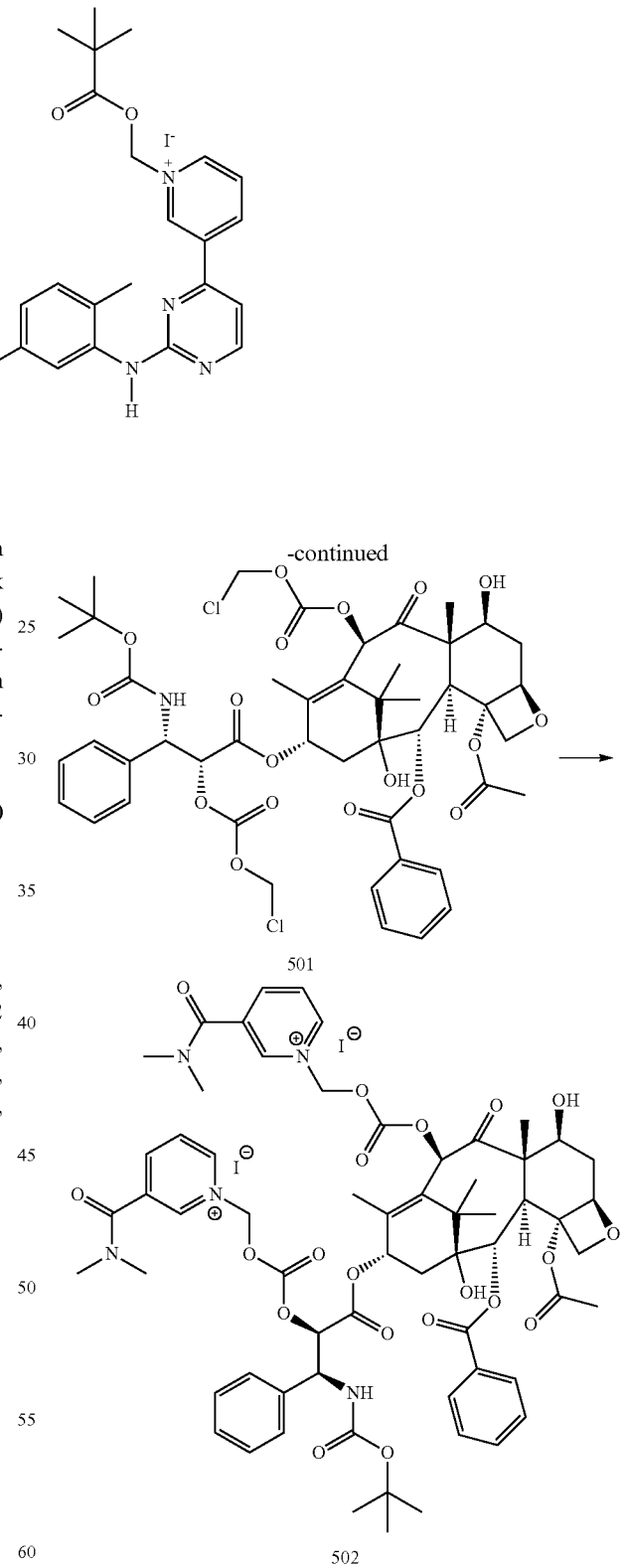

501

502

To a solution of docetaxel [500] (0.06 g, 0.074 mmol, 1.0 eq) in DCM (5 ml) was added pyridine (0.1 ml) at RT. The reaction mixture was cooled to −23° C., followed by the addition of chloromethyl chloroformate (0.054 g, 0.42 mmol, 6.0 eq) and stirred for 30 min at −23° C. The reaction mixture was washed with dil. HCl, followed by brine, dried over anhydrous Na$_2$SO$_4$ and solvent removed under vacuum to get the desired product [501].

The product was confirmed by $^1$H NMR.

To a solution of docetaxel [501] (0.075 g, 0.093 mmol, 1.0 eq) in ACN (5 ml) was added NaI (0.055 g, 0.372 mmol, 4.0 eq) and N,N-dimethyl nicotinamide (0.023 g, 0.186 mmol, 2.0 eq) at RT. The reaction mixture was 60° C. by brine, dried over night. Solvent was removed under vacuum, solid residue taken in DCM, inorganic impurities filtered off, DCM removed under vacuum and the product triturated with ether, filtered and vacuum dried to get the product [502].

Example Demonstrating the Effect of Modification of the Compounds:

The compounds as synthesized above are tested for their pK by the procedure as described above and their PK is provided at Table 7.

TABLE 7

PK of Modified Drugs

| Compound Number | Compound Name | PK Value (AUC)* nm/h | Dosage (mpk) | Vehicle |
|---|---|---|---|---|
| 4154 | Aspirin | 3839 | 30.00 | PEG400 |
| 318 | Aspirin Mod Drug | 1112 | 30.00 | PEG400 |
| 4114 | Paclitaxel | 186 | 10.00 | PEG400 |
| 311 | Paclitaxel Mod Drug | 1491 | 10.00 | 5% Tween 80, Ethanol:Normal Saline:: 1:30 |
| 9400 | Paclitaxel Mod Drug | 135 | 14.50 | PEG400 |
| 316 | Paclitaxol Mod Drug | 87 | 10.00 | 40% PEG400, 10% Ethanol, Distilled Water |
| 9405 | Paclitaxol Mod Drug | 519 | 10.00 | 40% PEG400, 10% Ethanol, Distilled Water |
| 4102 | Sildenafil | 1451 | 10.00 | Normal saline |
| 295 | Sildenafil Mod Drug | 146 | 10.00 | Normal saline |
| 9500 | Sildenafil Mod Drug | 382 | 10.00 | Normal saline |
| 9505 | Sildenafil Mod Drug | 261 | 10.00 | Normal saline |
| 9510 | Sildenafil Mod Drug | 519 | 10.00 | Normal saline |
| 4150 | SN-38 | BDL | 10.00 | PEG400 |
| 306 | SN-38 Mod Drug | BDL | 3.00 | PEG400 |
| 305 | SN-38 Mod Drug | BDL | 10.00 | PEG400 |
| 148 | Imatinib | 9199 | 3.00 | PEG400 |
| 41 | Imatinib mod drug | 5233 | 3.00 | PEG400 |

We claim:

1. A method of modifying physicochemical, biological, pharmacokinetics, and/or pharmaco dynamics properties of a pharmaceutical compound, comprising incubating the pharmaceutical compound with a modifying agent having the formula of compound 1,

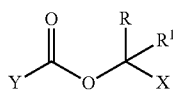

1 under conditions to cause Y—(CO)—O— to covalently bond to a tertiary nitrogen on the pharmaceutical compound, thereby forming a quaternary nitrogen, wherein X is selected from Cl, Br, I, OTs, or OMs;

Y is selected from R$^2$, OR$^2$, or N(R$^2$)$_2$; and

R and R$^1$ are independently H, C$_1$-C$_8$ straight or branched chain alkyl; C$_1$-C$_8$ straight or branched chain alkyl that has been substituted with 1-3 hetero atoms selected from O, N, S, SO, or SO$_2$; 3-7 membered cycloalkyl; 3-7 membered cyclo alkyl that has been substituted with 1-3 hetero atoms selected from O, N, S, SO, or SO$_2$ and/or lower alkyl, straight or branched alkyl, alkoxy; alkaryl, aryl, heteroaryl, or alkheteroaryl;

R and R$^1$ can also be joined to form a 3-7 membered carbocyclic ring optionally containing 1-2 heteroatoms selected from, O, N, S, SO, SO$_2$ and also be optionally substituted with alkoxy, F or Cl;

R$^2$ independently is H, C$_1$-C$_8$ straight or branch chain alkyl; C$_1$-C$_8$ straight or branched chain alkyl that has been substituted with 1-3 heteroatoms selected from O, N, S, SO, or SO$_2$; 3-7 membered cyclo alkyl; 3-7 membered cyclo alkyl that has been substituted with 1-3 heteroatoms selected from O, N, S, SO, or SO$_2$ and/or lower alkyl, straight or branched alkyl, alkoxy; alkaryl, aryl, heteroaryl, or alkheteroaryl; or is independently part of a 3-7 membered ring optionally containing additional 1-2 heteroatoms selected from, O, N, S, SO, SO$_2$ and also be optionally substituted with alkoxy, F or Cl;

wherein when Y=OR$^2$ then compound 1 is selected from the group consisting of:

i. chloromethyl isopropyl carbonate;
ii. benzyl chloromethyl carbonate;
iii. chloromethylmorpholinomethyl carbonate;
iv. chloromethyl isobutyl carbonate;
v. (S)-sec-butyl chloromethyl carbonate;
vi. (R)-sec-butyl chloromethyl carbonate;
vii. chloromethyl ((3S,5R)-3,5-dimethylmorpholino)methyl carbonate;
viii. chloromethyl 2-methylcyclopropyl carbonate;
ix. chloromethyl2-methoxyethyl carbonate;
x. chloromethyl propyl carbonate;
xi. chloromethylcyclobutyl carbonate;
xii. chloromethylcyclopropyl carbonate;
xiii. chloromethyl 2,2-dimethylcyclobutyl carbonate;
xiv. chloromethylcyclopentyl carbonate;
xv. chloromethyloxetan-3-yl carbonate;
xv. (S)-chloromethyltetrahydrofuran-3-yl carbonate;
xvii. chloromethylcyclohexylmethyl carbonate;
xviii. chloromethyl 3-methoxycyclohexyl carbonate;
xix. (R)-chloromethyltetrahydrofuran-3-yl carbonate;
xx. chloromethylethoxymethyl carbonate;
xxi. chloromethyloxepan-4-yl carbonate;
xxii. (1R,2S,4S)-bicyclo[2.2.1]heptan-2-ylchloromethyl carbonate;

xxiii. chloromethyl 2,3-dihydro-1H-inden-1-yl carbonate;
xxiv. benzyl chloromethyl carbonate;
xxv. (S)-chloromethyl 1-phenylethyl carbonate;
xxvi. chloromethylcyclohexyl carbonate;
xxvii. chloromethyl isobutyl carbonate;
xxviii. chloromethyl 4-methylcyclohexyl carbonate;
xxix. chloromethyl 2-(methylthio)ethyl carbonate;
xxx. chloromethyl 3-methylcyclohexyl carbonate;
xxxi. chloromethylpentan-2-yl carbonate;
xxxii. chloromethylneopentyl carbonate;
xxxiii. methyl 1-((chloromethoxy)carbonyloxy)cyclopropanecarboxylate;
xxxiv. chloromethylcyclopropylmethyl carbonate;
xxxv. chloromethyl 2,2-diethoxyethyl carbonate;
xxxvi. chloromethylcyclopentylmethyl carbonate;
xxxvii. methyl 2-((chloromethoxy)carbonyloxy)propanoate;
xxxviii. (S)-chloromethyl 2,2,4-trimethylcyclopent-3-enyl carbonate;
xxxix. chloromethyl 1,3-dioxolan-2-yl carbonate;
xl. chloromethyl (2,6-dimethylcyclohexyl)methyl carbonate;
xli. chloromethyl 2-(tetrahydro-2H-pyran-2-yl)ethyl carbonate;
xlii. chloromethyl(tetrahydro-2H-pyran-4-yl)methyl carbonate;
xliii. chloromethyltetrahydro-2H-pyran-4-yl carbonate;
xliv. chloromethyl 1-methylcyclopentyl carbonate;
xlv. chloromethyl 1-cyclopentylethyl carbonate;
xlvi. chloromethyl 3-methylcyclopentyl carbonate;
xlvii. chloromethyl 3,3-dimethylcyclohexyl carbonate;
xlviii. chloromethyl 2,5-dimethylcyclohexyl carbonate;
xlix. chloromethyl 1-(4-methylcyclohexyl)ethyl carbonate;
l. chloromethyl (3-methyloxetan-3-yl)methyl carbonate;
li. chloromethyl (3-methyloxetan-3-yl)methyl carbonate;
lii. chloromethyl 2-isopropoxyethyl carbonate;
liii. (chloromethyl carbonic) 5-((3aS,4S,6aR)-2-oxohexahydro-1H-thieno[3,4-d]imidazol-4-yl)pentanoic anhydride;
liv. 4-((chloromethoxy)carbonyloxy)-2-hydroxy-4-oxobutanoic acid;
lv. chloromethyl 4-formyl-2-methoxyphenyl carbonate;
lvi. chloromethyl 3-oxobutan-2-yl carbonate;
lvii. methyl 4-((chloromethoxy)carbonyloxy)benzoate;
lviii. (R)-2-amino-3-((chloromethoxy)carbonyloxy)propanoic acid;
lix. 3-tert-butyl-4-methoxyphenylchloromethyl carbonate;
lx. (R)-2-amino-3-(4-((chloromethoxy)carbonyloxy)phenyl)propanoic acid;
lxi. (R)-2-amino-4-((chloromethoxy)carbonyloxy)-4-oxobutanoic acid;
lxii. (E)-chloromethyl 3,7-dimethylocta-2,6-dienyl carbonate;
lxiii. methyl 4-((chloromethoxy)carbonyloxy)benzoate;
lxiv. chloromethyl 2-(4-methylcyclohex-3-enyl)propan-2-yl carbonate;
lxv. chloromethyl 3,7-dimethylocta-1,6-dien-3-yl carbonate;
lxvi. 4-allyl-2-methoxyphenylchloromethyl carbonate;
lxvii. chloromethyl (1R,2S,5R)-2-isopropyl-5-methylcyclohexyl carbonate;
lxviii. propyl 4-((chloromethoxy)carbonyloxy)benzoate; and (E)-chloromethyl 3,7-dimethylocta-2,6-dienyl carbonate;

when Y=R$^2$ then compound 1 is selected from the group consisting of:
i. Chloromethylcyclohexanecarboxylate;
ii. chloromethyl 2-cyclohexylacetate;
iii. chloromethyl 4-methylcyclohexanecarboxylate;
iv. chloromethyl 1-methylcyclohexanecarboxylate;
v. chloromethylcyclopentanecarboxylate;
vi. chloromethyl 1-(trifluoromethyl)cyclopentanecarboxylate;
vii. chloromethylcyclobutanecarboxylate;
viii. chloromethyl 2-ethylhexanoate;
ix. chloromethyl 3-cyclopentylpropanoate;
x. chloromethylcyclopropanecarboxylate;
xi. chloromethylpentanoate;
xii. chloromethyl 2-methylpentanoate;
xiii. chloromethyl 3,5,5-trimethylhexanoate;
xiv. chloromethyl 2,2-dimethylbutanoate;
xv. chloromethyl 2-methylbutanoate;
xvi. chloromethylhexanoate;
xvii. chloromethyl 2-ethylbutanoate;
xviii. chloromethyl butyrate;
xix. chloromethyl 3-phenylpropanoate;
xx. chloromethyl 2-phenylpropanoate;
xxi. (R)-chloromethyl 2-phenylpropanoate;
xxii. (S)-chloromethyl 2-phenylpropanoate;
xxiii. (1r,4r)-chloromethyl 4-methylcyclohexanecarboxylate;
xxiv. chloromethyl 4-methoxycyclohexanecarboxylate;
xxv. chloromethyl 4,4-difluorocyclohexanecarboxylate;
xxvi. chloromethyl 3-methoxycyclohexanecarboxylate;
xxvii. (2R)-chloromethyl 2-methylcyclopentanecarboxylate;
xxviii. (R)-chloromethyl 2-methylbutanoate;
xxix. (S)-chloromethyl 2-methylbutanoate;
xxx. (S)-chloromethyl 2-methoxy-2-phenylacetate;
xxxi. (S)-chloromethyl 2-phenylpropanoate;
xxxii. (S)-chloromethyl 2-phenylbutanoate;
xxxiii. (S)-chloromethyl 3-phenylbutanoate;
xxxiv. bis(chloromethyl) 2,2-dimethylmalonate;
xxxv. bis(chloromethyl) oxalate;
xxxvi. chloromethyl 2-cyclopropylacetate;
xxxvii. chloromethyl 2-cyclobutylacetate;
xxxviii. chloromethyl 2-cyclopentylacetate;
xxxix. chloromethyl 2-(tetrahydrofuran-3-yl)acetate;
xl. chloromethyl 2-(tetrahydro-2H-pyran-4-yl)acetate;
xli. chloromethyl 2-methylcyclopropanecarboxylate;
xlii. chloromethyl 2-(1-methylcyclobutyl)acetate;
xliii. chloromethyl 2-(1-methylcyclopropyl)acetate;
xliv. chloromethyl propionate;
xlv. chloromethyl acetate;
xlvi. chloromethylisobutyrate;
xlvii. chloromethyl 2-isopropyl-3-methylbutanoate;
xlviii. chloromethyl 3,5-dimethylcyclohexanecarboxylate;
xlix. chloromethyl 2-propylpentanoate;
l. chloromethyl 4-methoxybenzoate;
li. chloromethyl 4-methylbenzoate;
lii. chloromethyl 3-methylbenzoate;
liii. chloromethyl 2,2,2-trifluoroacetate;
liv. chloromethyl 5,5-dimethyl-3-oxohexanoate;
lv. bis(chloromethyl) cyclopropane-1,1-dicarboxylate;
lvi. chloromethyl 1,2-dihydrocyclobutabenzene-1-carboxylate;
lvii. chloromethyl 2-cyclopentenylacetate;
lviii. chloromethyl 2-phenylbutanoate;
lix. chloromethyl 2,2-difluoroacetate;
lx. chloromethyl 4-fluorobenzoate;

lxi. chloromethyl 3-cyclohexylpropanoate;
lxii. chloromethyl 2-cyclohexylacetate;
lxiii. chloromethyl 3-(tetrahydro-2H-pyran-4-yl)propanoate;
lxiv. chloromethyl 2-(tetrahydro-2H-pyran-3-yl)acetate; and
lxv. chloromethyl 3-(tetrahydro-2H-pyran-3-yl)propanoate and when Y=NR$^2$ then compound 1 is selected from the group consisting of:
i. chloromethylbenzylcarbamate;
ii. chloromethylisopropylcarbamate;
iii. chloromethyldiisopropylcarbamate;
iv. iodomethyldiisopropylcarbamate;
v. chloromethyl benzyl(methyl)carbamate;
vi. chloromethylpiperidine-1-carboxylate;
vii. (S)-chloromethyl (1-cyclohexylethyl)carbamate;
viii. (R)-chloromethyl (1-cyclohexylethyl)carbamate;
ix. chloromethyl (1-phenylethyl)carbamate;
x. (S)-chloromethyl (1-phenylethyl)carbamate;
xi. chloromethylcyclohexylcarbamate;
xii. (S)-chloromethyl (3-methylbutan-2-yl)carbamate;
xiii. (S)-chloromethyl sec-butylcarbamate;
xiv. chloromethyl 2-methylpiperidine-1-carboxylate;
xv. chloromethyl sec-butylcarbamate;
xvi. chloromethylmorpholine-4-carboxylate;
xvii. chloromethylpyrrolidine-1-carboxylate;
xviii. iodomethylisopropylcarbamate;
xix. chloromethyldimethylcarbamate;
xx. iodomethyldimethylcarbamate;
xxi. chloromethyl 4-methylpiperazine-1-carboxylate;
xxii. 1-chloroethyldiisopropylcarbamate;
xxiii. 1-chloroethylisopropylcarbamate;
xxiv. 1-chloroethylmorpholine-4-carboxylate;
xxv. 1-chloroethylpiperidine-1-carboxylate;
xxvi. chloromethyl 4-methylpiperidine-1-carboxylate; and
xxvii. bromomethylmorpholine-4-carboxylate.

2. A method according to claim 1, wherein Y=R$^2$ and compound 1, is selected from the group consisting of:
i. chloromethyl isopropyl carbonate;
ii. benzyl chloromethyl carbonate;
iii. chloromethyl morpholinomethyl carbonate;
iv. chloromethyl isobutyl carbonate;
v. chloromethylmethyl carbonate;
vi. (S)-sec-butyl chloromethyl carbonate;
vii. (R)-sec-butyl chloromethyl carbonate;
viii. chloromethyl ((3S,5R)-3,5-dimethylmorpholino)methyl carbonate;
ix. chloromethyl 2-methylcyclopropyl carbonate;
x. chloromethyl 2-methoxyethyl carbonate;
xi. chloromethyl propyl carbonate;
xii. chloromethyl cyclobutyl carbonate;
xiii. chloromethyl cyclopropyl carbonate;
xiv. chloromethyl 2,2-dimethylcyclobutyl carbonate;
xv. chloromethyl cyclopentyl carbonate;
xvi. chloromethyl oxetan-3-yl carbonate;
xvii. (S)-chloromethyl tetrahydrofuran-3-yl carbonate;
xviii. chloromethyl cyclohexylmethyl carbonate;
xix. chloromethyl 3-methoxycyclohexyl carbonate;
xx. (R)-chloromethyl tetrahydrofuran-3-yl carbonate;
xxi. chloromethyl ethoxymethyl carbonate;
xxii. chloromethyl oxepan-4-yl carbonate;
xxiii. (1R,2S,4S)-bicyclo[2.2.1]heptan-2-yl chloromethyl carbonate;
xxiv. chloromethyl 2,3-dihydro-1H-inden-1-yl carbonate;
xxv. benzyl chloromethyl carbonate;
xxvi. (S)-chloromethyl 1-phenylethyl carbonate;
xxvii. chloromethyl cyclohexyl carbonate;
xxviii. chloromethyl isobutyl carbonate;
xxix. chloromethyl 4-methylcyclohexyl carbonate;
xxx. chloromethyl 2-(methylthio)ethyl carbonate;
xxxi. chloromethyl 3-methylcyclohexyl carbonate;
xxxii. chloromethylpentan-2-yl carbonate;
xxxiii. chloromethyl neopentyl carbonate;
xxxiv. methyl 1-((chloromethoxy)carbonyloxy)cyclopropanecarboxylate;
xxxv. chloromethyl cyclopropylmethyl carbonate;
xxxvi. chloromethyl 2,2-diethoxyethyl carbonate;
xxxvii. chloromethyl cyclopentylmethyl carbonate;
xxxviii. methyl 2-((chloromethoxy)carbonyloxy)propanoate;
xxxix. (S)-chloromethyl 2,2,4-trimethylcyclopent-3-enyl carbonate;
xl. chloromethyl 1,3-dioxolan-2-yl carbonate;
xli. chloromethyl (2,6-dimethylcyclohexyl)methyl carbonate;
xlii. chloromethyl 2-(tetrahydro-2H-pyran-2-yl)ethyl carbonate;
xliii. chloromethyl(tetrahydro-2H-pyran-4-yl)methyl carbonate;
xliv. chloromethyl tetrahydro-2H-pyran-4-yl carbonate;
xlv. chloromethyl 1-methylcyclopentyl carbonate;
xlvi. chloromethyl 1-cyclopentylethyl carbonate;
xlvii. chloromethyl 3-methylcyclopentyl carbonate;
xlviii. chloromethyl 3,3-dimethylcyclohexyl carbonate;
xlix. chloromethyl 2,5-dimethylcyclohexyl carbonate;
l. chloromethyl 1-(4-methylcyclohexyl)ethyl carbonate;
li. chloromethyl (3-methyloxetan-3-yl)methyl carbonate;
lii. chloromethyl (3-methyloxetan-3-yl)methyl carbonate;
liii. chloromethyl 2-isopropoxyethyl carbonate;
liv. (chloromethyl carbonic) 5-((3aS,4S,6aR)-2-oxohexahydro-1H-thieno[3,4-d]imidazol-4-yl)pentanoic anhydride;
lv. 4-((chloromethoxy)carbonyloxy)-2-hydroxy-4-oxobutanoic acid;
lvi. chloromethyl 4-formyl-2-methoxyphenyl carbonate;
lvii. chloromethyl 3-oxobutan-2-yl carbonate;
lviii. methyl 4-((chloromethoxy)carbonyloxy)benzoate;
lix. (R)-2-amino-3-((chloromethoxy)carbonyloxy)propanoic acid;
lx. 3-tert-butyl-4-methoxyphenyl chloromethyl carbonate;
lxi. (R)-2-amino-3-(4-((chloromethoxy)carbonyloxy)phenyl)propanoic acid;
lxii. (R)-2-amino-4-((chloromethoxy)carbonyloxy)-4-oxobutanoic acid;
lxiii. (E)-chloromethyl 3,7-dimethylocta-2,6-dienyl carbonate;
lxiv. methyl 4-((chloromethoxy)carbonyloxy)benzoate;
lxv. chloromethyl 2-(4-methylcyclohex-3-enyl)propan-2-yl carbonate;
lxvi. chloromethyl 3,7-dimethylocta-1,6-dien-3-yl carbonate;
lxvii. 4-allyl-2-methoxyphenyl chloromethyl carbonate;
lxviii. chloromethyl (1R,2S,5R)-2-isopropyl-5-methylcyclohexyl carbonate;
lxix. propyl 4-((chloromethoxy)carbonyloxy)benzoate; and
lxx. (E)-chloromethyl 3,7-dimethylocta-2,6-dienyl carbonate.

3. A method according to claim 2, wherein compound 1 is selected from the group consisting of:
   i. chloromethyl isobutyrate;
   ii. chloromethyl 2,2-dimethylbutanoate;
   iii. chloromethyl 3,3-dimethylbutanoate;
   iv. chloromethyl 3-methylbutanoate;
   v. chloromethyl 2-methoxyacetate;
   vi. iodomethyl isobutyrate;
   vii. chloromethyl 2-phenylacetate;
   viii. chloromethyl nicotinate;
   ix. iodomethyl pivalate;
   x. 1-chloroethyl isobutyrate;
   xi. 1-chloropropyl isobutyrate;
   xii. chloromethyl acetate;
   xiii. ((methylsulfonyl)oxy)methyl 3-methylbutanoate;
   xiv. (tosyloxy)methyl 3-methylbutanoate; and
   xv. ((methylsulfonyl)oxy)methyl nicotinate.

4. A method according to claim 1, wherein Y=NR$^2$ and compound 1 is selected from the group consisting of:
   i. Chloromethyl cyclohexanecarboxylate;
   ii. chloromethyl 2-cyclohexylacetate;
   iii. chloromethyl 4-methylcyclohexanecarboxylate;
   iv. chloromethyl 1-methylcyclohexanecarboxylate;
   v. chloromethyl cyclopentanecarboxylate;
   vi. chloromethyl 1-(trifluoromethyl)cyclopentanecarboxylate;
   vii. chloromethyl cyclobutanecarboxylate;
   viii. chloromethyl 2-ethylhexanoate;
   ix. chloromethyl 3-cyclopentylpropanoate;
   x. chloromethyl cyclopropanecarboxylate;
   xi. chloromethyl pentanoate;
   xii. chloromethyl 2-methylpentanoate;
   xiii. chloromethyl 3,5,5-trimethylhexanoate;
   xiv. chloromethyl 2,2-dimethylbutanoate;
   xv. chloromethyl 2-methylbutanoate;
   xvi. chloromethyl hexanoate;
   xvii. chloromethyl 2-ethylbutanoate;
   xviii. chloromethyl butyrate;
   xix. chloromethyl 3-phenylpropanoate;
   xx. chloromethyl 2-phenylpropanoate;
   xxi. (R)-chloromethyl 2-phenylpropanoate;
   xxii. (S)-chloromethyl 2-phenylpropanoate;
   xxiii. (1r,4r)-chloromethyl 4-methylcyclohexanecarboxylate;
   xxiv. chloromethyl 4-methoxycyclohexanecarboxylate;
   xxv. chloromethyl 4,4-difluorocyclohexanecarboxylate;
   xxvi. chloromethyl 3-methoxycyclohexanecarboxylate;
   xxvii. (2R)-chloromethyl 2-methylcyclopentanecarboxylate;
   xxviii. (R)-chloromethyl 2-methylbutanoate;
   xxix. (S)-chloromethyl 2-methylbutanoate;
   xxx. (S)-chloromethyl 2-methoxy-2-phenylacetate;
   xxxi. (S)-chloromethyl 2-phenylpropanoate;
   xxxii. (S)-chloromethyl 2-phenylbutanoate;
   xxxiii. (S)-chloromethyl 3-phenylbutanoate;
   xxxiv. bis(chloromethyl) 2,2-dimethylmalonate;
   xxxv. bis(chloromethyl) oxalate;
   xxxvi. chloromethyl 2-cyclopropylacetate;
   xxxvii. chloromethyl 2-cyclobutylacetate;
   xxxviii. chloromethyl 2-cyclopentylacetate;
   xxxix. chloromethyl 2-(tetrahydrofuran-3-yl)acetate;
   xl. chloromethyl 2-(tetrahydro-2H-pyran-4-yl)acetate;
   xli. chloromethyl 2-methylcyclopropanecarboxylate;
   xlii. chloromethyl 2-(1-methylcyclobutyl)acetate;
   xliii. chloromethyl 2-(1-methylcyclopropyl)acetate;
   xliv. chloromethyl propionate;
   xlv. chloromethyl acetate;
   xlvi. chloromethyl isobutyrate;
   xlvii. chloromethyl 2-isopropyl-3-methylbutanoate;
   xlviii. chloromethyl 3,5-dimethylcyclohexanecarboxylate;
   xlix. chloromethyl 2-propylpentanoate;
   l. chloromethyl 4-methoxybenzoate;
   li. chloromethyl 4-methylbenzoate;
   lii. chloromethyl 3-methylbenzoate;
   liii. chloromethyl 2,2,2-trifluoroacetate;
   liv. chloromethyl 5,5-dimethyl-3-oxohexanoate;
   lv. bis(chloromethyl) cyclopropane-1,1-dicarboxylate;
   lvi. chloromethyl 1,2-dihydrocyclobutabenzene-1-carboxylate;
   lvii. chloromethyl 2-cyclopentenylacetate;
   lviii. chloromethyl 2-phenylbutanoate;
   lix. chloromethyl 2,2-difluoroacetate;
   lx. chloromethyl 4-fluorobenzoate;
   lxi. chloromethyl 3-cyclohexylpropanoate;
   lxii. chloromethyl 2-cyclohexylacetate;
   lxiii. chloromethyl 3-(tetrahydro-2H-pyran-4-yl)propanoate;
   lxiv. chloromethyl 2-(tetrahydro-2H-pyran-3-yl)acetate; and
   lxv. chloromethyl 3-(tetrahydro-2H-pyran-3-yl)propanoate.

5. A method according to claim 4, wherein compound 1 is selected from the group consisting of:
   i. chloromethyl benzylcarbamate;
   ii. chloromethyl isopropylcarbamate;
   iii. chloromethyl diisopropylcarbamate;
   iv. iodomethyl diisopropylcarbamate;
   v. chloromethyl benzyl(methyl)carbamate;
   vi. chloromethyl piperidine-1-carboxylate;
   vii. (S)-chloromethyl (1-cyclohexylethyl)carbamate;
   viii. (R)-chloromethyl (1-cyclohexylethyl)carbamate;
   ix. chloromethyl (1-phenylethyl)carbamate;
   x. (S)-chloromethyl (1-phenylethyl)carbamate;
   xi. chloromethyl cyclohexylcarbamate;
   xii. (S)-chloromethyl (3-methylbutan-2-yl)carbamate;
   xiii. (S)-chloromethyl sec-butylcarbamate;
   xiv. chloromethyl 2-methylpiperidine-1-carboxylate;
   xv. chloromethyl sec-butylcarbamate;
   xvi. chloromethyl morpholine-4-carboxylate;
   xvii. chloromethyl pyrrolidine-1-carboxylate;
   xviii. iodomethyl isopropylcarbamate;
   xix. chloromethyl dimethylcarbamate;
   xx. iodomethyl dimethylcarbamate;
   xxi. chloromethyl 4-methylpiperazine-1-carboxylate;
   xxii. 1-chloroethyl diisopropylcarbamate;
   xxiii. 1-chloroethyl isopropylcarbamate;
   xxiv. 1-chloroethyl morpholine-4-carboxylate;
   xxv. 1-chloroethyl piperidine-1-carboxylate;
   xxvi. chloromethyl 4-methylpiperidine-1-carboxylate; and
   xxvii. bromomethyl morpholine-4-carboxylate.

6. A method according to claim 1, wherein Y=OR$^2$ and compound 1 is selected from the group consisting of:
   i. chloromethyl isopropylcarbamate;
   ii. chloromethyl diisopropylcarbamate;
   iii. chloromethyl dimethylcarbamate;
   iv. chloromethyl isobutylcarbamate;
   v. chloromethyl methylcarbamate;
   vi. chloromethyl ethyl(isopropyl)carbamate;
   vii. chloromethylisobutyl(methyl)carbamate;
   viii. (S)-chloromethyl sec-butylcarbamate;
   ix. chloromethyl methylcarbamate;
   x. chloromethyl isopropyl(methyl)carbamate;

xi. chloromethyl propylcarbamate;
xii. chloromethyl 2-methoxyethylcarbamate;
xiii. chloromethyl methyl(propyl)carbamate;
xiv. chloromethyl diisobutylcarbamate;
xv. chloromethyl tert-butyl(isopropyl)carbamate;
xvi. chloromethyl di-sec-butylcarbamate;
xvii. chloromethyl aziridine-1-carboxylate;
xviii. chloromethyl 2-methylcyclopropylcarbamate;
xix. chloromethyl cyclopropylcarbamate;
xx. chloromethyl cyclopropylmethyl(propyl)carbamate;
xxi. chloromethyl cyclopropyl(methyl)carbamate;
xxii. chloromethyl azetidine-1-carboxylate;
xxiii. chloromethyl cyclobutylcarbamate;
xxv. chloromethyl 2,2-dimethylcyclobutylcarbamate;
xxv. chloromethyl 3-methoxyazetidine-1-carboxylate;
xxvi. chloromethyl cyclobutyl(methyl)carbamate;
xxvii. chloromethyl oxetan-3-ylcarbamate;
xxviii. (S)-chloromethyl 2-methylpyrrolidine-1-carboxylate;
xxix. chloromethyl cyclopentylcarbamate;
xxx. chloromethyl cyclopentyl(methyl)carbamate;
xxxi. chloromethyl tetrahydrofuran-3-ylcarbamate;
xxxii. chloromethyl piperidine-1-carboxylate;
xxxiii. (2R,6S)-chloromethyl 2,6-dimethylpiperidine-1-carboxylate;
xxxiv. (R)-chloromethyl 2-methylpiperidine-1-carboxylate;
xxxv. chloromethyl piperidine-1-carboxylate;
xxxvi. chloromethyl 3-methoxycyclohexylcarbamate;
xxxvii. chloromethyl cyclohexylmethylcarbamate;
xxxviii. chloromethyl cyclohexylmethyl(methyl)carbamate;
xxxix. chloromethyl morpholine-4-carboxylate;
xl. (3S,5R)-chloromethyl 3,5-dimethylmorpholine-4-carboxylate;
xli. (3R,5S)-chloromethyl 3,5-dimethylmorpholine-4-carboxylate;
xlii. (2S,6R)-chloromethyl 2,6-dimethylmorpholine-4-carboxylate;
xliii. chloromethyl 4-methylpiperazine-1-carboxylate;
xliv. chloromethylazepane-1-carboxylate;
xlv. chloromethylcycloheptylcarbamate;
xlvi. chloromethyl oxepan-4-ylcarbamate;
xlvii. chloromethyl (1R,2S,4S)-bicyclo[2.2.1]heptan-2-ylcarbamate;
xlviii. chloromethyl 2,3-dihydro-1H-inden-1-ylcarbamate;
xlix. chloromethyl benzylcarbamate;
l. (S)-chloromethyl 1-phenylethylcarbamate;
li. ethyl 2-((chloromethoxy)carbonylamino)-3-methylbutanoate;
lii. ethyl 2-((chloromethoxy)carbonylamino)-3-phenylpropanoate;
liii. (S)-diethyl 2-((chloromethoxy)carbonylamino)pentanedioate;
liv. ethyl((chloromethoxy)carbonylamino)propanoate;
lv. ethyl 2-amino-6-((chloromethoxy)carbonylamino)hexanoate;
lvi. ethyl 2-((chloromethoxy)carbonylamino)-4-methylpentanoate;
lvii. ethyl 2-((chloromethoxy)carbonylamino)-3-methylpentanoate;
lviii. (S)-dimethyl 2-((chloromethoxy)carbonylamino) succinate;
lix. (S)-ethyl 2-((chloromethoxy)carbonylamino)-5-guanidinopentanoate;
lx. (S)-ethyl 4-amino-2-((chloromethoxy)carbonylamino)-4-oxobutanoate;
lxi. (S)-ethyl 2-amino-5-((chloromethoxy)carbonylamino)pentanoate;
lxii. (S)-ethyl 5-amino-2-((chloromethoxy)carbonylamino)-5-oxopentanoate;
lxiii. ethyl 2-((chloromethoxy)carbonylamino)-4-(methylthio)butanoate;
lxiv. 1-chloromethyl 3-methyl 2-methyl-5,6-dihydropyridine-1,3(2H)-dicarboxylate;
lxv. (S)-chloromethyl (1-methylpyrrolidin-2-yl)methyl carbonate;
lxvi. (R)-chloromethyl (1-methylpyrrolidin-2-yl)methyl carbonate;
lxvii. (S)-(1-benzylpyrrolidin-2-yl)methyl chloromethyl carbonate;
lxviii. chloromethyl 1H-pyrrole-1-carboxylate;
lxix. chloromethyl 2-nicotinoylhydrazinecarboxylate;
lxx. (6S)-3-chloro-7-((chloromethoxy)carbonylamino)-8-oxo-5-thia-1-azabicyclo[4.2.0]oct-2-ene-2-carboxylic acid;
lxxi. (6S)-7-((chloromethoxy)carbonylamino)-8-oxo-3-vinyl-5-thia-1-azabicyclo[4.2.0]oct-2-ene-2-carboxylic acid;
lxxii. (6S)-7-((chloromethoxy)carbonylamino)-3-(methoxymethyl)-8-oxo-5-thia-1-azabicyclo[4.2.0]oct-2-ene-2-carboxylic acid;
lxxiii. (6R,7R)-7-((chloromethoxy)carbonylamino)-3-methoxy-8-oxo-5-thia-1-azabicyclo[4.2.0]oct-2-ene-2-carboxylic acid;
lxxiv. chloromethyl 3-(4-chlorophenyl)-1H-pyrazole-1-carboxylate;
lxxv. chloromethyl 3-(4-fluorophenyl)-1H-pyrazole-1-carboxylate;
lxxvi. chloromethyl 3-phenyl-1H-pyrazole-1-carboxylate;
lxxvii. chloromethyl 3-(4bromophenyl)-1H-pyrazole-1-carboxylate;
lxxviii. chloromethyl 2-cyano-1H-pyrrole-1-carboxylate;
lxxix. chloromethyl 4-oxopiperidine-1-carboxylate;
lxxx. 1-chloromethyl 3-ethyl 2-oxopiperidine-1,3-dicarboxylate;
lxxxi. chloromethyl 2,2,6,6-tetramethyl-4-oxopiperidine-1-carboxylate; and
lxxxii. chloromethyl 2-oxopiperidine-1-carboxylate.

7. A method according to claim 6, wherein compound 1 is selected from the group consisting of:
i. tert-butyl (chloromethyl) carbonate;
ii. chloromethyl ethyl carbonate;
iii. chloromethyl cyclohexyl carbonate;
iv. chloromethyl (1-methylcyclohexyl) carbonate;
v. chloromethyl cyclopentyl carbonate;
vi. chloromethyl tert-pentyl carbonate;
vii. chloromethyl (2,4-dimethylpentan-3-yl) carbonate;
viii. chloromethyl (cyclopropylmethyl) carbonate;
ix. chloromethyl (3-methylbutan-2-yl) carbonate;
x. (S)-sec-butyl (chloromethyl) carbonate;
xi. (R)-sec-butyl (chloromethyl) carbonate;
xii. chloromethyl cyclobutyl carbonate;
xiii. chloromethyl (1-methoxypropan-2-yl) carbonate;
xiv. sec-butyl (chloromethyl) carbonate;
xv. chloromethyl (1-methylcyclopentyl) carbonate;
xvi. chloromethyl isopropyl carbonate;
xvii. 1-chloroethyl isopropyl carbonate;
xviii. benzyl (iodomethyl) carbonate;
xix. (S)-iodomethyl (1-phenylethyl) carbonate; and
xx. (R)-iodomethyl (1-phenylethyl) carbonate.

8. A method according to claim 1, wherein the functional group on said pharmaceutical compound to be modified is selected from the group consisting of (a) a primary, secondary or tertiary amine; (b) a primary, secondary or tertiary alcohol; (c) a carboxylic acid; or (d) a nitrogen heteroatom.

9. A method according to claim 1, wherein the pharmaceutical compound to be modified is any of Tadalafil, Sildenafil, Amprenavir, Fosamprenavir, Buprobrion, Duloxetine, Finasteride, Latanoprost, Lopinavir, Raloxifene, Tropicamide, Geldanamycin, Metformin, Paclitaxel, Doxorubicin, Nelfinavir, Rapamycin, Piroxicam, Amlexanox, Rosoxacin, Etoricoxib, Sumatriptan, Vardenafil, Quinacrine, Atorvastatin, Valciclovir Hydrochloride, Atovaquone, Dihydroergotamine, Donepezil, Levofloxacin, Topotecan, Estradiol, Quetiapine, Olanzapine, Venlafaxine, Azelastine, Pioglitazone, Nevirapine, Rizatriptan, Escitalopram, Losartan, Saquinavir, Fluticasone/salmeterol, Rosuvastatin, Budesonide/Formoterol, Montelukast, Acetaminophen, Imatinib, Dimebon, SN-38, Curcumin, Hydroxy Fasudil, Fasudil, Aspirin, or Nicorandil.

10. A method according to claim 1, wherein the pharmaceutical compound to be modified is selected from Central Nervous System Drugs, CNS/Respiratory Stimulants, Analgesics, Narcotic Agonists, Narcotic agonist/antagonists, Nonsteroidal Anti-inflammatory/Analgesic Agents, Behavior-Modifying Agents, Tranquilizers/Sedatives, Anesthetic Agents, Inhalants, Narcotics, Reversal Agents, Anticonvulsants, Muscle Relaxants, Skeletal, Muscle Relaxants, Smooth, Euthanasia Agent, Cardiovascular Agents, Inotropic Agents, Antiarrhythmic Drugs, Anticholinergics, Vasodilating Agents, Agents Used in Treatment of Shock, Alpha-Adrenergic Blocking Agents, Beta-Adrenergic Blocking Agents, Respiratory Drugs, Bronchodilators, Sympathomimetics, Antihistamines, Antitussives, Renal and Urinary Tract, Agents for Urinary Incontinence/Retention, Urinary Alkalinizers, Urinary Acidifiers, Cholinergic Stimulants, Agents for Urolithiasis, Gastrointestinal Agents, Antiemetic Agents, Antacids, H2 Antagonists, Gastromucosal Protectants, Proton Pump Inhibitors, Appetite Stimulants, GI Antispasmodics-Anticholinergics, GI Stimulants, Laxatives, Saline, Bulk producing, Antidiarrheals, Hormones/Endocrine/Reproductive Agents, Sex Hormones, Anabolic steroids, Posterior Pituitary Hormones, Adrenal Cortical Steroids, Glucocorticoids, Antidiabetic Agents, Thyroid Drugs, Thyroid Hormones, Misc. Endocrine/Reproductive Drugs, Prostaglandins, Anti-infective Drugs, Antiparasitics, Anticoccidial Agents, Antibiotics, Anti-tuberculosis, Aminocyclitols, Cephalosporins, Macrolides, Penicillins, Tetracyclines, Lincosamides, Quinolones, Sulfonamides, Miscellaneous Antibacterials, Antifungal Agents, Antiviral Agents, Blood Modifying Agents, Clotting Agents, Anticoagulants, Erythropoietic Agents, Antineoplastics/Immunosuppresives, Alkylating Agents, Antidotes, Bone/Joint Agents, Dermatologic Agents (Systemic), Vitamins and Minerals/Nutrients, Systemic Acidifiers, Systemic Alkalinizers, anti-cancer agents, and anti-viral agents.

11. A method according to claim 1, wherein the modified pharmaceutical compound is altered and converted to a salt, solvate, a stereoisomer; or alternatively is present as its counter ion; or alternatively is a deuterated compound.

12. A method as claimed in claim 1, wherein one or more of the properties altered includes the pharmacokinetic and/or pharmacodynamic properties of the modified pharmaceutical compound in comparison to those of the pharmaceutical compound before modification.

13. The method of claim 1, wherein the modified pharmaceutical compound is selected from the group consisting of:

i. 3-(dimethylcarbamoyl)-1-((((2-(2,6-dioxopiperidin-3-yl)-1-oxoisoindolin-4-yl)carbamoyl)oxy)methyl)pyridin-1-ium;

ii. 3-(((3-(4-amino-1-oxoisoindolin-2-yl)-2,6-dioxopiperidin-1-yl)methoxy)carbonyl)-1-(((isopropylcarbamoyl)oxy)methyl)pyridin-1-ium;

iii. 1-(acetoxymethyl)-4-((4-ethoxy-3-(1-methyl-7-oxo-3-propyl-4,7-dihydro-1H-pyrazolo[4,3-d]pyrimidin-5-yl)phenyl)sulfonyl)-1-methylpiperazin-1-ium;

iv. (2R,3S)-1-(((2aR,4S,4aS,6R,9S,11S,12S,12aR,12bS)-12b-acetoxy-12-(benzoyloxy)-4,6,11-trihydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxet-9-yl)oxy)-3-((tert-butoxycarbonyl)amino)-1-oxo-3-phenylpropan-2-yl nicotinate;

v. (3-(4-amino-1-oxoisoindolin-2-yl)-2,6-dioxopiperidin-1-yl)methyl nicotinate vi. 4-((4-ethoxy-3-(1-methyl-7-oxo-3-propyl-4,7-dihydro-1H-pyrazolo[4,3-d]pyrimidin-5-yl)phenyl)sulfonyl)-1-(((isopropylcarbamoyl)oxy)methyl)-1-methylpiperazin-1-ium;

vii. 3-(((((1S,2R)-1-benzamido-3-(((2aR,4S,4aS,6R,9S,11S,12S,12aR,12bS)-6,12b-diacetoxy-12-(benzoyloxy)-4,11-dihydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxet-9-yl)oxy)-3-oxo-1-phenylpropan-2-yl)oxy)carbonyl)-1-(((isopropoxycarbonyl)oxy)methyl)pyridin-1-ium;

viii. 4-((4-ethoxy-3-(1-methyl-7-oxo-3-propyl-4,7-dihydro-1H-pyrazolo[4,3-d]pyrimidin-5-yl)phenyl)sulfonyl)-1-(((isopropoxycarbonyl)oxy)methyl)-1-methylpiperazin-1-ium;

ix. 4-((4-ethoxy-3-(1-methyl-7-oxo-3-propyl-4,7-dihydro-1H-pyrazolo[4,3-d]pyrimidin-5-yl)phenyl)sulfonyl)-1-((isobutyryloxy)methyl)-1-methylpiperazin-1-ium;

x. 3-(2-((5-benzamido-2-methylphenyl)amino)pyrimidin-4-yl)-1-((isobutyryloxy)methyl)pyridin-1-ium;

xi. 1-((((((1S,2R)-1-benzamido-3-(((2aR,4S,4aS,6R,9S,11S,12S,12aR,12bS)-6,12b-diacetoxy-12-(benzoyloxy)-4,11-dihydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxet-9-yl)oxy)-3-oxo-1-phenylpropan-2-yl)oxy)carbonyl)oxy)methyl)-3-(dimethylcarbamoyl)pyridin-1-ium;

xii. 3-(2-((5-benzamido-2-methylphenyl)amino)pyrimidin-4-yl)-1-(((piperidine-1-carbonyl)oxy)methyl)pyridin-1-ium;

xiii. 2-amino-1-(((diisopropylcarbamoyl)oxy)methyl)-5-(4-(4-(dimethylcarbamoyl)phenoxy)-6-morpholino-1,3,5-triazin-2-yl)pyridin-1-ium;

xiv. 3-(2-((5-benzamido-2-methylphenyl)amino)pyrimidin-4-yl)-1-(((pyrrolidine-1-carbonyl)oxy)methyl)pyridin-1-ium;

xv. 3-carbamoyl-1-((2-(1-(4-chlorobenzoyl)-5-methoxy-2-methyl-1H-indol-3-yl)acetoxy)methyl)pyridin-1-ium;

xvi. 3-(2-((5-benzamido-2-methylphenyl)amino)pyrimidin-4-yl)-1-(((diisopropylcarbamoyl)oxy)methyl)pyridin-1-ium;

xvii. (2-(1-(4-chlorobenzoyl)-5-methoxy-2-methyl-1H-indol-3-yl)acetoxy)methyl nicotinate;

xviii. 3-(((2-acetoxybenzoyl)oxy)methyl)-1H-imidazol-3-ium;

xix. 1-(((2-acetoxybenzoyl)oxy)methyl)-1-methyl-1H-imidazol-1-ium;

xx. 1-(((2-acetoxybenzoyl)oxy)methyl)-3-(methylcarbamoyl)pyridin-1-ium;
xxi. ((2-acetoxybenzoyl)oxy)methyl nicotinate;
xxii. 1-(((2-acetoxybenzoyl)oxy)methyl)-3-carbamoylpyridin-1-ium;
xxiii. Compound No. 337;

337

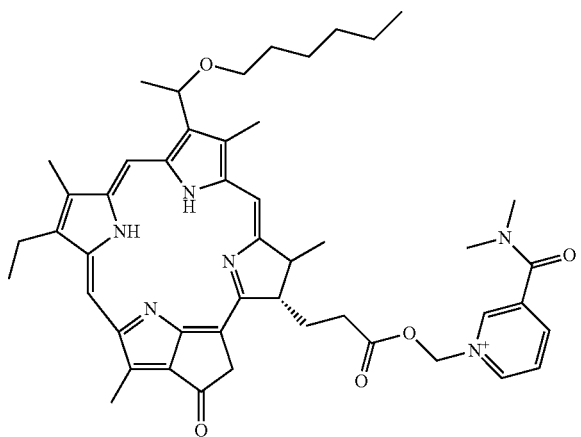

xxiv. 1-((((((1S,2R)-1-benzamido-3-(((2aR,4S,4aS,6R,9S,11S,12S,12aR,12bS)-6,12b-diacetoxy-12-(benzoyloxy)-4-((((3-(dimethylcarbamoyl)pyridin-1-ium-1-yl)methoxy)carbonyl)oxy)-11-hydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxet-9-yl)oxy)-3-oxo-1-phenylpropan-2-yl)oxy)carbonyl)oxy)methyl)-3-(dimethylcarbamoyl)pyridin-1-ium;
xxv. (R)-1-(((sec-butoxycarbonyl)oxy)methyl)-3-((2-(nitrooxy)ethyl)carbamoyl)pyridin-1-ium;
xxv. (S)-1-(((sec-butoxycarbonyl)oxy)methyl)-3-((2-(nitrooxy)ethyl)carbamoyl)pyridin-1-ium;
xxvii. (R)-1-((((1-cyclohexylethyl)carbamoyl)oxy)methyl)-3-((2-(nitrooxy)ethyl)carbamoyl)pyridin-1-ium;
xxviii. (S)-1-((((1-cyclohexylethyl)carbamoyl)oxy)methyl)-3-((2-(nitrooxy)ethyl)carbamoyl)pyridin-1-ium;
xxix. 1-(((isopropylcarbamoyl)oxy)methyl)-1-methyl-4-(2-methyl-10H-benzo[b]thieno[2,3-e][1,4]diazepin-4-yl)piperazin-1-ium;
xxx. 1-(((2-acetoxybenzoyl)oxy)methyl)-3-((2-(nitrooxy)ethyl)carbamoyl)pyridin-1-ium;
xxxi. 3-(2-hydroxy-2,2-diphenylacetoxy)-1-(((isopropylcarbamoyl)oxy)methyl)-1-methylpiperidin-1-ium;
xxxii. 1-((2-(1-(4-chlorobenzoyl)-5-methoxy-2-methyl-1H-indol-3-yl)acetoxy)methyl)-3-(dimethylcarbamoyl)pyridin-1-ium;
xxxiii. 3-(dimethylcarbamoyl)-1-(((2-(4-isobutylphenyl)propanoyl)oxy)methyl)pyridin-1-ium;
xxxiv. 1-(((2-(4-isobutylphenyl)propanoyl)oxy)methyl)-2-(methoxycarbonyl)-1-methylpyrrolidin-1-ium;
xxxv. 2-(((diisopropylcarbamoyl)oxy)methyl)-2,8-dimethyl-5-(2-(6-methylpyridin-3-yl)ethyl)-2,3,4,4a,5,9b-hexahydro-1H-pyrido[4,3-b]indol-2-ium;
xxxvi. 5-chloro-1'-(((isopropylcarbamoyl)oxy)methyl)-6'-methyl-3-(4-(methylsulfonyl)phenyl)-[2,3'-bipyridin]-1'-ium;
xxxvii. (S)-4-(9-fluoro-6-(methoxycarbonyl)-3-methyl-7-oxo-7-dihydro-2H-[1,4]oxazino[2,3,4-ij]quinolin-10-yl)-1-(((isopropylcarbamoyl)oxy)methyl)-1-methylpiperazin-1-ium;

xxxviii. 3-(((((1S,2S)-1-benzamido-3-(((2aR,4S,4aS,6R,9S,11S,12S,12aR,12bS)-6,12b-diacetoxy-12-(benzoyloxy)-4,11-dihydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxet-9-yl)oxy)-3-oxo-1-phenylpropan-2-yl)oxy)carbonyl)-1-(((diisopropylcarbamoyl)oxy)methyl)pyridin-1-ium;
xxxix. 5-chloro-6'-methyl-3-(4-(methylsulfonyl)phenyl)-1'-((pivaloyloxy)methyl)-[2,3'-bipyridin]-1'-ium;
xl. 1-((2-((2-(2,6-dichlorophenyl)amino)phenyl)acetoxy)methyl)-3-(dimethylcarbamoyl)pyridin-1-ium;
xli. 3-((((2-acetoxybenzoyl)oxy)methoxy)carbonyl)-1-((pivaloyloxy)methyl)pyridin-1-ium;
xlii. 1-(((2-acetoxybenzoyl)oxy)methyl)-3-(dimethylcarbamoyl)pyridin-1-ium;
xliii. 1-((((((4-acetamidophenoxy)carbonyl)oxy)methyl)-3-(dimethylcarbamoyl)pyridin-1-ium;
xliv. 3-((4-acetamidophenoxy)carbonyl)-1-((isobutyryloxy)methyl)pyridin-1-ium;
xlv. 3-(dimethylcarbamoyl)-1-((((4-((1E,3Z,6E)-3-hydroxy-7-(4-hydroxy-3-methoxyphenyl)-5-oxohepta-1,3,6-trien-1-yl)-2-methoxyphenoxy)carbonyl)oxy)methyl)pyridin-1-ium;
xlvi. 3-((4-acetamidophenoxy)carbonyl)-1-(((diisopropylcarbamoyl)oxy)methyl)pyridin-1-ium;
xlvii. (S)-1-(((isopropylcarbamoyl)oxy)methyl)-3-((((2-(6-methoxynaphthalen-2-yl)propanoyl)oxy)methoxy)carbonyl)pyridin-1-ium;
xlviii. (E)-3-(dimethylcarbamoyl)-1-(((2-methoxy-4-((8-methylnon-6-enamido)methyl)phenoxy)carbonyl)oxy)methyl)pyridin-1-ium;
xlix. 3-((((1S,2R)-1-benzamido-3-(((2aR,4S,4aS,6R,9S,11S,12S,12aR,12bS)-6,12b-diacetoxy-12-(benzoyloxy)-4,11-dihydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxet-9-yl)oxy)-3-oxo-1-phenylpropan-2-yl)oxy)carbonyl)-1-(((isopropylcarbamoyl)oxy)methyl)pyridin-1-ium;
l. (2aR,4S,4aS,6R,9S,11S,12S,12aR,12bS)-9-(((2R,3S)-3-benzamido-2-(nicotinoyloxy)-3-phenylpropanoyl)oxy)-12-(benzoyloxy)-4,11-dihydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxete-6,12b-diyl diacetate;
li. (E)-1-(((isopropylcarbamoyl)oxy)methyl)-3-((2-methoxy-4-((8-methylnon-6-enamido)methyl)phenoxy)carbonyl)pyridin-1-ium;
lii. 3,3'-(((((1E,3Z,6E)-3-hydroxy-5-oxohepta-1,3,6-triene-1,7-diyl)bis(2-methoxy-4,1-phenylene))bis(oxy))bis(carbonyl))bis(1-(((isopropylcarbamoyl)oxy)methyl)pyridin-1-ium);
liii. (S)-3-((((4,11-diethyl-4-hydroxy-3,14-dioxo-3,4,12,14-tetrahydro-1H-pyrano[3',4':6,7] indolizino[1,2-b]quinolin-9-yl)oxy)methoxy)carbonyl)-1-(((isopropylcarbamoyl)oxy)methyl)pyridin-1-ium;
liv. (S)-((4,11-diethyl-4-hydroxy-3,14-dioxo-3,4,12,14-tetrahydro-1H-pyrano[3',4':6,7] indolizino[1,2-b]quinolin-9-yl)oxy)methyl nicotinate;
lv. 1-(((morpholine-4-carbonyl)oxy)methyl)-3-((2-(nitrooxy)ethyl)carbamoyl)pyridin-1-ium;
lvi. 3-((2-(nitrooxy)ethyl)carbamoyl)-1-(((pyrrolidine-1-carbonyl)oxy)methyl)pyridin-1-ium;
lvii. ((6,7-bis(2-methoxyethoxy)quinazolin-4-yl)(3-ethynylphenyl)amino)methyl diisopropylcarbamate;
2-(((diisopropylcarbamoyl)oxy)methyl)-5-(2-(1-(((diisopropylcarbamoyl)oxy)methyl)-6-methylpyridin-1-ium-3-yl)ethyl)-2,8-dimethyl-2,3,4,5-tetrahydro-1H-pyrido[4,3-b]indol-2-ium;

lix. 3-(2-((5-benzamido-2-methylphenyl)amino)pyrimidin-4-yl)-1-(((isopropylcarbamoyl)oxy)methyl)pyridin-1-ium;
lx. 1-(((tert-butoxycarbonyl)oxy)methyl)-3-((2-(nitrooxy)ethyl)carbamoyl)pyridin-1-ium;
lxi. 3-((((2-acetoxybenzoyl)oxy)methoxy)carbonyl)-1-(((dimethylcarbamoyl)oxy)methyl)pyridin-1-ium;
lxii. 1-(((isopropylcarbamoyl)oxy)methyl)-3-((2-(nitrooxy)ethyl)carbamoyl)pyridin-1-ium;
lxiii. 1-(((dimethylcarbamoyl)oxy)methyl)-3-((2-(nitrooxy)ethyl)carbamoyl)pyridin-1-ium;
lxiv. 1-(((isopropoxycarbonyl)oxy)methyl)-3-((2-(nitrooxy)ethyl)carbamoyl)pyridin-1-ium;
lxv. 3-(2-((5-benzamido-2-methylphenyl)amino)pyrimidin-4-yl)-1-((pivaloyloxy)methyl)pyridin-1-ium;
lxvi. 1-(((ethoxycarbonyl)oxy)methyl)-3-((2-(nitrooxy)ethyl)carbamoyl)pyridin-1-ium;
lxv. 3-((2-(nitrooxy)ethyl)carbamoyl)-1-(((piperidine-1-carbonyl)oxy)methyl)pyridin-1-ium;
lxviii. 1-(((diisopropylcarbamoyl)oxy)methyl)-3-((2-(nitrooxy)ethyl)carbamoyl)pyridin-1-ium;
lxix. 1-((isobutyryloxy)methyl)-3-((2-(nitrooxy)ethyl)carbamoyl)pyridin-1-ium;
lxx. 1-methyl-4-(4-((4-methyl-3-((4-(1-((pivaloyloxy)methyl)pyridin-1-ium-3-yl)pyrimidin-2-yl)amino)phenyl)carbamoyl)benzyl)-1-((pivaloyloxy)methyl)piperazin-1-ium;
lxxi. 1-(((3-methylbutanoyl)oxy)methyl)-3-((2-(nitrooxy)ethyl)carbamoyl)pyridin-1-ium;
lxxii. 2-methyl-1-((9-methyl-4-oxo-2,3,4,9-tetrahydro-1H-carbazol-3-yl)methyl)-3-((pivaloyloxy)methyl)-1H-imidazol-3-ium;
lxxiii. 1-(((3,3-dimethylbutanoyl)oxy)methyl)-3-((2-(nitrooxy)ethyl)carbamoyl)pyridin-1-ium;
lxxiv. 1-methyl-4-((4-methyl-3-((4-(pyridin-3-yl)pyrimidin-2-yl)amino)phenyl)carbamoyl)benzyl)-1-((pivaloyloxy)methyl)piperazin-1-ium;
lxxv. 3-((2-(nitrooxy)ethyl)carbamoyl)-1-((pivaloyloxy)methyl)pyridin-1-ium; and
lxxvi. Compound 502

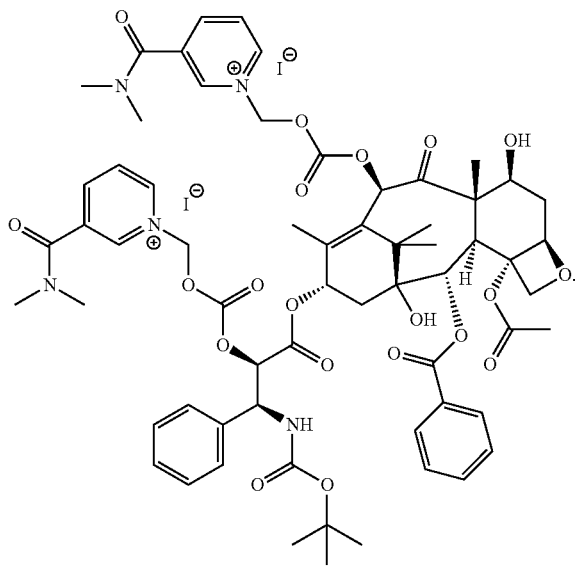

502

14. The method of claim 1, wherein the modified pharmaceutical compound is selected from the group consisting of:
i. 2-(((diisopropylcarbamoyl)oxy)methyl)-2,8-dimethyl-5-(2-(6-methylpyridin-3-yl)ethyl)-2,3,4,5-tetrahydro-1H-pyrido[4,3-b]indol-2-ium iodide;
ii. 2-(((diisopropylcarbamoyl)oxy)methyl)-5-(2-(1-(((diisopropylcarbamoyl)oxy)methyl)-6-methylpyridin-1-ium-3-yl)ethyl)-2,8-dimethyl-2,3,4,5-tetrahydro-1H-pyrido[4,3-b]indol-2-ium diiodide;
iii. 1-(((isopropylcarbamoyl)oxy)methyl)-1-methyl-4-(2-methyl-10H-benzo[b]thieno[2,3-e][1,4]diazepin-4-yl)piperazin-1-ium iodide;
iv. 1-(acetoxymethyl)-4-((4-ethoxy-3-(1-methyl-7-oxo-3-propyl-4,7-dihydro-1H-pyrazolo[4,3-d]pyrimidin-5-yl)phenyl)sulfonyl)-1-methylpiperazin-1-ium iodide;
v. 4-acetamidophenyl nicotinate;
vi. 3-((4-acetamidophenoxy)carbonyl)-1-(((diisopropylcarbamoyl)oxy)methyl)pyridin-1-ium iodide;
vii. 4-acetamidophenyl 2-bromoacetate;
viii. 1-(2-(4-acetamidophenoxy)-2-oxoethyl)-3-(dimethylcarbamoyl)pyridin-1-ium iodide;
ix. 4-acetamidophenyl (chloromethyl) carbonate;
x. 4-acetamidophenyl (iodomethyl) carbonate;
xi. 1-((((4-acetamidophenoxy)carbonyl)oxy)methyl)-3-(dimethylcarbamoyl)pyridin-1-ium iodide;
xii. (S)-((4,11-diethyl-4-hydroxy-3,14-dioxo-3,4,12,14-tetrahydro-1H-pyrano[3',4':6,7]indolizino[1,2-b]quinolin-9-yl)oxy)methyl nicotinate;
xiii. (S)-3-((((4,11-diethyl-4-hydroxy-3,14-dioxo-3,4,12,14-tetrahydro-1H-pyrano[3',4':6,7]indolizino[1,2-b]quinolin-9-yl)oxy)methoxy)carbonyl)-1-(((isopropylcarbamoyl)oxy)methyl)pyridin-1-ium iodide;
xiv. 4-((1E,4Z,6E)-5-hydroxy-7-(4-hydroxy-3-methoxyphenyl)-3-oxohepta-1,4,6-trien-1-yl)-2-methoxyphenyl nicotinate;
xv. E,3Z,6E)-3-hydroxy-5-oxohepta-1,3,6-triene-1,7-diyl)bis(2-methoxy-4,1-phenylene) dinicotinate;
xvi. 3,3'-(((((1E,3Z,6E)-3-hydroxy-5-oxohepta-1,3,6-triene-1,7-diyl)bis(2-methoxy-4,1-phenylene))bis(oxy))bis(carbonyl))bis(1-(((isopropylcarbamoyl)oxy)methyl)pyridin-1-ium) diiodide;
xvii. (2aR,4S,4aS,6R,9S,11S,12S,12aR,12bS)-9-(((2R,3S)-3-benzamido-2-(nicotinoyloxy)-3-phenylpropanoyl)oxy)-12-(benzoyloxy)-4,11-dihydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxete-6,12b-diyl diacetate;
xviii. 3-(((((1S,2R)-1-benzamido-3-(((2aR,4S,4aS,6R,9S,11S,12S,12aR,12bS)-6,12b-diacetoxy-12-(benzoyloxy)-4,11-dihydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxet-9-yl)oxy)-3-oxo-1-phenylpropan-2-yl)oxy)carbonyl)-1-(((isopropylcarbamoyl)oxy)methyl)pyridin-1-ium iodide;
xix. (2aR,4S,4aS,6R,9S,11S,12S,12aR,12bS)-9-(((2R,3S)-3-benzamido-2-(((chloromethoxy)carbonyl)oxy)-3-phenylpropanoyl)oxy)-12-(benzoyloxy)-4-(((chloromethoxy)carbonyl)oxy)-11-hydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxete-6,12b-diyl diacetate;

xx. (2aR,4S,4aS,6R,9S,11S,12S,12aR,12bS)-9-(((2R,3S)-3-benzamido-2-(((iodomethoxy)carbonyl)oxy)-3-phenylpropanoyl)oxy)-12-(benzoyloxy)-11-hydroxy-4-(((iodomethoxy)carbonyl)oxy)-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxete-6,12b-diyl diacetate;

xxi. mono(1-((((((1S,2R)-1-benzamido-3-(((2aR,4S,4aS,6R,9S,11S,12S,12aR,12bS)-6,12b-diacetoxy-12-(benzoyloxy)-4-((((3-(dimethylcarbamoyl)pyridin-1-ium-1-yl)methoxy)carbonyl)oxy)-11-hydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxet-9-yl)oxy)-3-oxo-1-phenylpropan-2-yl)oxy)carbonyl)oxy)methyl)-3-(dimethylcarbamoyl)pyridin-1-ium) doiodide;

xx. (2aR,4S,4aS,6R,9S,11S,12S,12aR,12bS)-9-(((2R,3S)-3-benzamido-2-(((chloromethoxy)carbonyl)oxy)-3-phenylpropanoyl)oxy)-12-(benzoyloxy)-4,11-dihydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxete-6,12b-diyl diacetate;

xxiii. 1-((((((1S,2R)-1-benzamido-3-(((2aR,4S,4aS,6R,9S,11S,12S,12aR,12bS)-6,12b-diacetoxy-12-(benzoyloxy)-4,11-dihydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxet-9-yl)oxy)-3-oxo-1-phenylpropan-2-yl)oxy)carbonyl)oxy)methyl)-3-(dimethylcarbamoyl)pyridin-1-ium iodide iodomethyl 2-(4-isobutylphenyl) propanoate;

xxiv. ((2-acetoxybenzoyl)oxy)methyl nicotinate;

xxv. 3-(((((2-acetoxybenzoyl)oxy)methoxy)carbonyl)-1-(((dimethylcarbamoyl)oxy)methyl)pyridin-1-ium iodide;

xxvi. Chloromethyl 2-acetoxybenzoate;

xxvii. 1-(((2-acetoxybenzoyl)oxy)-3-carboylpyridin-1-ium iodide;

xxviii. Chloromethyl 2-(-1-(4-chlorobenzoyl)-5methoxy-2-methyl-1H-indol-3yl) acetate;

xxix. 3-carbamoyl-1-((2-(-1-(4-chlorobenzoyl)-5methoxy-2-methyl-1H-indol-3yl)acetoxy)methyl)pyridine-1-ium iodide;

xxx. chloromethyl 2-(4-isobutylphenyl)propanoate;

xxxi. iodomethyl 2-(4-isobutylphenyl) propanoate;

xxxii. 3-(dimethylcarbamoyl)-1-(((2-(4-isobutylphenyl)propanoyl)oxy)methyl)pyridin-1-ium iodide;

xxxiii. chloromethyl 2-(2-((2,6-dichlorophenyl)amino)phenyl)acetate;

xxxiv. iodomethyl 2-(2-((2,6-dichlorophenyl)amino)phenyl)acetate;

xxxv. 1-((2-(2-((2,6-dichlorophenyl)amino)phenyl)acetoxy)methyl)-3-(dimethylcarbamoyl)pyridin-1-ium iodide;

xxxvi. Compound 337

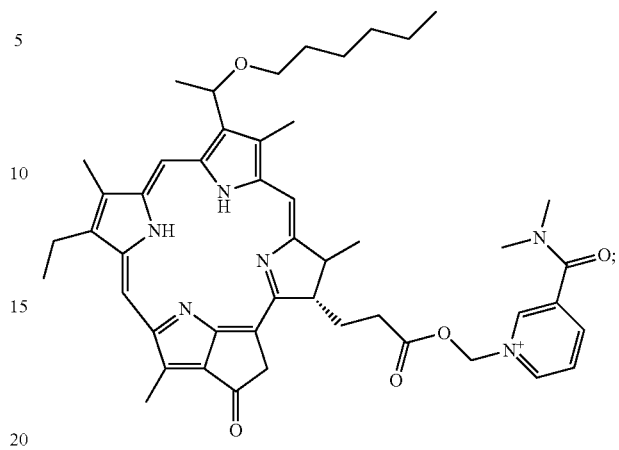

xxxvii. (3-(4-amino-1-oxoisoindolin-2-yl)-2,6-dioxopiperidin-1-yl)methyl nicotinate;

xxxviii. 3-(((3-(4-amino-1-oxoisoindolin-2-yl)-2,6-dioxopiperidin-1-yl)methoxy)carbonyl)-1-(((isopropylcarbamoyl)oxy)methyl)pyridin-1-ium iodide;

xxxix. 1-methyl-4-(4-((4-methyl-3-((4-(pyridin-3-yl)pyrimidin-2-yl)amino)phenyl)carbamoyl)benzyl)-1-((pivaloyloxy)methyl)piperazin-1-ium iodide;

xl. 1-methyl-4-(4-((4-methyl-3-((4-(1-((pivaloyloxy)methyl)pyridin-1-ium-3-yl)pyrimidin-2-yl)amino)phenyl)carbamoyl)benzyl)-1-((pivaloyloxy)methyl)piperazin-1-ium diiodide; and xli. Compound 502

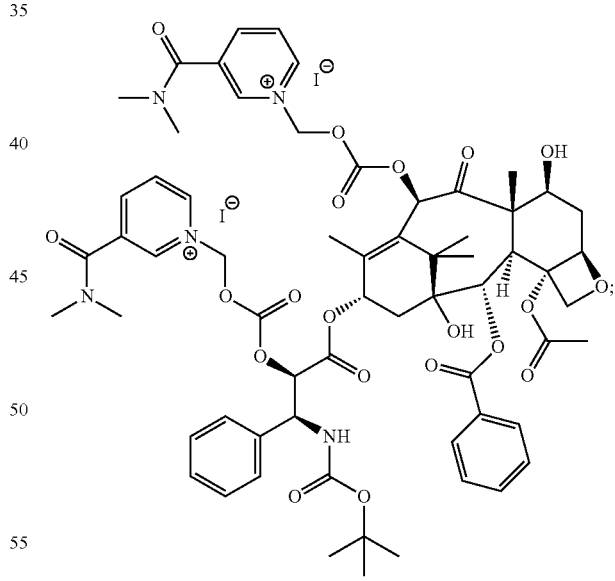

and when the modified pharmaceutical compound is present as a counter ion, then the counter ion is mesylate or iodide.

* * * * *